(12) United States Patent
Afacan et al.

(10) Patent No.: US 12,304,954 B2
(45) Date of Patent: May 20, 2025

(54) MULTIVALENT AND BISPECIFIC ANTIBODY CONSTRUCTS AND METHODS OF USE THEREOF

(71) Applicant: ZYMEWORKS BC INC., Vancouver (CA)

(72) Inventors: Nicole Afacan, Vancouver (CA); Chayne L. Piscitelli, Vancouver (CA); Thomas Spreter Von Kreudenstein, Vancouver (CA); Patricia Zwierzchowski, Vancouver (CA); Nina E. Weisser, Vancouver (CA); David Douda, Vancouver (CA); Kara White-Moyes, Seattle, WA (US); Harsh Pratap, Vancouver (CA)

(73) Assignee: Zymeworks BC Inc., Vancouver (CA)

( * ) Notice: Subject to any disclaimer, the term of this patent is extended or adjusted under 35 U.S.C. 154(b) by 0 days.

(21) Appl. No.: 18/747,102

(22) Filed: Jun. 18, 2024

(65) Prior Publication Data
US 2024/0327516 A1   Oct. 3, 2024

Related U.S. Application Data

(63) Continuation of application No. PCT/CA2023/051026, filed on Jul. 28, 2023.

(60) Provisional application No. 63/465,483, filed on May 10, 2023, provisional application No. 63/458,621, filed on Apr. 11, 2023, provisional application No. 63/393,633, filed on Jul. 29, 2022.

(51) Int. Cl.
| | |
|---|---|
| A61P 35/00 | (2006.01) |
| C07K 16/28 | (2006.01) |
| C07K 16/30 | (2006.01) |
| A61K 39/00 | (2006.01) |

(52) U.S. Cl.
CPC .......... *C07K 16/2809* (2013.01); *A61P 35/00* (2018.01); *C07K 16/30* (2013.01); *A61K 2039/505* (2013.01); *C07K 2317/31* (2013.01); *C07K 2317/55* (2013.01); *C07K 2317/565* (2013.01); *C07K 2317/622* (2013.01); *C07K 2317/734* (2013.01)

(58) Field of Classification Search
None
See application file for complete search history.

(56) References Cited

U.S. PATENT DOCUMENTS

| | | |
|---|---|---|
| 9,388,222 B2 | 7/2016 | Pastan et al. |
| 2018/0327508 A1 | 11/2018 | Wesche et al. |
| 2019/0359712 A1 | 11/2019 | Takahashi et al. |

FOREIGN PATENT DOCUMENTS

| | | | |
|---|---|---|---|
| WO | 2017/021356 A1 | 2/2017 | |
| WO | 2017055391 A1 | 4/2017 | |
| WO | 2020052692 A2 | 3/2020 | |
| WO | 2021231969 A1 | 11/2021 | |
| WO | WO-2023141713 A1 * | 8/2023 | ............. A61K 38/00 |

OTHER PUBLICATIONS

Van den Bremer, Human IgG is produced in a pro-form that requires clipping of C-terminal lysines for maximal complement activation; 2015, mAbs 7(4): 672-680. (Year: 2015).*
International Search Report and Written Opinion for PCT/CA2023/051026, mailed Oct. 19, 2023, 16 pages.
Yoon, A., et al., "A Novel T-Cell Engaging Bispecific Antibody for Treating Mesothelin-Postiive Solid Tumors", Biomolecules, Mar. 4, 2020, vol. 10(3): 399.
Zeng, V.G., et al., "Affinity tuned Xmab®2+1 anti-mesothelin x anti-CD3 bispecific antibody 1-43 induces selective T cell-dependent cellular cytotoxicity of hunan ovarian cancer cells", Proceedings of the Annual Meeting of the American Association for Cancer Research 2020, Cancer Res. Aug. 15, 2020, vol. 80(16_Supplement): Abstract #5654.
Suurs, F.V., et al., "Mesothelin/CD3 Half-Life-Extended Bispecific T-Cell Engager 1-43 Molecule Shows Specific Tumor Uptake and Distributes tu Mesuthelin and CD3-Expressing Tissues", J. Nucl. Med. Apr. 30, 2021, vol. 62, pp. 1797-1804.
Afacan, N.J., et al., "Abstract 2942: ZWI71, a T cell-engaging, bispecific antibody for the treatment of mesothelin-expressing solid tumors", Proceedings of the American Association for Cancer Research Annual Meeting 2023, Part 1 (Regular and Invited Abstracts), Cancer Res. 1, Apr. 2023 (Apr. 1, 2023), vol. 83(7 Supplement): Abstract #2942.
Early Research & Development Day Presentation, Oct. 20, 2022. Engineering and Preclinical Development of ZW171: A 2+1 Format Anti-MSLN T Cell Engager, Oral presentation, PEGS Boston, May 19, 2023.
Chowdhury P.S., et al., Isolation of a high-affinity stable single-chain Fv specific for mesothelin from DNA-immunized mice by phage display and construction of a recombinant immunotoxin with anti-tumor activity. Proc Natl Acad Sci U S A. 1998;95(2):669-674.

(Continued)

*Primary Examiner* — Daniel E Kolker
*Assistant Examiner* — James Ryland Melchior
(74) *Attorney, Agent, or Firm* — Goodwin Procter LLP

(57) ABSTRACT

The present disclosure relates to multivalent, e.g., trivalent, and bispecific antibody constructs capable of binding an antigen on a cytotoxic effector cell and a tumor-associated antigen (TAA) on a tumor cell. Pharmaceutical compositions comprising such antibody constructs and methods of preparing and using such constructs and compositions, e.g., for the treatment of cancer, are also disclosed.

30 Claims, 45 Drawing Sheets
Specification includes a Sequence Listing.

(56) References Cited

OTHER PUBLICATIONS

Chang K, et al. Molecular cloning of mesothelin, a differentiation antigen present on mesothelium, mesotheliomas, and ovarian cancers. Proc Natl Acad Sci U S A. 1996;93(1):136-140.

Hassan R, et al. Detection and quantitation of serum mesothelin, a tumor marker for patients with mesothelioma and ovarian cancer. Clin Cancer Res. 2006; 12(2):447-453.

Hassan R, et al. Mesothelin-targeting T cell receptor fusion construct cell therapy in refractory solid tumors: phase 1/2 trial interim results. Nat Med. 2023;29(8):2099-2109.

Hollevoet K, et al. Diagnostic performance of soluble mesothelin and megakaryocyte potentiating factor in mesothelioma. Am J Respir Crit Care Med. 2010; 181(6):620-625.

Huang H, et al. Mesothelial cell-derived antigen-presenting cancer-associated fibroblasts induce expansion of regulatory T cells in pancreatic cancer. Cancer Cell. 2022;40(6):656-673.

Inaguma S, et al. Comprehensive immunohistochemical study of mesothelin (MSLN) using different monoclonal antibodies 5B2 and MN-1 in 1562 tumors with evaluation of its prognostic value in malignant pleural mesothelioma. Oncotarget. 2017;8(16):26744-26754.

Quanz M, et al. Anetumab ravtansine inhibits tumor growth and shows additive effect in combination with targeted agents and chemotherapy in mesothelin-expressing human ovarian cancer models. Oncotarget. 2018;9 (75):34103-34121.

Sharon E, et al. Serum mesothelin and megakaryocyte potentiating factor in pancreatic and biliary cancers. Clin Chem Lab Med. 2012;50(4):721-725.

Shen J, et al. Insights Into the Role of Mesothelin as a Diagnostic and Therapeutic Target in Ovarian Carcinoma. Front Oncol. 2020; 10:1263.

Shimabukuro-Vornhagen A, et al. Cytokine release syndrome. J Immunother Cancer. 2018;6(1):56.

Smith Ker, et al., Soluble mesothelin neutralizes mesothelin antibody-based therapies. JCO 42(16 Suppl), 2565-2565(2024).

Weidemann S, et al. Mesothelin Expression in Human Tumors: A Tissue Microarray Study on 12,679 Tumors. Biomedicines. 2021;9(4):397.

\* cited by examiner

MULTIVALENT AND BISPECIFIC ANTIBODY CONSTRUCTS AND METHODS OF USE THEREOF

CROSS REFERENCE TO RELATED APPLICATIONS

This application is a continuation of PCT/CA2023/051026, filed Jul. 28, 2023, which claims priority to and the benefit of U.S. provisional application 63/465,483, filed May 10, 2023, U.S. provisional application 63/458,621, filed Apr. 11, 2023, and U.S. provisional application 63/393,633, filed Jul. 29, 2022, the entire contents of each of which are incorporated by reference herein for all purposes.

SEQUENCE LISTING

The instant application contains a Sequence Listing which has been filed electronically in XML format and is hereby incorporated by reference in its entirety. Said XML file copy, created on Sep. 28, 2023, is named V820416WO and is 105,702 bytes in size.

TECHNICAL FIELD

The present disclosure relates to multivalent and bispecific antibody constructs capable of targeting an antigen on the surface of a cytotoxic effector cell and a tumor-associated antigen (TAA) located on a tumor cell, as well as methods for producing and using such constructs, e.g., for the treatment of cancer.

BACKGROUND

Cancer continues to pose a major unmet medical need, despite the considerable progress that has been made in its treatment over the past decades. The TAA mesothelin (MSLN) can be targeted to treat MSLN$^+$ tumors, particularly solid tumors, including those characterized as mesothelioma, ovarian, lung, colon and pancreatic cancer, as well as triple negative breast cancer. While the current standard of care as well as more recently developed therapies for these indications have shown some clinical progress, which validated MSLN as a promising target for cancer treatment, significant systemic side effects and limited efficacy were reported, mainly due to the narrow therapeutic windows for these modalities.

SUMMARY

In various embodiments, the present disclosure relates to multivalent and bispecific antibody constructs capable of binding an antigen on the surface of a cytotoxic effector cell and a tumor-associated antigen (TAA) located on a tumor cell. In some embodiments, the present disclosure relates to a trivalent and bispecific antibody construct capable of binding cluster of differentiation 3 (CD3) on an immune cell (e.g., a T cell) and MSLN on a tumor cell.

In various embodiments, the present disclosure relates to an antibody construct, comprising: (i) a Fab domain capable of binding an antigen on a cytotoxic effector cell; (ii) a first scFv domain and a second scFv domain, wherein the first scFv domain and the second scFv domain are both capable of binding mesothelin (MSLN); and (iii) a dimeric Fc domain comprising a first Fc polypeptide and a second Fc polypeptide, wherein: a) the Fab domain is coupled to the N-terminus of the first Fc polypeptide, b) the first scFv domain is coupled to the N-terminus of the second Fc polypeptide, and c) the second scFv domain is coupled to an N-terminus of the Fab domain. In some embodiments, at least one of the first scFv domain and the second scFv domain comprises a $V_H$ domain comprising an HCDR1 sequence comprising or consisting of the sequence set forth in SEQ ID NO: 120, an HCDR2 sequence comprising or consisting of the sequence set forth in SEQ ID NO: 121, and an HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125. In various embodiments, the first scFv domain and the second scFv domain each comprise a $V_H$ domain comprising an HCDR1 sequence comprising or consisting of the sequence set forth in SEQ ID NO: 120, an HCDR2 sequence comprising or consisting of the sequence set forth in SEQ ID NO: 121, and an HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

The present disclosure, in various embodiments, relates to an antibody construct comprising: (i) a Fab domain capable of binding an antigen on a cytotoxic effector cell; (ii) a first scFv domain capable of binding MSLN and comprising a $V_H$ domain comprising an HCDR1 sequence comprising or consisting of the sequence set forth in SEQ ID NO: 120, an HCDR2 sequence comprising or consisting of the sequence set forth in SEQ ID NO: 121, and an HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125; (iii) a second scFv domain capable of binding a second tumor-associated antigen (TAA); and (iv) a dimeric Fc domain comprising a first Fc polypeptide and a second Fc polypeptide, wherein: a) the Fab domain is coupled to the N-terminus of the first Fc polypeptide, b) the first scFv domain is coupled to the N-terminus of the second Fc polypeptide, and c) the second scFv domain is coupled to an N-terminus of the Fab domain. In various embodiments, the second TAA to which the second scFv domain binds is also MSLN. Hence, in certain embodiments, the second scFv domain also comprises a $V_H$ domain comprising an HCDR1 sequence comprising or consisting of the sequence set forth in SEQ ID NO: 120, an HCDR2 sequence comprising or consisting of the sequence set forth in SEQ ID NO: 121, and an HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

In various embodiments of an antibody construct disclosed herein, the cytotoxic effector cell is a T cell. In such embodiments, the antigen to which the Fab domain binds can be CD3. In various embodiments, the Fab domain is capable of binding CD3 and comprises a $V_H$ domain comprising an HCDR1 sequence comprising or consisting of the sequence set forth in SEQ ID NO: 126, an HCDR2 sequence comprising or consisting of the sequence set forth in SEQ ID NO: 127, and an HCDR3 sequence comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131.

In various embodiments of an antibody construct disclosed herein, the first scFv domain and the second scFv domain each comprise a $V_H$ domain comprising or consisting of an amino acid sequence having at least about 90%, 95%, 97%, 99% or 100% sequence identity to the sequence set forth in SEQ ID NO: 103 and a $V_L$ domain comprising or consisting of an amino acid sequence having at least about 90%, 95%, 97%, 99% or 100% sequence identity to the sequence set forth in SEQ ID NO: 101. In certain embodiments, for the first scFv domain and the second scFv domain, the $V_L$ domain is coupled to the $V_H$ domain by a linker$^{scFv}$. Such linker$^{scFv}$ can comprise or consist of the amino acid sequence $(G_4S)_n$, wherein n is 1, 2, 3, 4 or 5 (SEQ ID NO:132). In certain embodiments, n is 3. In other embodiments, n is 4.

In some embodiments of an antibody construct disclosed herein, the first scFv domain (which can also be referred to herein as "scFv1"), the second scFv domain (which can also be referred to herein as "scFv2"), or both scFv domains, can have the domain structure, from N-terminus to C-terminus, of: $V_H$-linker$^{scFv}$-$V_L$. In some embodiments, the first scFv domain and the second scFv domain have the domain structure, from N-terminus to C-terminus, of: $V_H$-linker$^{scFv}$-$V_L$. In such embodiments, the first scFv domain and the second scFv domain of an antibody construct can each comprise or consist of an amino acid sequence having at least about 90%, 95%, 97%, 99% or 100% sequence identity to the sequence set forth in SEQ ID NO: 150.

In other embodiments of an antibody construct disclosed herein, the first scFv domain, the second scFv domain, or both scFv domains, can have the domain structure, from N-terminus to C-terminus, of: $V_L$-linker$^{scFv}$-$V_H$. In various embodiments, the first scFv domain and the second scFv domain have the domain structure, from N-terminus to C-terminus, of: $V_L$-linker$^{scFv}$-$V_H$. In such embodiments, the first scFv domain and the second scFv domain can each comprise or consist of an amino acid sequence having at least about 90%, 95%, 97%, 99% or 100% sequence identity to the sequence set forth in SEQ ID NO: 149.

In various embodiments of an antibody construct disclosed herein, the Fab domain comprises or consists of a heavy chain H, or portion thereof, comprising, from N- to C-terminus, a $V_H$ domain comprising or consisting of an amino acid sequence having at least about 90%, 95%, 97%, 99% or 100% sequence identity to the sequence set forth in SEQ ID NO: 105, and a $C_{H1}$ domain comprising or consisting of an amino acid sequence having at least about 90%, 95%, 97%, 99% or 100% sequence identity to the sequence set forth in SEQ ID NO: 106. The Fab domain further comprises a light chain L comprising, from N- to C-terminus, a $V_L$ domain comprising or consisting of an amino acid sequence having at least about 90%, 95%, 97%, 99% or 100% sequence identity to the sequence set forth in SEQ ID NO: 115, and a $C_L$ domain comprising or consisting of an amino acid sequence having at least about 90%, 95%, 97%, 99% or 100% sequence identity to the sequence set forth in SEQ ID NO: 116, wherein the light chain L pairs with the $V_H$-$C_{H1}$ domain sequence of the heavy chain H, thereby forming the Fab domain. In some embodiments, the light chain L of an antibody construct herein comprises or consists of an amino acid sequence having at least about 90%, 95%, 97%, 99% or 100% sequence identity to the sequence set forth in SEQ ID NO: 114.

In various embodiments of an antibody construct disclosed herein, the antibody construct comprises a first heavy chain H1 comprising, from N-terminus to C-terminus, scFv2-$V_H$-$C_{H1}$, in which the C-terminus of the second scFv domain is coupled to the N-terminus of the $V_H$ domain. In some embodiments, the C-terminus of the second scFv domain is coupled to the N-terminus of the $V_H$ domain via a linker$^{scFv-Fab}$, resulting in the heavy chain domain structure: scFv2-linker$^{scFv-Fab}$-$V_H$-$C_{H1}$. Such linker$^{scFv-Fab}$ can comprise or consist of the amino acid sequence $(G_4S)_n$, wherein n is 1, 2, 3, 4 or 5 (SEQ ID NO:132). In various embodiments, the first heavy chain H1 further comprises the first Fc polypeptide, and wherein the C-terminus of the $C_{H1}$ domain of the Fab domain is coupled to the N-terminus of the first Fc polypeptide, thereby forming the following domain structure for H1: scFv2-linker$^{scFv-Fab}$-$V_H$-$C_{H1}$-CH2-CH3. In certain embodiments, the $C_{H1}$ domain is coupled to the CH2 domain of the first Fc polypeptide by a linker$^{Fab-Fc}$. Such linker$^{Fab-Fc}$ can comprise or consist of an immunoglobulin (Ig) hinge region. In some embodiments, the Ig hinge region is an IgG hinge region. Such IgG hinge region can be an IgG1 hinge region. In some embodiments, the linker$^{Fab-Fc}$ comprises or consists of an amino acid sequence having at least about 70%, 80%, 90% or 100% sequence identity to the sequence set forth in SEQ ID NO: 107. Hence, in certain embodiments, H1 can comprise or consist of the following domain structure: scFv2-linker$^{scFv-Fab}$-$V_H$-$C_{H1}$-linker$^{Fab-Fc}$-CH2-CH3.

In various embodiments of an antibody construct disclosed herein, the dimeric Fc domain is a heterodimeric Fc domain. Such heterodimeric Fc domain comprises a first polypeptide and a second Fc polypeptide. Such first and second Fc polypeptides, unless otherwise specified, are interchangeable and can be coupled to either the Fab or the first scFv domain, as further described herein.

In certain embodiments, one of the first or second Fc polypeptide of the dimeric Fc domain is an IgG1-derived Fc polypeptide and comprises a first CH2 domain (e.g., CH2$_1$ domain) and a first CH3 domain (e.g., CH3$_1$ domain). Such first CH3 domain can comprise one or more amino acid substitutions compared to a corresponding wild-type IgG1 CH3 domain sequence. In some embodiments, the one or more amino acid substitutions are sets of amino acid substitutions selected from: L351Y_F405A_Y407V, T350V_L351Y_F405A_Y407V and T350V_L351Y_S400E_F405A_Y407V, wherein the numbering of amino acid residues in the first Fc polypeptide is according to the EU numbering system. In certain embodiments, the first CH2 domain comprises one or more amino acid substitutions compared to a corresponding wild-type IgG1 CH2 domain that reduce or eliminate binding to an Fc-receptor (e.g., an Fcγ-receptor).

In various embodiments herein, a trivalent and bispecific antibody construct comprises a first heavy chain H1 that comprises or consists of an amino acid sequence having at least about 90%, 95%, 97%, 99% or 100% sequence identity to the sequence set forth in SEQ ID NO: 100. In certain embodiments, such H1 comprises or consists of the amino acid sequence set forth in SEQ ID NO: 100.

In various embodiments of an antibody construct disclosed herein, the antibody construct further comprises a second heavy chain H2, comprising, from N-terminus to C-terminus, the first scFv domain coupled to the other one of the first or second Fc polypeptide, thereby forming the domain structure: scFv1-CH2-CH3. In certain embodiments, the C-terminus of the first scFv domain is coupled to the N-terminus of the second Fc polypeptide, e.g., the N-terminus of a second CH2 domain, via a linker$^{scFv\text{-}Fc}$. Such linker$^{scFv\text{-}Fc}$ can comprise or consist of an Ig hinge region. In some embodiments, the Ig hinge region is an IgG hinge region. Such IgG hinge region can be an IgG1 hinge region. Hence, in some embodiments, the linker$^{scFv\text{-}Fc}$ comprises or consists of an amino acid sequence having at least about 70%, 80%, 90% or 100% sequence identity to the sequence set forth in SEQ ID NO: 111. Accordingly, in some embodiments, H2 can comprise or consist of the following domain structure: scFv1-linker$^{scFv\text{-}Fc}$-CH2-CH3.

In various embodiments of an antibody construct disclosed herein, the other one of the first or second Fc polypeptide is also an IgG1-derived Fc polypeptide and comprises a second CH2 domain (e.g., $CH2_2$ domain) and a second CH3 domain (e.g., $CH3_2$ domain). In some embodiments, the second CH3 domain comprises one or more amino acid substitutions compared to a corresponding wild-type IgG1 CH3 domain sequence. In some embodiments, the one or more amino acid substitutions are selected from: T366L_K392M_T394W, T366L_K392L_T394W, T350V_T366L_K392L-_T394W, T350V_T366L_K392M_T394W and T350V_T366L_N390R_K392M_T394W, wherein the numbering of amino acid residues in the second Fc polypeptide is according to the EU numbering system. Hence, in various embodiments of antibody constructs comprising a heterodimeric Fc domain, the one or more amino acid substitutions in the first CH3 domain and the one or more amino acid substitutions in the second CH3 domain promote preferential pairing of the heavy chains H1 and H2 and formation of a heterodimeric Fc domain H1-H2, compared to the formation of a corresponding homodimeric Fc domain (e.g., one that is comprised of H1-H1 or H2-H2). Similar to the first CH2 domain of the first Fc polypeptide, the second CH2 domain can comprise one or more amino acid substitutions compared to a corresponding wild-type IgG1 CH2 domain that reduce or eliminate binding to an Fc-receptor (e.g., an Fcγ-receptor).

In various embodiments herein, a trivalent and bispecific antibody construct comprises a second heavy chain H2 that comprises or consists of an amino acid sequence having at least about 90%, 95%, 97%, 99% or 100% sequence identity to the amino acid sequence set forth in SEQ ID NO: 110. In certain embodiments, H2 comprises or consists of the amino acid sequence set forth in SEQ ID NO: 110.

In various embodiments of the present disclosure, the antibody construct is bispecific for CD3 and MSLN, and trivalent, i.e., monovalent for CD3 via the Fab domain, and bivalent for MSLN via the first scFv domain and second scFv domain.

In various embodiments of an antibody construct disclosed herein, the antibody construct comprises a first heavy chain (H1) comprising or consisting of an amino acid sequence having at least about 90%, 95%, 97%, 99% or 100% sequence identity to the sequence set forth in SEQ ID NO: 100, a second heavy chain (H2) comprising or consisting of an amino acid sequence having at least about 90%, 95%, 97%, 99% or 100% sequence identity to the sequence set forth in SEQ ID NO: 110, and a light chain (L1) comprising or consisting of an amino acid sequence having at least about 90%, 95%, 97%, 99% or 100% sequence identity to the sequence set forth in SEQ ID NO: 114.

In some embodiments, an antibody construct of the present disclosure comprises (i) a first heavy chain (H1) comprising or consisting of the amino acid sequence set forth in SEQ ID NO: 100, (ii) a second heavy chain (H2) comprising or consisting of the amino acid sequence set forth in SEQ ID NO: 110, and (iii) a light chain (L1) comprising or consisting of the amino acid sequence set forth in SEQ ID NO: 114.

In some embodiments, an antibody construct of the present disclosure comprises a first heavy chain (H1) comprising or consisting of the amino acid sequence set forth in SEQ ID NO: 171, a second heavy chain (H2) comprising or consisting of the amino acid sequence set forth in SEQ ID NO: 172, and a light chain (L1) comprising or consisting of the amino acid sequence set forth in SEQ ID NO: 114.

In other embodiments of an antibody construct disclosed herein, the antibody construct comprises a first heavy chain (H1) comprising or consisting of an amino acid sequence having at least about 90%, 95%, 97%, 99% or 100% sequence identity to the sequence set forth in SEQ ID NO: 117, a second heavy chain (H2) comprising or consisting of an amino acid sequence having at least about 90%, 95%, 97%, 99% or 100% sequence identity to the sequence set forth in SEQ ID NO: 119, and a light chain (L1) comprising or consisting of an amino acid sequence having at least about 90%, 95%, 97%, 99% or 100% sequence identity to the sequence set forth in SEQ ID NO: 114.

In various embodiments of a trivalent and bispecific antibody construct disclosed herein, such antibody construct is capable of one or more, two or more, or all of the following when present for about 72 hours at a concentration of about 10 picomole per liter (pM) in a cell population comprising immune cells expressing CD3 and tumor cells expressing about 500,000 MSLN/cell: A) inducing production of at least about 20 pg/mL, 30 pg/mL, or 40 pg/mL TNFα; B) inducing production of at least about 500 pg/mL, 1000 pg/mL, or 2000 pg/mL IFNγ; and/or C) inducing production of at least about 50 pg/mL, 1000 pg/mL, or 150 pg/mL IL-2.

In various embodiments of a trivalent and bispecific antibody construct disclosed herein, such antibody construct is capable of inducing at least 10-fold higher T-cell mediated cytotoxicity against MSLN-expressing tumor cells compared to an analogous antibody constructs that comprises two anti-MSLN Fab domains instead of the first and second anti-MSLN scFv domains.

In various embodiments of a trivalent and bispecific antibody construct disclosed herein, such antibody construct has a binding affinity for MSLN of about 0.7 nM, 0.8 nM, 0.9 nM, or about 1 nM as measured by surface plasmon resonance (SPR).

In certain embodiments of a trivalent and bispecific antibody construct disclosed herein, such antibody construct has a binding affinity for CD3 of about 30 nM, 40 nM, 50 nM, or about 60 nM as measured by SPR.

In certain embodiments of a trivalent and bispecific antibody construct disclosed herein, such antibody construct is capable of inducing production of a pro-inflammatory cytokine by a cytotoxic effector cell in a MSLN-dependent manner, wherein the MSLN-dependent activation of the cytotoxic effector cell is determined by measuring a reduction in cytokine production of at least about 20-fold, 50-fold, 100-fold, or at least about 1000-fold between a first cell population comprising a first tumor cell and immune cells and in a second cell population comprising a second tumor cell and immune cells, wherein the first tumor cell has a MSLN-expression that is at least about 3, 4 or 5-fold higher than that of the second tumor cell.

In certain embodiments of a trivalent and bispecific antibody construct disclosed herein, when such antibody construct is administered to a mammalian subject, the construct is capable of reducing the volume of a MSLN-expressing tumor in the subject by at least about 5% over a time period of at least 20 days following administration of the antibody construct to the subject at a dose of about 1 mg/kg, 1.5 mg/kg or about 3 mg/kg, and when administered 4-times every week. In some embodiments, such reduction in tumor volume is at least about 7%, 10%, 15%, 20%, 25%, 30%, 35%, 40%, 50%, 60%, or at least about 70%. In some embodiments, the mammalian subject is a rodent or a non-human primate.

In some embodiments herein, a trivalent and bispecific antibody construct of the present disclosure can have a stability of at least about 97%, 98% or 99%, i.e., at least about 97%, 98% or 99% of intact antibody construct is measured, after incubation of the antibody construct at 40° C. for 14 days in an aqueous solution or buffer system comprising sucrose, and as measured using SEC.

In some embodiments, the present disclosure relates to a pharmaceutical composition comprising a trivalent and bispecific antibody construct of the present disclosure, and a pharmaceutically acceptable carrier, excipient, diluent, or combination thereof.

Certain embodiments of the present disclosure relate to a nucleic acid molecule or a set of nucleic acid molecules encoding the one or more polypeptide chains of an antibody construct described herein. In some embodiments, described herein is a nucleic acid molecule or a set of nucleic acid molecules encoding the one or more polypeptide chains of a bispecific and trivalent antibody construct described herein, e.g., construct v32523 or v21812. In some embodiments, described herein is a nucleic acid molecule or a set of nucleic acid molecules encoding the three polypeptide chains of the bispecific and trivalent antibody construct v32523, which amino acid sequences are set forth in SEQ ID NOs: 100, 110 and 114, or in SEQ ID NOs: 171, 172 and 114, as further described herein.

Further described herein is a vector or a set of vectors comprising a nucleic acid molecule or a set of nucleic acid molecules encoding the one or more polypeptide chains of an antibody construct described herein.

Further described herein is a host cell comprising a nucleic acid molecule or a set of nucleic acid molecules encoding the one or more polypeptide chains of an antibody construct described herein, and/or a vector or a set of vectors comprising a nucleic acid molecule or a set of nucleic acid molecules encoding the one or more polypeptide chains of an antibody construct described herein. In some embodiments, the host cell can be a mammalian host cell.

Certain embodiments of the present disclosure relate to a method of producing an antibody construct described herein. In some embodiments, such method relates to the production of a trivalent and bispecific antibody construct that comprises two anti-MSLN scFv domains and one anti-CD3 Fab domain, as further described herein. In some embodiments, a method of producing such trivalent and bispecific antibody construct comprises (a) obtaining a host cell culture comprising at least one host cell comprising one or more nucleic acid molecules encoding the one or more polypeptide chains of the antibody construct; and (b) recovering the antibody construct from the host cell culture. In some embodiments, such method can further comprise purifying the antibody construct using, e.g., a chromatographic purification method as described herein.

In some embodiments, the amino acid sequences of one or more heavy chains of an antibody construct herein can comprise an additional C-terminal lysine residue for production in a host cell. Hence, in some embodiments, the amino acid sequences set forth in SEQ ID NO: 100 and SEQ ID NO: 110 can further comprise a C-terminal lysine ("K") residue. Exemplary amino acid sequences for the two heavy chains H1 and H2 of antibody construct v32523 that comprise a C-terminal lysine residue are set forth in SEQ ID NOs: 171 and 172, respectively. Such C-terminal lysine residue may be enzymatically cleaved from the one or more heavy chains subsequent to expression in the host cell. In some embodiments, the trivalent and bispecific antibody construct comprising the heavy chain amino acid sequences set forth in SEQ ID NOs: 171 and 172, and the light chain amino acid sequence set forth in SEQ ID NO: 114 can be referred to as v38490.

Additional embodiments of the present disclosure relate to a method of eliciting an anti-tumor immune response in a cell population comprising immune cells expressing CD3 and tumor cells expressing MSLN, the method comprising contacting the cell population with an effective amount of a trivalent and bispecific antibody construct of the present disclosure. In some embodiments, the anti-tumor immune response provides a dose-dependent reduction in live tumor cells in the cell population of at least about 30%, 40%, 50%, or 60% when the concentration of the antibody construct in the cell population ranges (e.g., is increased) from about $10^{-2}$ picomolar (pM) to about $10^2$ pM, wherein the expression of MSLN of the tumor cells is at least about 15,000 MSLN/cell and the ratio of immune cells to tumor cells in the cell population is about 5:1.

Certain embodiments of the present disclosure relate to a method of inhibiting the proliferation of tumor cells expressing MSLN, the method comprising contacting a cell population comprising the tumor cells and immune cells expressing CD3 with an effective amount of a trivalent and bispecific antibody construct of the present disclosure. In certain embodiments, the proliferation of tumor cells is inhibited when an increase in live tumor cell count of at most about 5% is observed in the cell population over a period of at least about 5, 10, 20, or 48 hours using a concentration of the antibody construct of at most about $10^{-2}$ pM, $10^{-1}$ pM, or 1 pM, wherein the expression of MSLN of the tumor cells is at least about 15,000 MSLN/cell and the ratio of immune cells to tumor cells in the cell population is about 5:1. In some embodiments, proliferation of tumor cells is inhibited when a decrease in live tumor cell count of at least about 5%, 10%, 15%, 20%, 25%, 30%, 35%, 40%, 45%, or at least about 50% is measured over the given period of time.

Other embodiments of the present disclosure relate to a method of killing tumor cells expressing MSLN, the method comprising contacting a cell population comprising the tumor cells and immune cells expressing CD3 with an effective amount of a trivalent and bispecific antibody construct of the present disclosure. In such embodiments, tumor cell killing is observed when a dose-dependent reduction in live tumor cells in the cell population of at least about 30%, 40%, 50%, or 60% is measured when the concentration of the antibody construct ranges (e.g., is increased) from about $10^{-2}$ pM to about $10^2$ pM, wherein the expression of MSLN of the tumor cells is at least about 15,000 MSLN/cell and the ratio of immune cells to tumor cells in the cell population is about 5:1.

In certain embodiments of these methods, the immune cells comprise or consist of T cells. Such T cell populations can comprise one or more different types of T cells known in the art.

In certain embodiments of the methods described herein, the trivalent and bispecific antibody constructs bind CD3 on an immune cell and MSLN on a tumor cell. In various embodiments, such binding of both antigens on different cells can comprise simultaneous binding of CD3 and MSLN, which, in some embodiments, can establish a TCR-independent immune synapse capable of inducing anti-tumor cytotoxic activity of the T cell against the tumor cell.

In some embodiments, the present disclosure relates to a method of inhibiting the growth of a MSLN-expressing tumor or reducing the volume of such tumor in a subject, the method comprising administering to the subject an effective amount of a trivalent and bispecific antibody construct of the present disclosure. In various embodiments, the antibody construct engages CD3 on immune cells and MSLN on tumor cells in the subject which elicits an anti-tumor immune response in the subject, and thereby inhibits the growth of the tumor or reduces the volume of the tumor in the subject. In some embodiments, inhibition of tumor growth and/or reduction in tumor volume is elicited, at least in part, by binding of the antibody construct to CD3 on an immune cell and to MSLN on a tumor cell and formation of a TCR-independent artificial immune synapse within a tumor environment in the subject. As described herein, the immune cell can be a T cell. In various embodiments, and as further described herein, immune cell (e.g., T cell) activation can elicit a release of one or more cytokines from the activated immune cells, such as TNFα, IFNγ, and/or IL-2. In various embodiments, tumor growth in the subject is inhibited (e.g., no more than 5% tumor growth over the course of the study) for at least about 20 days, 30 days, or at least about 50 days using 4-times weekly (Q7Dx4) administration of the antibody construct to the subject. In certain embodiments, the tumor volume is reduced by at least about 10%, 20%, 30%, 40%, or at least about 50% about 15 days after start of treatment. In such embodiments, about 1 mg/kg, 1.5 mg/kg or about 3 mg/kg of antibody construct is administered to the subject. The subject in the methods described herein can be a rodent, a non-human primate, or a human. In some embodiments, the antibody construct is administered intravenously.

In some embodiments, the present disclosure relates to a trivalent and bispecific antibody construct according to any of the embodiments described herein for use in the treatment of cancer.

In some embodiments, the present disclosure relates to the use of an antibody construct according to any of the embodiments described herein in the manufacture of a medicament for the treatment of cancer.

In some of these embodiments, the cancer is a MSLN-expressing cancer.

BRIEF DESCRIPTION OF THE DRAWINGS

The implementations disclosed herein are illustrated by way of example, and not by way of limitation, in the accompanying drawings. The description and drawings are only for the purpose of illustration and as an aid to understanding and are not intended as a definition of the limits of the antibody constructs, pharmaceutical compositions, and methods of the present disclosure.

FIG. 1A shows a schematic representation of the geometry and format of a trivalent and bispecific antibody construct of this disclosure capable of monovalent binding to CD3 (via one Fab domain) and bivalent binding to MSLN (via 2 scFv domains), according to various embodiments of this disclosure (e.g., as described herein for variants v21812, v32523, etc.). FIG. 1B shows a schematic representation of the geometry and format of a trivalent and bispecific antibody construct capable of monovalent binding to CD3 (via one Fab domain) and bivalent binding to MSLN (via 2 Fab domains), e.g., as used in the 2+1 Fab$^3$ TCB benchmark construct, v29191, or the Fab$^3$ reference construct v21791. FIG. 1C shows a schematic representation of the geometry and format of a bivalent and bispecific antibody construct capable of monovalent binding to CD3 (e.g., via one scFv domain) and monovalent binding to MSLN (e.g., via one Fab domain), e.g., as used in construct v21815 herein. FIG. 1D shows a schematic representation of the geometry and format of a trivalent and trispecific MH6T-TriTAC benchmark polypeptide construct, v31805, capable of monovalent binding to CD3 (e.g., via one scFv domain), monovalent binding to MSLN (e.g., via one $V_{HH}$ domain) and monovalent binding to human serum albumin (HSA or Alb, e.g., via one $V_{HH}$ domain).

FIG. 5D shows that the trivalent and bispecific construct v21812 induced significantly higher IL-2 release from T cells when compared to both the triple-Fab (Fab$^3$; anti-CD3 Fab×anti-MSLN Fab$^2$) construct v21791 as well as the 1+1 anti-CD3 scFv×anti-MSLN Fab construct v21815. Cytokine release was assessed by co-culturing OVCAR3 tumor cells with human pan-T cells and treatment of the cell population with the respective test article for 3 days.

FIG. 7A shows that the trivalent and bispecific anti-(MSLN×CD3) antibody construct v21812 showed the highest cell killing activity of high MSLN-expressing OVCAR-3 cells in a pan T cell co-culture compared to (i) the two variants with lower affinity MSLN paratopes, v29045 and v29048, (ii) the trivalent and bispecific Fab$^3$ benchmark construct (2+1 Fab$^3$ TCB benchmark, v29191), and (iii) a negative control (v31926, anti-CD3/anti-HA construct). FIG. 7B shows that the trivalent and bispecific anti-(MSLN×CD3) antibody construct v21812 showed the highest cell killing activity of modest MSLN-expressing H292 cells in a pan T cell co-culture, which was similar to that of the anti-(MSLN×CD3) benchmark antibody construct MH6T-TriTAC (v31805, see, e.g., FIG. 1D for format), and further compared to (i) the two variants with lower affinity anti-MSLN paratopes, v29045 and v29048, (ii) the trivalent and bispecific Fab$^3$ benchmark construct (v29191), as well as (iii) the negative control (v31926). FIG. 7C shows that all tested constructs did not have any significant effect on live cell count when tested in a MSLN-negative tumor cell line IGROV-1/pan T cell co-culture.

FIG. 12A shows the percent tumor cell killing elicited by the antibody construct v32523 in MSLN$^{high}$ expressing H292 cells compared to MSLN$^{Low}$ expressing OVTOKO and MCF7 cells, wherein FIG. 12B shows a head-to-head comparison of tumor cell killing of the two tested constructs v32523 and v31805 in MSLN$^{high}$ expressing H292 cells and MSLN$^{Low}$ expressing A375 cells. T cell dependent cellular cytotoxicity of the trivalent and bispecific construct v32523* was also tested in the presence of H292 lung cancer cells (FIG. 12C, ~170,000 MSLN/cell), OVCAR8 ovarian cancer cells (FIG. 12D, ~85,000 MSLN/cell), HCT-116 colon cancer cells (FIG. 12E, ~35,000 MSLN/cell) and H2452 mesothelioma cells (FIG. 12F, ~11,000 MSLN/cell), and compared to a negative control (*test article data are shown as square-dotted lines).

production in T cells co-incubated with MSLN+ H292 and MSLN+ HCT116 cells, respectively, for 72 h (E:T ratio of 5:1). The data show that the trivalent and bispecific antibody construct v32523 induced a profoundly lower amount of both cytokines in the lower MSLN-expressing cell line HCT116, demonstrating the property of the antibody constructs described herein to provide a TAA- (e.g., MSLN-) dependent T cell mediated cytotoxicity. Such antigen-dependent properties may enable strong anti-tumor immune responses in high MSLN-expressing environments, while off-target tissues with no or low MSLN-expression may not—or at least to a far lower degree—exposed to T cell mediated cytotoxic effects.

Figure 15:
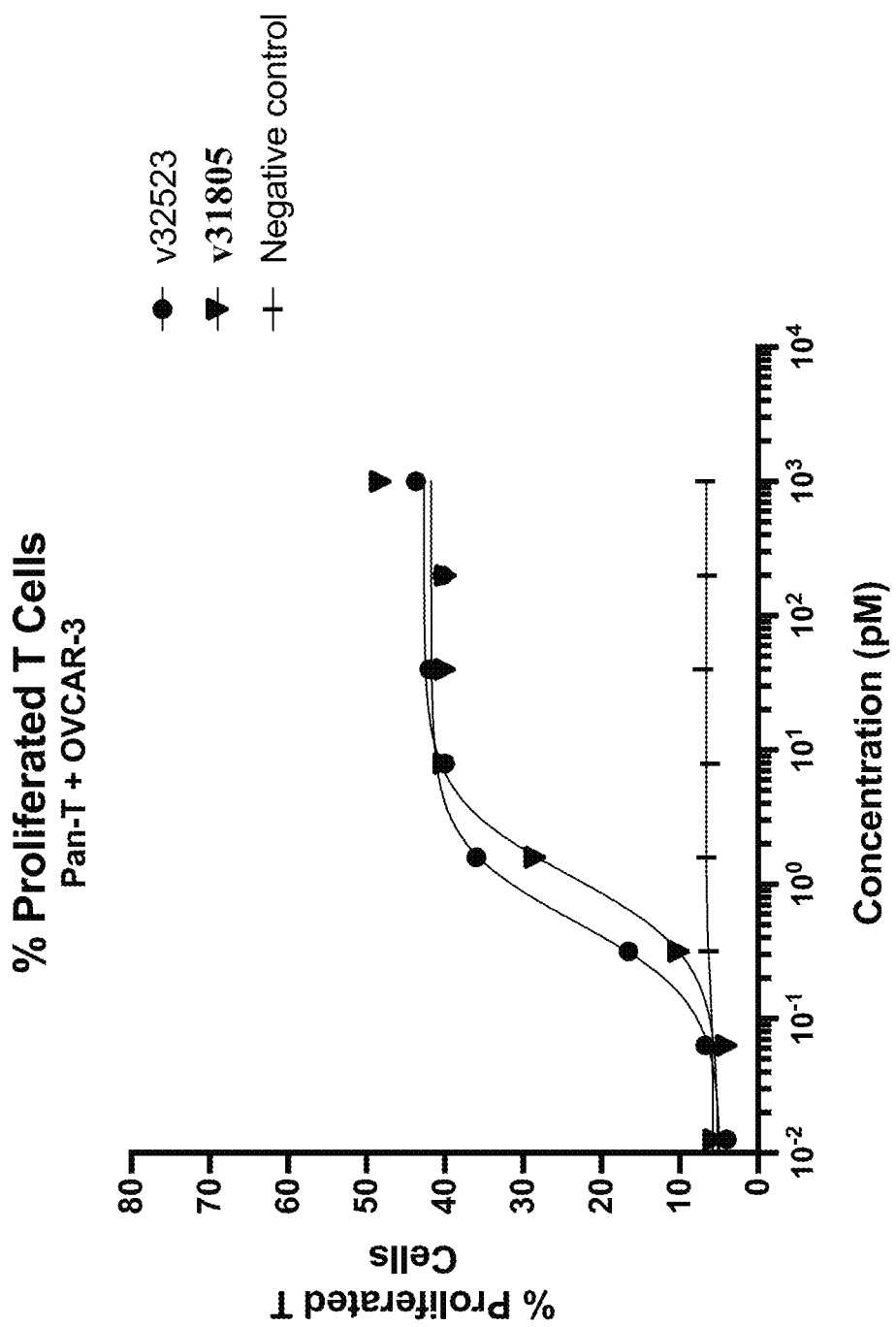

FIG. 15 shows that the trivalent and bispecific antibody construct v32523 as well as the v31805 (MH6T-TriTAC) benchmark control construct induced proliferation of T cells in a comparable and dose-dependent manner when co-incubated with MSLN+ OVCAR-3 cells (E:T ratio of 10:1) for 72 h.

Figure 16A:
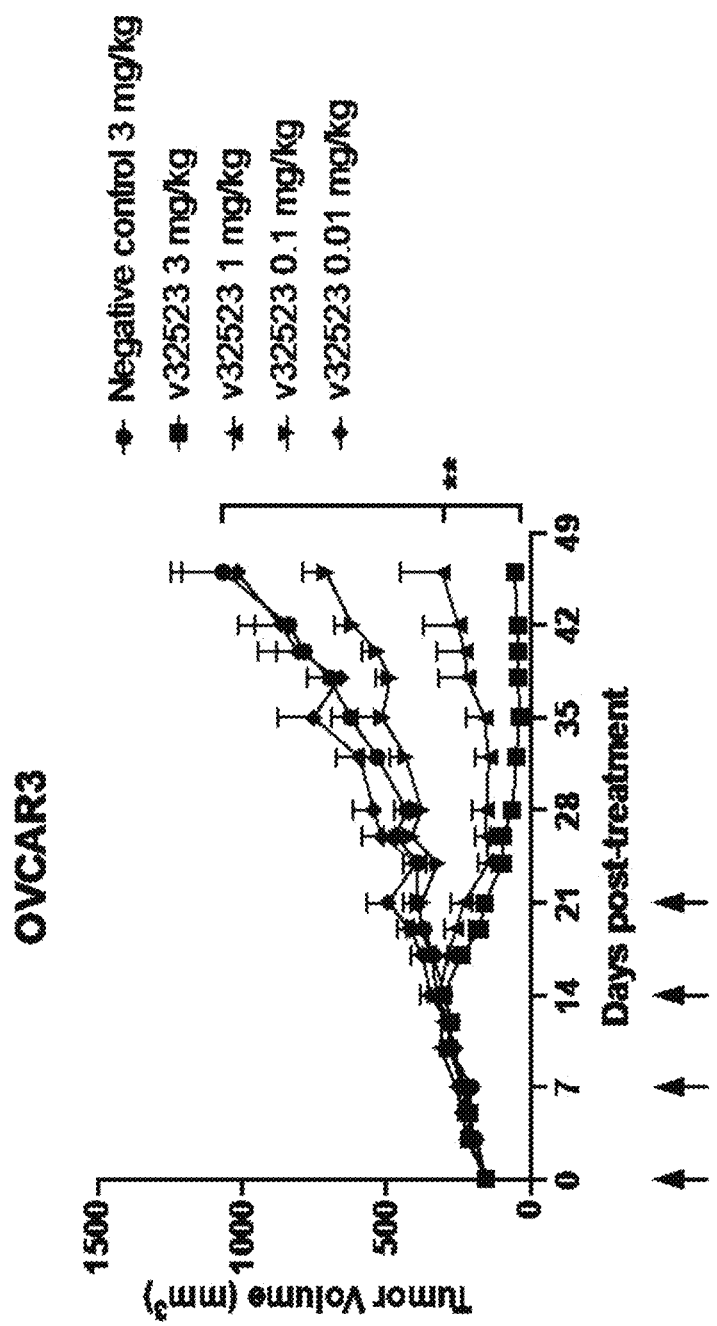
Figure 16B:
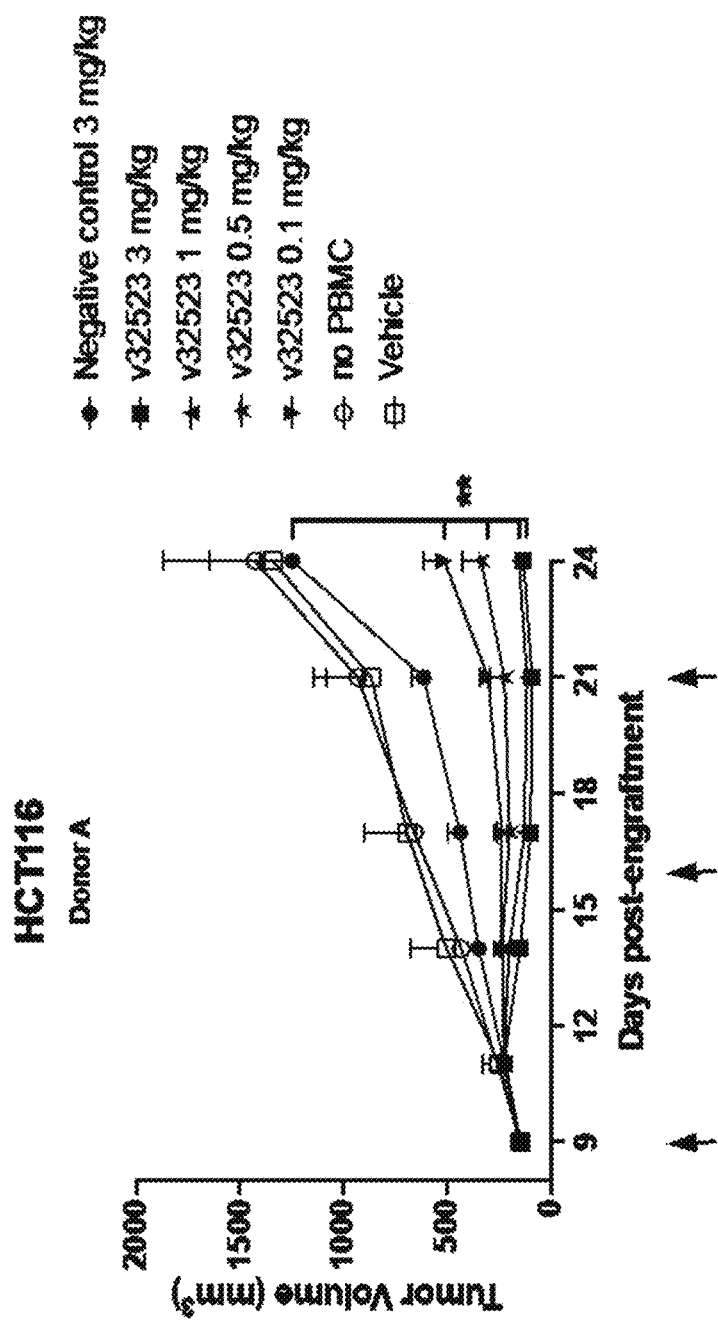

FIGS. 16A-16B show that the trivalent and bispecific antibody construct v32523 of the present disclosure significantly inhibited tumor growth and reduced tumor volume at doses as low as 1 mg/kg or 3 mg/kg in both OVCAR-3-tumor bearing NOG mice (high MSLN expression, FIG. 16A) and HCT116-tumor bearing NOG mice (medium MSLN expression, FIG. 16B), engrafted with human PBMCs (arrows indicate administration time points).

Figure 17A:
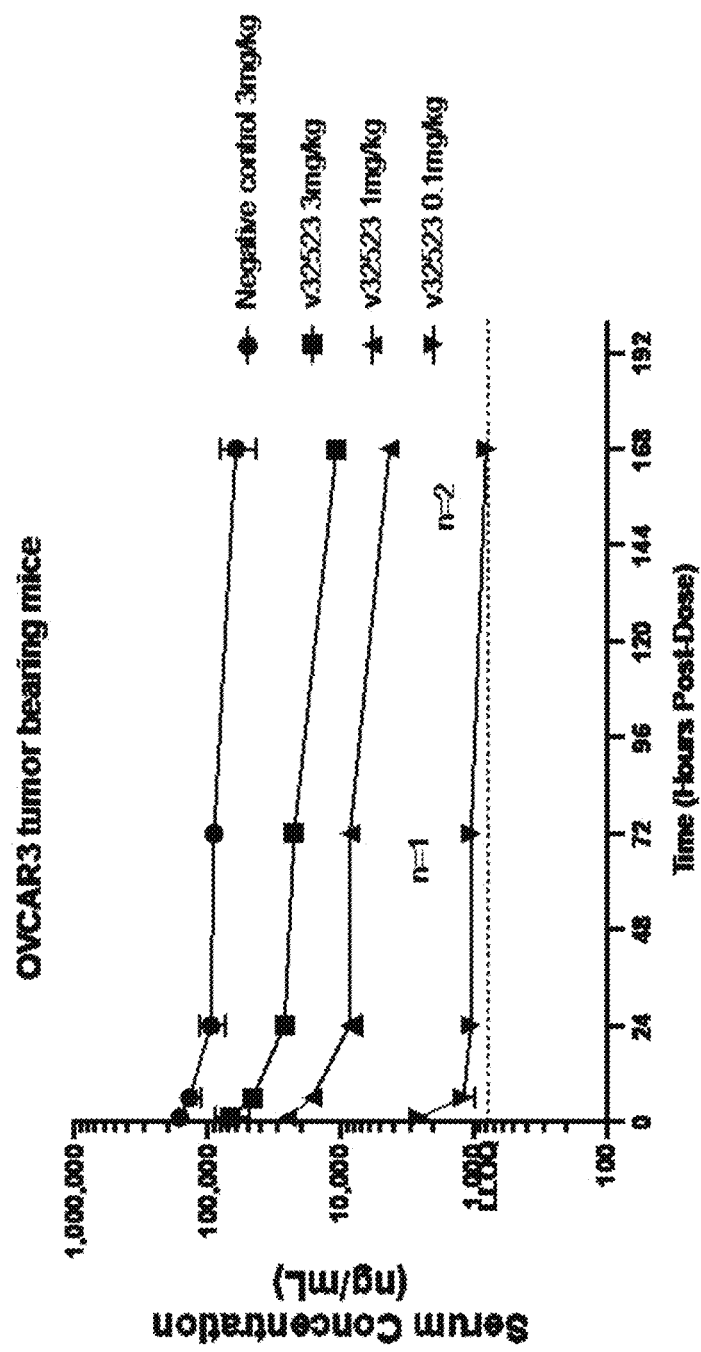
Figure 17B:
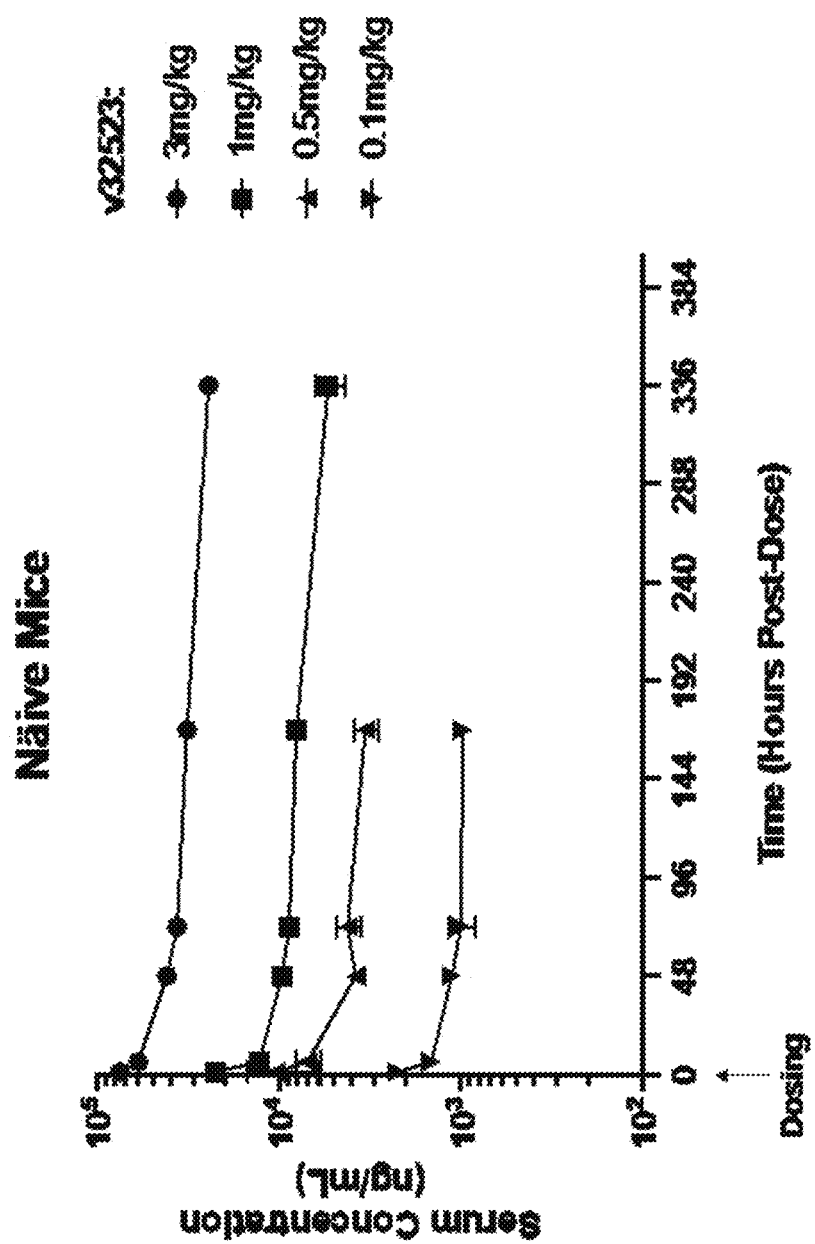
Figure 17C:
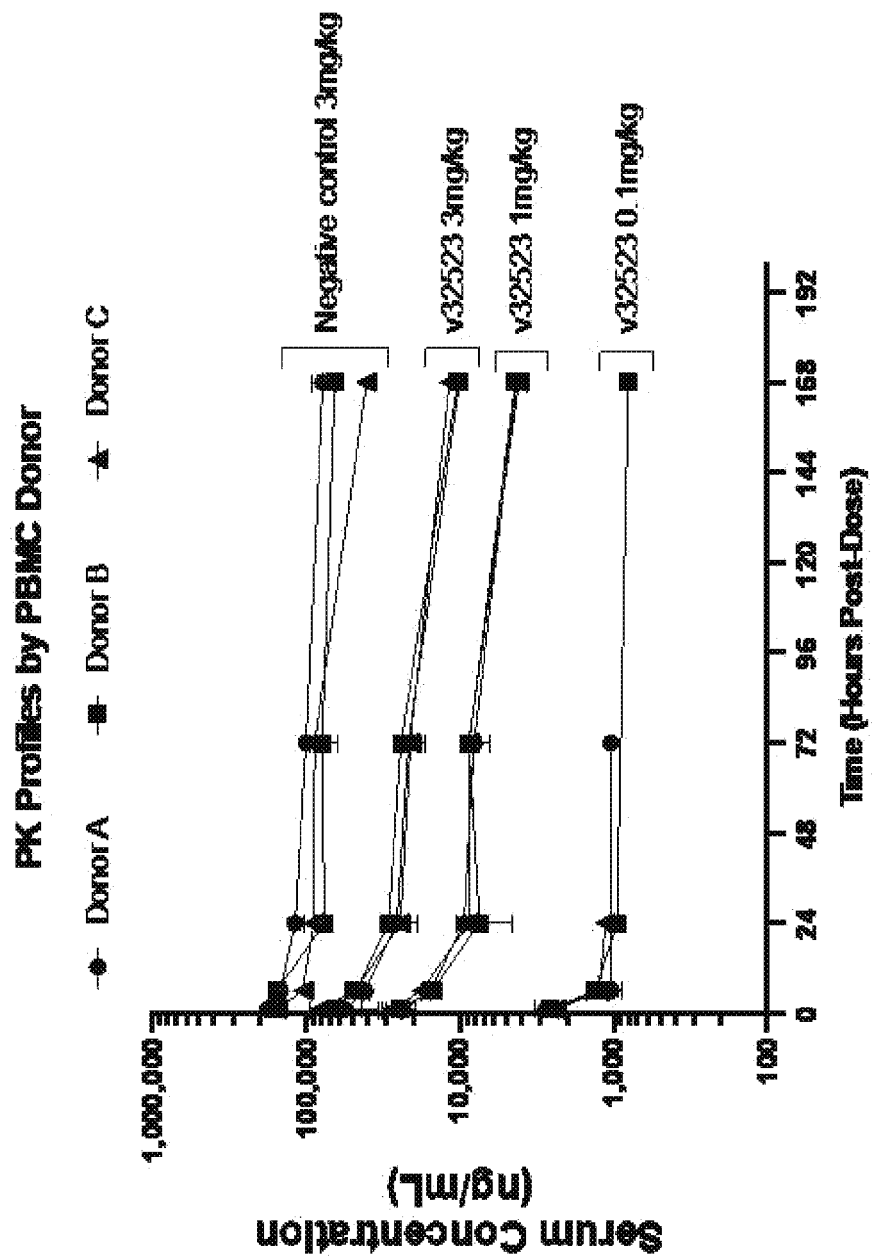

FIGS. 17A-17C show the pharmacokinetic profiles and serum concentrations at various time points post-injection using varying doses of the trivalent and bispecific antibody construct v32523 in both OVCAR-3 tumor bearing mice (FIG. 17A, at doses of 0.1, 1 and 3 mg/kg) and naïve mice (FIG. 17B, at doses of 0.1, 0.5, 1 and 3 mg/kg). FIG. 17C shows the pharmacokinetic profile and serum concentrations at various time point post-injection of varying doses (i.e., 0.1, 1 and 3 mg/kg) of the trivalent and bispecific antibody construct v32523 by PBMC donors A, B and C. The effective lower limit of quantitation (LLOQ) was determined to be about 781 ng/mL.

Figure 18:
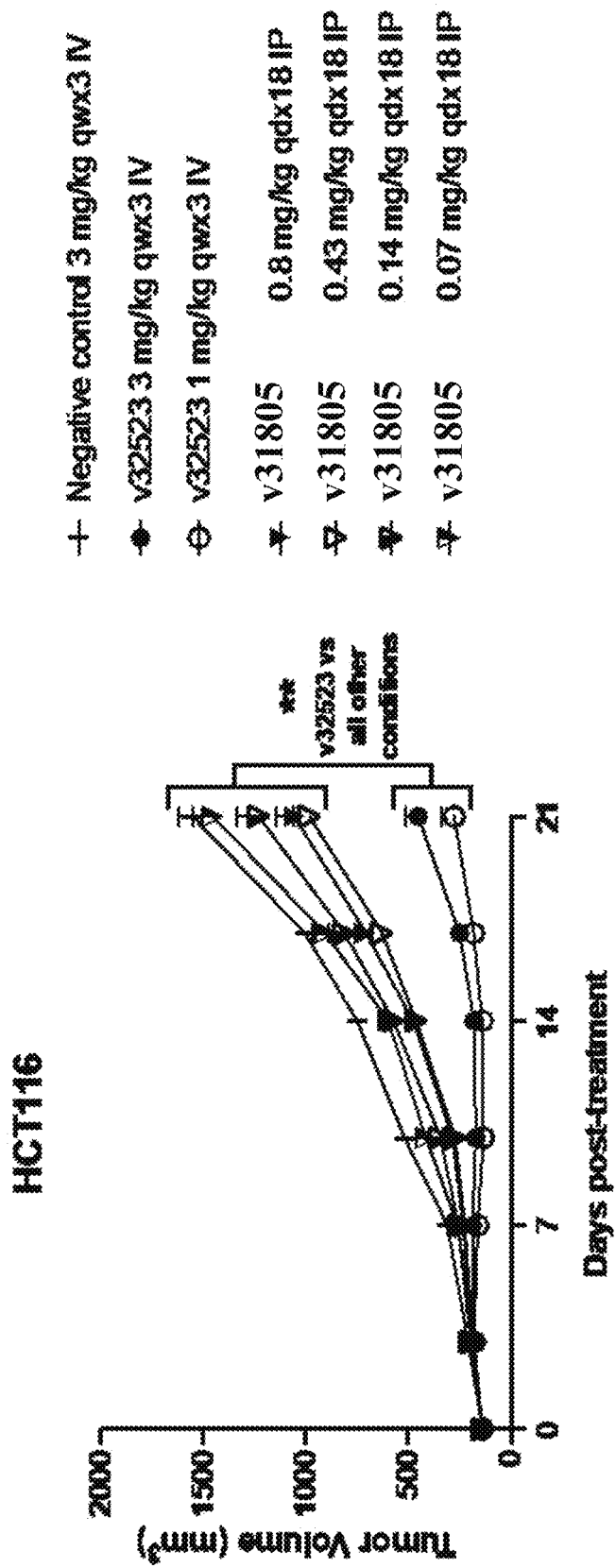

FIG. 18 shows that the trivalent and bispecific antibody construct v32523 of the present disclosure exhibited significantly greater anti-tumor activity at both doses (i.v. administration) of 1 mg/kg and 3 mg/kg, when compared to the benchmark control v31805 (MH6T-TriTAC) at various equivalent doses in HCT116-tumor bearing mice engrafted with human PBMCs. Doses of construct v31805 were matched to those of v32523 by PK analysis to account for the different in vivo half-lives and to allow head-to-head comparisons of the two constructs.

Figure 19:
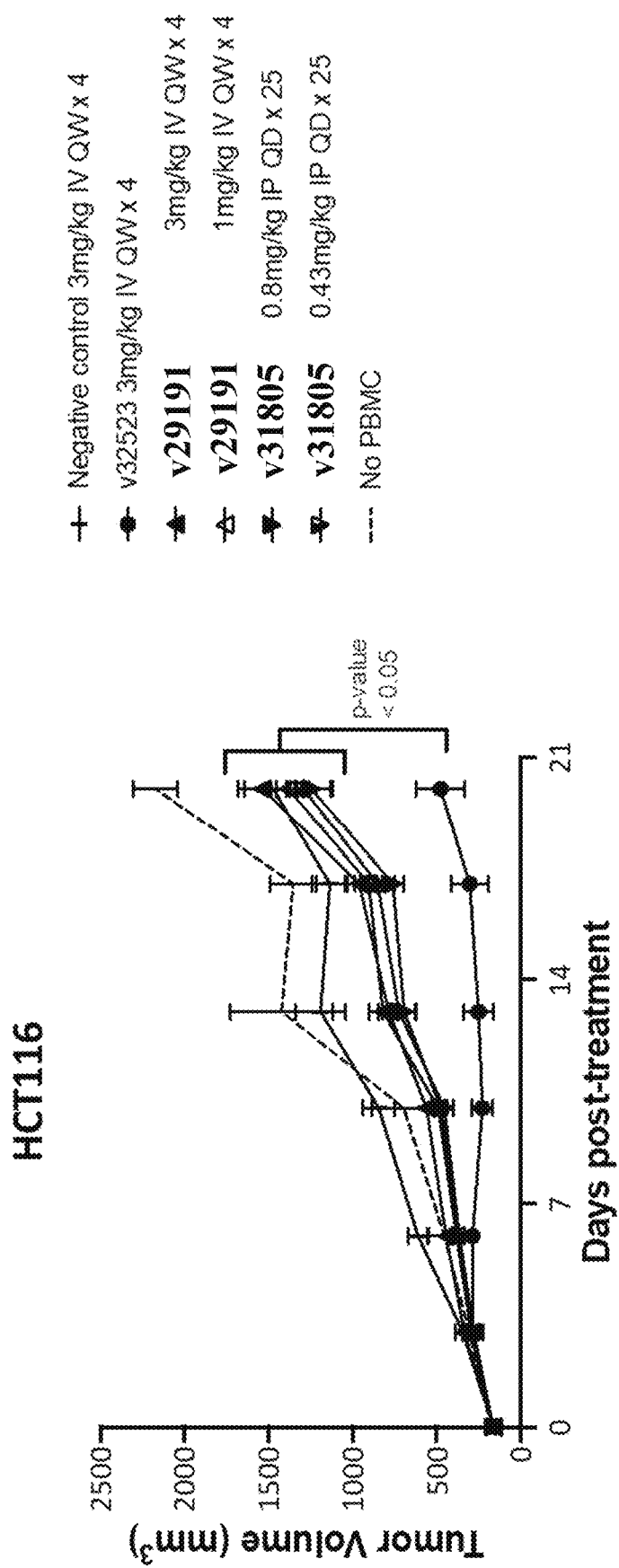

FIG. 19 shows that the trivalent and bispecific antibody construct v32523 of the present disclosure exhibited significantly greater anti-tumor activity (i.v., 3 mg/kg) compared to the benchmark controls v31805 (MH6T-TriTAC) and v29191 (2+1 Fab³) at equivalent dose levels in HCT116-tumor bearing mice engrafted with human PBMCs.

Figure 20:
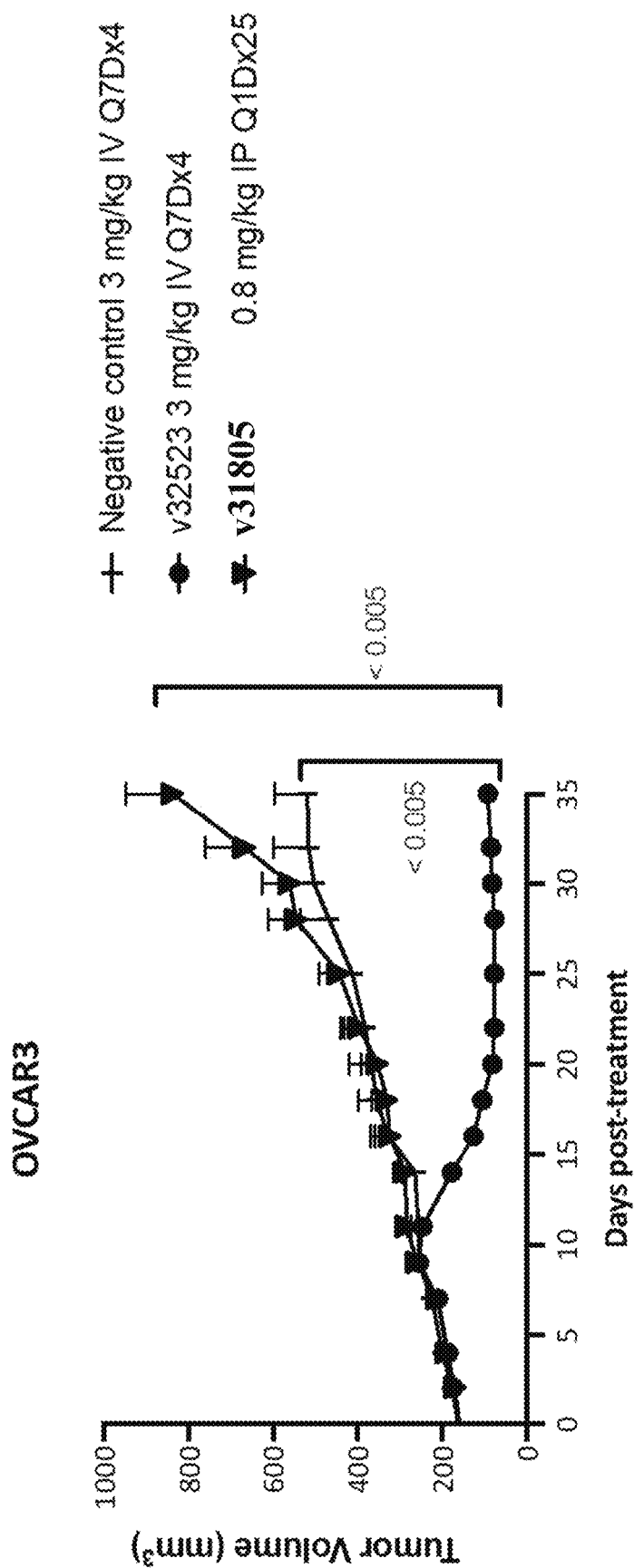

FIG. 20 shows that the trivalent and bispecific antibody construct v32523 of the present disclosure exhibited significantly greater anti-tumor activity (i.v., 3 mg/kg), as measured by a significant reduction in tumor volume, when compared to the benchmark control construct v31805 at equivalent doses in OVCAR-3 tumor bearing mice engrafted with human PBMCs.

Figure 21A:
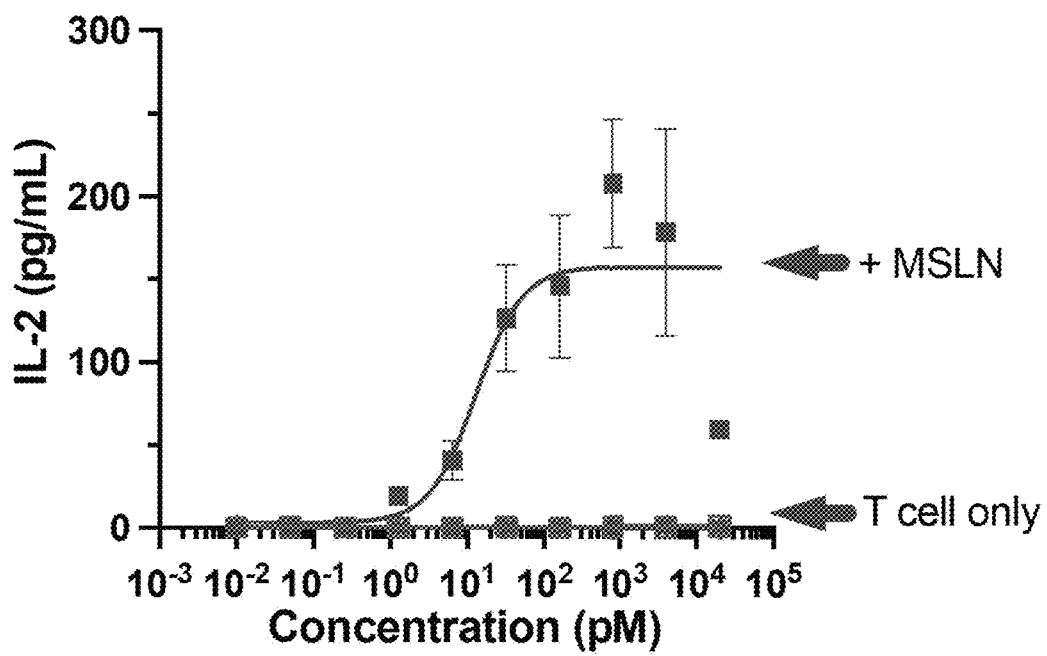
Figure 21B:
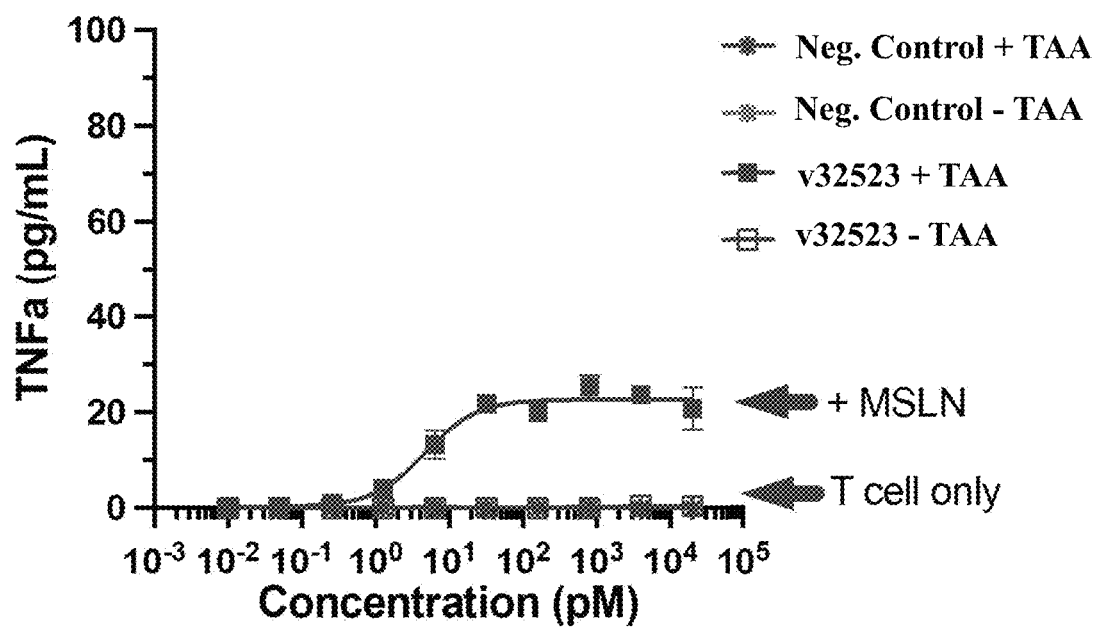
Figure 21C:
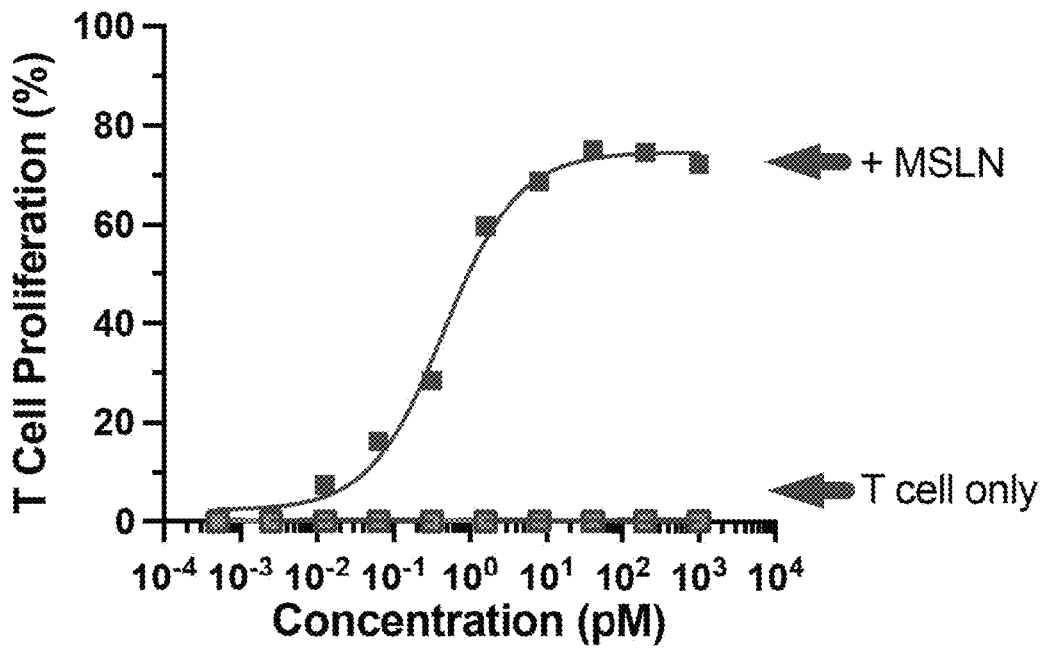

FIGS. 21A-21C show that the trivalent and bispecific antibody construct v32523 induced MSLN-dependent cytokine production (IL-2 (FIG. 21A) and TNFα (FIG. 21B)) and T cell proliferation (FIG. 21C) under conditions in which either (i) T cells only were present or (ii) T cells co-cultured with MSLN+ tumor cells. Cytokine production was assessed by co-culturing MSLN expressing tumor cell lines with human pan-T cells and treating those cells with v32523 or negative control for 3 days. T cell proliferation was assessed by co-culturing CFSE-labeled T cells with OVCAR3 cells and treating those cells with v32523 for 5 days. Proliferation was measured by flow cytometry.

Figure 22A:
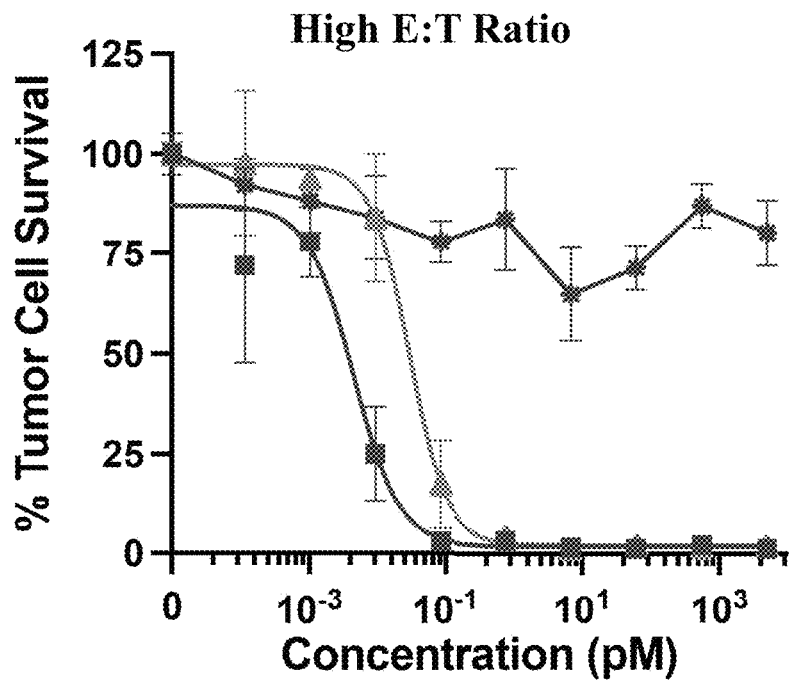
Figure 22B:
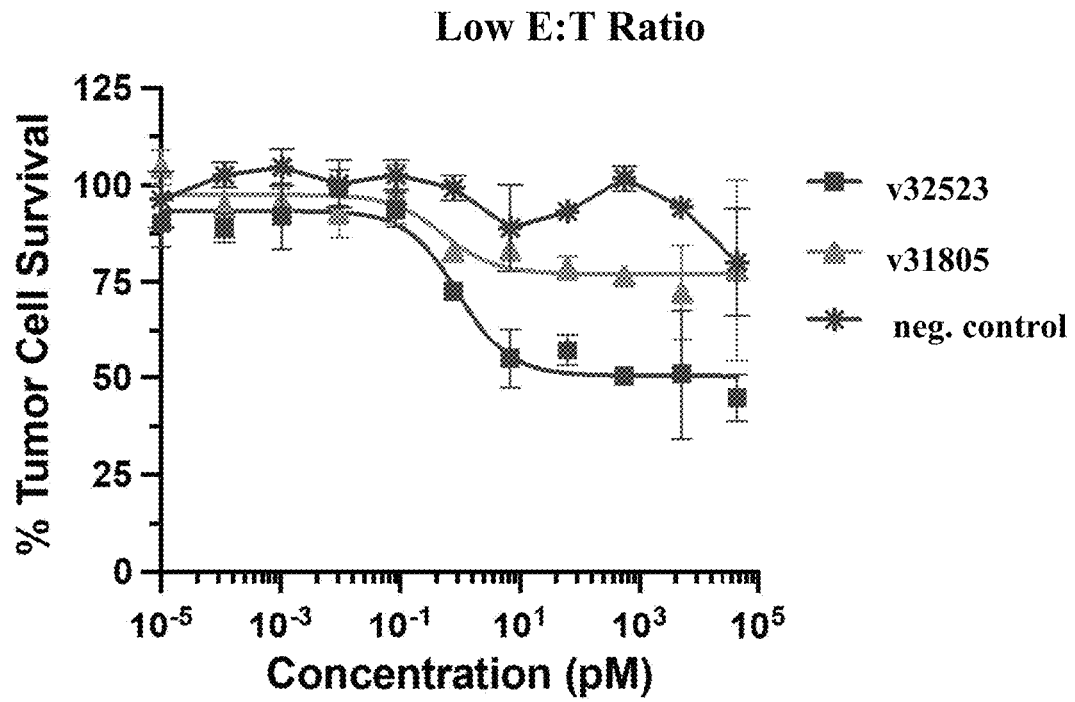

FIGS. 22A-22B show that the trivalent and bispecific construct v32523 exhibited greater anti-tumor activity when compared to the clinical benchmark construct v31805 and when tested in high (5:1, FIG. 22A) and low (1:5, FIG. 22B) E:T ratio environments (FIGS. 22A-22B used identical figure legends to identify testing conditions).

Figure 23A:
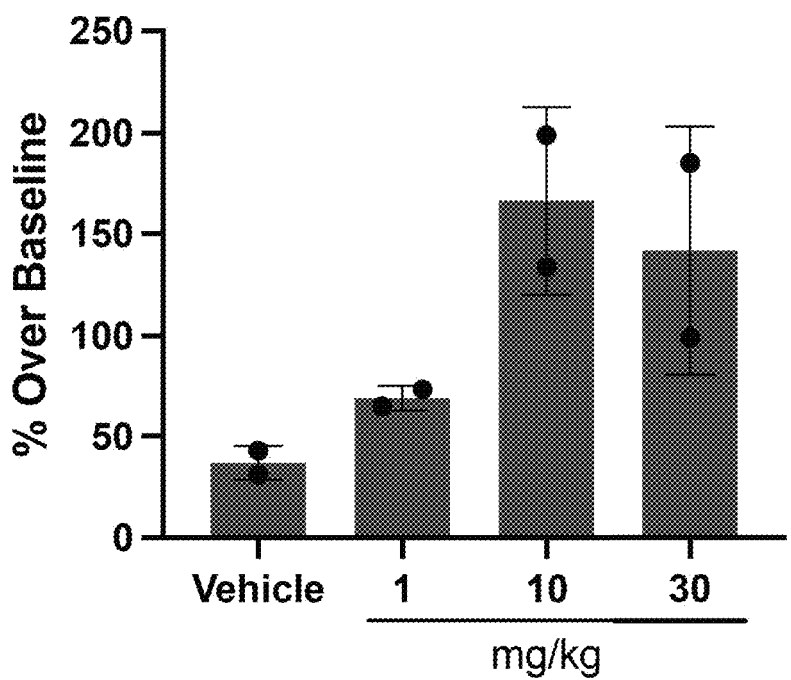
Figure 23B:
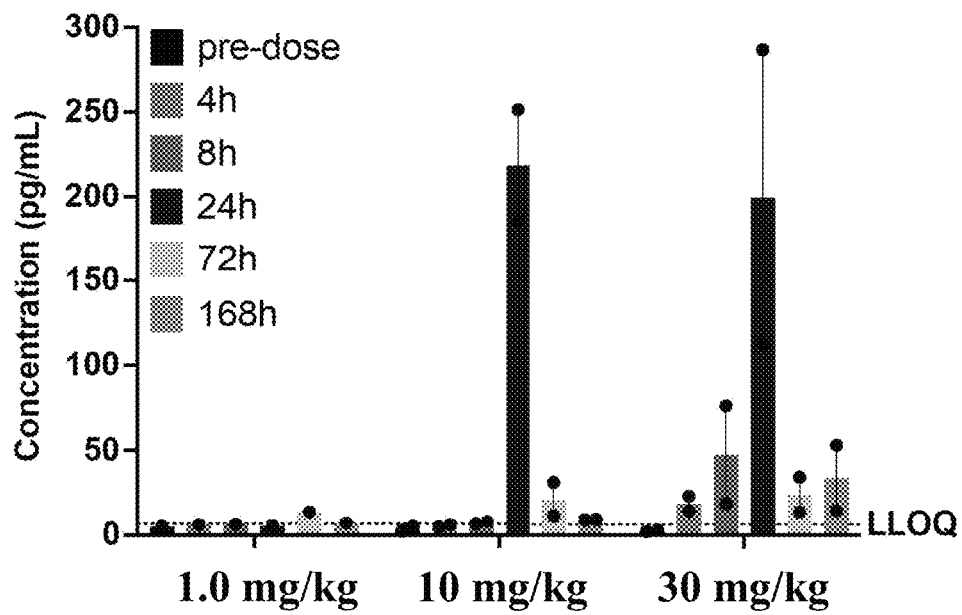
Figure 23C:
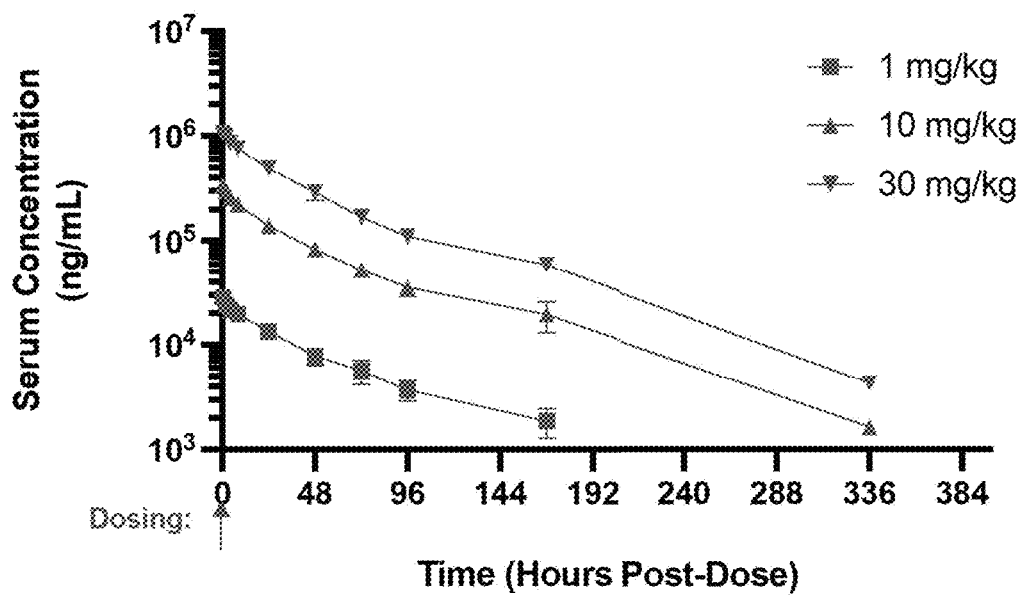

FIGS. 23A-23C show (i) serum levels of fibrinogen (FIG. 23A), (ii) transient increases in IL-6 (FIG. 23B), and (iii) serum half-life (FIG. 23C) of the trivalent and bispecific antibody construct v38490 in cynomolgus monkeys following injection of 1 mg/kg, 10 mg/kg, and 30 mg/kg doses.

Figure 24A:
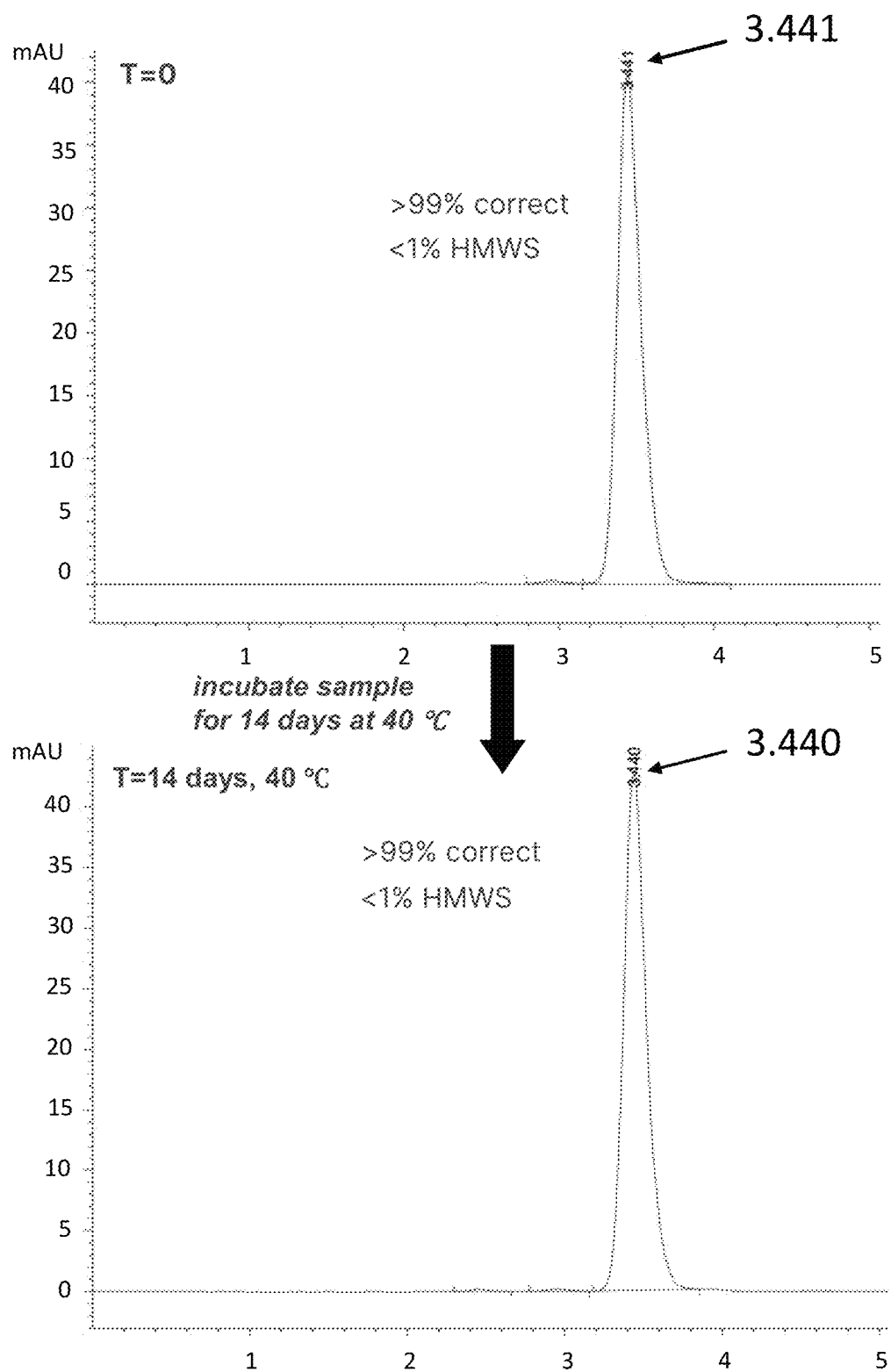
Figure 24B:
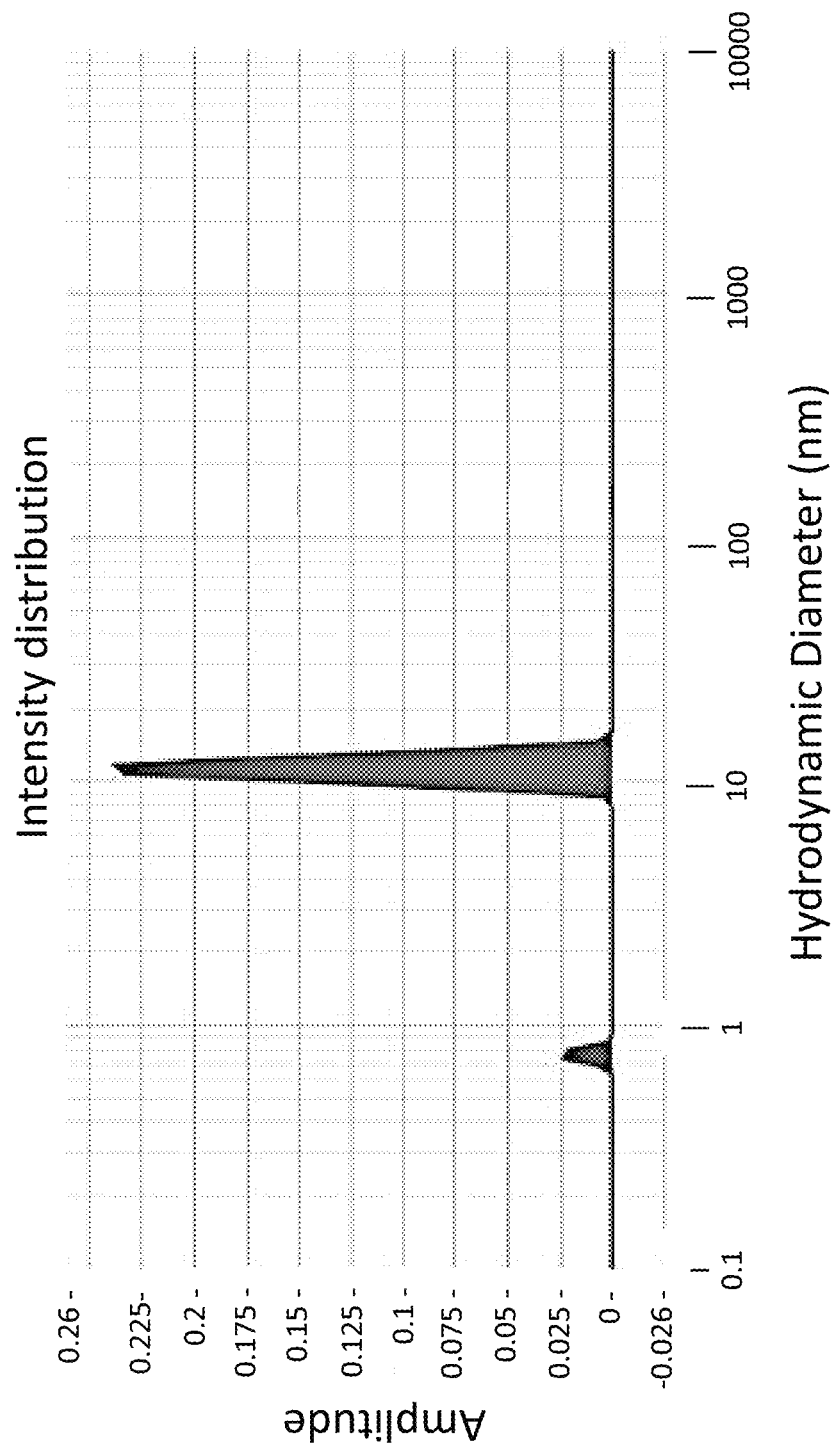

FIGS. 24A-24B show that the trivalent and bispecific antibody construct v32523 maintained monodispersity after incubation in A5Su buffer at 40° C. for 14 days, as shown by size-exclusion chromatography (SEC, FIG. 24A) and dynamic light scatter (DLS, FIG. 24B) analysis, demonstrating a purity of v32523 post-incubation of at least about 99%, with less than about 1% of other high molecular weight species (HMWS), as measured by SEC.

DETAILED DESCRIPTION

The present disclosure relates to multivalent and bispecific antibody constructs that may address the unmet medical need for improved treatment options for MSLN+ tumors. Specifically, the antibody constructs described herein may allow a wider therapeutic window due to less side-effects compared to conventional constructs, potentially enabling the use of more effective doses. As further demonstrated herein, it was unexpectedly found that such improved properties—at least to a large extent—were achieved by improving an antibody construct's format. In some embodiments, modulating a construct's format can induce a more TAA- (e.g., MSLN-) dependent T cell activity in vitro and/or in vivo, which can provide more tumor-focused T cell mediated cytotoxicity while significantly lowering cytotoxic activity in non-tumor (e.g., MSLN-low or MSLN-negative) tissue.

As further described herein, at least one of the remaining technical problems in the treatment of MSLN+ tumors can be regarded as an imbalance between a molecule's cytotoxic activity against MSLN+ tumor cells and its activity in low MSLN-expressing tissues. Among other aspects, which includes an enhanced anti-tumor activity, the antibody constructs of the present disclosure have been designed and produced to address this shortcoming by providing the ability to direct cytotoxic effector cells (e.g., CD3+ immune cells such as T cells) to tumor cells in a more TAA- (e.g., MSLN-) dependent manner, e.g., when compared to conventional approaches. In vitro and in vivo experiments described herein demonstrate the unexpected and superior performance (e.g., low TAA-independent activity, high tumor-cell killing in a TAA-dependent manner and in vivo tolerability) of the multivalent (e.g., trivalent) and bispecific antibody constructs over existing clinical benchmark constructs. Further disclosed herein are antibody constructs with specific formats and geometries, and it is demonstrated how in vitro and in vivo performance (e.g., anti-tumor activity, TAA-specific tumor killing, etc.) of a construct can depend on its format, e.g., by using anti-TAA scFv domains instead of anti-TAA Fab domains, etc.

The present disclosure further describes pharmaceutical compositions comprising a multivalent and bispecific antibody construct of this disclosure, such as a trivalent and bispecific antibody construct, as well as methods of producing and using such constructs and compositions for the treatment of TAA-positive tumors.

Generally, it is to be understood that the positive recitation of a feature in one embodiment serves as a basis for excluding the feature in an alternative embodiment. In particular, where a list of options is presented for a given embodiment or claim, it is to be understood that one or more option can be deleted from the list and the shortened list can form an alternative embodiment, whether or not such an alternative embodiment is specifically referred to.

It is further contemplated that any embodiment discussed herein can be implemented with respect to any antibody construct, method, use, or composition disclosed herein, and vice versa. Furthermore, modifications of the specific embodiments described herein that would be apparent to those skilled in the art are intended to be included within the scope of the claims recited herein.

Definitions

Unless defined otherwise, all technical and scientific terms used herein have the same meaning as commonly understood by one of ordinary skill in the art.

The term "about," as used herein in the context of a numerical value or range, generally refers to ±10%, 9%, 8%, 7%, 6%, 5%, 4%, 3%, 2%, or ±1% of the numerical value or range recited or claimed, unless otherwise specified. In various embodiments, the term "about" refers to an approximately ±10% variation from a given value or range. In other embodiments, the term "about" refers to an approximately ±5% variation from a given value or range. In yet other embodiments, the term "about" refers to an approximately ±1% variation from a given value or range. Unless specified otherwise, it is to be understood that such a variation is always included in any given value provided herein, whether it is specifically referred to or not.

The use of the word "a" or "an," when used herein in conjunction with the term "comprising," can mean "one," but it is also consistent with the meaning of "one or more," "at least one" and "one or more than one."

As used herein, the terms "comprising," "having," "including" and "containing," and grammatical variations thereof, when used herein in connection with a construct, composition, use or method, are inclusive or open-ended and do not exclude additional, unrecited elements and/or method steps. The term "consisting essentially of" when used herein in connection with a construct, composition, use or method, denotes that additional features, elements and/or method steps can be present, but that these additions do not materially affect the manner in which the recited construct, composition, method or use functions. The term "consisting of," when used herein in connection with a construct, composition, use or method, excludes the presence of additional elements and/or method steps. An antibody construct, composition, use, or method described herein as comprising certain elements and/or steps can also, in certain embodiments, consist essentially of those elements and/or steps, and in other embodiments, consist of those elements and/or steps, whether or not these embodiments are specifically referred to.

The terms "subject" and "patient" can be used interchangeably herein and generally refer to an animal in need of treatment. An animal in need of treatment can be a human or a non-human animal, such as a mammal, bird, or fish. In certain embodiments, the subject or patient is a mammal. In some embodiments, the subject is a human. In other embodiments, the subject is a rodent or a non-human primate.

An "effective amount" of an antibody construct described herein, or of a pharmaceutical composition comprising such antibody construct, in respect of a particular result to be achieved is an amount sufficient to achieve the desired result. For example, an "effective amount" of an antibody construct or pharmaceutical composition when referred to in respect of the killing of cancer cells, refers to an amount of antibody construct or composition sufficient to produce a killing effect. In some embodiments, achievement of the desired result (e.g., cancer cell killing) can be confirmed by measurements using one or more of the relevant methods described herein and/or those known to individuals skilled in the art.

The terms "Fc region," "Fc" and "Fc domain," are used interchangeably herein and refer to a C-terminal region of an immunoglobulin heavy chain that contains at least a portion of a constant region. In various embodiments, an Fc domain herein can be dimeric. Such dimeric Fc domain can comprise a first Fc polypeptide and a second Fc polypeptide, wherein each Fc polypeptide can comprise a CH2 domain and/or a CH3 domain. Such dimeric Fc can either be homodimeric, i.e., comprising first and second Fc polypeptides that have identical amino acid sequences, or heterodimeric, i.e., comprising first and second Fc polypeptides that have different amino acid sequences, e.g., sequences that share about 95%, 96%, 97%, 98%, or 99% sequence identity. In some embodiments, an antibody construct of the present disclosure comprises a homodimeric Fc domain. In yet other embodiments, and as further described herein, an antibody construct comprises a heterodimeric Fc domain in which at least one of the CH2 and/or CH3 domains of the first and second Fc polypeptides have amino acid sequences that share about 99% or less, 98% or less, or about 97% or less sequence identity.

The term "bispecific," as used herein in the context of an antibody construct, refers to a biologically functional protein (e.g., an antibody construct as described herein) which is "at least bispecific," i.e., it comprises at least a first binding domain and a second binding domain, wherein such first and second binding domain can bind specifically two distinct epitopes, e.g., a first epitope and a second epitope. Such first and second epitopes can be located on the same antigen or on different antigens, e.g., a first epitope on CD3 and a second epitope on MSLN. Accordingly, in some embodiments, antibody constructs according to the present disclosure can comprise specificities for at least two different antigens, epitopes or other targets. In certain embodiments, an antibody construct of this disclosure is bispecific for two different epitopes, wherein each epitope is located on a different antigen (e.g., CD3 and MSLN). The term "bispecific" in the context of an antibody construct herein also encompasses multispecific antibody constructs such as trispecific antibody constructs, the latter ones including three binding domains each binding a distinct epitope or target, or constructs having more than three (e.g., four, five, etc.) specificities.

The term "trivalent," as used herein in the context of an antibody construct, refers to a biologically functional protein (e.g., an antibody construct as described herein) which is "at least trivalent," i.e., it comprises three binding domains, e.g., at least a first binding domain, a second binding domain and a third binding domain, wherein each of the first, second, and third binding domains is capable of specifically binding an epitope and/or antigen, e.g., CD3, MSLN, etc. The three binding domains can either have specificities for three different epitopes or antigens, or two or more of the three binding domains have a specificity for the same epitope or antigen. Hence, the valency in the context of an antibody construct herein, e.g., being mono-, bi-, or trivalent, describes the total number of antigen binding domains of the antibody construct. Accordingly, the valency of an antibody construct has to be at least equal to its specificity, i.e., a bispecific antibody construct has to be at least bivalent. In embodiments herein in which the antibody construct is trivalent and bispecific, two of the construct's three binding domains are capable of bivalently binding a first epitope or antigen (e.g., MSLN), and the third binding domain engages monovalently a different epitope and/or antigen (e.g., CD3).

As used herein, the abbreviations "H," "H1," "H2," "L1," and so forth, are generally used as generic heavy and light chain identifiers, respectively. As an example, "H1" and "H2" can broadly refer to a first heavy chain and a second heavy chain of an antibody construct herein, respectively, and thus are not intended to be limited in any way to specific heavy chain amino acid (or polynucleotide) sequences. Rather, such chain identifiers may be used herein to describe and distinguish two or more polypeptide chains of an antibody construct.

The term "amino acid modification," as used herein in the context of an amino acid sequence of a polypeptide, generally refers to an amino acid sequence of a polypeptide in which one or more amino acid substitutions, one or more amino acid insertions, and/or one or more amino acid deletions have been introduced relative to a corresponding unmodified (e.g., WT or reference) amino acid sequence of the polypeptide.

Antibody Constructs

In various embodiments, the present disclosure relates to multivalent and bispecific antibody constructs capable of targeting an antigen on the surface of a cytotoxic effector cell and a tumor-associated antigen (TAA) located on a tumor cell. In various embodiments, an antibody construct of this disclosure is trivalent and bispecific comprising at least three binding domains. Such trivalent and bispecific antibody constructs can be capable of monovalent binding of an antigen on the surface of a cytotoxic effector cell and bivalent for binding of a TAA located on a tumor cell. The two binding domains that are capable of bivalently binding the TAA can either be directed against the same TAA or to two different TAAs. In various embodiments, both anti-TAA binding domains are directed against the same TAA. In some embodiments, both anti-TAA binding domains are directed against the same epitope on the TAA (e.g., MSLN).

In certain other embodiments, a trivalent and bispecific antibody construct can be capable of monovalent binding of a TAA on the surface of a tumor cell and bivalent for binding of an antigen on the surface of a cytotoxic effector cell.

In various embodiments, a trivalent and bispecific antibody construct comprises (i) a first binding domain capable of monovalently binding an antigen on a cytotoxic effector cell, and (ii) a second binding domain and a third binding domain capable of bivalently binding a TAA on a tumor cell. In some embodiments, the antigen on the cytotoxic effector cell is CD3, wherein the cytotoxic effector cell can be an immune cell such as a T cell, and the TAA is MSLN.

In some embodiments, the present disclosure relates to trivalent and bispecific antibody constructs comprising (i) a first binding domain capable of binding CD3 on the surface of a cytotoxic effector cell and (ii) a second binding domain and a third binding domain, wherein at least one of second and third binding domain is capable of binding MSLN. In various embodiments, both the second binding domain and the third binding domain are capable of binding MSLN. Such constructs described herein that are monovalent for CD3 and bivalent for MSLN can have the ability to direct immune cells (e.g., T cells) to tumor cells and elicit a localized, MSLN-dependent and immune cell-mediated anti-tumor immune response. In certain embodiments, an antibody construct of this disclosure may not elicit a significant TAA-independent T cell or immune response in the absence or at low abundance of the TAA, thereby having the ability to reduce off-target effects and enable wider therapeutic windows when compared to other, existing approaches that are less TAA-dependent in their anti-tumor immune response. The term "significant" in the context of a TAA-independent immune response generally refers to an immune response elicited by the antibody construct that is equal to or less than 10%, 5%, or 3% of an immune response elicited in environments containing medium or high TAA-expressing cells or tissue, as further described herein.

Previously, certain bispecific antibodies capable of directing T cells to tumor cells were identified and tested for their efficacy in the treatment of cancers. Blinatumomab is an example of a bispecific anti-CD3-CD19 antibody in a format called BiTE™ (Bi-specific T-cell Engager) that was identified for the treatment of B-cell diseases such as relapsed B-cell non-Hodgkin lymphoma and chronic lymphocytic leukemia (see, e.g., Baeuerle et al (2009) Cancer Research12:4941-4944) and is FDA approved. T cell engagers directed against other tumor-associated target antigens have also been made, and several have entered clinical trials, for example, AMG110/MT110 EpCAM for lung cancer, gastric cancer and colorectal cancer, AMG211/MEDI565 CEA for gastrointestinal adenocarcinoma, and AMG 212/BAY2010112 PSMA for prostate cancer (see, e.g., Suruadevara, C. M. et al, Oncoimmunology. 2015 June; 4(6): e1008339). While these studies showed some clinical efficacy, they were hampered by severe dose-limiting toxicities primarily due to cytokine release syndrome (CRS). This resulted in narrow therapeutic windows for these agents.

The T cell-engaging antibody constructs of the present disclosure aim to address these shortcomings, e.g., by providing reduced or even non-measurable T cell activation in the absence or at low abundance of the TAA to be targeted, e.g., MSLN, thereby focusing their cytotoxic effects primarily to the tumor (micro-) environment, which it assumed to not only provide higher anti-cancer activity but to also allow a broader therapeutic window with a significant reduction in off-target effects when compared to conventional T cell engaging approaches.

In various embodiments, a T cell-engaging trivalent and bispecific antibody construct of the present disclosure can be capable of binding CD3 (monovalently) on a T cell and MSLN (bivalently) on a tumor cell and can—when bound to CD3 and MSLN—form a TCR-independent artificial immune synapse between the T cell and the tumor cell. This can cause the T cell to become activated and exert a cytotoxic effect on the tumor cell leading to tumor cell killing, as further described herein.

A. Format and Geometry of Antibody Constructs

In certain embodiments, the present disclosure describes multivalent and bispecific antibody constructs having a format and geometry specifically designed for improved in vivo tumor killing and tolerability properties (e.g., reduced off-target effects) compared to conventional constructs with different format and/or geometry. Combined with an improved format, the antigen affinity of each binding domain present in a trivalent and bispecific antibody constructs described herein was rationally selected to provide strong anti-tumor activity in TAA-expressing tissue while limiting the construct's activity in tissue that has low TAA-expression.

Generally, the format of an antibody construct as described herein refers to the type(s) and number(s) of antibody construct domains (e.g., scFv, Fab, Fc, etc.) it comprises, which further defines the construct's valency for its targets (e.g., CD3, MSLN, etc.) as well as its specificity, i.e., being bispecific, trispecific, etc., and bivalent, trivalent, etc. As further described herein, an antibody construct's format can also be indicated as a combination of numerical values indicating its valency and specificity for certain targets, including formats described as 1+1 (a), 2+1 (b), 2+2 (c), etc., referring, in the same order, to antibody constructs (a) capable of monovalent ("1") binding to a first antigen and monovalent ("1") to a second antigen, (b) bivalent ("2") binding to a first antigen and monovalent ("1") to a second antigen, and (c) bivalent ("2") binding to a first antigen and bivalent ("2") to a second antigen. The geometry of a construct herein is generally defined as the relative and three-dimensional orientation and positioning of the various domains of the antibody construct. As an example, an antibody construct comprising a Fab domain, an scFv domain, and a dimeric Fc domain can have different geometries in which the domains are differently interconnected to one another resulting in a different relative orientation. In one such embodiment, both the Fab domain and the scFv domain can each be coupled to the N-termini of the dimeric Fc domain (e.g., each to an N-terminus of a first or second Fc polypeptide). In another embodiment, one of the Fab domain and the scFv domain can be coupled to an N-terminus of the Fc domains, whereas the other is coupled to a C-terminus of the dimeric Fc domain. In yet another embodiment, all three domains can be coupled in tandem, e.g., the Fab domain can be coupled to an N-terminus of the Fc domain, and the scFv domain can be coupled to an N-terminus of the Fab domain.

In various embodiments, the present disclosure describes a bispecific antibody construct comprising (i) a first binding domain capable of binding CD3, (ii) a second binding domain capable of binding MSLN, and (iii) a heterodimeric Fc domain comprising a first Fc polypeptide and a second Fc polypeptide. In some embodiments, the first binding domain capable of binding CD3 is a Fab domain comprising a heavy chain comprising a first heavy chain variable domain ($V_H$) and a heavy chain constant domain ($C_{H1}$), paired with a light chain comprising a first light chain variable domain ($V_L$) and a first light chain constant domain ($C_L$). In some embodiments, the second binding domain capable of binding MSLN is an scFv domain comprising a second heavy chain variable domain ($V_H$) and a second light chain variable domain ($V_L$). In some embodiments, the first binding domain is coupled to the N-terminus of the first Fc polypeptide of the heterodimeric Fc domain via the C-terminus of $C_{H1}$, and the second binding domain is coupled to the N-terminus of the second Fc polypeptide of the heterodimeric Fc domain, either via the C-terminus of the second heavy chain variable domain ($V_H$) or the C-terminus of the second light chain variable domain ($V_L$), depending on their relative orientation and the domain structure of the scFv domain.

In some embodiments, the first binding domain is a Fab domain and can be coupled to the first Fc polypeptide either directly or via a linker$^{Fab\text{-}Fc}$. Similarly, the second binding domain is an scFv domain and can be coupled to the second Fc polypeptide either directly or via a linker$^{scFv\text{-}Fc}$. In various embodiments, the first binding domain and the second binding domain are coupled to the first and second Fc polypeptides via linker$^{Fab\text{-}Fc}$ and linker$^{scFv\text{-}Fc}$ respectively. In some embodiments, linker$^{Fab\text{-}Fc}$ and linker$^{scFv\text{-}Fc}$ comprise or consist of a different amino acid sequence, as further described herein. In other embodiments, linker$^{Fab\text{-}Fc}$ and linker$^{scFv\text{-}Fc}$ comprise or consist of an identical amino acid sequence.

In various embodiments of the present disclosure, an antibody construct can be bispecific and multivalent. In some embodiments, such construct is bivalent and bispecific. In various other embodiments herein, an antibody construct of the present disclosure is trivalent and bispecific.

A trivalent and bispecific antibody construct of the present disclosure can further comprise a third binding domain. Such third binding domain can be capable of binding a different TAA compared to the second binding domain. In other embodiments, the third binding domain is capable of binding the same TAA as the second binding domain. In various embodiments, the second binding domain and the third binding domain are both capable of binding MSLN. The third binding domain can be a Fab domain, or it can be a second scFv domain. In some embodiments, the third binding domain is a Fab domain. In various other embodiments, the third binding domain is a second scFv domain, resulting in an antibody construct comprising one Fab domain and two scFv domains, i.e., a first scFv domain (also referred to herein as "scFv1") and a second scFv domain (also referred to herein as "scFv2"), wherein such first and second scFv domains are capable of binding MSLN.

In various embodiments, a trivalent and bispecific antibody construct of this disclosure can be monovalent for CD3 and bivalent for MSLN. Such antibody construct can comprise (i) a first binding domain capable of binding CD3 on a cytotoxic effector cell, (ii) a second binding domain capable of binding MSLN, (iii) a third binding domain capable of binding MSLN, and (iv) a heterodimeric Fc domain comprising a first Fc polypeptide and a second Fc polypeptide. In various embodiments, the first binding domain is a Fab domain, and the second and third binding domains are each scFv domains, i.e., a first scFv domain and a second scFv domain. In some embodiments, the second and third binding domains comprise or consist of $V_H$ and $V_L$ amino acid sequences that each share at least about 80%, 90%, 95%, 97%, 99%, or 100% sequence identity. Hence, in some embodiments, the second $V_H$ and $V_L$ domains of the second binding domain (e.g., first scFv domain, or "scFv1") and the third $V_H$ and $V_L$ domains of the third binding domain (e.g., second scFv domain, or "scFv2") comprise or consist of identical amino acid sequences, i.e., comprise identical anti-MSLN paratope $V_H$ and $V_L$ sequences. In some embodiments, the second binding domain and the third binding domain of a trivalent and bispecific antibody construct herein are capable of binding to the same epitope on MSLN. In other embodiments, however, a trivalent and bispecific antibody construct herein can comprise a second binding domain and a third binding domain that are each capable of binding to a different epitope on MSLN. In yet other embodiments, a trivalent and bispecific antibody construct may comprise a second binding domain and a third binding domain that each comprise different anti-MSLN paratopes but may still bind to the same MSLN epitope.

In various embodiments of the present disclosure, a trivalent and bispecific antibody construct comprises (i) a first binding domain capable of binding CD3 on a cytotoxic effector cell (e.g., an immune cell such as a T cell), (ii) a second binding domain capable of binding MSLN, (iii) a third binding domain capable of binding MSLN, and (iv) a heterodimeric Fc domain comprising a first Fc polypeptide and a second Fc polypeptide, wherein the first binding domain is coupled to the first Fc polypeptide via a first linker, the second binding domain is coupled to the second Fc polypeptide via a second linker, and the third binding domain is coupled either directly or via a third linker to either (a) the first binding domain, (b) the second binding domain, or (c) the heterodimeric Fc domain.

In various embodiments, the third binding domain is coupled via a third linker to the first binding domain.

In various embodiments of a trivalent and bispecific antibody construct of the present disclosure, the first binding domain capable of binding CD3 is a Fab domain comprising a heavy chain comprising a first heavy chain variable domain ($V_H$) and a heavy chain constant domain ($C_{H1}$), paired with a light chain (L1) comprising a first light chain variable domain ($V_L$) and a light chain constant domain ($C_L$), and the second and third binding domains capable of binding MSLN are each scFv domains, i.e., a first scFv domain and a second scFv domain. Hence, the second binding domain (e.g., first scFv domain) can comprise a second heavy chain variable domain ($V_H$) and a second light chain variable domain ($V_L$), and the third binding domain (e.g., second scFv domain) can comprise a third heavy chain variable domain ($V_H$) and a third light chain variable domain ($V_L$).

In some embodiments of a trivalent and bispecific antibody construct, the Fab domain is coupled via the C-terminus of its $C_{H1}$ domain to the N-terminus of the first Fc polypeptide via a first linker (e.g., linker$^{Fab\text{-}Fc}$). The first scFv domain can be coupled via the C-terminus of either its $V_H$ domain or its $V_L$ domain (e.g., depending on the relative orientation of $V_H$ and $V_L$ sequences in the first scFv domain) to the N-terminus of the second Fc polypeptide via a second linker (e.g., linker$^{scFv\text{-}Fc}$). Similarly, the second scFv domain can be coupled via the C-terminus of either its $V_H$ domain or its $V_L$ domain (e.g., depending on the relative orientation of $V_H$ and $V_L$ sequences in the second scFv domain) to an N-terminus of the Fab domain via a third linker (e.g., linker$^{scFv\text{-}Fab}$). Since the Fab domain comprises a heavy and a light chain, the second scFv domain can be coupled to either the N-terminus of the heavy chain or the N-terminus of the light chain of the Fab domain. However, in various embodiments, the second scFv domain is coupled to the N-terminus of the heavy chain of the Fab domain, e.g., the N-terminus of the $V_H$ domain of the heavy chain.

In various embodiments, the linkers (e.g., linker$^{Fab}$Fc, linker$^{scFv\text{-}Fc}$ linker$^{scFv\text{-}Fab}$, etc.) connecting the various domains of the antibody construct are all peptide (or peptidic) linkers, i.e., are linkers that comprise or consist of an amino acid sequence of at least two, three, four, five, ten, fifteen, twenty, twenty-five, thirty, forty or more consecutive amino acid residues. In some embodiments, the linker$^{Fab\text{-}Fc}$ and linker$^{scFv\text{-}Fc}$ that couple various binding domains to a dimeric Fc domain are peptide linkers that can comprise or consist of an immunoglobulin hinge region, such as an IgG or IgG1 hinge region, as further described herein.

In some embodiments, a trivalent and bispecific antibody construct of this disclosure can comprise or consist of two, three, or more polypeptide chains that can be separately expressed and then assemble (e.g., via heavy and/or light chain pairing) to form the antibody construct including its various domains. In various embodiments, a trivalent and bispecific antibody construct described herein can comprise or consist of three polypeptide chains, two heavy chains (e.g., referred to as H1 and H2) and one light chain (e.g., referred to as L1). In such embodiments, H1 can comprise the domain structure (from N- to C-terminus): scFv2-$V_H$-$C_{H1}$-CH2-CH3, wherein the second scFv domain (scFv2) is coupled to the N-terminus of $V_H$ of the Fab domain via the C-terminus of either $V_{H\text{-}scFv2}$ or $V_{L\text{-}scFv2}$, depending on their relative orientation within scFv$_2$. In such embodiments, H1 can comprise or consist of the domain structure: $(V_L\text{-}V_H)_{scFv2}$-$V_H$-$C_{H1}$-CH2-CH3. In other embodiments, H1 can comprise or consist of the domain structure: $(V_H\text{-}V_L)_{scFv2}$-$V_H$-$C_{H1}$-CH2-CH3. Furthermore, H2 can comprise the domain structure (from N- to C-terminus): scFv$_1$-CH2-CH3, wherein the first scFv domain can be coupled to the N-terminus of CH2 via the C-terminus of either $V_{H\text{-}scFv1}$ or $V_{L\text{-}scFv1}$, depending on their relative orientation within scFv$_1$. In such embodiments, H2 can comprise or consist of the domain structure: $(V_L\text{-}V_H)_{scFv1}$-CH2-CH3. In other embodiments, H2 can comprise or consist of the domain structure: $(V_H\text{-}V_L)_{scFv1}$-CH2-CH3. The light chain L1 can comprise the domain structure (from N- to C-terminus): $V_L$-$C_L$. $V_H$—$C_{H1}$ of H1 and L1 can form the Fab domain (i.e., the first binding domain) that is capable of binding CD3. Fab domain formation can include covalent interactions (e.g., disulfide bonds), as well as non-covalent interactions between amino acid residues of H1 and L1, or a combination of both. Additionally, the CH2 and CH3 domains of H1 (e.g., corresponding to either a portion or the entire first Fc polypeptide) and the CH2 and CH3 domains of H2 (e.g., corresponding to either a portion or the entire second Fc polypeptide) can form the heterodimeric Fc domain, wherein the CH3 domain of H1 and the CH3 domain of H2 can each comprise one or more asymmetric amino acid substitutions that promote formation of the heterodimeric Fc domain over formation of a homodimeric Fc domain, as further described herein.

FIG. 1 provides a schematic representation of the geometry (relative orientation and connectivity of binding domains) and format (e.g., valency, presence/absence of Fc domain, etc.) of various antibody constructs contemplated and described herein. Specifically, FIG. 1A shows a schematic representation of the geometry and format of a trivalent and bispecific antibody construct according to various embodiments of this disclosure, which is composed of three polypeptide chains, H1, H2, and L1, and is capable of binding CD3 (monovalent via one Fab domain) and MSLN (bivalent via 2 scFv domains).

In various embodiments, the present disclosure describes an antibody construct, wherein the antibody construct comprises: (i) a Fab domain capable of binding an antigen on a cytotoxic effector cell, (ii) a first scFv domain and a second scFv domain, wherein the first scFv domain and the second scFv domain are both capable of binding MSLN; and (iii) a heterodimeric Fc domain comprising a first Fc polypeptide and a second Fc polypeptide, wherein (a) the Fab domain is coupled to the N-terminus of the first Fc polypeptide, (b) the first scFv domain is coupled to the N-terminus of the second Fc polypeptide, and (c) the second scFv domain is coupled to the N-terminus of the Fab domain.

In further embodiments, the present disclosure describes an antibody construct, comprising: (i) a Fab domain capable of binding to an antigen on a cytotoxic effector cell, (ii) a first scFv domain and a second scFv domain, wherein the first scFv domain and the second scFv domain are both capable of binding MSLN, and wherein at least one of the first scFv domain and the second scFv domain comprises a $V_H$ domain comprising an heavy chain complementarity determining region 1 (HCDR1) sequence comprising or consisting of the sequence set forth in SEQ ID NO: 120, an HCDR2 sequence comprising or consisting of the sequence set forth in SEQ ID NO: 121, and an HCDR3 sequence comprising or consisting of the sequence set forth in SEQ ID NO: 122, and a $V_L$ domain comprising an light chain complementarity determining region 1 (LCDR1) sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125, and (iii) a heterodimeric Fc domain comprising a first Fc polypeptide and a second Fc polypeptide, wherein (a) the Fab domain is coupled to the N-terminus of the first Fc polypeptide, (b) the first scFv domain is coupled to the N-terminus of the second Fc polypeptide, and (c) the second scFv domain is coupled to the N-terminus of the Fab domain.

In certain embodiments, both the first scFv domain and the second scFv domain each comprise a $V_H$ domain comprising an HCDR1 sequence comprising or consisting of the sequence set forth in SEQ ID NO: 120, an HCDR2 sequence comprising or consisting of the sequence set forth in SEQ ID NO: 121, and an HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

In some of these embodiments, the antigen on the cytotoxic effector cell is CD3. The cytotoxic effector cell can be an immune cell, e.g., a T cell.

In various embodiments, the present disclosure describes an antibody construct, comprising: (i) a Fab domain capable of binding CD3, wherein the Fab domain comprises a $V_H$ domain comprising an HCDR1 sequence comprising or consisting of the sequence set forth in SEQ ID NO: 126, an HCDR2 sequence comprising or consisting of the sequence set forth in SEQ ID NO: 127, and an HCDR3 comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131; (ii) a first scFv domain and a second scFv domain, wherein the first and the second scFv domains are both capable of binding MSLN; and (iii) a heterodimeric Fc domain comprising a first Fc polypeptide and a second Fc polypeptide, wherein: (a) the Fab domain is coupled to the N-terminus of the first Fc polypeptide, (b) the first scFv domain is coupled to the N-terminus of the second Fc polypeptide, and (c) the second scFv domain is coupled to the N-terminus of the Fab domain.

In various embodiments, the present disclosure describes an antibody construct, comprising: (i) a Fab domain capable of binding CD3, wherein the Fab domain comprises a $V_H$ domain comprising an HCDR1 sequence comprising or consisting of the sequence set forth in SEQ ID NO: 126, an HCDR2 sequence comprising or consisting of the sequence set forth in SEQ ID NO: 127, and an HCDR3 sequence comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131; (ii) a first scFv domain and a second scFv domain, wherein the first and the second scFv domains are both capable of binding MSLN and both scFv domains comprise a $V_H$ domain comprising an HCDR1 sequence comprising or consisting of the sequence set forth in SEQ ID NO: 120, an HCDR2 sequence comprising or consisting of the sequence set forth in SEQ ID NO: 121, and an HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125; and (iii) a heterodimeric Fc domain comprising a first Fc polypeptide and a second Fc polypeptide, wherein: (a) the Fab domain is coupled to the N-terminus of the first Fc polypeptide, (b) the first scFv domain is coupled to the N-terminus of the second Fc polypeptide, and (c) the second scFv domain is coupled to the N-terminus of the Fab domain.

In such embodiments, the antibody construct can be trivalent and bispecific.

In some embodiments, a trivalent and bispecific antibody construct described herein can comprise three polypeptide chains, two heavy chains (e.g., H1 and H2) and one light chain (e.g., L1). H1 can comprise or consist of the domain structure (from N- to C-terminus): $(V_L\text{-}V_H)_{scFv2}\text{-}V_H\text{-}C_{H1}\text{-}CH2\text{-}CH3$, wherein "scFv2" indicates the second scFv domain capable of binding MSLN. H2 can comprise or consist of the domain structure (from N- to C-terminus): $(V_L\text{-}V_H)_{scFv1}\text{-}CH2\text{-}CH3$, wherein "scFv1" indicates the first scFv domain capable of binding MSLN. L1 can comprise of consist of the domain structure (from N- to C-terminus): $V_L\text{-}C_L$. $V_H\text{-}C_{H1}$ of H1 and $V_L\text{-}C_L$ of L1 can (e.g., covalently) pair (e.g., via one or more disulfide bonds) to form the Fab domain that is capable of binding CD3. The CH2 and CH3 domains of H1, which—at least in part—form the first Fc polypeptide, and the CH2 and CH3 domains of H2, which—at least in part—form the second Fc polypeptide, can form the heterodimeric Fc domain, wherein the CH3 domain of H1 and the CH3 domain of H2 can each comprise one or more asymmetric amino acid substitutions that promote formation of the heterodimeric Fc domain (e.g., formation of H1-H2 heterodimeric Fc), as compared to respective homodimeric Fc domains (e.g., formation of H1-H1 or H2-H2 homodimeric Fc's).

In some embodiments, a trivalent and bispecific antibody construct described herein can comprise three polypeptide chains, two heavy chains (e.g., H1 and H2) and one light chain (e.g., L1). H1 can comprise or consist of the domain structure (from N- to C-terminus): $(V_H\text{-}V_L)_{scFv2}\text{-}V_H\text{-}C_{H1}\text{-}CH2\text{-}CH3$, wherein "scFv2" indicates the second scFv domain capable of binding MSLN. H2 can comprise or consist of the domain structure (from N- to C-terminus): $(V_H\text{-}V_L)_{scFv1}\text{-}CH2\text{-}CH3$, wherein "scFv1" indicates the first scFv domain capable of binding MSLN. L1 can comprise of consist of the domain structure (from N- to C-terminus): $V_L\text{-}C_L$. $V_H\text{-}C_{H1}$ of H1 and $V_L\text{-}C_L$ of L1 can (e.g., covalently) pair (e.g., via one or more disulfide bonds) to form the Fab domain that is capable of binding CD3. The CH2 and CH3 domains of H1, which—at least in part—form the first Fc polypeptide, and the CH2 and CH3 domains of H2, which— at least in part—form the second Fc polypeptide, can form the heterodimeric Fc domain, wherein the CH3 domain of H1 and the CH3 domain of H2 can each comprise one or more asymmetric amino acid substitutions that promote formation of the heterodimeric Fc domain (e.g., formation of H1-H2 heterodimeric Fc), as compared to respective homodimeric Fc domains (e.g., formation of H1-H1 or H2-H2 homodimeric Fc's).

Hence, in various embodiments, an antibody construct of the present disclosure can comprise or consist of the three polypeptide chains, H1, H2 and L1, wherein (i) H1 comprises or consists of the domain structure (from N- to C-terminus): $(V_L\text{-}V_H)_{scFv2}\text{-}V_H\text{-}C_{H1}\text{-}CH2\text{-}CH3$, (ii) H2 comprises or consists of the domain structure (from N- to C-terminus): $(V_L\text{-}V_H)_{scFv1}\text{-}CH2\text{-}CH3$, and (iii) L1 comprises or consists of the domain structure (from N- to C-terminus): $V_L\text{—}C_L$, wherein $V_H\text{—}C_{H1}$ of H1 and $V_L\text{—}C_L$ of L1 form the Fab domain capable of binding CD3, scFv1 and scFv2 are each capable of binding MSLN, and the first Fc polypeptide and second Fc polypeptide form the heterodimeric Fc domain, wherein the CH3 domain of H1 and the CH3 domain of H2 each comprise one or more asymmetric amino acid substitutions that promote formation of the heterodimeric Fc domain over a corresponding homodimeric Fc domain.

In various embodiments, a trivalent and bispecific antibody construct described herein can further comprise one or more linkers, as described herein, that covalently couple two or more domains of the construct to each other. In such embodiments, the Fab domain can be coupled to the first Fc polypeptide of the heterodimeric Fc domain via a first linker, the first scFv domain can be coupled to the second Fc polypeptide of the heterodimeric Fc domain via a second linker, and the second scFv domain can be coupled to the Fab domain via a third linker. The first linker coupling a Fab domain to an Fc polypeptide can be referred to herein as linker$^{Fab\text{-}Fc}$ (i.e., indicating the linker coupled a Fab domain to an Fc polypeptide). The second linker coupling an scFv domain to an Fc polypeptide can be referred to herein as linker$^{scFv\text{-}Fc}$. Similarly, the third linker coupling an scFv domain to a Fab domain can be referred to herein as linker$^{scFv\text{-}Fab}$.

Thus, in some embodiments, a first polypeptide chain H1 of an antibody construct herein can comprise one or more peptide linkers. In such embodiments, a $C_{H1}$ sequence (e.g., of a Fab domain) can be coupled to a CH2 domain of the first Fc polypeptide via the first linker, e.g., a linker$^{Fab\text{-}Fc}$, thereby coupling the Fab domain to the first Fc polypeptide. Such linker$^{Fab\text{-}Fc}$ can be a peptide linker. In some embodiments, the linker$^{Fab\text{-}Fc}$ can comprise or consist of an immunoglobulin hinge region, such as an IgG or IgG1 hinge region. In some embodiments, the linker$^{Fab\text{-}Fc}$ comprises or consists of an amino acid sequence having at least about 80%, 90%, 95%, 97%, 99%, or 100% sequence identity to the amino acid sequence set forth in SEQ ID NO: 107. Furthermore, in various embodiments, the second scFv domain (e.g., scFv$_2$) can be coupled, either via the $V_H$ or $V_L$ sequence of scFv$_2$, to a $V_H$ sequence of a Fab domain via a linker$^{scFv\text{-}Fab}$. The linker$^{scFv\text{-}Fab}$ can be a peptide linker. In various embodiments, the linker$^{scFv\text{-}Fab}$ comprises or consists of the amino acid sequence $(Gly_4Ser)_n$ (or in single letter amino acid code: $(G_4S)_n$, SEQ ID NO: 132), wherein n is an integer from 1 to 5. In various embodiments, the linker$^{scFv\text{-}Fab}$ comprises or consists of the amino acid sequence $(Gly_4Ser)$ (SEQ ID NO: 104). In various embodiments, a first and/or second scFv domain (e.g., scFv1 or scFv2) itself can comprise a fourth linker that couples the $V_L$ domain to the $V_H$ domain. Such linker$^{scFv}$ can be referred to as linker$^{scFv}$. The linker$^{scFv}$ can be a peptide linker. In some embodiments, the linker$^{scFv}$ can comprise or consist of the amino acid sequence $(Gly_4Ser)_n$(SEQ ID NO: 132), wherein n is an integer from 1 to 5. In various embodiments, the linker$^{scFv}$ comprises or consists of the amino acid sequence $(Gly_4Ser)_4$ (SEQ ID NO: 102).

In some embodiments, the H1 polypeptide chain of a trivalent and bispecific antibody construct herein can comprise or consist of the domain structure (from N- to C-terminus): $(V_L\text{-linker}^{scFv}\text{-}V_H)_{scFv2}\text{-linker}^{scFv\text{-}Fab}\text{-}V_H\text{-}C_{H1}\text{-linker}^{Fab\text{-}Fc}\text{-}CH2\text{-}CH3$, wherein "scFv2" indicates the second scFv domain capable of binding MSLN.

In various embodiments, a second polypeptide chain H2 of an antibody construct herein can comprise one or more peptide linkers. In such embodiments, the first scFv$_1$ domain, either via its $V_H$ or $V_L$ domain, can be coupled to the CH2 domain of the second Fc polypeptide via a fifth linker, which can also be referred to as linker$^{scFv\text{-}Fc}$, thereby coupling the first scFv domain (scFv1) to the second Fc polypeptide. Such linker$^{scFv\text{-}Fc}$ can be a peptide linker. In some embodiments, the linker$^{scFv\text{-}Fc}$ can comprise or consist of an immunoglobulin hinge region, such as an IgG or IgG1 hinge region. In some embodiments, the linker$^{scFv\text{-}Fc}$ comprises or consists of an amino acid sequence having at least about 80%, 90%, 95%, 97%, 99%, or 100% sequence identity to the amino acid sequence set forth in SEQ ID NO: 111 or SEQ ID NO: 112. Moreover, the first scFv domain (scFv1) can comprise a linker$^{scFv1}$ that couples the $V_L$ domain to the $V_H$ domain (wherein the N- to C-terminal order of $V_H$ and $V_L$ can differ). Such linker$^{scFv1}$ can be a peptide linker, and it can be identical or the different in sequence to the linker$^{scFv}$ that is present in scFv2 (which can be referred to as linker$^{scFv2}$). In some embodiments, the linker$^{scFv1}$ can comprise or consist of the amino acid sequence $(Gly_4Ser)_n$(SEQ ID NO: 132), wherein n is an integer from 1 to 5. In various embodiments, the linker$^{scFv1}$ comprises or consists of the amino acid sequence $(Gly_4Ser)_4$ (SEQ ID NO: 102), in which case the first and second scFv domains comprise an identical linker$^{scFv}$.

In some embodiments, the H2 polypeptide chain of a trivalent and bispecific antibody construct herein can comprise or consist of the domain structure (from N- to C-terminus): $(V_L\text{-linker}^{scFv}\text{-}V_H)_{scFv1}\text{-linker}^{scFv\text{-}Fc}\text{-}CH2\text{-}CH3$, wherein "scFv1" indicates the first scFv domain capable of binding MSLN.

In various embodiments, a trivalent and bispecific antibody construct of the present disclosure can comprise or consist of three polypeptide chains, which can be referred to as H1, H2 and L1, and wherein (i) H1 comprises or consists of the domain structure (from N- to C-terminus): $(V_L\text{-linker}^{scFv}\text{-}V_H)_{scFv2}\text{-linker}^{scFv\text{-}Fab}\text{-}V_H\text{-}C_{H1}\text{-linker}^{Fab\text{-}Fc}\text{-}CH2\text{-}CH3$, (ii) H2 comprises or consists of the domain structure (from N- to C-terminus): $(V_L\text{-linker}^{scFv}\text{-}V_H)_{scFv1}\text{-linker}^{scFv\text{-}Fc}\_CH2\text{-}CH3$, and (iii) L1 comprises or consists of the domain structure-(from N- to C-terminus): $V_L\text{—}C_L$, wherein $V_H\text{—}C_{H1}$ of H1 and $V_L\text{—}C_L$ of L1 form the Fab domain capable of binding CD3, scFv1 and scFv2 are each capable of binding MSLN, and the first Fc polypeptide and second Fc polypeptide form a heterodimeric Fc domain, wherein the CH3 domain of H1 and the CH3 domain of H2 each comprise one or more asymmetric amino acid substitutions that promote formation of the heterodimeric Fc domain and pairing of H1-H2 over a corresponding homodimeric Fc domain (e.g., resulting in H1-H1 or H2-H2 formation).

In some embodiments, the present disclosure relates to a trivalent and bispecific antibody construct that can comprise: (i) a Fab domain capable of binding CD3, (ii) a first scFv domain and a second scFv domain, wherein the first and the second scFv domains are both capable of binding MSLN, and wherein at least one of the first and second scFv domain comprises a $V_L$ domain comprising or consisting of an amino acid sequence having at least about 80%, 90%, 95%, 97%, 99% or 100% sequence identity to the sequence set forth in SEQ ID NO: 101, and a $V_H$ domain comprising or consisting of an amino acid sequence having at least about 80%, 90%, 95%, 97%, 99% or 100% sequence identity to the sequence set forth in SEQ ID NO: 103, and (iii) a heterodimeric Fc domain comprising a first Fc polypeptide and a second Fc polypeptide, and wherein: (a) the Fab domain is coupled to the N-terminus of the first Fc polypeptide, (b) the first scFv domain is coupled to the N-terminus of the second Fc polypeptide, and (c) the second scFv domain is coupled to an N-terminus of the Fab domain. In some embodiments, both the first and the second scFv domains each comprise a $V_L$ domain comprising or consisting of an amino acid sequence having at least about 80%, 90%, 95%, 97%, 99% or 100% sequence identity to the sequence set forth in SEQ ID NO: 101, and a $V_H$ domain comprising or consisting of an amino acid sequence having at least about 80%, 90%, 95%, 97%, 99% or 100% sequence identity to the sequence set forth in SEQ ID NO: 103. In such embodiments, the $V_L$ domains and $V_H$ domains of the first and second scFv domains, scFv1 and scFv2, can each comprise or consist of an amino acid sequence having at least about 90% sequence identity to the sequences set forth in SEQ ID NOs: 101 and 103, respectively. In some embodiments, the $V_L$ domains and $V_H$ domains of the first and second scFv domains, scFv1 and scFv2, can each comprise or consist of an amino acid sequence having at least about 95% sequence identity to the sequences set forth in SEQ ID NOs: 101 and 103, respectively. In some embodiments, the $V_L$ domains and $V_H$ domains of the first and second scFv domains, scFv1 and scFv2, can each comprise or consist of an amino acid sequence having at least about 97% sequence identity to the sequences set forth in SEQ ID NOs: 101 and 103, respectively. In some embodiments, the $V_L$ domains and $V_H$ domains of the first and second scFv domains, scFv1 and scFv2, can each comprise or consist of an amino acid sequence having at least about 99% sequence identity to the sequences set forth in SEQ ID NOs: 101 and 103, respectively. In yet other embodiments, the $V_L$ domains and $V_H$ domains of the first and second scFv domains, scFv1 and scFv2, can comprise or consist of the amino acid sequences set forth in SEQ ID NOs: 101 and 103, respectively.

In various embodiments herein, a trivalent and bispecific antibody construct can comprise: (i) a Fab domain capable of binding CD3, wherein the Fab domain comprises a $V_L$ domain comprising or consisting of an amino acid sequence having at least about 80%, 90%, 95%, 97%, 99% or 100% sequence identity to the sequence set forth in SEQ ID NO: 105, and a $V_H$ domain comprising or consisting of an amino acid sequence having at least about 80%, 90%, 95%, 97%, 99% or 100% sequence identity to the sequence set forth in SEQ ID NO: 115, (ii) a first scFv domain and a second scFv domain, wherein the first and the second scFv domains are both capable of binding mesothelin, and (iii) a heterodimeric Fc domain comprising a first Fc polypeptide and a second Fc polypeptide, wherein: (a) the Fab domain is coupled to the N-terminus of the first Fc polypeptide, (b) the first scFv domain is coupled to the N-terminus of the second Fc polypeptide, and (c) the second scFv domain is coupled to the N-terminus of the Fab domain. In some embodiments, the $V_L$ domain and the $V_H$ domain of the Fab domain comprise or consist of an amino acid sequence having at least about 90% sequence identity to the sequences set forth in SEQ ID NOs: 105 and 115, respectively. In some embodiments, the $V_L$ domain and the $V_H$ domain of the Fab domain comprise or consist of an amino acid sequence having at least about 95% sequence identity to the sequences set forth in SEQ ID NOs: 105 and 115, respectively. In some embodiments, the $V_L$ domain and the $V_H$ domain of the Fab domain comprise or consist of an amino acid sequence having at least about 97% sequence identity to the sequences set forth in SEQ ID NOs: 105 and 115, respectively. In some embodiments, the $V_L$ domain and the $V_H$ domain of the Fab domain comprise or consist of an amino acid sequence having at least about 99% sequence identity to the sequences set forth in SEQ ID NOs: 105 and 115, respectively. In yet other embodiments, the $V_L$ domain and the $V_H$ domain of the Fab domain comprise or consist of amino acid sequences having the sequences set forth in SEQ ID NOs: 105 and 115, respectively.

In various embodiments described herein, a trivalent and bispecific antibody construct can comprise or consist of a set of three polypeptide chains, e.g., H1, H2 and L1, having the amino acid sequences set forth in (i) SEQ ID NOs: 100, 110 and 114, (ii) SEQ ID NOs: 171, 172 and 114, or (iii) SEQ ID NOs: 117, 119 and 114, or variant sequences thereof, e.g., those having at least about 80% sequence identity.

In embodiments in which an antibody construct comprises the three polypeptide chains, H1, H2 and L1, (i) H1 can comprise or consist of an amino acid sequence having at least about 80%, 90%, 95%, 97%, 99% or 100% sequence identity to the sequence set forth in SEQ ID NO: 100, (ii) H2 can comprise or consist of an amino acid sequence having at least about 80%, 90%, 95%, 97%, 99% or 100% sequence identity to the sequence set forth in SEQ ID NO: 110, and (iii) L1 can comprise or consist of an amino acid sequence having at least about 80%, 90%, 95%, 97%, 99% or 100% sequence identity to the sequence set forth in SEQ ID NO: 114.

In some embodiments, H1 comprises or consists of an amino acid sequence having at least about 80%, 90%, 95%, 97%, 99% or 100% sequence identity to the sequence set forth in SEQ ID NO: 100, H2 comprises or consists of the amino acid sequence set forth in SEQ ID NO: 110, and L1 comprises or consists of the amino acid sequence set forth in SEQ ID NO: 114. In such embodiments, H1 can comprise or consist of an amino acid sequence having at least about 90% sequence identity to the sequence set forth in SEQ ID NO: 100. In other embodiments, H1 comprises or consists of an amino acid sequence having at least about 95% sequence identity to the sequence set forth in SEQ ID NO: 100. In some embodiments, H1 comprises or consists of an amino acid sequence having at least about 97% sequence identity to the sequence set forth in SEQ ID NO: 100. In some embodiments, H1 comprises or consists of an amino acid sequence having at least about 99% sequence identity to the sequence set forth in SEQ ID NO: 100. In some embodiments, H1 comprises or consists of the amino acid sequence set forth in SEQ ID NO: 100.

In some embodiments, H1 comprises or consists of the amino acid sequence set forth in SEQ ID NO: 100, H2 comprises or consists of an amino acid sequence having at least about 80%, 90%, 95%, 97%, 99% or 100% sequence identity to the amino acid sequence set forth in SEQ ID NO: 110, and L1 comprises or consists of the amino acid sequence set forth in SEQ ID NO: 114. In such embodiments, H2 can comprise or consist of an amino acid sequence having at least about 90% sequence identity to the sequence set forth in SEQ ID NO: 110. In other embodiments, H2 comprises or consists of an amino acid sequence having at least about 95% sequence identity to the sequence set forth in SEQ ID NO: 110. In some embodiments, H2 comprises or consists of an amino acid sequence having at least about 97% sequence identity to the sequence set forth in SEQ ID NO: 110. In some embodiments, H2 comprises or consists of an amino acid sequence having at least about 99% sequence identity to the sequence set forth in SEQ ID NO: 110. In some embodiments, H2 comprises or consists of the amino acid sequence set forth in SEQ ID NO: 110.

In some embodiments, H1 comprises or consists of the amino acid sequence set forth in SEQ ID NO: 100, H2 comprises or consists of the amino acid sequence set forth in SEQ ID NO: 110, and L1 comprises or consists of an amino acid sequence having at least about 80%, 90%, 95%, 97%, 99% or 100% sequence identity to the amino acid sequence set forth in SEQ ID NO: 114. In such embodiments, L1 can comprise or consist of an amino acid sequence having at least about 90% sequence identity to the sequence set forth in SEQ ID NO: 114. In other embodiments, L1 comprises or consists of an amino acid sequence having at least about 95% sequence identity to the sequence set forth in SEQ ID NO: 114. In some embodiments, L1 comprises or consists of an amino acid sequence having at least about 97% sequence identity to the sequence set forth in SEQ ID NO: 114. In some embodiments, L1 comprises or consists of an amino acid sequence having at least about 99% sequence identity to the sequence set forth in SEQ ID NO: 114. In some embodiments, L1 comprises or consists of the amino acid sequence set forth in SEQ ID NO: 114.

Hence, in some embodiments, the present disclosure describes a trivalent and bispecific antibody construct consisting of the three polypeptide chains, H1, H2 and L1, wherein (i) H1 comprises or consists of the amino acid sequence set forth in SEQ ID NO: 100, (ii) H2 comprises or consists of the amino acid sequence set forth in SEQ ID NO: 110, and (iii) L1 comprises or consists of the amino acid sequence set forth in SEQ ID NO: 114. In some embodiments, such trivalent and bispecific antibody construct can be variant v32523.

In other embodiments, the present disclosure describes a trivalent and bispecific antibody construct consisting of the three polypeptide chains, H1, H2 and L1, wherein (i) H1 comprises or consists of the amino acid sequence set forth in SEQ ID NO: 117, (ii) H2 comprises or consists of the amino acid sequence set forth in SEQ ID NO: 119, and (iii) L1 comprises or consists of the amino acid sequence set forth in SEQ ID NO: 114. In some embodiments, such trivalent and bispecific antibody construct can be variant v21812.

In some embodiments, one or more heavy chains of an antibody construct herein can further comprise a C-terminal lysine residue. Exemplary heavy chain sequences that contain such additional C-terminal lysine residue are set forth in SEQ ID NOs: 171 and 172, and refer to the first and second heavy chains, respectively, of the construct v32523 in which both heavy chain further contain the C-terminal lysine. As further described herein, such C-terminal lysine residues may be cleaved (e.g., enzymatically cleaved) following expression of the antibody construct heavy chains.

The antibody constructs of this disclosure can be capable of simultaneously binding CD3 on an immune cell (e.g., a T cell) and MSLN on a tumor cell. Such simultaneous binding can direct the anti-tumor activity of the T cell to the tumor cell and/or tumor microenvironment. The simultaneous binding of CD3 and MSLN, combined with the rationally selected antigen affinities of the constructs described herein, can provide a TAA- (e.g., MSLN-) dependent anti-tumor activity, i.e., simultaneous binding of CD3 and MSLN can elicit the tumor killing effect in a localized area, i.e., at the tumor site and/or in the tumor environment. Hence, the T cell engaging antibody constructs of this disclosure can be used to treat a MSLN-positive tumor while causing significantly less off-target effects following administration to a subject in need thereof, and when compared to existing T cell engager constructs (e.g., the benchmark constructs described herein as v29191 (Roche) and v31805 (Harpoon)).

As further described herein, an antibody construct can comprise a heterodimeric Fc domain comprising a first Fc polypeptide comprising a first CH2 domain and a first CH3 domain and a second Fc polypeptide comprising a second CH2 domain and a second CH3 domain, wherein at least one of the first and second Fc polypeptide can comprise one or more amino acid modifications in the first or second CH3 domain, respectively, wherein such one or more amino acid modifications can promote the formation of the heterodimeric Fc domain comprising the first and the second Fc polypeptides over a corresponding homodimeric Fc domain which contains two copies of the first Fc polypeptide or the second Fc polypeptide. As further described herein, in some embodiments, the first and second Fc polypeptide each comprise at least one, two, three, four, or five amino acid modifications, wherein such amino acid modifications are relative to a corresponding wildtype Fc polypeptide.

In various embodiments, an antibody construct of the present disclosure can comprise one or more amino acid modifications in the first CH2 domain of the first Fc polypeptide, the second CH2 domain of the second Fc polypeptide, or in both CH2 domains. Such CH2 domain modifications can, as further described herein, alter the interaction of the antibody construct with an Fc-receptor. In various embodiments, the one or more amino acid modifications, to either one or both of the CH2 domains, can reduce or "knock out" the endogenous Fc receptor function of the Fc domain. Hence, in various embodiments, either one or both of the CH2 domains of an antibody construct comprise one or more amino acid substitutions that reduce or abate interactions of the Fc domain with Fc receptors, such as the Fc-gamma receptor (FcγR).

In some embodiments, described herein is an antibody construct, comprising: (i) a Fab domain capable of binding CD3 on a cytotoxic effector cell, wherein the Fab domain comprises a $V_H$ domain comprising a HCDR1 sequence comprising or consisting of the sequence set forth in SEQ ID NO: 126, a HCDR2 sequence comprising or consisting of the sequence set forth in SEQ ID NO: 127, and a HCDR3 sequence comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131; (ii) a first scFv domain (scFv1) and a second scFv domain (scFv2), wherein the first scFv domain and the second scFv domain are capable of binding mesothelin (MSLN), and (iii) a dimeric Fc domain comprising a first Fc polypeptide and a second Fc polypeptide, wherein: the Fab domain is coupled to the N-terminus of the first Fc polypeptide, the first scFv domain is coupled to the N-terminus of the second Fc polypeptide, and the second scFv domain is coupled to an N-terminus of the Fab domain.

In some embodiments, at least one of the first scFv domain and the second scFv domain, or both scFv domains, comprise (i) a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and (ii) a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

In certain embodiments, described herein is an antibody construct, comprising: (i) a Fab domain capable of binding CD3 on a cytotoxic effector cell, wherein the Fab domain comprises a $V_H$ domain comprising a HCDR1 sequence comprising or consisting of the sequence set forth in SEQ ID NO: 126, a HCDR2 sequence comprising or consisting of the sequence set forth in SEQ ID NO: 127, and a HCDR3 sequence comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131; (ii) a first scFv domain (scFv1) and a second scFv domain (scFv2), wherein the first scFv domain and the second scFv domain are capable of binding mesothelin (MSLN), and wherein the first scFv domain and the second scFv domain each comprise a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125; and (iii) a dimeric Fc domain comprising a first Fc polypeptide and a second Fc polypeptide, wherein: the Fab domain is coupled to the N-terminus of the first Fc polypeptide, the first scFv domain is coupled to the N-terminus of the second Fc polypeptide, and the second scFv domain is coupled to an N-terminus of the Fab domain.

In yet further embodiments, the present disclosure describes a trivalent and bispecific antibody construct comprising: a first heavy chain (H1) polypeptide comprising or consisting of the amino acid sequence set forth in SEQ ID NO: 100, a second heavy chain (H2) polypeptide comprising or consisting of the amino acid sequence set forth in SEQ ID NO: 110, and a light chain (L1) polypeptide comprising or consisting of the amino acid sequence set forth in SEQ ID NO: 114.

B. Domains of an Antibody Construct

As further described herein, an antibody construct of the present disclosure can comprise one or more antibody domains. In various embodiments, an antibody construct comprises a plurality (i.e., two or more) of antibody domains. Such plurality of antibody domains can comprise (i) one or more Fc domains, wherein an Fc domain can comprise a first Fc polypeptide and a second Fc polypeptide, (ii) one or more Fab domains, wherein a Fab domain can comprise a heavy chain portion comprising a heavy variable domain ($V_H$) and a heavy constant domain ($C_{H1}$) and a light chain comprising a light variable domain ($V_L$) and light constant domain ($C_L$), and (iii) one or more scFv domains, wherein an scFv domain can comprise a heavy chain variable domain ($V_H$) and a light chain variable domain ($V_L$). The various domains an antibody construct can comprise are further described herein.

An immunoglobulin (Ig) structural unit is typically composed of two pairs of polypeptide chains, each pair having one "light" chain (about 25 kilodalton (kD)) and one "heavy" chain (about 50-70 kD). Light chains can be classified as either kappa or lambda. The "class" of an immunoglobulin refers to the type of constant domain possessed by its heavy chain. There are five major classes of antibodies: IgA, IgD, IgE, IgG and IgM, and several of these can be further divided into subclasses (isotypes), for example, IgG1, IgG2, IgG3, IgG4, IgA1 and IgA2. The heavy chain constant domains that correspond to the different classes of immunoglobulins are called alpha (α), delta (δ), epsilon (ε), gamma (γ) and mu (μ), respectively.

In various embodiments, an antibody construct described herein is based on an IgG class immunoglobulin, for example, an IgG1, IgG2, IgG3 or IgG4 immunoglobulin. In some embodiments, an antibody constructs described herein is based on an IgG1, IgG2 or IgG4 immunoglobulin. In certain embodiments, an antibody constructs described herein is based on an IgG1 immunoglobulin. In the context of the present disclosure, when an antibody construct is based on a specified immunoglobulin isotype, it refers to an antibody construct that comprises either all or merely a portion of the constant region (i.e., Fc domain) of the specified immunoglobulin isotype. It is to be understood that an antibody construct can also comprise hybrids of isotypes and/or subclasses, according to certain embodiments of this disclosure.

Generally, in antibodies, the N-terminal domain of each polypeptide chain usually defines a variable region (e.g., $V_H$ or $V_L$) of about 100 to 110 or more amino acids in length that is primarily responsible for antigen recognition. The terms variable light chain ($V_L$) and variable heavy chain ($V_H$) refer to these domains in the light and heavy chain, respectively. As described herein, in various embodiments, an antibody construct can comprise two or more variable domain sequences that are coupled to one another in tandem and in a single polypeptide chain format, e.g., as disclosed for constructs in which an scFv domain is coupled to a Fab domain in a single chain configuration. Such construct can comprise the domain structure, from N- to C-terminus: $[(V_H\text{-}V_L)/(V_L\text{-}V_H)]_{scFv}\text{-}V_H\text{-}C_{H1}$ (wherein "/" is equivalent to "or" in this description).

Accordingly, in some embodiments, an antibody construct of the present disclosure that is derived from an immunoglobulin molecule can comprise different Ig domains within its heavy and light chains. Heavy chain domains can include the Fc domain (or Fc region), e.g., comprising a CH2 domain and CH3 domain, a hinge domain (or hinge region), and a heavy chain Fab domain comprising the variable heavy domain ($V_H$) and the constant heavy domain ($C_{H1}$), and light chain domains can include the variable light domain ($V_L$) and the light constant domain ($C_L$). In some embodiments, and according to certain nomenclatures, the "Fc domain" can include the CH2 and CH3 domains as well as a hinge domain (or hinge region).

In each of the $V_H$ and $V_L$ domains of an antibody construct herein are three loops which are hypervariable in sequence and form an antigen-binding site. Each of these loops is referred to as a "hypervariable region" or "HVR," or "complementarity determining region" or "CDR." The terms hypervariable region (HVR) and complementarity determining region (CDR) are used herein interchangeably in reference to the portions of the variable region that form the antigen-binding site. With the exception of CDR1 in $V_H$, CDRs generally comprise the amino acid residues that form the hypervariable loops. The $V_H$ and $V_L$ domains consist of relatively invariant stretches called framework regions (FRs) of between about 15 to 30 amino acids in length separated by the shorter CDRs, which are each typically between about 5 and 15 amino acids in length, although can occasionally be longer or shorter. The three CDRs and four FRs that make up each $V_H$ and $V_L$ domain are arranged from N- to C-terminus as follows: FR1-CDR1-FR2-CDR2-FR3-CDR3-FR4.

Several different definitions and numbering conventions of the CDR regions in immunoglobulin molecules are in common use, including those described by Kabat et al. (1983, *Sequences of Proteins of Immunological Interest*, NIH Publication No. 369-847, Bethesda, MD), by Chothia et al. (1987, *J Mol Biol*, 196:901-917), as well as the IMGT, AbM and Contact definitions. These different definitions include overlapping or subsets of amino acid residues when compared against each other. By way of example, CDR definitions according to Kabat, Chothia, IMGT, AbM and Contact are provided in TABLE 1 below.

Accordingly, as can be readily apparent to one skilled in the art, the exact numbering and placement of CDRs can differ based on the numbering system employed. However, it is to be understood that the disclosure herein of a variable heavy domain ($V_H$) includes the disclosure of the associated (inherent) heavy chain CDRs (HCDRs) as defined by any of the known numbering systems. Similarly, disclosure herein of a variable light domain ($V_L$) includes the disclosure of the associated (inherent) heavy chain CDRs (HCDRs) as defined by any of the known numbering systems. One skilled in the art can appreciate that a limited number of amino acid substitutions can be introduced into the CDR sequences or to the $V_H$ or $V_L$ sequences of known antibodies without the antibody losing its ability to bind its target. Candidate amino acid substitutions can be identified by computer modeling or by techniques such as alanine scanning, with the resulting variants being tested for binding activity (e.g., expressed as binding affinity, e.g., given as the measured $EC_{50}$ value) by standard techniques. As an example, in certain embodiments, the MSLN binding domain(s) of antibody constructs described herein can comprise a set of CDRs (i.e., heavy chain CDR1, CDR2 and CDR3, and light chain CDR1, CDR2 and CDR3) that have 90% or greater, 95% or greater, 98% or greater, 99% or greater, or 100% sequence identity to the amino acid sequences set forth in SEQ ID NOs: 120-125, respectively, wherein the binding domain retains or substantially retains the ability to bind MSLN. In this context, the term "substantially" refers to a change in binding affinity of less than about 5%, less than about 4%, less than about 3%, less than about 2%, or less than about 1%, when compared to an unmodified binding domain.

TABLE 1

Common CDR Definitions[1]

| | Heavy Chain | | | Light Chain | | |
|---|---|---|---|---|---|---|
| Definition | CDR1[2] | CDR2 | CDR3 | CDR1 | CDR2 | CDR3 |
| Kabat | H31-H35B | H50-H65 | H95-H102 | L24-L34 | L50-L56 | L89-L97 |
| Chothia | H26-H32, H33 or H34 | H52-H56 | H95-H102 | L24-L34 | L50-L56 | L89-L97 |
| IMGT | H26-H33, H34, H35, H35A or H35B | H51-H57 | H93-102 | L27-L32 | L50-L52 | L89-L97 |
| AbM | H26-H35B | H50-H58 | H95-H102 | L24-L34 | L50-L56 | L89-L97 |
| Contact | H30-H35B | H47-H58 | H95-H101 | L30-L36 | L46-L55 | L89-L96 |

[1]Either the Kabat or Chothia numbering system can be used for HCDR2, HCDR3 and the light chain CDRs for all definitions except Contact, which uses Chothia numbering.
[2]Using Kabat numbering. The position in the Kabat numbering scheme that demarcates the end of the Chothia and IMGT CDR-H1 loop varies depending on the length of the loop due to the placement of insertions outside of those CDR definitions at positions 35A and 35B in Kabat. The IMGT and Chothia CDR-H1 loop can be unambiguously defined using Chothia numbering. CDR-H1 definitions using Chothia numbering are: Kabat H31-H35, Chothia H26-H32, AbM H26-H35, IMGT H26-H33, Contact H30-H35.

In some embodiments, the antibody constructs described herein comprise at least one immunoglobulin domain from a mammalian immunoglobulin, such as a bovine immunoglobulin, a human immunoglobulin, a camelid immunoglobulin, a rat immunoglobulin, or a mouse immunoglobulin. In some embodiments, an antibody construct herein can be a chimeric construct comprising two or more immunoglobulin domains, in which at least one domain is from a first mammalian immunoglobulin, for example a human immunoglobulin, and at least a second domain is from a second mammalian immunoglobulin, for example, a mouse or rat immunoglobulin. In other embodiments, an antibody construct can be derived from immunoglobulins that are from different species, for example, an antibody construct can be chimeric or humanized. A "chimeric antibody construct" refers to an antibody that typically comprises at least one variable domain from a rodent antibody (usually a murine antibody) and at least one constant domain from a human antibody. A "humanized antibody construct" is a type of chimeric antibody that contains minimal sequence derived from a non-human antibody. In some embodiments, an antibody construct herein can comprise at least one immunoglobulin constant domain from a human immunoglobulin. In some embodiments, all domains of an antibody construct described herein can be (or be derived from) from a human immunoglobulin.

In some embodiments, and as further described elsewhere herein, modifications (e.g., to the amino acid sequence) to one or more domains of an antibody construct can be made to further refine the antibody construct's properties and performance (e.g., antigen affinity, stability, pharmacokinetics, etc.). For example, framework region (FR) residues of a human immunoglobulin can be replaced by corresponding non-human residues, or the humanized antibodies can comprise residues that are not found in either the recipient antibody or the donor antibody. In general, a variable domain in a humanized antibody or a humanized antibody domain comprises all or substantially all of the hypervariable regions from a non-human immunoglobulin and all or substantially all of the FRs from a human immunoglobulin sequence. As further described herein, modifications in the Fc domain can enable preferential pairing of the Fc polypeptides to form a heterodimeric Fc domain rather than a homodimeric Fc domain.

In some embodiments, the present disclosure relates to antibody constructs that can have different valencies, e.g., can be bivalent, trivalent, tetravalent, or have a higher valency. Hence, in various embodiments, an antibody construct herein comprises two or more, or three or more antigen binding domains, i.e., is at least bivalent or at least trivalent, respectively. An antibody construct herein can also comprise different valencies combined with certain antigen specificities. As an example, a bivalent and bispecific antibody construct herein can comprise two binding domains, e.g., a first binding domain (e.g., a Fab domain) and a second binding domain (e.g., an scFv domain). Such two binding domains can each have a unique binding specificity for an antigen, e.g., one domain for a first antigen (e.g., CD3) and a second domain for a second antigen (e.g., MSLN). In various embodiments of this disclosure, an antibody construct can be bispecific and multivalent, and thus such antibody construct can comprise two or more binding domains, such as three binding domains. Each of the two or more binding domains can have a unique binding specificity for an antigen (either the same epitope/antigen or different ones). In some embodiments, at least two of the two or more binding domains have a binding specificity for two different antigens, e.g., for CD3 and MSLN. In various embodiments, an antibody construct herein can be trivalent and bispecific, that is the antibody comprises three binding domains, wherein one of the three binding domains has specificity for, or is capable of binding to, a first antigen (e.g., CD3), and the other two binding domains have specificity for, or are capable of binding to, a second antigen (e.g., MSLN).

In embodiments in which an antibody construct herein comprises two binding domains that bind to the same target molecule (e.g., MSLN), the two binding domains can bind to the same epitope on the target molecule, or they can bind to different epitopes on the target molecule. In some embodiments, an antibody construct herein comprises two binding domains that bind to different epitopes on the target molecule (e.g., MSLN), which can be characterized as "biparatopic" binding. In other embodiments, however, an antibody construct herein comprises two binding domains that bind to the same epitope of an antigen (e.g., MSLN). In such embodiments, the two binding domains can comprise heavy and light chain CDRs that share at least about 90%, 95%, 97%, 99%, or 100% amino acid sequence identity. In further embodiments, the $V_H$ and $V_L$ domains of the two binding domains (e.g., first and second scFv domains) that bind the same epitope on a target (e.g., MSLN) can share at least about 90%, 95%, 97%, 99%, or 100% amino acid sequence identity, so that, in some of these embodiments, the full amino acid sequences of the first scFv and the second scFv share at least about 90%, 95%, 97%, 99%, or 100% amino acid sequence identity.

As described herein, an antibody construct of the present disclosure can comprise (i) one or more Fab domains, (ii) one or more scFv domains, and (iii) an Fc domain comprising a first Fc polypeptide and a second Fc polypeptide. In various embodiments, a trivalent and bispecific antibody construct as described herein comprises (i) a Fab domain capable of binding to a first antigen, (ii) a first scFv domain and a second scFv domain, both capable of binding to a second antigen, and (iii) a heterodimeric Fc domain comprising a first Fc polypeptide and a second Fc polypeptide.

Generally, a "Fab domain," as used herein, contains the constant domain ($C_L$) of the light chain and the first constant domain ($C_{H1}$) of the heavy chain along with the variable domains $V_L$ and $V_H$ on the light and heavy chains, respectively, which comprise the CDRs as described herein. In some embodiments, a Fab domain can be a single chain Fab. A single chain Fab can be a Fab molecule in which the Fab light chain and the Fab heavy constant chain are connected by a peptide linker to form a single polypeptide chain. In such embodiments, typically, the C-terminus of the Fab light chain is connected to the N-terminus of the Fab heavy chain in the single-chain Fab molecule, however, other formats are also encompassed herein. In various embodiments herein, however, a Fab domain of an antibody construct is formed by two separately expressed polypeptide chains, i.e., a light chain and a heavy chain (or portion thereof). The heavy chain and light chain parts of the Fab domain can, however, be interconnected by covalent bonds, such as disulfide bonds.

An "scFv domain," as used herein, generally comprises a heavy chain variable domain ($V_H$) and a light chain variable domain ($V_L$) in a single polypeptide chain format. The scFv can optionally comprise a peptide linker between the $V_H$ and $V_L$ domains which can assist the scFv in forming a functional structure for antigen binding. Hence, in various embodiments, an scFv domain herein can include a $V_L$ domain that is coupled via its C-terminus to the N-terminus of a $V_H$ domain by a linker$^{scFv}$, i.e., an scFv domain can have the domain structure: $V_L$-linker$^{scFv}$-$V_H$, or alternatively, an scFv can comprise a $V_H$ connected by its C-terminus to the N-terminus of a $V_L$ by a linker$^{scFv}$, i.e., having the domain structure: $V_H$-linker$^{scFv}$-$V_L$.

In some embodiments, an antibody construct described herein can further comprise another domain or moiety that may not be derived from an immunoglobulin molecule. Such non-Ig domain can be referred to as a non-Ig moiety. Such non-Ig moiety can be a detectable label (e.g., a radiolabel or fluorescent label), a low molecular weight (<750 Da) drug molecule, another peptide (e.g., signal peptide(s)) or polypeptide molecule, or combinations thereof.

Fc Domains

As described herein, an antibody construct of this disclosure can comprise an Fc domain comprising a first Fc polypeptide and a second Fc polypeptide. In various embodiments, the Fc domain is a heterodimeric Fc domain comprising a first Fc polypeptide and a second Fc polypeptide, wherein the first Fc polypeptide and the second Fc polypeptide share about 90%, 95%, 97%, or about 99% amino acid sequence identity, e.g., each comprising one or more asymmetric amino acid substitutions that can promote preferential pairing for the Fc polypeptides to form the heterodimeric Fc domain compared to formation of a respective homodimeric Fc domain.

The term "Fc domain" or "Fc region," as used herein, includes native (or wildtype) sequence Fc domains as well as variant Fc domains comprising one or more amino acid modifications relative to a corresponding native or wildtype Fc domain. Unless otherwise specified herein, numbering of amino acid residues in the Fc domain or constant region is according to the EU numbering system, also called the EU index, as described, e.g., in Kabat et al., Sequences of Proteins of Immunological Interest, 5th Ed. Public Health Service, National Institutes of Health, Bethesda, MD (1991). An "Fc polypeptide" of a dimeric (e.g., heterodimeric) Fc domain refers to one of the two polypeptide chains (e.g., a first and second Fc polypeptide) forming the dimeric (e.g., heterodimeric) Fc domain. In some embodiments, Fc polypeptides can comprise a C-terminal constant region of an immunoglobulin heavy chain that is capable of stable self-association. In various embodiments, and as further described herein, an Fc polypeptide (e.g., a first or a second Fc polypeptide) comprises at least one of a CH2 domain sequence and/or a CH3 domain sequence. In certain embodiments, an Fc polypeptide of an antibody construct described herein comprises a CH2 domain sequence and a CH3 domain sequence.

As disclosed herein, an antibody construct can comprise an Fc domain, wherein such Fc domain can be a heterodimeric Fc domain. The Fc domain, e.g., heterodimeric Fc domain, of an antibody construct, unless otherwise specified, comprises a first Fc polypeptide and a second Fc polypeptide. Generally, each Fc polypeptide of a (e.g., heterodimeric) Fc domain can comprise a CH2 domain, a CH3 domain, or, as described in various embodiments herein, both a CH2 domain and a CH3 domain.

In certain embodiments, an antibody construct comprises an Fc domain based on a human IgG Fc domain. In some embodiments, an antibody construct comprises an Fc domain based on a human IgG1 Fc domain. In various embodiments, an antibody construct comprises a heterodimeric IgG Fc domain comprising two different Fc polypeptides, e.g., a first Fc polypeptide and a second polypeptide, wherein the first and second Fc polypeptides have different amino acid sequences, e.g., amino acid sequences that have about 90%, 95%, 97%, or 99% sequence identity when compared and aligned to one another, e.g., as further described herein for heterodimeric Fc domains. In some embodiments, the differences in the amino acid sequences of a first and second Fc polypeptide can be due to asymmetric amino acid substitutions that can be introduced into each Fc polypeptide chain to promote preferential paring of the heavy chains to form the heterodimeric Fc domain, compared to a corresponding homodimeric Fc domain.

In various embodiments, an antibody construct herein comprises an Fc domain that is a modified IgG Fc domain, and in which the CH3 domain of at least one Fc polypeptide comprises one or more amino acid modifications compared to a respective wildtype CH3 domain. In some embodiments, an antibody construct herein comprises an Fc domain based on a modified IgG Fc domain in which the CH2 domain of at least one Fc polypeptide comprises one or more amino acid modifications compared to a respective wildtype CH2 domain. In some embodiments, an antibody construct comprises an Fc domain based on a modified IgG Fc domain in which both the CH3 domain and the CH2 domain of at least one Fc polypeptide comprises one or more amino acid modifications compared to respective wildtype CH3 and CH2 domains. In various embodiments, both Fc polypeptides of a heterodimeric Fc domain can comprise one or more amino acid modifications in their CH3 domains. In some embodiments, both Fc polypeptides of a heterodimeric Fc domain can comprise one or more amino acid modifications in their CH2 domains. In yet other embodiments, both Fc polypeptides of a heterodimeric Fc domain can comprise one or more amino acid modifications in both their CH2 domains and CH3 domains.

Modified Fc Domains

In some embodiments, the present disclosure relates to antibody constructs that can comprise a heterodimeric immunoglobulin Fc domain comprising a modified heterodimeric CH3 domain, wherein the modified heterodimeric CH3 domain comprises one or more asymmetric amino acid modifications, i.e., one or both the first and the second Fc polypeptide each comprise one or more amino acid modifications in their CH3 domain sequences compared to respective wildtype sequences. As used herein, the term "asymmetric amino acid modification" generally refers to a modification in which an amino acid at a specific position on the first Fc polypeptide is different to the amino acid at the corresponding position on the second Fc polypeptide. These asymmetric amino acid modifications can comprise modifications of only one of the two amino acids at the corresponding position on each Fc polypeptide, or they can comprise modifications of both amino acids at the corresponding positions on each of the first and second Fc polypeptides. In various embodiments, an "asymmetric amino acid modification" is an asymmetric amino acid substitution.

In some embodiments, an antibody construct herein comprises a heterodimeric Fc domain comprising a modified CH3 domain (i.e., a heterodimeric CH3 domain consisting of the two CH3 domain sequences of the first and second Fc polypeptides), wherein the modified CH3 domain comprises one or more asymmetric amino acid modifications that promote formation of the heterodimeric Fc domain (e.g., pairing of a first Fc polypeptide with a second Fc polypeptide) over formation of a corresponding homodimeric Fc domain (e.g., pairing of a first Fc polypeptide with another first Fc polypeptide). Amino acid modifications that can be made to the CH3 domain of an Fc domain in order to promote formation of a heterodimeric Fc domain are known in the art and include, for example, those described in International Publication No. WO 96/027011 ("knobs into holes"), Gunasekaran et al., 2010, *J Biol Chem*, 285, 19637-46 ("electrostatic steering"), Davis et al., 2010, *Prot Eng Des Sel*, 23(4):195-202 (strand exchange engineered domain (SEED) technology) and Labrijn et al., 2013, *Proc Natl Acad Sci USA*, 110(13):5145-50 (Fab-arm exchange). Other examples include approaches combining positive and negative design strategies to produce stable asymmetrically modified Fc regions as described in International Publication Nos. WO 2012/058768 and WO 2013/063702.

In certain embodiments, an antibody construct herein comprises a heterodimeric Fc domain comprising a modified heterodimeric CH3 domain in which at least one, or both of the Fc polypeptide chains comprise one or more amino acid modifications, as described in International Publication No. WO 2012/058768 or International Patent Publication No. WO 2013/063702.

In some embodiments, an antibody construct herein comprises a heterodimeric human IgG1 Fc domain having a modified CH3 domain. TABLE 2 herein provides the amino acid sequence of a human IgG1 Fc domain sequence (e.g., a sequence that a first and/or a second Fc polypeptide can be derived from), corresponding to amino acids 231 to 447 of a full-length human IgG1 heavy chain (e.g., one that comprises $V_H$, $C_{H1}$, Hinge, CH2 and CH3 domains), and identified by SEQ ID NO: 1. The CH2 domain is typically defined as comprising amino acids 231-340 of the full-length human IgG1 heavy chain and the CH3 domain is typically defined as comprising amino acids 341-447 of the full-length human IgG1 heavy chain.

As described herein, an antibody construct can comprise a heterodimeric Fc domain having a modified CH3 domain comprising one or more asymmetric amino acid modifications that promote formation of the heterodimeric Fc domain over formation of a homodimeric Fc domain, and in which the modified CH3 domain comprises a first Fc polypeptide including amino acid modifications at positions F405 and Y407, relative to SEQ ID NO: 1, and a second Fc polypeptide including amino acid modifications at positions T366 and T394, relative to SEQ ID NO: 1. In various embodiments, the one or more amino acid modifications comprise one or more amino acid substitutions. Hence, in some embodiments, the amino acid modification at position F405 of the first Fc polypeptide of the modified CH3 domain is F405A, F405I, F405M, F405S, F405T or F405V. In some embodiments, the amino acid modification at position Y407 of the first Fc polypeptide of the modified CH3 domain is Y407I or Y407V. In some embodiments, the amino acid modification at position T366 of the second Fc polypeptide of the modified CH3 domain is T366I, T366L or T366M. In some embodiments, the amino acid modification at position T394 of the second Fc polypeptide of the modified CH3 domain is T394W. In some embodiments, the modified CH3 domain of a first Fc polypeptide further includes an amino acid modification at position L351, relative to SEQ ID NO: 1. In some embodiments, the amino acid modification at position L351 in the first Fc polypeptide of the modified CH3 domain is L351Y. In some embodiments, the second Fc polypeptide of the modified CH3 domain further includes an amino acid modification at position K392, relative to SEQ ID NO: 1. In some embodiments, the amino acid modification at position K392 in the second Fc polypeptide of the modified CH3 domain is K392F, K392L or K392M. In some embodiments, one or both of the first and second Fc polypeptides of the modified CH3 domain further comprises the amino acid modification T350V.

TABLE 2

Exemplary Human IgG1 Fc Domain Sequences and Variants Thereof

| | | |
|---|---|---|
| Human IgG1 Fc Domain sequence of amino acid residues 231-447 (EU-numbering) | APELLGGPSVFLFPPKPKDTLMISRTPEVTC VVVDVSHEDPEVKFNWYVDGVEVHNAKTKPR EEQYNSTYRVVSVLTVLHQDWLNGKEYKCKV SNKALPAPIEKTISKAKGQPREPQVYTLPPS RDELTKNQVSLTCLVKGFYPSDIAVEWESNG QPENNYKTTPPVLDSDGSFFLYSKLTVDKSR WQQGNVFSCSVMHEALHNHYTQKSLSLSPGK (SEQ ID NO: 1) | |

| Variant # | Poly-peptide Chain* | Mutations |
|---|---|---|
| 1 | A | L351Y_F405A_Y407V |
|   | B | T366L_K392M_T394W |
| 2 | A | L351Y_F405A_Y407V |
|   | B | T366L_K392L_T394W |
| 3 | A | T350V_L351Y_F405A_Y407V |
|   | B | T350V_T366L_K392L_T394W |
| 4 | A | T350V_L351Y_F405A_Y407V |
|   | B | T350V_T366L_K392M_T394W |

TABLE 2-continued

Exemplary Human IgG1 Fc Domain Sequences and Variants Thereof

| 5 | A | T350V_L351Y_S400E_F405A_Y407V |
|---|---|---|
|   | B | T350V_T366L_N390R_K392M_T394W |

*"A" corresponds to one of the first and second Fc polypeptide chains and "B" to corresponds to the other of the first and second Fc polypeptide chains of an antibody construct described herein.

In certain embodiments, an antibody construct herein comprises a heterodimeric Fc domain having a modified CH3 domain comprising one or more asymmetric amino acid modifications that promote formation of the heterodimeric Fc domain over formation of a homodimeric Fc domain, and in which the modified CH3 domain comprises a first Fc polypeptide including the amino acid modification F405A, F405I, F405M, F405S, F405T or F405V together with the amino acid modification Y407I or Y407V, and relative to SEQ ID NO: 1, and a second Fc polypeptide including the amino acid modification T366I, T366L or T366M, together with the amino acid modification T394W, and relative to SEQ ID NO: 1. In some embodiments, the first Fc polypeptide of the modified CH3 domain further includes the amino acid modification L351Y. In some embodiments, the second Fc polypeptide of the modified CH3 domain further includes the amino acid modification K392F, K392L or K392M. In some embodiments, one or both of the first and second Fc polypeptides having a modified CH3 domain further comprises the amino acid modification T350V.

In certain embodiments, an antibody construct herein comprises a heterodimeric Fc domain comprising a modified CH3 domain having a first Fc polypeptide that comprises amino acid modifications at positions F405 and Y407, and optionally further comprises an amino acid modification at position L351, and a second Fc polypeptide that comprises amino acid modifications at positions T366 and T394, and optionally further comprises an amino acid modification at position K392, as described above, and the first Fc polypeptide further comprises an amino acid modification at one or both of positions S400 or Q347 and/or the second Fc polypeptide further comprises an amino acid modification at one or both of positions K360 or N390, wherein the amino acid modification at position S400 is S400E, S400D, S400R or S400K; the amino acid modification at position Q347 is Q347R, Q347E or Q347K; the amino acid modification at position K360 is K360D or K360E, and the amino acid modification at position N390 is N390R, N390K or N390D, relative to SEQ ID NO: 1.

In some embodiments, an antibody construct comprises a heterodimeric Fc domain comprising a modified CH3 domain comprising the modifications of any one of Variant 1, Variant 2, Variant 3, Variant 4 or Variant 5, as shown in TABLE 2.

In various embodiments, an antibody construct of the present disclosure can comprise a heterodimeric Fc domain comprising a first Fc polypeptide (A) and a second Fc polypeptide (B), wherein the first Fc polypeptide (A) and the second Fc polypeptide (B) comprise the amino acid substitutions in their CH3 domains according to variant #1 as shown in TABLE 2. In other embodiments, an antibody construct of the present disclosure can comprise a heterodimeric Fc domain comprising a first Fc polypeptide (A) and a second Fc polypeptide (B), wherein the first Fc polypeptide (A) and the second Fc polypeptide (B) comprise the amino acid substitutions in their CH3 domains according to variant #2 as shown in TABLE 2. In some embodiments, an antibody construct of the present disclosure can comprise a heterodimeric Fc domain comprising a first Fc polypeptide (A) and a second Fc polypeptide (B), wherein the first Fc polypeptide (A) and the second Fc polypeptide (B) comprise the amino acid substitutions in their CH3 domains according to variant #3 as shown in TABLE 2. In some embodiments, an antibody construct of the present disclosure can comprise a heterodimeric Fc domain comprising a first Fc polypeptide (A) and a second Fc polypeptide (B), wherein the first Fc polypeptide (A) and the second Fc polypeptide (B) comprise the amino acid substitutions in their CH3 domains according to variant #4 as shown in TABLE 2. In yet other embodiments, an antibody construct of the present disclosure can comprise a heterodimeric Fc domain comprising a first Fc polypeptide (A) and a second Fc polypeptide (B), wherein the first Fc polypeptide (A) and the second Fc polypeptide (B) comprise the amino acid substitutions in their CH3 domains according to variant #5 as shown in TABLE 2.

In certain embodiments, the CH3 domain of a first Fc polypeptide of an antibody construct herein has an amino acid sequence that is at least about 80%, about 85%, about 90%, about 95%, about 97%, or at least about 99% identical to the amino acid sequence set forth in SEQ ID NO: 109. In certain embodiments, the CH3 domain of a second Fc polypeptide of an antibody construct herein has an amino acid sequence that is at least about 80%, about 85%, about 90%, about 95%, about 97%, or at least about 99% identical to the amino acid sequence set forth SEQ ID NO: 113. In some embodiments, the CH3 domain of a first Fc polypeptide of an antibody construct herein has the amino acid sequence set forth in SEQ ID NO: 109 and a second Fc polypeptide of the antibody construct herein has the amino acid sequence set forth SEQ ID NO: 113.

It is noted that the descriptors "a first Fc polypeptide" and "a second Fc polypeptide" in this section and the present disclosure as a whole can be generally used interchangeably for both Fc polypeptides of an Fc domain, unless specified otherwise. Such descriptors are generally used herein to distinguish between the two Fc polypeptides of an Fc domain and are not intended to limit one specific Fc polypeptide to a certain set of asymmetric mutations.

In certain embodiments, an antibody construct herein comprises a heterodimeric Fc domain based on an IgG Fc domain having a modified CH2 domain (i.e., a heterodimeric CH2 domain consisting of the two CH2 domain sequences of the respective first and second Fc polypeptides). In some embodiments, an antibody construct comprises an Fc domain based on an IgG Fc domain having a modified CH2 domain, wherein the modification(s) of the CH2 domain result(s) in altered (e.g., reduced or abated) binding to one or more Fc receptors (FcRs) such as receptors of the FcγRI, FcγRII and FcγRIII subclasses.

Several amino acid modifications to the CH2 domain of the first and/or second Fc polypeptide(s) of an Fc domain that selectively alter the affinity of such Fc domain for different Fcγ receptors are known in the art. Amino acid modifications that result in increased binding and amino acid modifications that result in decreased binding can both be useful in certain indications. For example, increasing binding affinity of an Fc for FcγRIIIa (an activating receptor) can result in increased antibody dependent cell-mediated cytotoxicity (ADCC), which in turn can result in increased lysis of the target cell. Decreased binding to FcγRIIb (an inhibitory receptor) likewise can be beneficial in some circumstances. In certain indications, a decrease in, or elimination of, ADCC and complement-mediated cytotoxicity (CDC) can be desirable. In such embodiments, modified CH2 domains comprising amino acid modifications that result in increased binding to FcγRIIb or amino acid modifications that can decrease or eliminate binding of the Fc region to all of the Fcγ receptors ("knock-out" variants) can be useful.

Non-limiting examples of amino acid modifications to the CH2 domain that alter binding of the Fc domain by Fcγ receptors include, but are not limited to, the following: S298A/E333A/K334A and S298A/E333A/K334A/K326A (increased affinity for FcγRIIIa) (Lu, et al., 2011, *J Immunol Methods*, 365(1-2):132-41); F243L/R292P/Y300L/V305I/P396L (increased affinity for FcγRIIIa) (Stavenhagen, et al., 2007, *Cancer Res*, 67(18):8882-90); F243L/R292P/Y300L/L235V/P396L (increased affinity for FcγRIIIa) (Nordstrom J L, et al., 2011, *Breast Cancer Res*, 13(6):R123); F243L (increased affinity for FcγRIIIa) (Stewart, et al., 2011, *Protein Eng Des Sel.*, 24(9):671-8); S298A/E333A/K334A (increased affinity for FcγRIIIa) (Shields, et al., 2001, *J Biol Chem*, 276(9):6591-604); S239D/I332E/A330L and S239D/I332E (increased affinity for FcγRIIIa) (Lazar, et al., 2006, *Proc Natl Acad Sci USA*, 103(11):4005-10), and S239D/S267E and S267E/L328F (increased affinity for FcγRIIb) (Chu, et al., 2008, *Mol Immunol*, 45(15):3926-33). Additional modifications that affect Fc domain binding to Fcγ receptors are described in *Therapeutic Antibody Engineering* (Strohl & Strohl, Woodhead Publishing series in Biomedicine No 11, ISBN 1 907568 37 9, October 2012, page 283).

In various embodiments, an antibody construct of the present disclosure comprises a heterodimeric Fc domain based on an IgG Fc domain having a modified CH2 domain, in which the modified CH2 domain comprises one or more amino acid modifications that can result in decreased or eliminated binding of the Fc domain to one or more, or all of the Fcγ receptors (i.e., a "knock-out" or "KO" variant).

Various publications describe strategies that have been used to engineer antibodies to produce "knock-out" Fc variants (see, for example, Strohl, 2009, *Curr Opin Biotech* 20:685-691, and Strohl & Strohl, "*Antibody Fc engineering for optimal antibody performance*" In Therapeutic Antibody Engineering, Cambridge: Woodhead Publishing, 2012, pp 225-249). These strategies include reduction of effector function through modification of glycosylation, use of IgG2/IgG4 scaffolds, or the introduction of mutations in the hinge or CH2 domain of the Fc (see also, U.S. Patent Publication No. 2011/0212087, International Publication No. WO 2006/105338, U.S. Patent Publication No. 2012/0225058, U.S. Patent Publication No. 2012/0251531, and Strop et al., 2012, *J. Mol. Biol.*, 420: 204-219).

In some embodiments, an antibody construct's Fc domain can comprise one or more of known amino acid modifications to reduce FcγR and/or complement binding of the Fc domain. In some embodiments, such modifications can include those identified in TABLE 3.

TABLE 3

Modifications to Reduce Fcγ Receptor or Complement Binding

| Company | Mutations |
|---|---|
| GSK | N297A |
| Ortho Biotech | L234A/L235A |
| Protein Design labs | IgG2 V234A/G237A |
| Wellcome Labs | IgG4 L235A/G237A/E318A |
| GSK | IgG4 S228P/L236E |
| Merck | IgG2 H268Q/V309L/A330S/A331S |

TABLE 3-continued

Modifications to Reduce Fcγ Receptor or Complement Binding

| Company | Mutations |
|---|---|
| Bristol-Myers | C220S/C226S/C229S/P238S |
| Seattle Genetics | C226S/C229S/E3233P/L235V/L235A |
| Medimmune | L234F/L235E/P331S |

Additional examples herein include Fc domains engineered to include the amino acid modifications L235A/L236A/D265S, e.g., based on the sequence set forth in SEQ ID NO: 1. In addition, asymmetric amino acid modifications in the CH2 domain that decrease binding of the Fc to all Fcγ receptors are described in International Publication No. WO 2014/190441.

In certain embodiments, the CH2 domain of a first and a second Fc polypeptide herein comprises or consists of an amino acid sequence having at least about 80%, about 85%, about 90%, about 95%, about 97%, or at least about 99% sequence identity to the sequence set forth in SEQ ID NO: 108. In some embodiments, the CH2 domain of a first and/or a second Fc polypeptide herein comprises or consists of the sequence set forth in SEQ ID NO: 108.

In certain embodiments, an antibody construct herein comprises a heterodimeric Fc domain in which native glycosylation has been modified. As is known in the art, glycosylation of an Fc can be modified to increase or decrease effector function. For example, mutation of the conserved asparagine residue at position 297 to alanine, glutamine, lysine, or histidine (i.e., N297A, Q, K or H) results in an aglycoslated Fe that lacks all effector function (Bolt et al., 1993, *Eur. J. Immunol.*, 23:403-411; Tao & Morrison, 1989, *J. Immunol.*, 143:2595-2601). Conversely, removal of fucose from heavy chain N297-linked oligosaccharides has been shown to enhance ADCC, based on improved binding to FcγRIIIa (see, for example, Shields et al., 2002, *J Biol Chem.*, 277:26733-26740, and Niwa et al., 2005, *J. Immunol. Methods*, 306:151-160). Such low fucose antibody constructs can be produced, for example in knock-out Chinese hamster ovary (CHO) cells lacking fucosyltransferase (FUT8) (Yamane-Ohnuki et al., 2004, *Biotechnol. Bioeng.*, 87:614-622), in the variant CHO cell line, Lee 13, that has a reduced ability to attach fucose to N297-linked carbohydrates (International Publication No. WO 03/035835), or in other cells that generate afucosylated antibodies (see, for example, Li et al., 2006, *Nat Biotechnol*, 24:210-215; Shields et al., 2002, ibid, and Shinkawa et al., 2003, *J. Biol. Chem.*, 278:3466-3473). In addition, International Publication No. WO 2009/135181 describes the addition of fucose analogs to culture medium during antibody production to inhibit incorporation of fucose into the carbohydrate on the antibody.

In certain embodiments, a trivalent and bispecific antibody construct of this disclosure can bind a neonatal Fc receptor (e.g., FcRn).

Linkers

As described herein, an antibody construct of the present disclosure can comprise one or more linkers. In various embodiments, such one or more linkers are peptide (or peptitic) linkers comprising or consisting of an amino acid sequence of 1, 2, 3, 5, 10, 15, 20, 25, 30 or more consecutive amino acid residues. Such peptide linkers can couple, or link, two or more peptides or polypeptides to each other. Hence, in various embodiments, a linker herein can couple a first polypeptide sequence, e.g., a heavy chain constant domain ($C_{H1}$), to a second polypeptide sequence, e.g., an Fc polypeptide. Thus, in some embodiments, a linker can be used to couple one domain of an antibody construct to another domain, e.g., a Fab domain to an Fc domain, e.g., via a linker$^{Fab\text{-}Fc}$, an scFv domain to a Fab domain, e.g., via a linker$^{scFv\text{-}Fab}$ a $V_H$ domain to a $V_L$ domain, e.g., via a linker$^{scFv}$, and so forth.

In embodiments in which a linker couples, e.g., a heavy chain variable domain ($V_H$) to, e.g., a light chain variable domain ($V_L$), the linker can be of sufficient length to allow both domains to elicit their biological function. In addition to providing a spacing function, a linker herein (e.g., a peptide linker) can provide flexibility or rigidity suitable for properly orienting the one or more domains of an antibody construct, both within the antibody construct itself and between the antibody construct and its biological target(s) (e.g., T cell and/or cancer antigens).

Further, a linker herein (e.g., a peptide linker) can support (i) expression of a full-length fusion protein, e.g., a full-length polypeptide chain H1, L1, H2, etc. of an antibody construct, and (ii) provide increased stability of the purified protein both in vitro and in vivo, e.g., following administration to a subject in need thereof, such as a human or rodent. The one or more linkers used in antibody constructs herein are generally non-immunogenic or poorly immunogenic in mammalian subjects that an antibody construct may be administered to. In certain embodiments, one or more of the linkers used in an antibody construct herein can comprise part or all of a human immunoglobulin hinge region, a stalk region of C-type lectins, a family of type II membrane proteins, or combinations thereof. In certain embodiments, one or more of the linkers used in an antibody construct herein can comprise part or all of a human immunoglobulin hinge region, such as an IgG or IgG1 hinge region, such as a linker$^{Fab\text{-}Fc}$ or linker$^{scFv\text{-}Fc}$.

In certain embodiments, each linker of the one or more linkers used in an antibody construct herein can comprise or consist of an amino acid sequence having a length of 2 to about 50 amino acids. In some embodiments, each linker of the one or more linkers used in an antibody construct herein can comprise or consist of an amino acid sequence having a length from about 3 to about 40 amino acids, from about 10 to about 50 amino acids, from about 2 to about 40 amino acids, from about 5 to about 30 amino acids, from about 5 to about 25 amino acids, from about 4 to about 30 amino acids, from about 10 to about 30 amino acids, or from about 15 to about 25 amino acids. In some embodiments, the one or more linkers of an antibody construct can each comprise an amino acid sequence comprising or consisting of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive amino acids.

In certain embodiments, a linker of an antibody construct herein comprises of consists of the amino acid sequence (EAAAK)$_n$ wherein n is an integer from 1 to 5 (SEQ ID NO: 133). In some embodiments, a linker comprises or consists of the sequence EAAAK (SEQ ID NO: 134). In some embodiments, a linker comprises or consists of the sequence EAAAKEAAAK (SEQ ID NO: 135). In some embodiments, a linker comprises a polyproline linker, e.g., having an amino acid sequence of PPP (SEQ ID NO: 136) or PPPP (SEQ ID NO: 137). In certain embodiments, a linker is a glycine (G)-proline (P) polypeptide linker, e.g., comprising or consisting of one or more of GPPPG (SEQ ID NO: 138), GGPPPGG (SEQ ID NO: 139), GPPPPG (SEQ ID NO: 140), or GGPPPPGG (SEQ ID NO: 141). In some embodiments, a linker herein is a (Gly$_n$Ser)$_m$linker, wherein n and m are independently integers from 1 to 5 (SEQ ID NO: 142). In certain embodiments, a linker comprises or consists of an amino acid sequence of $(Gly_3Ser)_n(Gly_4Ser)_1$ (SEQ ID NO: 143), $(Gly_3Ser)_1(Gly_4Ser)_n$ (SEQ ID NO: 144), or $(Gly_3Ser)_n(Gly_4Ser)_n$ (SEQ ID NO: 145), wherein each n is independently an integer from 1 to 5. In certain embodiments, a linker herein is suitable for connecting two different domains of an antibody construct and comprises a sequence comprising glycine-serine linkers, for example, but not limited to, $(G_mS)_n$-GG (SEQ ID NO: 146), $(SG_n)_m$ (SEQ ID NO: 147), or $(SEG_n)_m$ (SEQ ID NO: 148), wherein m and n are independently integers from 0 to 20, from 1 to 10, or from 1 to 5.

Hence, in some embodiments, an antibody construct described herein comprises one or more linkers, e.g., 1, 2, 3, 4, or 5 linkers which comprise or consist of the amino acid sequence $(Gly_4Ser)_n$, wherein n is an integer from 1 to 5 (SEQ ID NO: 132), 1 to 4, or 1 to 3. In such embodiments, n can be 1 (SEQ ID NO: 104). In other embodiments, n is 3 (SEQ ID NO: 118). In yet other embodiments, n is 4 (SEQ ID NO: 102).

In certain embodiments herein, one or more of the linkers an antibody construct comprises can be an amino acid sequence obtained, derived, or designed from an antibody hinge region sequence. In some embodiments, such linker can have at least one cysteine capable of participating or forming in at least one disulfide bond under physiological conditions or other standard peptide conditions (e.g., peptide purification conditions, conditions for peptide storage). In certain embodiments, a linker corresponding to, or similar to, an immunoglobulin hinge peptide retains a cysteine that corresponds to the hinge cysteine disposed toward the amino (or N-) terminus of that hinge. In further embodiments, a linker is derived from an IgG1 hinge and can be modified to remove any cysteine residues, or the linker is an IgG1 hinge that has one cysteine or two cysteines corresponding to hinge cysteines.

In certain embodiments, a linker of an antibody construct described herein can comprise an "altered wildtype immunoglobulin hinge region" or an "altered immunoglobulin hinge region". Such altered hinge regions can refer to (a) a wild type immunoglobulin hinge region with up to 30 percent amino acid changes (e.g., up to 25 percent, 20 percent, 15 percent, 10 percent, or 5 percent amino acid substitutions, insertions and/or deletions), (b) a portion of a wild type immunoglobulin hinge region that is at least 10 amino acids (e.g., at least 12, 13, 14 or 15 amino acids) in length with up to 30 percent amino acid changes (e.g., up to 25 percent, 20 percent, 15 percent, 10 percent, or 5 percent amino acid substitutions and/or deletions), (c) a portion of a wild type immunoglobulin hinge region that comprises the core hinge region, which portion can be 4, 5, 6, 7, 8, 9, 10, 11, 12, 13, 14, or 15, or at least 4, 5, 6, 7, 8, 9, 10, 11, 12, 13, 14, or 15 amino acids in length, or (d) a combination of any of (a)-(c). In certain embodiments, one or more cysteine residues in a wildtype immunoglobulin hinge region, such as an IgG1 hinge comprising the upper and core regions, can be substituted by one or more other amino acid residues (e.g., one or more serine residues). An altered immunoglobulin hinge region can alternatively or additionally have a proline residue of a wildtype immunoglobulin hinge region, such as an IgG1 hinge comprising the upper and core regions, substituted by another amino acid residue (e.g., a serine residue).

Hence, in some embodiments, an antibody construct of this disclosure comprises a linker comprising or consisting of an amino acid sequence having at least about 80%, 90%, 95%, 97%, 99%, or 100% sequence identity to the sequence set forth in SEQ ID NO: 107. In some embodiments, an antibody construct comprises a linker comprising or consisting of an amino acid sequence having at least about 80%, 90%, 95%, 97%, 99%, or 100% sequence identity to the sequence set forth in SEQ ID NO: 111. In some embodiments, an antibody construct comprises a linker comprising or consisting of an amino acid sequence having at least about 80%, 90%, 95%, 97%, 99%, or 100% sequence identity to the sequence set forth in SEQ ID NO: 112.

In various embodiments, an antibody construct of this disclosure comprises a linker that couples a Fab domain to a first Fc polypeptide, linker$^{Fab-Fc}$, wherein the linker$^{Fab-Fc}$ comprises or consists of the amino acid sequence set forth in SEQ ID NO: 107, and another linker coupling a first scFv domain to a second Fc polypeptide, linker$^{scFv-Fc}$, wherein the linker$^{scFv-Fc}$ comprises or consists of the amino acid sequence set forth in SEQ ID NO: 111.

In other embodiments, an antibody construct of this disclosure comprises a linker that couples a Fab domain to a first Fc polypeptide, linker$^{Fab-Fc}$, wherein the linker$^{Fab-Fc}$ comprises or consists of the amino acid sequence set forth in SEQ ID NO: 107, and another linker coupling a first scFv domain to a second Fc polypeptide, linker$^{scFv-Fc}$, wherein the linker$^{scFv-Fc}$ comprises or consists of the amino acid sequence set forth in SEQ ID NO: 112.

Binding Domains Directed Against Tumor-Associated Antigens

As described herein, an antibody construct of the present disclosure can comprise one or more binding domains capable of binding one or more tumor-associated antigens (TAAs). In various embodiments, an antibody construct herein is trivalent and bispecific and comprises a first binding domain, a second binding domains, and a third binding domain, wherein one or more of such binding domains are capable of binding a tumor-associated antigen (TAA). In various embodiments, two of such binding domains are capable of binding to a TAA. The TAA can be any antigenic substance expressed on a tumor cell surface.

Hence, in embodiments in which at least two binding domains of an antibody construct herein are capable of binding a TAA, both binding domains can bind to different TAAs. In various other embodiments, both anti-TAA binding domains can bind to the same TAA, i.e., the antibody construct is bivalent for that TAA. As further described herein, in such embodiments, both anti-TAA binding domains can be capable of binding the same epitope of the TAA (e.g., capable of bivalent binding of two TAA molecules (e.g., two MSLN molecules) on the same epitope). In other embodiments, both anti-TAA binding domains can be capable of binding to two different epitopes of the same TAA.

As described herein, in various embodiments, the two anti-TAA binding domains of an antibody construct can be capable of binding MSLN. In various embodiments, the anti-MSLN binding domains of such construct are scFv domains, and capable of binding to the same epitope of MSLN, on either the same MSLN protein or on two different MSLN proteins.

In some embodiments, the present disclosure relates to antibody constructs in which both anti-MSLN binding domains can have the same, or a similar (i.e., within about ±5%), binding affinity for MSLN, or both domains can have different binding affinities for MSLN. Such different binding affinities can differ by at least about 2%, 5% different, or 10% e.g., as measured as $EC_{50}$ values.

Hence, in various embodiments, at least one anti-MSLN binding domain of a construct herein can have a binding affinity for MSLN of about 0.5 nM, 0.6 nM, 0.7, nM, 0.8 nM, 0.9 nM, 1 nM, 2 nM, 3 nM, 4 nM, 5 nM, or about 10 nM. In some embodiments, both anti-MSLN binding domains can have a binding affinity for MSLN of about 0.5 nM, 0.6 nM, 0.7, nM, 0.8 nM, 0.9 nM, 1 nM, 2 nM, 3 nM, 4 nM, 5 nM, or about 10 nM. In some embodiments, the at least one, or both, binding domain(s) against MSLN have an affinity for MSLN of about 3 nM. In some embodiments, the at least one, or both, binding domain(s) against MSLN have an affinity for MSLN from about 0.5 nM to about 5 nM, from about 1 nM to about 10 nM, from about 1 nM to about 5 nM, or from about 2 nM to about 4 nM. In some embodiments, both binding domains against MSLN have an affinity for MSLN from about 2 nM to about 4 nM.

As used throughout this disclosure, the term "binding affinity" in the context of an antibody construct herein, or a portion thereof (e.g., a binding domain), for binding to a certain antigen (e.g., CD3, MSLN, etc.) broadly corresponds to a dissociation constant ($K_D$) value measured using one or more binding assays known in the art, such as SPR, FACS, etc. The term "$K_D$" (given in units such as: molar "M", mM, pM, nM, pM, etc.) refers to the dissociation equilibrium constant of a particular antibody construct-antigen interaction. There is an inverse relationship between $K_D$ and binding affinity, therefore the smaller the $K_D$ value, the higher, i.e., stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. Unless otherwise indicated, binding affinities of antibody constructs herein for their targets, e.g., CD3, MSLN, etc., are provided as the $EC_{50}$ value for binding those targets. As used herein, the term "$EC_{50}$" refers to the half maximal effective concentration, which includes the concentration of an antibody construct which induces a response halfway between the baseline and maximum after a specified exposure time. The $EC_{50}$ value essentially represents the concentration of an antibody construct at which 50% of its maximal effect is observed. Hence, the $EC_{50}$ value generally equals the concentration of an antibody construct of the present disclosure that gives half-maximal binding to cells expressing CD3 or a tumor-associated antigen such as MSLN, as determined by e.g., an SPR or a FACS binding assay.

As described herein, the two anti-MSLN binding domains of an antibody constructs herein can each comprise or consist of an scFv domain. In various embodiments, the two anti-MSLN binding domains each consist of an scFv domain, i.e., a first scFv domain and a second scFv domain, each comprising a $V_H$ domain, a $V_L$ domain, and a linker that couples the C-terminus of the $V_L$ domain to the N-terminus of the $V_H$ domain, or the C-terminus of the $V_H$ domain to the N-terminus of the $V_L$ domain. In various embodiments, the two anti-MSLN scFv domains comprise or consist of an identical amino acid sequence. In such embodiments, the two anti-MSLN binding domains bind the same epitope on MSLN and can each comprise a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising a LCDR1 sequence comprising or consisting of the sequence set forth in SEQ ID NO: 123, a LCDR2 sequence comprising or consisting of the sequence set forth in SEQ ID NO: 124, and a LCDR3 sequence comprising or consisting of the sequence set forth in SEQ ID NO: 125. In these embodiments, both anti-MSLN scFv domains can possess the same, or similar, binding affinity to MSLN.

In some embodiments, the CDRs of an anti-MSLN paratope comprise one or more amino acid modifications in one or more of the CDR sequences set forth in SEQ ID NOs: 120-125, wherein at least about 80%, 90%, or 95% binding affinity to MSLN is retained compared to the paratope with no amino acid modifications.

In some embodiments, the two anti-MSLN binding domains are scFv domains (e.g., a first and a second scFv domain) that comprise or consist of amino acid sequences that share at about 80%, 90%, 95%, 97%, 99%, or 100% sequence identity.

In such embodiments, both anti-MSLN binding domains, i.e., the first scFv domain and the second scFv domain, can comprise a $V_H$ domain comprising or consisting of an amino acid sequence having at least about 80%, 90%, 95%, 97%, 99%, or 100% sequence identity to the amino acid sequence set forth in SEQ ID NO: 103. In certain embodiments, both anti-MSLN binding domains can comprise a $V_H$ domain comprising or consisting of an amino acid sequence having at least about 90% sequence identity to the amino acid sequence set forth in SEQ ID NO: 103. In some embodiments, both anti-MSLN binding domains can comprise a $V_H$ domain comprising or consisting of an amino acid sequence having at least about 95% sequence identity to the amino acid sequence set forth in SEQ ID NO: 103. In some embodiments, both anti-MSLN binding domains can comprise a $V_H$ domain comprising or consisting of an amino acid sequence having at least about 97% sequence identity to the amino acid sequence set forth in SEQ ID NO: 103. In some embodiments, both anti-MSLN binding domains can comprise a $V_H$ domain comprising or consisting of an amino acid sequence having at least about 99% sequence identity to the amino acid sequence set forth in SEQ ID NO: 103. In some embodiments, both anti-MSLN binding domains can comprise a $V_H$ domain comprising or consisting of the amino acid sequence set forth in SEQ ID NO: 103.

In further embodiments, both anti-MSLN binding domains, i.e., the first scFv domain and the second scFv domain, can comprise a $V_L$ domain comprising or consisting of an amino acid sequence having at least about 80%, 90%, 95%, 97%, 99%, or 100% sequence identity to the amino acid sequence set forth in SEQ ID NO: 102. In some embodiments, both anti-MSLN binding domains can comprise a $V_L$ domain comprising or consisting of an amino acid sequence having at least about 90% sequence identity to the amino acid sequence set forth in SEQ ID NO: 102. In some embodiments, both anti-MSLN binding domains can comprise a $V_L$ domain comprising or consisting of an amino acid sequence having at least about 95% sequence identity to the amino acid sequence set forth in SEQ ID NO: 102. In some embodiments, both anti-MSLN binding domains can comprise a $V_L$ domain comprising or consisting of an amino acid sequence having at least about 97% sequence identity to the amino acid sequence set forth in SEQ ID NO: 102. In some embodiments, both anti-MSLN binding domains can comprise a $V_L$ domain comprising or consisting of an amino acid sequence having at least about 99% sequence identity to the amino acid sequence set forth in SEQ ID NO: 102. In some embodiments, both anti-MSLN binding domains can comprise a $V_L$ domain comprising or consisting of the amino acid sequence set forth in SEQ ID NO: 102.

Hence, in various embodiments, an antibody construct of the present disclosure comprises a first scFv domain and a second scFv domain, wherein the first scFv domain and the second scFv domain are both capable of binding the same epitope on MSLN, and wherein the first scFv domain and the second scFv domain each comprise or consist of an amino acid sequence having at about 80%, 90%, 95%, 97%, 99%, or 100% sequence identity to the amino acid sequence set forth in SEQ ID NO: 149. In some embodiments, the first scFv domain and the second scFv domain each comprise or consist of an amino acid sequence having at about 90%, 95%, 97%, 99%, or 100% sequence identity to the amino acid sequence set forth in SEQ ID NO: 149. In some embodiments, the first scFv domain and the second scFv domain each comprise or consist of an amino acid sequence having at about 90% sequence identity to the amino acid sequence set forth in SEQ ID NO: 149. In some embodiments, the first scFv domain and the second scFv domain each comprise or consist of an amino acid sequence having at about 95% sequence identity to the amino acid sequence set forth in SEQ ID NO: 149. In some embodiments, the first scFv domain and the second scFv domain each comprise or consist of an amino acid sequence having at about 97% sequence identity to the amino acid sequence set forth in SEQ ID NO: 149. In some embodiments, the first scFv domain and the second scFv domain each comprise or consist of an amino acid sequence having at about 99% sequence identity to the amino acid sequence set forth in SEQ ID NO: 149. In various embodiments, the first scFv domain and the second scFv domain each comprise or consist of the amino acid sequence set forth in SEQ ID NO: 149.

In some embodiments, the first scFv domain and the second scFv domain of an antibody construct herein which are both capable of binding MSLN each consist of the amino acid sequence set forth in SEQ ID NO: 149.

Binding Domains Directed Against Antigens on Cytotoxic Effector Cells

As further described herein, an antibody construct of the present disclosure can comprise at least one binding domain capable of binding to a molecule, e.g., a polypeptide, on the surface of a cytotoxic effector cell. Such cytotoxic effector cell can be an immune cell. The immune cell can be a T cell, a macrophage, a dendritic cell, a neutrophil, a B-cell, or an NK cell. In various embodiments, an antibody construct of the present disclosure comprises at least one binding domain capable of binding an antigen on a T cell. In various embodiments, such antigen is CD3.

In some embodiments, the present disclosure relates to trivalent and bispecific antibody constructs comprising a first binding domain capable of binding CD3 and a second and a third binding domain both capable of binding MSLN. The antibody constructs described herein can also be referred to as "T cell engagers," "TCEs" or "T cell engager molecules" referring to the construct's ability to bind both CD3 on a T cell and MSLN on a tumor cell, and thereby direct T cell-mediated cytotoxic activity to a tumor environment which contains cells expressing MSLN.

In various embodiments, an anti-CD3 binding domain of an antibody construct herein can have an affinity for CD3 given as an $EC_{50}$ value for binding CD3 that is not more than about 1 nM, 5 nM, 10 nM, 20 nM, or not more than about 30 nM. In various embodiments, an anti-CD3 binding domain herein has an affinity for CD3 given as an $EC_{50}$ value for binding CD3 that is from about 20 nM to about 80 nM, from about 30 nM to about 60 nM, or from about 40 nM to about 50 nM. In some embodiments, an anti-CD3 binding domain herein has an affinity for CD3 given as an $EC_{50}$ value for binding CD3 that is about 30 nM, 40 nM, 50 nM, or about 60 nM. In various embodiments, an antibody construct herein comprises an anti-CD3 binding domain that has an $EC_{50}$ value for binding CD3 from about 20 nM to about 40 nM, e.g., of about 30 nM.

In various embodiments, an antibody construct herein comprises a Fab domain capable of binding CD3 on a T cell, wherein such Fab domain has an $EC_{50}$ value for binding CD3 from about 20 nM to about 40 nM, e.g., of about 30 nM, and comprises a $V_H$ domain comprising a HCDR1 sequence comprising or consisting of the sequence set forth in SEQ ID NO: 126, a HCDR2 sequence comprising or consisting of the sequence set forth in SEQ ID NO: 127, and a HCDR3 sequence comprising or consisting of the sequence set forth in SEQ ID NO: 128, and a $V_L$ domain comprising a LCDR1 sequence comprising or consisting of the sequence set forth in SEQ ID NO: 129, a LCDR2 sequence comprising or consisting of the sequence set forth in SEQ ID NO: 130, and a LCDR3 sequence comprising or consisting of the sequence set forth in SEQ ID NO: 131.

In some embodiments, the CDRs of an anti-CD3 paratope herein comprise one or more amino acid modifications in one or more of the CDR sequences set forth in SEQ ID NOs: 126-131, wherein at least about 80%, 90%, or 95% binding affinity to CD3 is retained compared to the paratope with no amino acid modifications.

In certain embodiments, and as further described herein, the anti-CD3 Fab domain of an antibody construct can comprise or consist of a heavy chain portion comprising a $V_H$ domain and $C_{H1}$ domain and a light chain comprising a $V_L$ domain and $C_L$ domain.

The $V_H$ domain of an anti-CD3 Fab domain of an antibody construct herein can comprise or consist of an amino acid sequence having at least about 80%, 90%, 95%, 97%, 99%, or 100% sequence identity to the amino acid sequence set forth in SEQ ID NO: 105. In some embodiments, the $V_H$ domain of such Fab domain comprises or consists of an amino acid sequence having at least about 90% sequence identity to the amino acid sequence set forth in SEQ ID NO: 105. In some embodiments, the $V_H$ domain of such Fab domain comprises or consists of an amino acid sequence having at least about 95% sequence identity to the amino acid sequence set forth in SEQ ID NO: 105. In some embodiments, the $V_H$ domain of such Fab domain comprises or consists of an amino acid sequence having at least about 97% sequence identity to the amino acid sequence set forth in SEQ ID NO: 105. In some embodiments, the $V_H$ domain of such Fab domain comprises or consists of an amino acid sequence having at least about 99% sequence identity to the amino acid sequence set forth in SEQ ID NO: 105. In yet other embodiments, the $V_H$ domain of such Fab domain comprises or consists of the amino acid sequence set forth in SEQ ID NO: 105.

The $V_L$ domain of an anti-CD3 Fab domain of an antibody construct herein, which can be part of a light chain (e.g., L1) that pairs with an anti-CD3 domain of a heavy chain, can comprise or consist of an amino acid sequence having at least about 80%, 90%, 95%, 97%, 99%, or 100% sequence identity to the amino acid sequence set forth in SEQ ID NO: 115. In some embodiments, the $V_L$ domain of such Fab domain comprises or consists of an amino acid sequence having at least about 90% sequence identity to the amino acid sequence set forth in SEQ ID NO: 115. In some embodiments, the $V_L$ domain of such Fab domain comprises or consists of an amino acid sequence having at least about 95% sequence identity to the amino acid sequence set forth in SEQ ID NO: 115. In some embodiments, the $V_L$ domain of such Fab domain comprises or consists of an amino acid sequence having at least about 97% sequence identity to the amino acid sequence set forth in SEQ ID NO: 115. In some embodiments, the $V_L$ domain of such Fab domain comprises or consists of an amino acid sequence having at least about 99% sequence identity to the amino acid sequence set forth in SEQ ID NO: 115. In various embodiments, the $V_L$ domain of such Fab domain comprises or consists of the amino acid sequence set forth in SEQ ID NO: 115.

The $C_{H1}$ domain of an anti-CD3 Fab domain of an antibody construct herein can comprise or consist of an amino acid sequence having at least about 80%, 90%, 95%, 97%, 99%, or 100% sequence identity to the amino acid sequence set forth in SEQ ID NO: 106. In some embodiments, the $C_{H1}$ domain of such Fab domain comprises or consists of an amino acid sequence having at least about 90% sequence identity to the amino acid sequence set forth in SEQ ID NO: 106. In some embodiments, the $C_{H1}$ domain of such Fab domain comprises or consists of an amino acid sequence having at least about 95% sequence identity to the amino acid sequence set forth in SEQ ID NO: 106. In some embodiments, the $C_{H1}$ domain of such Fab domain comprises or consists of an amino acid sequence having at least about 97% sequence identity to the amino acid sequence set forth in SEQ ID NO: 106. In some embodiments, the $C_{H1}$ domain of such Fab domain comprises or consists of an amino acid sequence having at least about 99% sequence identity to the amino acid sequence set forth in SEQ ID NO: 106. In some embodiments, the $C_{H1}$ domain of such Fab domain comprises or consists of the amino acid sequence set forth in SEQ ID NO: 106.

The $C_L$ domain of an anti-CD3 Fab domain of an antibody construct herein can comprise or consist of an amino acid sequence having at least about 80%, 90%, 95%, 97%, 99%, or 100% sequence identity to the amino acid sequence set forth in SEQ ID NO: 116. In some embodiments, the $C_L$ domain of such Fab domain comprises or consists of an amino acid sequence having at least about 90% sequence identity to the amino acid sequence set forth in SEQ ID NO: 116. In some embodiments, the $C_L$ domain of such Fab domain comprises or consists of an amino acid sequence having at least about 95% sequence identity to the amino acid sequence set forth in SEQ ID NO: 116. In some embodiments, the $C_L$ domain of such Fab domain comprises or consists of an amino acid sequence having at least about 97% sequence identity to the amino acid sequence set forth in SEQ ID NO: 116. In some embodiments, the $C_L$ domain of such Fab domain comprises or consists of an amino acid sequence having at least about 99% sequence identity to the amino acid sequence set forth in SEQ ID NO: 116. In yet other embodiments, the $C_L$ domain of such Fab domain comprises or consists of the amino acid sequence set forth in SEQ ID NO: 116.

Hence, in various embodiments, an antibody construct herein comprises an anti-CD3 Fab domain comprising (i) a $V_H$ domain comprising or consisting of an amino acid sequence having at least about 95%, 97%, 99%, or 100% sequence identity to the amino acid sequence set forth in SEQ ID NO: 105, (ii) a $V_L$ domain comprising or consisting of an amino acid sequence having at least about 95%, 97%, 99%, or 100% sequence identity to the amino acid sequence set forth in SEQ ID NO: 115, (iii) a $C_{H1}$ domain comprising or consisting of an amino acid sequence having at least about 95%, 97%, 99%, or 100% sequence identity to the amino acid sequence set forth in SEQ ID NO: 106, and (iv) CL domain comprising or consisting of an amino acid sequence having at least about 95%, 97%, 99%, or 100% sequence identity to the amino acid sequence set forth in SEQ ID NO: 116.

In certain embodiments, an antibody construct herein comprises an anti-CD3 Fab domain comprising (i) a $V_H$ domain comprising or consisting of the amino acid sequence set forth in SEQ ID NO: 105, (ii) a $V_L$ domain comprising or consisting of the amino acid sequence set forth in SEQ ID NO: 115, (iii) a $C_{H1}$ domain comprising or consisting of the amino acid sequence set forth in SEQ ID NO: 106, and (iv) CL domain comprising or consisting of the amino acid sequence set forth in SEQ ID NO: 116.

In various embodiments, and as further described herein, an anti-CD3 Fab domain of an antibody construct can form when a portion of a heavy chain (e.g., H1) that comprises a $V_H$ domain and a $C_{H1}$ domain pairs with a light chain (L1) that comprises a $V_L$ domain and a CL domain. In some embodiments, the heavy chain H1 of which a portion can form an anti-CD3 Fab domain has the amino acid sequence set forth in SEQ ID NO: 100, and the corresponding light chain L1 that pairs with the anti-CD3 portion of the heavy chain to form the anti-CD3 Fab domain has the amino acid sequence set forth in SEQ ID NO: 114.

C. Properties of Antibody Constructs

A trivalent and bispecific antibody construct of the present disclosure can possess one or more properties that can make such antibody construct superior when tested in vivo and/or in vitro and when compared to other, known constructs currently in use, e.g., for the treatment of cancers, and in terms of anti-tumor activity and occurrence of side effects when the construct is administered to a subject in need thereof.

As described herein, an antibody construct of this disclosure can be capable of binding CD3 on a cytotoxic effector cell (e.g., a T cell) and MSLN located on a tumor cell. In some embodiments, such binding occurs simultaneously, e.g., the antibody construct can be simultaneously bound to both CD3 on the cytotoxic effector cell and to MSLN on a tumor cell. In various embodiments, the cytotoxic effector cell is an immune cell such as a T cell, and the tumor cell is a MSLN-expressing solid tumor cell.

In various embodiments, the antibody constructs described herein have been engineered and designed to possess a certain format (e.g., 2(scFv)+1(Fab) for MSLN and CD3, respectively) and geometry that allows for an avidity-driven engagement of MSLN via two anti-MSLN scFv domains each located in on a different arm of the antibody construct. Furthermore, extensive evaluation studies have shown that the use of anti-MSLN paratopes with moderate, single digit nanomolar affinity for MSLN, e.g., from about 2 nM to about 4 nM, in combination with the antibody format provided surprisingly potent T cell mediated anti-tumor activity in the presence of tumor cells with moderate to high MSLN expression, whereas low anti-tumor activity was observed in environments with low MSLN-expressing tumor cells. This superior and TAA-dependent anti-tumor activity appeared to be unique to the constructs described herein and was not observed in the tested benchmark constructs that possessed a different format and/or geometry. It was furthermore found that combining such MSLN binding profile with a single anti-CD3 binding domain that has a moderate to low affinity for CD3 in the double digit nanomolar range, e.g., from about 20 nM to about 40 nM, showed the most favorable balance between T cell mediated anti-tumor activity and selectivity for moderate or high MSLN-expressing tumor cells over low-MSLN expressing tissue. Such properties may provide an enhanced cytotoxic effect elicited by the immune cell at a target site, e.g., where tumor cells expressing the TAA (e.g., MSLN) are present, and when compared to other organs or tissue(s) where no or a significantly lower number of cells with high MSLN expression are present. Hence, the trivalent and bispecific antibody constructs described herein that comprise one anti-CD3 Fab binding domain and two anti-MSLN scFv binding domains in a configuration in which both anti-MSLN scFv domains are located at the N-terminal regions of the antibody construct (e.g., at the N-termini of two heavy chains), may provide superior in vivo anti-tumor activity and tolerability when compared to existing benchmark molecules that may also target both CD3 and MSLN but possess different molecular formats and/or geometries as well as different antigen affinities.

Hence, an antibody construct of the present disclosure can be characterized as a trivalent and bispecific T cell engaging molecule capable of forming a TCR-independent artificial immune synapse between the immune cell, e.g., T cell, and the tumor cell when bound to CD3 on the immune cell and MSLN on the tumor cell. This can cause the T cell to become activated and to exert a cytotoxic effect on the tumor cell, which can lead to tumor cell lysis, as further described herein.

In some embodiments, a trivalent and bispecific antibody construct of the present disclosure comprising an anti-CD3 Fab domain and two anti-MSLN scFv domains can be capable of one or more of the following in a cell population comprising immune cells expressing CD3 and tumor cells expressing MSLN and when present in a concentration of about 10 pM: A) inducing production of at least about 20 pg/mL, 30 pg/mL, or 40 pg/mL TNFα; B) inducing production of at least about 500 pg/mL, 1000 pg/mL, or 2000 pg/mL IFNγ; and/or C) inducing production of at least about 50 pg/mL, 1000 pg/mL, or 150 pg/mL IL-2. In some embodiments, the antibody construct comprises two or more of the properties A, B, and C. In yet other embodiments, the antibody construct comprises all of the properties A, B, and C. In some of these embodiments, the immune cells can comprise T cells and the tumor cells can express at least about 500,000 MSLN/cell.

In various embodiments, a trivalent and bispecific antibody construct of the present disclosure comprising an anti-CD3 Fab domain and two anti-MSLN scFv domains can have a binding affinity for MSLN of about 0.7 nM, 0.8 nM, 0.9 nM, or about 1 nM as measured by surface plasmon resonance (SPR). In some embodiments, such trivalent and bispecific antibody construct of the present disclosure can further have a binding affinity for CD3 of about 30 nM, 40 nM, 50 nM, or 60 nM, or from about 30 nM to about 60 nM.

Hence, in some embodiments, a trivalent and bispecific antibody construct of the present disclosure comprising an anti-CD3 Fab domain and two anti-MSLN scFv domains and having the domain structure scFv2-Fab-CH2$_1$-CH3$_1$ in the first heavy chain, and scFv1-CH2$_2$-CH3$_2$ in the second heavy chain, and comprising (i) the anti-MSLN paratope with HCDRs and LCDRs set forth in SEQ ID NOs: 120-125, respectively, and the anti-CD3 paratope with HCDRs and LCDRs set forth in SEQ ID NOs: 126-131, respectively, can have a binding affinity for MSLN of about 0.7 nM, 0.8 nM, 0.9 nM, or about 1 nM, and a binding affinity for CD3 of at most about 30 nM, 40 nM, 50 nM, or 60 nM, as measured by SPR. The relative orientation of the binding domains of such antibody construct can provide a specific, avidity-based engagement with both CD3$^+$ T cells and MSLN$^+$ tumor cells that can allow for a MSLN-dependent T cell activation, e.g., as measured by cytokine release of the activated T cells, and/or the tumor cell killing activity based on MSLN-expression by the tumor cells. As further described and demonstrated herein, and without being bound by any theory, the use of two anti-MSLN scFv's and one anti-CD3 Fab in the configuration described herein, and as shown, e.g., in FIG. 1A, can provide a more potent and more MSLN-dependent anti-tumor response when compared to other, previously reported constructs, e.g., corresponding Fab$^3$ constructs that contain two anti-MSLN Fabs (instead of the two anti-MSLN scFv domains used in the presently described constructs) as well as one anti-CD3 Fab domain. The present disclosure, including experimental data provided herein, demonstrates the remarkable and surprising impact that a construct's format and geometry in combination with its antigen affinities can have on its in vivo properties, e.g., by head-to-head comparison of trivalent and bispecific constructs of which one comprises one anti-CD3 Fab domain and two anti-MSLN scFv domains (e.g., v21812, v32523, etc.) and another contains one anti-CD3 Fab domain and two anti-MSLN Fab domains (e.g., v29191, v21791), and, in some embodiments, even comparing constructs with different geometries but identical anti-CD3/MSLN paratope sequences to show differences that are entirely format-driven.

Accordingly, in some embodiments, a trivalent and bispecific antibody construct of the present disclosure comprising an anti-CD3 Fab domain and two anti-MSLN scFv domains can be capable of inducing production of a pro-inflammatory cytokine by a T cell in a MSLN-dependent manner, wherein the MSLN-dependent activation of the cytotoxic effector cell is determined by measuring a reduction in cytokine production of at least about 20-fold, 50-fold, 100-fold, or at least about 1000-fold between a first cell population comprising a first tumor cell and immune cells and in a second cell population comprising a second tumor cell and immune cells, wherein the first tumor cell has a MSLN-expression that is at least about 3, 4 or 5-fold higher than that of the second tumor cell.

In further embodiments, a trivalent and bispecific antibody construct of the present disclosure comprising an anti-CD3 Fab domain and two anti-MSLN scFv domains can be capable of inducing at least 5-fold, 10-fold, 15-fold, or 20-fold higher T-cell mediated cytotoxicity against tumor cells in an in vitro study when compared under the same experimental conditions to an analogous antibody constructs that comprises two anti-MSLN Fab domains instead of the first and second anti-MSLN scFv domains of the herein disclosed construct.

The cytotoxic activity of an antibody construct described herein against a MSLN$^+$ cell line can be given as a half maximal inhibitory concentration (IC$_{50}$). As an example, such IC$_{50}$ value can be used as a measure of how much of an antibody construct is needed to reduce the number of live MSLN$^+$ cells by 50%. Several methods of determining the IC$_{50}$ for an antibody construct are known in the art and are described herein, e.g., the use of cell viability assays and measurements to determine the concentration at which the live tumor cell count is reduced by 50%. Generally, a high IC$_{50}$ indicates that more of an antibody construct is required to reduce live tumor cell count by, e.g., 50%, and thus that the antibody construct's ability to induce anti-tumor cytotoxic activity is relatively low. Conversely, a low IC$_{50}$ indicates that less of an antibody construct is required to reduce live tumor cell count by, e.g., 50%, and thus that the antibody construct's ability to induce anti-tumor cytotoxic activity is relatively high.

In some embodiments, a trivalent and bispecific antibody construct of the present disclosure comprising an anti-CD3 Fab domain and two anti-MSLN scFv domains can have an $IC_{50}$ for T cell induced tumor cell killing from about 1 pM to about 0.005 pM, from about 1 pM to about 0.01 pM, from about 0.5 pM to about 0.005 pM, from about 0.1 pM to about 0.01 pM or from about 0.1 pM to about 0.05 pM. In certain embodiments, a trivalent and bispecific antibody construct of the present disclosure comprising an anti-CD3 Fab domain and two anti-MSLN scFv domains can have an $IC_{50}$ for T cell induced tumor cell killing from about 1 pM to about 0.01 pM or from about 0.5 pM to about 0.01 pM. In some embodiments, the tumor cells are $MSLN^+$ tumor cells with an average number of equal to or more than about 100,000 MSLN/cell, such as H292 or OVCAR3 cells, as described herein.

In some embodiments, a trivalent and bispecific antibody construct of the present disclosure comprising an anti-CD3 Fab domain and two anti-MSLN scFv domains can be capable of either (i) inhibiting the growth of a tumor (e.g., <5% increase in tumor volume) and/or (ii) reducing the volume of the tumor by at least about 5%, 10%, 15%, 20%, 25%, 30%, 40%, or by at least about 50% in a subject and when measured over a time period of at least about 20 days following administration of the antibody construct to the subject at a dose of about 1 mg/kg, 1.5 mg/kg or about 3 mg/kg, wherein the tumor comprises cells expressing at least about 100,000 MSLN/cell. In various embodiments, such trivalent and bispecific antibody construct achieves a reduction in tumor volume that is significantly greater than that of a construct comprising a $Fab^3$ format, i.e., comprising 2 anti-MSLN Fabs and one anti-CD3 Fab. As further described herein, a difference is significant when the calculated p-value is <0.05, e.g., <0.005.

In some embodiments, a trivalent and bispecific antibody construct of the present disclosure comprising an anti-CD3 Fab domain and two anti-MSLN scFv domains can exhibit a greater anti-tumor activity when compared to a 1+1 format-based bispecific construct (e.g., a construct comprising one anti-CD3 (scFv or Fab) domain and one anti-MSLN (scFv or Fab) domain) in an environment in which soluble MSLN is present. Such experimental scenario can mimic the in vivo shedding of MSLN from tumor cells expressing MSLN, which can lead to circulating MSLN in the serum of a subject having a MSLN expressing tumor. Hence, the shed MSLN can be referred to as soluble MSLN and can comprise or consist of an extracellular portion of the membrane-bound MSLN located on tumor cells. In some of these embodiments, the trivalent and bispecific antibody construct of the present disclosure comprising an anti-CD3 Fab domain and two anti-MSLN scFv domains can exhibit a greater anti-tumor activity compared to a 1+1 format-based construct when soluble MSLN is present in a concentration of about 50 ng/mL, 100 ng/mL, or about 150 ng/mL. In some embodiments, under such conditions the anti-tumor activity of the trivalent and bispecific construct can be about 10-fold, 20-fold, 50-fold, or about 100-fold greater than that of a corresponding 1+1 format-based construct.

In some embodiments, a trivalent and bispecific antibody construct of the present disclosure comprising an anti-CD3 Fab domain and two anti-MSLN scFv domains can elicit cytokine release from an immune cell (e.g., a T cell) in a MSLN-dependent manner. In such embodiments, measurable cytokine release can be detected only when the construct is present with T cells and tumor cells expressing MSLN, and when compared to the construct being present with T cell and tumor cells with no MSLN expression. In further embodiments, a trivalent and bispecific antibody construct of the present disclosure comprising an anti-CD3 Fab domain and two anti-MSLN scFv domains can induce T cell proliferation in a MSLN-dependent manner; e.g., no measurable T cell proliferation of T cell may be detected in the absence of MSLN expressing tumor cells, whereas T cell proliferation of at least about 40%, 50%, 60%, 70%, or at least about 80% can be measured under conditions when MSLN expressing tumor cells are present.

In some embodiments, a trivalent and bispecific antibody construct of the present disclosure comprising an anti-CD3 Fab domain and two anti-MSLN scFv domains can be tolerated in cynomolgus monkeys at doses of about 1 mg/kg, 10 mg/kg and 30 mg/kg. Upon intravenous administration of the trivalent and bispecific antibody construct, v32523, to cynomolgus monkeys at doses of 1, 10 and 30 mg/kg a transient increase in one or more biomarkers can be observed. Such one or more biomarkers can include one or more of IL-6, monocyte chemoattractant protein 1 (MCP-1) and granulocyte-macrophage colony-stimulating factor (GM-CSF). In certain embodiments, serum IL-6 concentrations can range from about 150 pg/mL to about 250 ng/mL about 24 hours after injection of 10 or 30 mg/kg an antibody construct, e.g., v32523. Other effects of administering a trivalent and bispecific antibody construct can include an increase in fibrinogen levels, e.g., of about 38%, 68%, 166% and 142% at day 4 after injection of 0.1, 1, 10 and 30 mg/kg antibody construct, respectively, and compared to pre-dose levels.

In further embodiments, a trivalent and bispecific antibody construct of the present disclosure comprising an anti-CD3 Fab domain and two anti-MSLN scFv domains can have an in vivo serum half-life in cynomolgus monkeys of about 2.3, 2.6, or 3 days.

In various embodiments herein, the trivalent and bispecific antibody construct can be the construct v32523 or v21812, as further described herein.

Sequence Identity

As described in other parts of this disclosure, certain embodiments herein relate to an isolated polypeptide or a set of isolated polypeptides (e.g., polypeptide chains H1, H2, L1, etc., or portions, e.g., domains, thereof) of an antibody construct, as well as to a polynucleotide or a set of polynucleotides encoding an antibody construct described herein. A polynucleotide in this context can encode all or part of an antibody construct, such as one or more polypeptide chains (e.g., H1, H2, L1, etc.) of an antibody construct.

The terms "nucleic acid," "nucleic acid molecule" and "polynucleotide" are used interchangeably herein and refer to a polymeric form of nucleotides of any length, either deoxyribonucleotides or ribonucleotides, or analogues thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers.

A polynucleotide that "encodes" a given polypeptide is a polynucleotide that is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence can be located 3' to the coding sequence.

In certain embodiments, the present disclosure relates to polynucleotide and/or polypeptide sequences that are identical or substantially identical to another polynucleotide and/or polypeptide sequence. The term "identical," in the context of two or more polynucleotide or polypeptide sequences, refers to two or more sequences or subsequences that are the same, i.e., have the identical sequence of nucleotide or amino acid monomers (i.e., 100% sequence identity), respectively. Polypeptide or polynucleotide sequences herein share "sequence identity" if they have a percentage or a certain number of amino acid residues or nucleotides, respectively, that are at least about 80%, about 85%, about 90%, about 95%, about 97%, or at least about 99% identity over a specified region when compared and aligned for maximum correspondence over a comparison window or over a designated region as measured using one of the commonly used sequence comparison algorithms as known to persons of ordinary skill in the art or by manual alignment and visual inspection. This definition also refers to the complement of a test polynucleotide sequence. A certain sequence identity can exist over a region that is at least about 50 amino acids or nucleotides in length, or over a region that is from about 75 to about 100 amino acids or nucleotides in length, or, where not specified, across the entire sequence of a polypeptide or polynucleotide. For sequence comparison, typically test sequences are compared to a designated reference sequence. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent (%) sequence identities for the test sequence(s) relative to the reference sequence, based on the program parameters.

The term "comparison window," as used herein, refers to a segment of a sequence comprising contiguous amino acid or nucleotide positions which can be from about 20 to about 1000 contiguous amino acid or nucleotide positions, for example from about 50 to about 600 or from about 100 to about 300 or from about 150 to about 200 contiguous amino acid or nucleotide positions over which a test sequence can be compared to a reference sequence of the same number of contiguous positions after the two sequences are optimally aligned. Longer segments up to and including the full-length sequence may also be used as a comparison window in certain embodiments. Methods of alignment of sequences for comparison are known to those of ordinary skill in the art. Optimal alignment of sequences for comparison can be conducted, for example, by the local homology algorithm of Smith & Waterman, 1970, *Adv. Appl. Math.*, 2:482c; by the homology alignment algorithm of Needleman & Wunsch, 1970, *J. Mol. Biol.*, 48:443; by the search for similarity method of Pearson & Lipman, 1988, *Proc. Natl. Acad. Sci. USA*, 85:2444, or by computerized implementations of these algorithms (for example, GAP, BESTFIT, FASTA or TFASTA in the Wisconsin Genetics Software Package, Genetics Computer Group, Madison, WI), or by manual alignment and visual inspection (see, for example, Ausubel et al., Current Protocols in Molecular Biology, (1995 supplement), Cold Spring Harbor Laboratory Press). Examples of available algorithms suitable for determining percent sequence identity are the BLAST and BLAST 2.0 algorithms, which are described in Altschul et al., 1997, *Nuc. Acids Res.*, 25:3389-3402, and Altschul et al., 1990, *J. Mol. Biol.*, 215:403-410, respectively. Software for performing BLAST analyses is publicly available through the website for the National Center for Biotechnology Information (NCBI).

Certain embodiments described herein relate to variant sequences (e.g., variant $V_H$ domains, variant Fc polypeptides, etc.) that comprise one or more amino acid modification, e.g., one or more amino acid insertions, one or more amino acid deletions, and/or one or more amino acid substitutions, when compared to, e.g., a reference sequence such as a wildtype sequence. In certain embodiments, the one or more amino acid modification of a variant sequence comprises one or more amino acid substitutions when compared to a reference such as a wildtype sequence. In such embodiments, the one or more amino acid substitutions are one or more non-conservative substitutions. In other embodiments, the one or more amino acid substitutions are one or more conservative substitutions. In general, a "conservative substitution," as used herein, is considered to be a substitution of one amino acid with another amino acid having similar physical, chemical and/or structural properties. Common conservative substitutions are listed under Column 1 of TABLE 4. One skilled in the art will appreciate that the main factors in determining what constitutes a conservative substitution are usually the size of the amino acid side chain and its physical/chemical properties, but that certain environments allow for substitution of a given amino acid with a broader range of amino acids than those listed in Column 1 of TABLE 4. These additional amino acids tend to either have similar properties to the amino acid being substituted but to vary more widely in size or be of similar size but vary more widely in physical/chemical properties. This broader range of conservative substitutions is listed under Column 2 of TABLE 4.

TABLE 4

Conservative Amino Acid Substitutions

| Original Amino Acid | Column 1 | Column 2 |
|---|---|---|
| Ala (A) | Gly, Ile, Leu, Met, Norleucine, Val | Cys, Gly, Ile, Leu, Met, Norleucine, Phe, Trp, Tyr, Val |
| Arg (R) | His, Lys | His, Lys |
| Asn (N) | Cys, Gln, Ser, Thr | Asp, Cys, Gln, Glu, Ser, Thr |
| Asp (D) | Glu | Asn, Cys, Gln, Glu, Ser, Thr |
| Cys (C) | Asn, Gln, Ser, Thr | Asn, Asp, Gln, Glu, Ser, Thr |
| Gln (Q) | Asn, Cys, Ser, Thr | Asn, Asp, Cys, Glu, Ser, Thr |
| Glu (E) | Asp | Asp, Asn, Cys, Gln, Ser, Thr |
| Gly (G) | Pro | Ala, Ile, Leu, Met, Norleucine, Pro, Val |
| His (H) | Arg, Lys | Arg, Lys, Phe, Trp, Tyr |
| Ile (I) | Ala, Gly, Leu, Met, Norleucine, Val | Ala, Cys, Gly, Leu, Met, Norleucine, Phe, Trp, Tyr, Val |
| Leu (L) | Ala, Gly, Ile, Met, Norleucine, Val | Ala, Cys, Gly, Ile, Met, Norleucine, Phe, Trp, Tyr, Val |
| Lys (K) | Arg, His | Arg, His |
| Met (M) | Ala, Gly, Ile, Leu, Norleucine, Val | Ala, Cys, Gly, Ile, Leu, Norleucine, Phe, Trp, Tyr, Val |
| Phe (F) | Tyr, Trp | Ala, Cys, Gly, His, Ile, Leu, Met, Norleucine, Trp, Tyr, Val |
| Pro (P) | Gly | Gly |
| Ser (S) | Asn, Cys, Gln, Thr | Asp, Asn, Cys, Gln, Glu, Thr |
| Thr (T) | Asn, Cys, Gln, Ser | Asp, Asn, Cys, Gln, Glu, Ser |
| Trp (W) | Phe, Tyr | Ala, Cys, Gly, His, Ile, Leu, Met, Norleucine, Phe, Tyr, Val |
| Tyr (Y) | Phe, Trp | Ala, Cys, Gly, His, Ile, Leu, Met, Norleucine, Phe, Trp, Val |
| Val (V) | Ala, Gly, Ile, Leu, Met, Norleucine | Ala, Cys, Gly, Ile, Leu, Met, Norleucine, Phe, Trp, Tyr |

The skilled person can readily ascertain the most appropriate group of substituents to select from in view of the particular protein environment in which the amino acid substitution is being made.

Pharmaceutical Compositions

In some embodiments, the present disclosure relates to pharmaceutical compositions that can comprise one or more of the antibody constructs described herein. In various embodiments, a pharmaceutical composition herein can further comprise a pharmaceutically acceptable excipient, carrier, buffer, stabiliser, or other materials well known to those skilled in the art. Such materials are generally non-toxic and do not interfere with the efficacy of the active ingredient (i.e., antibody construct). The precise nature of a carrier or other material can depend on the route of administration. Hence, a pharmaceutical composition herein can be formulated for various used and administration routes, e.g., for oral, intravenous, cutaneous, subcutaneous, nasal, intramuscular, or intraperitoneal administration routes.

A pharmaceutical composition for oral administration can be in tablet, capsule, powder, or liquid form. A tablet can include a solid carrier such as gelatin or an adjuvant. Liquid pharmaceutical compositions generally include a liquid carrier such as water, petroleum, animal or vegetable oils, mineral oil, or synthetic oil. Physiological saline solution, dextrose or other saccharide solution or glycols such as ethylene glycol, propylene glycol or polyethylene glycol can be included.

For intravenous, cutaneous, or subcutaneous injection, or injection at the site of affliction (e.g., at a tumor site), the active ingredient (i.e., antibody construct) can be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

For antibody constructs according to the present disclosure that are administered to a subject, administration is preferably in a "therapeutically effective amount" that is sufficient to show benefit to the individual, as further described herein. The actual amount administered, and rate and time-course of administration, can depend on the nature and severity of the disease (e.g., cancer) being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

In some embodiments, a pharmaceutical composition can comprise a second active ingredient (e.g., another protein or small molecule) in addition to an antibody construct described herein.

Kits

The present disclosure also describes kits comprising one or more of the antibody constructs described herein, or a pharmaceutical composition as described herein that comprises such antibody construct(s), wherein such kit can further comprise instructions for use. Thus, in certain embodiments, described herein are kits comprising vectors for expressing an antibody construct described herein and instructions for use. In certain embodiments, described herein are kits comprising host cells comprising a vector for expressing an antibody construct and instructions for use. In some embodiments, the present disclosure relates to kits comprising a purified antibody construct and instructions for use. The purified antibody construct can be lyophilized or provided in a dry form, such as a powder or granules, and the kit can additionally contain a suitable solvent for reconstitution of the lyophilized or dried component(s).

A kit can further comprise a container and a label and/or package insert on or associated with the container. The label or package insert contains instructions customarily included in commercial packages of therapeutic products, providing information or instructions about the indications, usage, dosage, administration, contraindications and/or warnings concerning the use of such therapeutic products (e.g., an antibody construct described herein). The label or package insert can further include a notice in the form prescribed by a governmental agency regulating the manufacture, use or sale of pharmaceuticals or biological products, which notice reflects approval by the agency of manufacture, for use or sale for human or animal administration. The container can hold a composition comprising an antibody construct of this disclosure. In some embodiments, the container can have a sterile access port. For example, the container can be an intravenous solution bag or a vial having a stopper that can be pierced by a hypodermic injection needle.

In addition to the container containing a composition comprising an antibody construct, the kit can further comprise one or more additional containers comprising other components of the kit. For example, a pharmaceutically acceptable buffer (such as bacteriostatic water for injection) (BWFI), phosphate-buffered saline, Ringer's solution, or dextrose solution), or other buffers or diluents can be included in such kit.

Suitable containers can include, for example, bottles, vials, syringes, intravenous solution bags, and the like. The containers can be formed from a variety of materials such as glass or plastic. If appropriate, one or more components (e.g., an antibody construct) of the kit can be lyophilized or provided in a dry form, such as a powder or granules, and the kit can additionally contain a suitable solvent for reconstitution of the lyophilized or dried component(s).

A kit herein can further include other materials desirable from a commercial or user standpoint, such as filters, needles, and syringes.

Methods of Preparing an Antibody Construct

In some embodiments, the present disclosure relates to methods for preparing the antibody constructs described herein. In various embodiments, an antibody construct of the present disclosure can be produced using standard recombinant methods known in the art (see, for example, U.S. Pat. No. 4,816,567 and "Antibodies: A Laboratory Manual," $2^{nd}$ Edition, Ed. Greenfield, Cold Spring Harbor Laboratory Press, New York, 2014).

For recombinant production of an antibody construct described herein, a polynucleotide or set of polynucleotides encoding the antibody construct can be generated and inserted into one or more vectors for further cloning and/or expression in a host cell. Polynucleotide(s) encoding the antibody construct can be produced by standard methods known in the art (see, for example, Ausubel et al., *Current Protocols in Molecular Biology*, John Wiley & Sons, New York, 1994 & update, and "*Antibodies: A Laboratory Manual,*" $2^{nd}$ Edition, Ed. Greenfield, Cold Spring Harbor Laboratory Press, New York, 2014). As would be appreciated by one of skill in the art, the number of polynucleotides required for expression of the antibody construct may be dependent on the format and/or geometry of the antibody construct, including, for example, the number of polypeptide chains that the antibody construct is comprised of. For example, when an antibody construct comprises three polypeptide chains (e.g., H1, H2 and L1), three polynucleotides each encoding one polypeptide chain can be used. In embodiments in which two or more polynucleotides are used, such two or more polynucleotides can be incorporated into one vector or into more than one vector (e.g., two or three separate vectors).

Generally, for expression, the polynucleotide or set of polynucleotides encoding an antibody construct herein can be incorporated into an expression vector together with one or more regulatory elements, such as transcriptional elements, which can be used for efficient transcription of the polynucleotide(s). Examples of such regulatory elements include, but are not limited to, promoters, enhancers, terminators, and polyadenylation signals. One skilled in the art will appreciate that the choice of regulatory elements can be dependent on the host cell selected for expression of the polypeptides of the antibody construct and that such regulatory elements can be derived from a variety of sources, including bacterial, fungal, viral, mammalian or insect genes. The expression vector can optionally further contain heterologous nucleic acid sequences that facilitate expression or purification of the expressed protein. Examples include, but are not limited to, signal peptides and affinity tags such as metal-affinity tags, histidine tags, avidin/streptavidin encoding sequences, glutathione-S-transferase (GST) encoding sequences and biotin encoding sequences. The expression vector can be an extrachromosomal vector or an integrating vector. Hence, in some embodiments, the amino acid sequences of the polypeptide chains of an expressed antibody construct described herein, e.g., chains H1, H2, L1, etc., can comprise a signal peptide sequence. Such signal peptide sequences may vary depending on the expression system and conditions used for producing an antibody construct. Exemplary signal peptide sequences can comprise the amino acid sequence METDTLLLWVLLLWVPGSTG (SEQ ID NO: 49) or MRPTWAWWLFLVLLLALWAPARG (SEQ ID NO: 50), e.g., for H1, H2, etc., or MRPTWAWWLFLVLLLALWAPARG (SEQ ID NO: 50) or MGWSCIILFLVATATGVHS (SEQ ID NO: 51), e.g., for L1, L2, etc. In certain embodiments, one or more heavy chains (e.g., H1, H2, etc.) of an antibody construct described herein can comprise a C-terminal lysine residue following expression of the polypeptide chains inside the cell. In various embodiments, such C-terminal lysine residue may be enzymatically cleaved from the polypeptide chains prior to further processing (e.g., purification, formulation, etc.) and prior to use of the corresponding antibody construct, e.g., prior to administration of the construct to a subject in need thereof.

Certain embodiments for producing an antibody construct of the present disclosure relate to vectors (such as expression vectors) comprising one or more polynucleotides encoding at least a portion of an antibody construct described herein. The polynucleotide(s) can be comprised by a single vector or by more than one vector. In some embodiments, the polynucleotides are comprised by a multicistronic vector. Expression vectors that can be used to express polynucleotides include but are not limited to pTT5 and pUC15 cells comprising vectors encoding an antibody construct.

Suitable host cells for cloning or expression of the antibody construct polypeptides include various prokaryotic or eukaryotic cells as known in the art. Eukaryotic host cells include, for example, mammalian cells, plant cells, insect cells and yeast cells (such as *Saccharomyces* or *Pichia* cells). Prokaryotic host cells include, for example, *E. coli, A. salmonicida* or *B. subtilis* cells. In certain embodiments, an antibody construct can be produced in bacteria, in particular when glycosylation and Fc effector function are not needed or desired for the indented purpose of the antibody construct, as described for example in U.S. Pat. Nos. 5,648,237, 5,789,199, and 5,840,523, and in Charlton, *Methods in Molecular Biology*, Vol. 248, pp. 245-254, B.K.C. Lo, ed., Humana Press, Totowa, N.J., 2003. Eukaryotic microbes such as filamentous fungi or yeast are suitable expression host cells in certain embodiments, in particular fungi and yeast strains whose glycosylation pathways have been "humanized" resulting in the production of an antibody with a partially or fully human glycosylation pattern (see, for example, Gerngross, 2004, *Nat. Biotech.* 22:1409-1414, and L1 et al., 2006, *Nat. Biotech.* 24:210-215).

Suitable host cells for the expression of glycosylated antibody constructs are, in various embodiments, eukaryotic cells. For example, U.S. Pat. Nos. 5,959,177, 6,040,498, 6,420,548, 7,125,978 and 6,417,429 describe PLANTIBODIES™ technology for producing antibodies and portions thereof (e.g., scFvs, Fabs, etc.) in transgenic plants. Mammalian cell lines adapted to grow in suspension are particularly useful for the expression of antibody constructs described herein. Examples include, but are not limited to, monkey kidney CV1 line transformed by SV40 (COS-7), human embryonic kidney (HEK) line 293 or 293 cells (see, for example, Graham et al., 1977, *J. Gen Virol.*, 36:59), baby hamster kidney cells (BHK), mouse sertoli TM4 cells (see, for example, Mather, 1980, *Biol Reprod*, 23:243-251); monkey kidney cells (CV1), African green monkey kidney cells (VERO-76), human cervical carcinoma (HeLa) cells, canine kidney cells (MDCK), buffalo rat liver cells (BRL 3A), human lung cells (W138), human liver cells (Hep G2), mouse mammary tumour (MMT 060562), TRI cells (see, for example, Mather et al., 1982, *Annals N.Y. Acad Sci*, 383: 44-68), MRC 5 cells, FS4 cells, Chinese hamster ovary (CHO) cells (including DHFR⁻ CHO cells, see Urlaub et al., 1980, *Proc Natl Acad Sci USA*, 77:4216), and myeloma cell lines (such as Y0, NS0 and Sp2/0). Exemplary mammalian host cell lines suitable for production of antibodies are reviewed in Yazaki & Wu, *Methods in Molecular Biology*, Vol. 248, pp. 255-268 (B.K.C. Lo, ed., Humana Press, Totowa, N.J., 2003).

In certain embodiments, the host cell used to produce an antibody construct herein is a transient or stable higher eukaryotic cell line, such as a mammalian cell line. In some embodiments, the host cell is a mammalian HEK293T, CHO, HeLa, NS0 or COS cell. In some embodiments, the host cell is a stable cell line that allows for mature glycosylation of the antibody construct.

The host cells comprising the expression vector(s) encoding the antibody construct can be cultured using routine methods to produce the antibody construct. Alternatively, in some embodiments, host cells comprising the expression vector(s) encoding the antibody construct can be used therapeutically or prophylactically to deliver the antibody construct to a subject, or polynucleotides or expression vectors can be administered to a cell from a subject ex vivo and the cell then returned to the body of the subject.

In some embodiments, a host cell comprises (for example, has been transformed with) a vector comprising a polynucleotide that encodes a $V_L$ and a $V_H$ of a binding domain of an antibody construct described herein. In some embodiments, a host cell comprises (for example, has been transformed with) a vector comprising a polynucleotide that encodes a full-length polypeptide chain of an antibody construct described herein, e.g., H1, H2, or L1 as described herein. In another example, a host cell comprises a first vector comprising a polynucleotide that encodes the $V_L$ of a binding domain and a second vector comprising a polynucleotide that encodes the corresponding $V_H$ of the binding domain. In various embodiments, the host cell is eukaryotic, for example, a Chinese Hamster Ovary (CHO) cell, a human embryonic kidney (HEK) cell or a lymphoid cell (e.g., Y0, NS0, Sp20 cell). In certain embodiments, the host cell is Expi293™ (Thermo Fisher, Waltham, MA). In certain embodiments, the host cell used herein is CHO-S cells (National Research Council Canada) or HEK293 cells.

Certain embodiments of the present disclosure relate to a method of making an antibody construct comprising culturing a host cell into which one or more polynucleotides encoding the antibody construct, or one or more expression vectors encoding the antibody construct, have been introduced, under conditions suitable for expression of the antibody construct. Such method can further comprise recovering the antibody construct from the host cell (or from host cell culture medium). In some embodiments, such method can further comprise purifying the antibody construct.

Cell culture media that can be used include, but are not limited to, DMEM (Thermo Fisher, Waltham, MA), Opti-MEM™ (Thermo Fisher, Waltham, MA), Opti-MEM™ I Reduced Serum Medium (Thermo Fisher, Waltham, MA), RPMI-1640 medium, Expi293™ Expression Medium (Thermo Fisher, Waltham, MA), and FreeStyle CHO expression medium (Thermo Fisher Scientific, Waltham, MA). The cell culture medium can be supplemented with serum, e.g., fetal bovine serum (FBS), amino acids, e.g., L-glutamine, antibiotics, e.g., penicillin, and streptomycin, and/or anti-mycotics, e.g., amphotericin, or any other supplements routinely used in the to support cell culture.

A. Purification of Antibody Constructs

In various embodiments, an antibody construct of the present disclosure is purified after expression. Proteins, such as an antibody construct of the present disclosure, can be isolated or purified in a variety of ways known to those skilled in the art (see, for example, *Protein Purification: Principles and Practice*, 3$^{rd}$ Ed., Scopes, Springer-Verlag, NY, 1994). Standard purification methods that can be used for the antibody constructs disclosed herein include chromatographic techniques, including ion exchange, hydrophobic interaction, affinity, sizing or gel filtration, and reverse-phase, carried out at atmospheric pressure or at high pressure using systems such as FPLC and HPLC. Additional purification methods include electrophoretic, immunological, precipitation, dialysis and chromatofocusing techniques. Ultrafiltration and diafiltration techniques, in conjunction with protein concentration, can also be used. As is well known in the art, a variety of natural proteins bind Fc domains and other structural elements of an antibody construct, and, in some embodiments, these proteins can be used for purification of an antibody construct. For example, the bacterial proteins A and G can bind to the Fc domain of some antibody constructs. Likewise, the bacterial protein L can bind to the Fab domain of some antibody constructs. Purification can also be enabled by a particular fusion partner. For example, antibody constructs can be purified using glutathione resin if a GST fusion is employed, Ni$^{+2}$ affinity chromatography if a His-tag is employed or immobilized anti-flag antibody if a flag-tag is used. The degree of purification necessary may vary depending on the use of the antibody constructs. Hence, in some embodiments, no purification may be necessary.

In certain embodiments, an antibody construct of this disclosure is substantially pure. The term "substantially pure" (or "substantially purified") when used in reference to an antibody construct described herein, refers to an antibody construct as substantially or essentially free of components that normally accompany or interact with the protein as found in its naturally occurring environment, such as a native cell, or a host cell in the case of a recombinantly produced antibody construct. In certain embodiments, an antibody construct that is substantially pure is an antibody construct purified to have less than about 30%, less than about 25%, less than about 20%, less than about 15%, less than about 10%, less than about 5%, or less than about 2% (by dry weight) of other contaminating protein species.

Assessment of antibody construct purity and/or homogeneity can be performed by any method known in the art, including, but not limited to, non-reducing/reducing CE-SDS, non-reducing/reducing SDS-PAGE, Ultra-high performance liquid chromatography-size exclusion chromatography (UPLC-SEC), High Performance Liquid Chromatography (HPLC), mass spectrometry, multi angle light scattering (MALS), and dynamic light scattering (DLS).

B. Post-Translational Modifications

In certain embodiments, an antibody construct described herein can comprise one or more post-translational modifications. Such post-translational modifications can occur in vivo, or they be conducted in vitro after isolation of the antibody construct from the host cell.

Post-translational modifications can include various modifications as are known in the art (see, for example, *Proteins—Structure and Molecular Properties*, 2nd Ed., T. E. Creighton, W. H. Freeman and Company, New York, 1993; *Post-Translational Covalent Modification of Proteins*, B. C. Johnson, Ed., Academic Press, New York, pgs. 1-12, 1983; Seifter et al., 1990, *Meth. Enzymol.*, 182:626-646, and Rattan et al., 1992, *Ann. N.Y. Acad. Sci.*, 663:48-62). In those embodiments in which an antibody construct comprises one or more post-translational modifications, the antibody construct can comprise the same type of modification at one or several sites (e.g., amino acid residues), or it can comprise different modifications at different sites.

Examples of post-translational modifications can include glycosylation, acetylation, phosphorylation, amidation, derivatization by known protecting/blocking groups, formylation, oxidation, reduction, proteolytic cleavage or specific chemical cleavage by cyanogen bromide, trypsin, chymotrypsin, papain, V8 protease or NaBH$_4$.

Other examples of post-translational modifications can include, for example, addition or removal of N-linked or O-linked carbohydrate chains, chemical modifications of N-linked or O-linked carbohydrate chains, processing of N-terminal or C-terminal ends, attachment of chemical moieties to the amino acid backbone, and addition or deletion of an N-terminal methionine residue resulting from prokaryotic host cell expression. Post-translational modifications can also include modification with a detectable label, such as an enzymatic, fluorescent, isotopic or affinity label to allow for detection and isolation of the protein. Examples of suitable enzyme labels include, but are not limited to, horseradish peroxidase, alkaline phosphatase, beta-galactosidase and acetylcholinesterase. Examples of suitable prosthetic group complexes include, but are not limited to, streptavidin/biotin and avidin/biotin. Examples of suitable fluorescent materials include, but are not limited to, umbelliferone, fluorescein, fluorescein isothiocyanate, rhodamine, dichlorotriazinylamine fluorescein, dansyl chloride and phycoerythrin. An example of a luminescent material is luminol, examples of bioluminescent materials include luciferase, luciferin and aequorin, and examples of suitable radioactive materials include iodine, carbon, sulfur, tritium, indium, technetium, thallium, gallium, palladium, molybdenum, xenon, and fluorine.

Additional examples of post-translational modifications can include acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, gamma-carboxylation, GPI anchor formation, hydroxylation, iodination, methylation, myristylation, pegylation, prenylation, racemization, selenoylation, sulfation, transfer-RNA mediated addition of amino acids to proteins such as arginylation, and ubiquitination.

Methods of Use

In some embodiments, the present disclosure relates to methods of using an antibody construct of the present disclosure. In certain embodiments, described herein are methods of using an antibody construct described herein for the treatment of a disease or condition in a subject in need thereof. Such method can comprise administering an antibody construct, or a pharmaceutical composition comprising an antibody construct, to a subject in need thereof. In certain embodiments, the subject is a mammal. In certain embodiments, the subject is human or a rodent.

In some embodiments, the present disclosure relates to a method of treating a cancer in a subject in need thereof, the method comprising administering to the subject an antibody construct of the present disclosure, or a pharmaceutical composition comprising the antibody construct. Cancers that can be treated using the methods and antibody constructs disclosed herein can include, but are not limited to, hematologic neoplasms (including leukemias, myelomas and lymphomas), carcinomas (including adenocarcinomas and squamous cell carcinomas), melanomas and sarcomas. Carcinomas and sarcomas are also frequently referred to as "solid tumors". In certain embodiments, the cancer is a solid tumor. In certain embodiments, the cancer is leukemia. In certain embodiments, the cancer is lymphoma.

When used in a method described herein, an antibody construct of this disclosure can exert either a cytotoxic or cytostatic effect and can result in one or more of a reduction in the size of a tumor, the slowing or prevention of an increase in the size of a tumor, an increase in the disease-free survival time between the disappearance or removal of a tumor and its reappearance, prevention of an initial or subsequent occurrence of a tumor (for example, metastasis), an increase in the time to progression, reduction of one or more adverse symptom associated with a tumor, an increase in the overall survival time of a subject having a tumor, or a combination of the above.

The methods described herein can comprise administering an antibody construct to a subject in need thereof. An antibody construct can be administered to a subject by any appropriate route of administration. As will be appreciated by the person of skill in the art, the route and/or mode of administration can vary depending upon the desired therapeutic results. In various embodiments, antibody constructs of this disclosure can be administered by systemic administration or local administration. Local administration can be at the site of a tumor or into a tumor draining lymph node. Generally, the antibody constructs can be administered by parenteral administration, for example, by intravenous, intramuscular, intradermal, intraperitoneal, subcutaneous, or spinal administration, such as by injection or infusion.

A treatment (e.g., of a cancer in a subject) can be achieved by administration of a therapeutically effective amount of an antibody construct. A "therapeutically effective amount," as used herein, generally refers to an amount of an antibody construct described herein that is effective, at dosages and for periods of time necessary, to achieve a desired therapeutic result. A therapeutically effective amount can vary according to factors such as the disease state, age, sex, and weight of the subject. A therapeutically effective amount is also one in which any potential toxic or detrimental effects of the antibody constructs are outweighed by the therapeutically beneficial effects. "Sufficient amount" generally refers to an amount sufficient to produce a desired effect, e.g., an amount sufficient to generate an anti-tumor immune response to a target (e.g., tumor) cell or tissue, e.g., by engaging an immune cell (e.g., T cell) using a trivalent and bispecific antibody construct described herein.

A suitable dosage of an antibody construct described herein can be determined by a skilled medical practitioner. The selected dosage level may depend upon a variety of pharmacokinetic factors including the activity (e.g., antigen affinity(ies)) of the particular antibody construct employed, the route of administration, the time of administration, the rate of excretion of the construct, the duration of the treatment, other drugs, compounds and/or materials used in combination with the antibody construct, e.g., anti-cancer agents, the age, sex, weight, condition, general health and prior medical history of the subject being treated, and like factors well known in the medical arts.

In some embodiments, a method of treating a disease (e.g., a cancer) in a subject comprises administering a second active ingredient (e.g., another protein or small molecule) in addition to an antibody construct described herein. Such second active ingredient can be administered simultaneously or sequentially with an antibody construct dependent upon the condition to be treated.

In some embodiments, the present disclosure relates to a method of eliciting an anti-tumor immune response in a cell population comprising immune cells expressing CD3 and tumor cells expressing MSLN, the method comprising contacting the cell population with an effective amount of the antibody construct of the present disclosure. In some embodiments, such antibody construct binds CD3 on the immune cell and MSLN on the tumor cell and comprises: (i) a Fab domain capable of binding CD3 on a cytotoxic effector cell; (ii) a first scFv domain and a second scFv domain, wherein the first and the second scFv domains are capable of binding MSLN; and (iii) a dimeric Fc domain comprising a first Fc polypeptide and a second Fc polypeptide, wherein: (a) the Fab domain is coupled to the N-terminus of the first Fc polypeptide, (b) the first scFv domain is coupled to the N-terminus of the second Fc polypeptide, and (c) the second scFv domain is coupled to an N-terminus (e.g., the N-terminus of the heavy or light chain) of the Fab domain. In various embodiments, the anti-tumor immune response provides a dose-dependent reduction in live tumor cells in the cell population of at least 30%, 40%, 50%, or 60% when the concentration of the antibody construct in the cell population is increased from about $10^{-2}$ pM to about $10^2$ pM, wherein the expression of MSLN of the tumor cells is at least about 15,000 MSLN/cell and the ratio of immune cells to tumor cells in the cell population is about 5:1.

In some embodiments, the present disclosure relates to a method of inhibiting the proliferation of tumor cells expressing MSLN, the method comprising contacting a cell population comprising the tumor cells and immune cells expressing CD3 with an effective amount of the antibody construct of the present disclosure. In various embodiments, such antibody construct binds CD3 on the immune cell and MSLN on the tumor cell and comprises: (i) a Fab domain capable of binding CD3 on a cytotoxic effector cell; (ii) a first scFv domain and a second scFv domain, wherein the first and the second scFv domains are capable of binding MSLN; and (iii) a dimeric Fc domain comprising a first Fc polypeptide and a second Fc polypeptide, wherein: (a) the Fab domain is coupled to the N-terminus of the first Fc polypeptide, (b) the first scFv domain is coupled to the N-terminus of the second Fc polypeptide, and (c) the second scFv domain is coupled to an N-terminus of the Fab domain. As defined herein, the proliferation of tumor cells is inhibited when an increase in live tumor cell count of at most about 5%, 3%, or at most about 1% is observed in the cell population over a period of at least about 5, 10, 20, or 48 hours using a concentration of the antibody construct of at most about $10^{-2}$ pM, $10^{-1}$ pM, or 1 pM, wherein the expression of MSLN of the tumor cells is at least about 15,000 MSLN/cell and the ratio of immune cells to tumor cells in the cell population is about 5:1.

In some embodiments, the present disclosure relates to a method of killing tumor cells expressing MSLN, such method comprising contacting a cell population comprising the tumor cells and immune cells expressing CD3 with an effective amount of the antibody construct of the present disclosure. In various embodiments, such antibody construct binds CD3 on the immune cell and MSLN on the tumor cell and comprises: (i) a Fab domain capable of binding CD3 on a cytotoxic effector cell; (ii) a first scFv domain and a second scFv domain, wherein the first and the second scFv domains are capable of binding MSLN; and (iii) a dimeric Fc domain comprising a first Fc polypeptide and a second Fc polypeptide, wherein: (a) the Fab domain is coupled to the N-terminus of the first Fc polypeptide, (b) the first scFv domain is coupled to the N-terminus of the second Fc polypeptide, and (c) the second scFv domain is coupled to an N-terminus of the Fab domain. In various embodiments, such tumor cell killing is observed when a dose-dependent reduction in live tumor cells in the cell population of at least about 30%, 40%, 50%, or 60% is measured when the concentration of the antibody construct is increased from about $10^{-2}$ pM to about $10^2$ pM, wherein the expression of MSLN of the tumor cells is at least about 15,000 MSLN/cell and the ratio of immune cells to tumor cells in the cell population is about 5:1.

In any of the methods described herein, the immune cells comprise or consist of one or more types of T cells.

As described herein, in various embodiments, an antibody construct described herein can be administered to a subject in need thereof, for example, a subject having cancer, in order to modulate an immune response in the subject. The immune response that can be modulated using an antibody construct of this disclosure can be an anti-tumor immune response in the subject, e.g., in various embodiments, such modulated immune response can occur locally at a tumor site. Thus, in certain embodiments, an antibody construct described herein can initiate and/or upregulate a local immune response, e.g., an anti-tumor response of a subject's immune system in order to elicit a localized cytotoxic effect against the tumor at the tumor site.

In various embodiments, an antibody construct described herein, e.g., a trivalent and bispecific antibody construct capable of monovalent binding to CD3 (via one Fab domain) and bivalent binding to MSLN (via two scFv domains), can have a broader therapeutic window, compared to comparable conventional molecules, e.g., v31805 (MH6T-TriTAC), that can allow administration of higher doses leading potentially to increased anti-tumor effects without inducing side effects and off-target. Such broader therapeutic window can be due to certain properties of the antibody constructs described herein, including higher ratios of anti-tumor activity compared to cytokine induction, i.e., higher tumor cell killing activities can be achieved at lower cytokine induction levels.

In some embodiments, the present disclosure relates to a method of inhibiting the growth of a MSLN-expressing tumor and/or reducing the volume of the tumor in a subject in need thereof, the method comprising administering to the subject an effective amount of the antibody construct of the present disclosure. In various embodiments, such in vivo anti-tumor is elicited by an antibody construct that binds (e.g., simultaneously) CD3 on the immune cell and MSLN on the tumor cell and comprises: (i) a Fab domain capable of binding CD3 on a cytotoxic effector cell; (ii) a first scFv domain and a second scFv domain, wherein the first and the second scFv domains are capable of binding MSLN; and (iii) a dimeric Fc domain comprising a first Fc polypeptide and a second Fc polypeptide, wherein: (a) the Fab domain is coupled to the N-terminus of the first Fc polypeptide, (b) the first scFv domain is coupled to the N-terminus of the second Fc polypeptide, and (c) the second scFv domain is coupled to an N-terminus of the Fab domain.

In various embodiments, and as further described elsewhere herein, inhibition of tumor growth and/or a reduction in tumor volume in a subject can be elicited by simultaneous binding of the antibody construct to CD3 on an immune cell and to MSLN on a tumor cell and formation of a TCR-independent artificial immune synapse within a tumor environment in the subject, thereby eliciting an anti-tumor cytotoxic effect mediated by the activated immune cell and directed against the tumor cell. The immune cell can be a T cell.

In various embodiments, tumor growth can be inhibited in the subject for at least 20 days, 30 days, or 50 days using 4-times weekly (Q7Dx4) administration of the antibody construct to the subject. Furthermore, in some embodiments, the tumor volume can be reduced by at least 20%, 30%, 40%, or at least about 50% about 15 days after start of treatment. Such therapeutic effects can be achieved when administering the antibody construct at a dose of about 1 mg/kg, 1.5 mg/kg or about 3 mg/kg to the subject. The subject can be a rodent, a non-human primate, or a human.

In further embodiments, and in relation to a method described herein, administration of a sufficient amount of an antibody construct to a subject in need thereof can provide one or more of the following to activate or upregulate an immune response: (i) modulation of T-cell receptor signaling, (ii) modulation of T-cell activation, (iii) modulation of pro-inflammatory cytokines, (iv) modulation of interferon-γ production by T cells, (v) modulation of T-cell suppression, (vi) modulation of M2-type tumor associated macrophages (TAM) or myeloid-derived suppressor cell (MDSC) survival and/or differentiation, and/or (vii) modulation of cytotoxic or cytostatic effects on cells, e.g., cancer cells.

In some embodiments, the present disclosure relates to methods of modulating an immune response in a cell or in a subject using one or more of the trivalent and bispecific antibody construct(s) of the present disclosure, wherein such modulation can comprise one or more of (i) immune cell activation, (ii) stimulation of T-cell receptor signaling, (iii) stimulation of antibody-dependent cellular cytotoxicity (ADCC), (iv) T cell-dependent cytotoxicity (TDCC), (v) cell-dependent cytotoxicity (CDC), (vi) antibody-dependent cellular phagocytosis (ADCP), and combinations of the above. As described herein, in certain embodiments, an antibody construct activates T effector cells. In some embodiments, and as demonstrated herein, an antibody construct increases production of one or more cytokines and/or signalling molecules, such as GM-CSF, TNF-α, MIP-1β, IFN-γ, IL-2, IL-12, IL-17, IL-21 and/or C-X-C motif ligand 13 (CXCL13) by T effector cells.

As described herein, in various embodiments, an antibody construct of the present disclosure comprises an Fc domain comprising a first and a second Fc polypeptide, wherein one or more of the Fc polypeptides can comprise a modified CH2 domain (e.g., compared to a WT domain) that comprises one or more amino acid modifications that can result in a decrease or elimination of binding of the Fc domain to one or more, or to all of the Fcγ receptors (also referred to herein as an Fc "knock-out" or "KO" variant).

Experimental Methods

In some embodiments, the present disclosure relates to experimental methods for analyzing and/or detecting an antibody construct of the present disclosure. Such methods can be used, for example, to assess in vitro and/or in vivo properties of an antibody construct such as its pharmacokinetic (PK) and pharmacodynamic (PD) properties. Other properties and characteristics of an antibody construct can be evaluated such as its stability under certain conditions (e.g., temperature, pH, etc.), its solubility, or its behaviour in the presence of certain other chemical components such as other proteins or cells.

Specific binding of an antibody construct described herein to an antigen (e.g., CD3, MSLN) can be measured, for example, through an enzyme-linked immunosorbent assay (ELISA), a surface plasmon resonance (SPR) technique (employing, for example, a BIAcore instrument) (Liljeblad et al., 2000, *Glyco J*, 17:323-329), or a traditional binding assay (Heeley, 2002, *Endocr Res*, 28:217-229). In certain embodiments, specific binding is defined as the extent of binding to an unrelated protein being less than about 10%, 5%, or less than about 2% of the binding to the target antigen (e.g., CD3, MSLN, etc.) as measured by SPR, for example. In certain embodiments, specific binding of an antibody construct herein for a particular antigen, or an epitope is defined by a dissociation constant ($K_D$) of ≤1 µM, for example, ≤500 nM, ≤200 nM, ≤100 nM, ≤50 nM, ≤25 nM, or ≤5 nM. In some embodiments, specific binding of an antibody construct for a particular antigen or an epitope is defined by a dissociation constant ($K_D$) from about $10^{-6}$ M to about $10^{-10}$ M, from about $10^{-6}$ M to about $10^{-9}$ M, from about $10^{-8}$ M to about $10^{-10}$ M, or from about $10^{-7}$ M to about $10^{-9}$ M.

Additional experimental methods characterizing and evaluating the trivalent and bispecific antibody constructs of the present disclosure are described in EXAMPLES 1-20 herein.

Certain Embodiments of this Disclosure

The present disclosure further describes antibody constructs, pharmaceutical compositions comprising such constructs, as well as methods of using such constructs according to any one or more of embodiments 1-124.

Embodiment 1. An antibody construct, comprising: a Fab domain capable of binding an antigen on a cytotoxic effector cell; a first scFv domain and a second scFv domain, wherein the first scFv domain and the second scFv domain are capable of binding mesothelin (MSLN); and a dimeric Fc domain comprising a first Fc polypeptide and a second Fc polypeptide, wherein: the Fab domain is coupled to the N-terminus of the first Fc polypeptide, the first scFv domain is coupled to the N-terminus of the second Fc polypeptide, and the second scFv domain is coupled to an N-terminus of the Fab domain.

Embodiment 2. The antibody construct of embodiment 1, wherein at least one of the first scFv domain and the second scFv domain comprises a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

Embodiment 3. The antibody construct of embodiment 2, wherein the first scFv domain and the second scFv domain each comprise a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

Embodiment 4. An antibody construct, comprising: a Fab domain capable of binding an antigen on a cytotoxic effector cell; a first scFv domain capable of binding MSLN and comprising a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125; a second scFv domain capable of binding a second tumor-associated antigen (TAA); and a dimeric Fc domain comprising a first Fc polypeptide and a second Fc polypeptide, wherein: the Fab domain is coupled to the N-terminus of the first Fc polypeptide, the first scFv domain is coupled to the N-terminus of the second Fc polypeptide, and the second scFv domain is coupled to an N-terminus of the Fab domain.

Embodiment 5. The antibody construct of embodiment 4, wherein the second TAA is also MSLN.

Embodiment 6. The antibody construct of any one of embodiments 4-5, wherein the second scFv domain comprises a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

Embodiment 7. The antibody construct of any one of embodiments 1-6, wherein the cytotoxic effector cell is a T cell.

Embodiment 8. The antibody construct of any one of embodiments 1-7, wherein the antigen to which the Fab domain binds is CD3.

Embodiment 9. The antibody construct of any one of embodiments 1-8, wherein the Fab domain comprises a $V_H$ domain comprising a HCDR1 sequence comprising or consisting of the sequence set forth in SEQ ID NO: 126, a HCDR2 sequence comprising or consisting of the sequence set forth in SEQ ID NO: 127, and a HCDR3 sequence comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131.

Embodiment 10. The antibody construct of any one of embodiments 1-9, wherein the first scFv domain and the second scFv domain each comprise a $V_H$ domain comprising an amino acid sequence having at least about 90%, 95%, 97%, 99% or 100% sequence identity to the sequence set forth in SEQ ID NO: 103, and a $V_L$ domain comprising an amino acid sequence having at least about 90%, 95%, 97%, 99% or 100% sequence identity to the sequence set forth in SEQ ID NO: 101.

Embodiment 11. The antibody construct of embodiment 10, wherein, for the first scFv domain and the second scFv domain, the $V_L$ domain is coupled to the $V_H$ domain by a linker$^{scFv}$.

Embodiment 12. The antibody construct of embodiment 11, wherein the linker$^{scFv}$ comprises or consists of the amino acid sequence $(G_4S)_n$, and wherein n is 1, 2, 3, 4 or 5 (SEQ ID NO: 132).

Embodiment 13. The antibody construct of any one of embodiments 10-12, wherein the first scFv domain and the second scFv domain have the domain structure, from N-terminus to C-terminus, of $V_H$-linker$^{scFv}$-$V_L$ or $V_L$-linker$^{scFv}$-$V_H$.

Embodiment 14. The antibody construct of any one of embodiments 10-13, wherein the first scFv domain and the second scFv domain each comprise or consist of an amino acid sequence having at least about 90%, 95%, 97%, 99% or 100% sequence identity to the sequence set forth in SEQ ID NO: 149.

Embodiment 15. The antibody construct of any one of embodiments 1-14, wherein the Fab domain comprises a $V_H$ domain comprising an amino acid sequence having at least about 90%, 95%, 97%, 99% or 100% sequence identity to the sequence set forth in SEQ ID NO: 105 and a $C_{H1}$ domain comprising an amino acid sequence having at least about 90%, 95%, 97%, 99% or 100% sequence identity to the sequence set forth in SEQ ID NO: 106.

Embodiment 16. The antibody construct of embodiment 15, wherein the Fab domain further comprises a light chain (L1) comprising a $V_L$ domain comprising an amino acid sequence having at least about 90%, 95%, 97%, 99% or 100% sequence identity to the sequence set forth in SEQ ID NO: 115 and a $C_L$ domain comprising an amino acid sequence having at least about 90%, 95%, 97%, 99% or 100% sequence identity to the sequence set forth in SEQ ID NO: 116, wherein the light chain (L1) pairs with the $V_H$-$C_{H1}$ domain of the heavy chain, thereby forming the Fab domain.

Embodiment 17. The antibody construct of any one of embodiments 15-16, wherein the light chain (L1) comprises or consists of an amino acid sequence having at least about 90%, 95%, 97%, 99% or 100% sequence identity to the sequence set forth in SEQ ID NO: 114.

Embodiment 18. The antibody construct of any one of embodiments 1-17, wherein the antibody construct comprises a first heavy chain (H1) comprising, from N-terminus to C-terminus, scFv2-$V_H$-$C_{H1}$, in which the C-terminus of the second scFv domain (scFv2) is coupled to the N-terminus of the $V_H$ domain.

Embodiment 19. The antibody construct of embodiment 18, wherein the C-terminus of the second scFv domain is coupled to the N-terminus of the $V_H$ domain via a linker$^{scFv-Fab}$.

Embodiment 20. The antibody construct of embodiment 19, wherein the linker$^{scFv-Fab}$ comprises or consists of the amino acid sequence $(G_4S)_n$, and wherein n is 1, 2, 3, 4 or 5 (SEQ ID NO: 132).

Embodiment 21. The antibody construct of any one of embodiments 18-20, wherein the first heavy chain (H1) further comprises the first Fc polypeptide, and wherein the C-terminus of the $C_{H1}$ domain is coupled to the N-terminus of the first Fc polypeptide, thereby forming the following domain structure for H1: scFv2-$V_H$-$C_{H1}$-CH2-CH3.

Embodiment 22. The antibody construct of embodiment 21, wherein the $C_{H1}$ domain is coupled to first Fc polypeptide by a linker$^{Fab-Fc}$.

Embodiment 23. The antibody construct of embodiment 22, wherein the linker$^{Fab-Fc}$ comprises or consists of an Ig hinge region.

Embodiment 24. The antibody construct of embodiment 23, wherein the Ig hinge region is an IgG hinge region.

Embodiment 25. The antibody construct of embodiment 24, wherein the IgG hinge region is an IgG1 hinge region.

Embodiment 26. The antibody construct of any one of embodiments 22-25, wherein the linker$^{Fab-Fc}$ comprises or consists of an amino acid sequence having at least about 70%, 80%, 90% or 100% sequence identity to the sequence set forth in SEQ ID NO: 107.

Embodiment 27. The antibody construct of any one of embodiments 1-26, wherein the dimeric Fc domain is a heterodimeric Fc domain comprising the first Fc polypeptide and the second Fc polypeptide.

Embodiment 28. The antibody construct of any one of embodiments 1-27, wherein the first Fc polypeptide is an IgG1-derived Fc polypeptide and comprises a first CH2 domain and a first CH3 domain.

Embodiment 29. The antibody construct of embodiment 28, wherein the first CH3 domain comprises one or more amino acid substitutions compared to a corresponding wild-type IgG1 CH3 domain sequence.

Embodiment 30. The antibody construct of any one of embodiments 28-29, wherein the first CH2 domain comprises one or more amino acid substitutions compared to a corresponding wild-type IgG1 CH2 domain that reduce or eliminate binding to an Fc-receptor.

Embodiment 31. The antibody construct of any one of embodiments 18-30, wherein the first heavy chain (H1) comprises or consists of an amino acid sequence having at least about 90%, 95%, 97%, 99% or 100% sequence identity to the sequence set forth in SEQ ID NO: 100.

Embodiment 32. The antibody construct of any one of embodiments 1-31, wherein the antibody construct further comprises a second heavy chain (H2) comprising, from N-terminus to C-terminus, the first scFv domain coupled to the second Fc polypeptide, thereby forming the domain structure: scFv1-CH2-CH3.

Embodiment 33. The antibody construct of embodiment 32, wherein the C-terminus of the first scFv domain is coupled to the N-terminus of the second Fc polypeptide via a linker$^{scFv\text{-}Fc}$.

Embodiment 34. The antibody construct of embodiment 33, wherein the linker$^{scFv\text{-}Fc}$ comprises or consists of an Ig hinge region.

Embodiment 35. The antibody construct of embodiment 34, wherein the Ig hinge region is an IgG hinge region.

Embodiment 36. The antibody construct of embodiment 35, wherein the IgG hinge region is an IgG1 hinge region.

Embodiment 37. The antibody construct of any one of embodiments 33-36, wherein the linker$^{scFv\text{-}Fc}$ comprises or consists of an amino acid sequence having at least about 70%, 80%, 90% or 100% sequence identity to the sequence set forth in SEQ ID NO: 111.

Embodiment 38. The antibody construct of any one of embodiments 32-37, wherein the second Fc polypeptide is also an IgG1-derived Fc polypeptide and comprises a second CH2 domain and a second CH3 domain.

Embodiment 39. The antibody construct of embodiment 38, wherein the second CH3 domain comprises one or more amino acid substitutions compared to a corresponding wild-type IgG1 CH3 domain sequence.

Embodiment 40. The antibody construct of any one of embodiments 38-39, wherein the second CH2 domain comprises one or more amino acid substitutions compared to a corresponding wild-type IgG1 CH2 domain that reduce or eliminate binding to an Fc-receptor.

Embodiment 41. The antibody construct of any one of embodiments 1-40, wherein the first Fc polypeptide and the second Fc polypeptide each comprise a CH3 sequence, and wherein one of the Fc polypeptides comprises amino acid substitutions in its CH3 sequence selected from: L351Y_F405A_Y407V, T350V_L351Y_F405A_Y407V and T350V_L351Y_S400E_F405A_Y407V, and the other Fc polypeptide comprises amino acid substitutions in its CH3 sequence selected from T366L_K392M_T394W, T366L_K392L_T394W, T350V_T366L_K392L_T394W, T350V_T366L_K392M_T394W and T350V_T366L_N390R_K392M_T394W, and wherein the numbering of amino acid residues in the Fc polypeptide sequences is according to the EU numbering system.

Embodiment 42. The antibody construct of embodiment 41, wherein the amino acid substitutions in the CH3 sequences of the Fc polypeptides promote preferential pairing of the heavy chains H1 and H2 and formation of a heterodimeric Fc domain, compared to the formation of a homodimeric Fc domain.

Embodiment 43. The antibody construct of any one of embodiments 32-42, wherein the second heavy chain (H2) comprises or consists of an amino acid sequence having at least about 90%, 95%, 97%, 99% or 100% sequence identity to the sequence set forth in SEQ ID NO: 110.

Embodiment 44. The antibody construct of any one of embodiments 1-43, wherein the antibody construct is bispecific for CD3 and MSLN, monovalent for CD3, and bivalent for MSLN.

Embodiment 45. The antibody construct of any one of embodiments 1-44, wherein the antibody construct comprises a first heavy chain (H1) comprising or consisting of an amino acid sequence having at least about 90%, 95%, 97%, 99% or 100% sequence identity to the sequence set forth in SEQ ID NO: 100, a second heavy chain (H2) comprising or consisting of an amino acid sequence having at least about 90%, 95%, 97%, 99% or 100% sequence identity to the sequence set forth in SEQ ID NO: 110, and a light chain (L1) comprising or consisting of an amino acid sequence having at least about 90%, 95%, 97%, 99% or 100% sequence identity to the sequence set forth in SEQ ID NO: 114.

Embodiment 46. The antibody construct of claim 45, wherein the first heavy chain (H1) comprises or consists of the amino acid sequence set forth in SEQ ID NO: 100.

Embodiment 47. The antibody construct of any one of embodiments 45-46, wherein the second heavy chain (H2) comprises or consists of the amino acid sequence set forth in SEQ ID NO: 110.

Embodiment 48. The antibody construct of any one of claims 45-47, wherein the light chain (L1) comprises or consists of the amino acid sequence set forth in SEQ ID NO: 114.

Embodiment 49. The antibody construct of any one of embodiments 1-44, wherein the antibody construct comprises (i) first heavy chain (H1) comprising or consisting of the amino acid sequence set forth in SEQ ID NO: 171, (ii) a second heavy chain (H2) comprising or consisting of the amino acid sequence set forth in SEQ ID NO: 172, and (iii) a light chain (L1) comprising or consisting of the amino acid sequence set forth in SEQ ID NO: 114.

Embodiment 50. The antibody construct of any one of embodiments 1-9, wherein the antibody construct comprises a first heavy chain (H1) comprising or consisting of an amino acid sequence having at least about 90%, 95%, 97%, 99% or 100% sequence identity to the sequence set forth in SEQ ID NO: 117, a second heavy chain (H2) comprising or consisting of an amino acid sequence having at least about 90%, 95%, 97%, 99% or 100% sequence identity to the sequence set forth in SEQ ID NO: 119, and a light chain (L1) comprising or consisting of an amino acid sequence having at least about 90%, 95%, 97%, 99% or 100% sequence identity to the sequence set forth in SEQ ID NO: 114.

Embodiment 51. The antibody construct of any one of embodiments 18-50, wherein one or more of the heavy chains H1 and H2 further comprise a C-terminal lysine residue.

Embodiment 52. The antibody construct of any one of embodiments 1-51, wherein the antibody construct is capable of one or more, two or more, or all of the following when present at a concentration of about 10 pM in a cell population comprising immune cells expressing CD3 and tumor cells expressing about 500,000 MSLN/cell: A) inducing production of at least about 20 pg/mL, 30 pg/mL, or 40 pg/mL TNFα; B) inducing production of at least about 500 pg/mL, 1000 pg/mL, or 2000 pg/mL IFNγ; or C) inducing production of at least about 50 pg/mL, 1000 pg/mL, or 150 pg/mL IL-2.

Embodiment 53. The antibody construct of any one of embodiments 1-52, wherein the antibody construct is capable of inducing at least 10-fold higher T-cell mediated cytotoxicity against tumor cells compared to an analogous antibody constructs that comprises two anti-MSLN Fab domains instead of the first and second anti-MSLN scFv domains.

Embodiment 54. The antibody construct of any one of embodiments 1-53, wherein the antibody construct has a binding affinity ($K_D$) for MSLN of about 0.7 nM, 0.8 nM, 0.9 nM, 1 nM or about 1.1 nM as measured by SPR.

Embodiment 55. The antibody construct of any one of embodiments 8-54, wherein the antibody construct has a binding affinity ($K_D$) for CD3 of about 30 nM, 40 nM, 50 nM, or about 60 nM as measured by SPR.

Embodiment 56. The antibody construct of any one of embodiments 1-55, wherein the antibody construct is capable of inducing production of a pro-inflammatory cytokine by the cytotoxic effector cell in a MSLN-dependent manner, wherein the MSLN-dependent activation of the cytotoxic effector cell is determined by measuring a reduction in cytokine production of at least about 20-fold, 50-fold, 100-fold, or at least about 1000-fold between a first cell population comprising a first tumor cell and immune cells and in a second cell population comprising a second tumor cell and immune cells, wherein the first tumor cell has a MSLN-expression that is at least about 3, 4 or 5-fold higher than that of the second tumor cell.

Embodiment 57. The antibody construct of any one of embodiments 1-56, wherein the antibody construct, when administered to a subject, is capable of reducing the volume of a MSLN-expressing tumor in the subject by at least about 5% over a time period of at least 20 days following administration of the antibody construct to the subject at a dose of about 1 mg/kg, 1.5 mg/kg or about 3 mg/kg, 4-times every week.

Embodiment 58. A pharmaceutical composition comprising the antibody construct of any one of embodiments 1-57, and a pharmaceutically acceptable carrier, excipient, diluent, or combination thereof.

Embodiment 59. A nucleic acid molecule or a set of nucleic acid molecules encoding one or more, two or more, or three or more polypeptide chains that form the antibody construct of any one of embodiments 1-57.

Embodiment 60. A vector or a set of vectors comprising the nucleic acid molecule or the set of nucleic acid molecules of embodiment 59.

Embodiment 61. A cell comprising the nucleic acid molecule or the set of nucleic acid molecules of embodiment 59 or the vector or set of vectors of embodiment 60.

Embodiment 62. A method of producing an antibody construct of any one of claims 1-57, the method comprising: (a) obtaining a host cell culture comprising at least one host cell comprising one or more nucleic acid molecules encoding one or more, two or more, three or more polypeptide chains that form the antibody construct; and (b) recovering the antibody construct from the host cell culture.

Embodiment 63. The method of embodiment 62, further comprising, subsequent to step (b), purifying the antibody construct.

Embodiment 64. A method of eliciting an anti-tumor immune response in a cell population comprising immune cells expressing CD3 and tumor cells expressing MSLN, the method comprising contacting the cell population with an effective amount of the antibody construct of any one of embodiments 1-57.

Embodiment 65. The method of embodiment 64, wherein the anti-tumor immune response provides a dose-dependent reduction in live tumor cells in the cell population of at least 30%, 40%, 50%, or 60% when the concentration of the antibody construct in the cell population is increased from about $10^{-2}$ µM to about 102 µM, wherein the expression of MSLN of the tumor cells is at least about 15,000 MSLN/cell and the ratio of immune cells to tumor cells in the cell population is about 5:1.

Embodiment 66. A method of inhibiting the proliferation of tumor cells expressing MSLN, the method comprising contacting a cell population comprising the tumor cells and immune cells expressing CD3 with an effective amount of the antibody construct of any one of embodiments 1-57.

Embodiment 67. The method of embodiment 66, wherein the proliferation of tumor cells is inhibited when an increase in live tumor cell count of at most about 5% is observed in the cell population over a period of at least about 5, 10, 20, or 48 hours using a concentration of the antibody construct of at most about 10-2 µM, $10^{-1}$ µM, or 1 µM, wherein the expression of MSLN of the tumor cells is at least about 15,000 MSLN/cell and the ratio of immune cells to tumor cells in the cell population is about 5:1.

Embodiment 68. A method of killing tumor cells expressing MSLN, the method comprising contacting a cell population comprising the tumor cells and immune cells expressing CD3 with an effective amount of the antibody construct of any one of embodiments 1-57.

Embodiment 69. The method of embodiment 68, wherein tumor cell killing is observed when a dose-dependent reduction in live tumor cells in the cell population of at least about 30%, 40%, 50%, or 60% is measured when the concentration of the antibody construct is increased from about 102 µM to about 102 µM, wherein the expression of MSLN of the tumor cells is at least about 15,000 MSLN/cell and the ratio of immune cells to tumor cells in the cell population is about 5:1.

Embodiment 70. The method of any one of embodiments 64-69, wherein the immune cells comprise T cells.

Embodiment 71. The method of any one of embodiments 64-70, wherein the antibody construct binds CD3 on an immune cell and MSLN on a tumor cell.

Embodiment 72. A method of inhibiting the growth of a MSLN-expressing tumor or reducing the volume of the tumor in a subject, the method comprising administering to the subject an effective amount of the antibody construct of any one of embodiments 1-57.

Embodiment 73. The method of embodiment 72, wherein the antibody construct engages CD3 on immune cells and MSLN on tumor cells in the subject which elicits an anti-tumor immune response in the subject, and thereby inhibits the growth of the tumor or reduces the volume of the tumor in the subject.

Embodiment 74. The method of embodiment 73, wherein inhibition of tumor growth or reduction in tumor volume is elicited by simultaneous binding of the antibody construct to CD3 on an immune cell and to MSLN on a tumor cell and formation of a TCR-independent artificial immune synapse within a tumor environment in the subject.

Embodiment 75. The method of embodiment 74, wherein the immune cell is a T cell.

Embodiment 76. The method of any one of embodiments 72-75, wherein tumor growth is inhibited for at least 20 days, 30 days, or 50 days using 4-times weekly (Q7Dx4) administration of the antibody construct to the subject.

Embodiment 77. The method of any one of embodiments 72-76, wherein the tumor volume is reduced by at least 20%, 30%, 40%, or at least about 50% about 15 days after start of treatment.

Embodiment 78. The method of any one of embodiments 72-77, wherein about 1 mg/kg, 1.5 mg/kg or about 3 mg/kg of antibody construct is administered to the subject.

Embodiment 79. The method of any one of embodiments 72-78, wherein the subject is a rodent, a non-human primate, or a human.

Embodiment 80. An antibody construct of any one of embodiments 1-57 for use in the treatment of cancer.

Embodiment 81. Use of an antibody construct of any one of embodiments 1-57 in the manufacture of a medicament for the treatment of cancer.

Embodiment 82. An antibody construct, comprising: (i) a Fab domain capable of binding CD3 on a cytotoxic effector cell, wherein the Fab domain comprises a $V_H$ domain comprising a HCDR1 sequence comprising or consisting of the sequence set forth in SEQ ID NO: 126, a HCDR2 sequence comprising or consisting of the sequence set forth in SEQ ID NO: 127, and a HCDR3 sequence comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131; (ii) a first scFv domain (scFv1) and a second scFv domain (scFv2), wherein the first scFv domain and the second scFv domain are capable of binding mesothelin (MSLN), and (iii) a dimeric Fc domain comprising a first Fc polypeptide and a second Fc polypeptide, wherein: the Fab domain is coupled to the N-terminus of the first Fc polypeptide, the first scFv domain is coupled to the N-terminus of the second Fc polypeptide, and the second scFv domain is coupled to an N-terminus of the Fab domain.

Embodiment 83. The antibody construct of embodiment 82, wherein at least one of the first scFv domain and the second scFv domain comprise (i) a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and (ii) a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

Embodiment 84. The antibody construct of embodiment 82 or embodiment 83, wherein the first scFv domain and the second scFv domain each comprise a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125.

Embodiment 85. An antibody construct, comprising: (i) a Fab domain capable of binding CD3 on a cytotoxic effector cell, wherein the Fab domain comprises a $V_H$ domain comprising a HCDR1 sequence comprising or consisting of the sequence set forth in SEQ ID NO: 126, a HCDR2 sequence comprising or consisting of the sequence set forth in SEQ ID NO: 127, and a HCDR3 sequence comprising or consisting of the sequence set forth in SEQ ID NO: 128, and a $V_L$ domain comprising an LCDR1 sequence comprising or consisting of the sequence set forth in SEQ ID NO: 129, an LCDR2 sequence comprising or consisting of the sequence set forth in SEQ ID NO: 130, and an LCDR3 sequence comprising or consisting of the sequence set forth in SEQ ID NO: 131; (ii) a first scFv domain (scFv1) and a second scFv domain (scFv2), wherein the first scFv domain and the second scFv domain are capable of binding mesothelin (MSLN), and wherein the first scFv domain and the second scFv domain each comprise a $V_H$ domain comprising a HCDR1 sequence comprising or consisting of the sequence set forth in SEQ ID NO: 120, a HCDR2 sequence comprising or consisting of the sequence set forth in SEQ ID NO: 121, and a HCDR3 sequence comprising or consisting of the sequence set forth in SEQ ID NO: 122, and a $V_L$ domain comprising an LCDR1 sequence comprising or consisting of the sequence set forth in SEQ ID NO: 123, an LCDR2 sequence comprising or consisting of the sequence set forth in SEQ ID NO: 124, and an LCDR3 sequence comprising or consisting of the sequence set forth in SEQ ID NO: 125; and (iii) a dimeric Fc domain comprising a first Fc polypeptide and a second Fc polypeptide, wherein: the Fab domain is coupled to the N-terminus of the first Fc polypeptide, the first scFv domain is coupled to the N-terminus of the second Fc polypeptide, and the second scFv domain is coupled to an N-terminus of the Fab domain.

Embodiment 86. The antibody construct of any one of embodiments 82-85, wherein the first scFv domain or the second scFv domain comprises (i) a $V_H$ domain comprising an amino acid sequence having at least about 90%, 95%, 97%, 99% or 100% sequence identity to the sequence set forth in SEQ ID NO: 103, and (ii) a $V_L$ domain comprising an amino acid sequence having at least about 90%, 95%, 97%, 99% or 100% sequence identity to the sequence set forth in SEQ ID NO: 101.

Embodiment 87. The antibody construct of any one of embodiments 82-86, wherein the first scFv domain and the second scFv domain each comprise (i) a $V_H$ domain comprising an amino acid sequence having at least about 90%, 95%, 97%, 99% or 100% sequence identity to the sequence set forth in SEQ ID NO: 103, and (ii) a $V_L$ domain comprising an amino acid sequence having at least about 90%, 95%, 97%, 99% or 100% sequence identity to the sequence set forth in SEQ ID NO: 101.

Embodiment 88. The antibody construct of any one of embodiments 82-87, wherein the first scFv domain and the second scFv domain each comprise (i) a $V_H$ domain comprising or consisting of the amino acid sequence set forth in SEQ ID NO: 103, and (ii) a $V_L$ domain comprising or consisting of the amino acid sequence set forth in SEQ ID NO: 101.

Embodiment 89. The antibody construct of any one of embodiments 86-88, wherein the first scFv domain and the second scFv domain further comprise a linker$^{scFv}$ that couples the $V_L$ domain to the $V_H$ domain.

Embodiment 90. The antibody construct of embodiment 89, wherein the linker$^{scFv}$ comprises or consists of the amino acid sequence $(G_4S)_n$, and wherein n is 1, 2, 3, 4 or 5 (SEQ ID NO:132).

Embodiment 91. The antibody construct of any one of embodiments 89-90, wherein the first scFv domain and the second scFv domain have the domain structure, from N-terminus to C-terminus, of $V_H$-linker$^{scFv}$-$V_L$ or $V_L$-linker$^{scFv}$-$V_H$.

Embodiment 92. The antibody construct of embodiment 91, wherein the first scFv domain and the second scFv domain have the domain structure, from N-terminus to C-terminus, of $V_H$-linker$^{scFv}$-$V_L$.

Embodiment 93. The antibody construct of embodiment 91, wherein the first scFv domain and the second scFv domain have the domain structure, from N-terminus to C-terminus, of $V_L$-linker$^{scFv}$-$V_H$.

Embodiment 94. The antibody construct of any one of embodiments 82-93, wherein the Fab domain comprises (i) a $V_H$ domain comprising or consisting of an amino acid sequence having at least about 90%, 95%, 97%, 99% or 100% sequence identity to the sequence set forth in SEQ ID NO: 105, (ii) a $C_{H1}$ domain comprising or consisting of an amino acid sequence having at least about 90%, 95%, 97%, 99% or 100% sequence identity to the sequence set forth in SEQ ID NO: 106, (iii) a $V_L$ domain comprising or consisting of an amino acid sequence having at least about 90%, 95%, 97%, 99% or 100% sequence identity to the sequence set forth in SEQ ID NO: 115, and a (iv) $C_L$ domain comprising or consisting of an amino acid sequence having at least about 90%, 95%, 97%, 99% or 100% sequence identity to the sequence set forth in SEQ ID NO: 116.

Embodiment 95. The antibody construct of any one of embodiments 82-94, wherein the antibody construct comprises a first heavy chain (H1) comprising, from N-terminus to C-terminus, scFv2-$V_H$-$C_{H1}$, in which the C-terminus of the second scFv domain (scFv2) is coupled to the N-terminus of the $V_H$ domain of the Fab heavy chain.

Embodiment 96. The antibody construct of embodiment 95, wherein the C-terminus of scFv2 is coupled to the N-terminus of the $V_H$ domain via a linker$^{scFv\text{-}Fab}$.

Embodiment 97. The antibody construct of embodiment 96, wherein the linker$^{scFv\text{-}Fab}$ comprises or consists of the amino acid sequence $(G_4S)_n$, and wherein n is 1, 2, 3, 4 or 5 (SEQ ID NO:132).

Embodiment 98. The antibody construct of any one of embodiments 95-97, wherein H1 further comprises the first Fc polypeptide comprising a first CH2 sequence (CH21) and a first CH3 sequence (CH31), and wherein the C-terminus of the $C_{H1}$ domain is coupled to the N-terminus of the first Fc polypeptide, thereby forming the following domain structure for H1 (from N- to C-terminus): scFv2-$V_H$-$C_{H1}$-$CH2_1$-$CH3_1$.

Embodiment 99. The antibody construct of embodiment 98, wherein the $C_{H1}$ domain is coupled to the CH2 sequence of the first Fc polypeptide via a linker$^{Fab\text{-}Fc}$.

Embodiment 100. The antibody construct of embodiment 99, wherein the linker$^{Fab\text{-}Fc}$ comprises or consists of an Ig hinge region.

Embodiment 101. The antibody construct of any one of embodiments 95-100, wherein H1 comprises or consists of an amino acid sequence having at least about 90%, 95%, 97%, 99% or 100% sequence identity to the sequence set forth in SEQ ID NO: 100.

Embodiment 102. The antibody construct of any one of embodiments 82-101, wherein the antibody construct further comprises a second heavy chain (H2) comprising, from N-terminus to C-terminus, the first scFv domain (scFv1) coupled to the second Fc polypeptide comprising a second CH2 sequence ($CH2_2$) and a second CH3 sequence ($CH3_2$), thereby forming the domain structure: scFv1-$CH2_2$-$CH3_2$.

Embodiment 103. The antibody construct of embodiment 102, wherein the C-terminus of scFv1 is coupled to the N-terminus of the second Fc polypeptide via a linker$^{scFv\text{-}Fc}$.

Embodiment 104. The antibody construct of embodiment 103, wherein the linker$^{scFv\text{-}Fc}$ comprises or consists of an Ig hinge region.

Embodiment 105. The antibody construct of any one of embodiments 102-104, wherein H2 comprises or consists of an amino acid sequence having at least about 90%, 95%, 97%, 99% or 100% sequence identity to the sequence set forth in SEQ ID NO: 110.

Embodiment 106. The antibody construct of any one of embodiments 82-105, wherein the first Fc polypeptide, the second Fc polypeptide, or both the first and the second Fc polypeptides, is an IgG1-derived Fc polypeptide.

Embodiment 107. The antibody construct of any one of embodiments 82-106, wherein the dimeric Fc domain is a heterodimeric Fc domain in which the amino acid sequence of the first Fc polypeptide differs by at least one amino acid residue from the amino acid sequence of the second Fc polypeptide.

Embodiment 108. The antibody construct of embodiment 107, wherein the first Fc polypeptide, the second Fc polypeptide, or both Fc polypeptides, comprise(s) one or more amino acid substitutions in the CH3 domain compared to a corresponding wild-type IgG1 CH3 domain sequence, wherein the one or more amino acid substitutions promote preferential pairing of the first and second Fc polypeptides to form the heterodimeric Fc domain.

Embodiment 109. The antibody construct of embodiment 108, wherein one Fc polypeptide comprises a set of amino acid substitutions selected from: L351Y_F405A_Y407V, T350V_L351Y_F405A_Y407V and T350V_L351Y_S400E_F405A_Y407V, and the other Fc polypeptide comprises a set of amino acid substitutions selected from: T366L_K392M_T394W, T366L_K392L_T394W, T350V_T366L_K392L_T394W, T350V_T366L_K392M_T394W and T350V_T366L_N390R_K392M_T394W, and wherein the numbering of amino acid residues in the Fc polypeptides is according to the EU numbering system.

Embodiment 110. The antibody construct of any one of embodiments 98-109, wherein the first Fc polypeptide, the second Fc polypeptide, or both Fc polypeptides, comprise(s) one or more amino acid substitutions in the CH2 domain compared to a corresponding wild-type IgG1 CH2 domain sequence, wherein the one or more amino acid substitutions reduce or eliminate binding of the antibody construct to an Fcγ-receptor.

Embodiment 111. The antibody construct of any one of embodiments 82-110, wherein the antibody construct comprises a first heavy chain (H1) comprising or consisting of an amino acid sequence having at least about 90%, 95%, 97%, 99% or 100% sequence identity to the sequence set forth in SEQ ID NO: 100, a second heavy chain (H2) comprising or consisting of an amino acid sequence having at least about 90%, 95%, 97%, 99% or 100% sequence identity to the sequence set forth in SEQ ID NO: 110, and a light chain (L1) comprising or consisting of an amino acid sequence having at least about 90%, 95%, 97%, 99% or 100% sequence identity to the sequence set forth in SEQ ID NO: 114.

Embodiment 112. The antibody construct of any one of embodiments 95-111, wherein one or more of the heavy chains H1 and H2 further comprise a C-terminal lysine residue.

Embodiment 113. An antibody construct, comprising: a first heavy chain (H1) polypeptide comprising or consisting of the amino acid sequence set forth in SEQ ID NO: 100, a second heavy chain (H2) polypeptide comprising or consisting of the amino acid sequence set forth in SEQ ID NO: 110, and a light chain (L1) polypeptide comprising or consisting of the amino acid sequence set forth in SEQ ID NO: 114.

Embodiment 114. The antibody construct of any one of embodiments 82-113, wherein the antibody construct is capable of one or more, two or more, or all of the following, when present at a concentration of about 10 Pm in a cell population comprising immune cells expressing CD3 and tumor cells expressing about 500,000 MSLN/cell: A) inducing production of at least about 20 pg/Ml, 30 pg/Ml, or 40 pg/Ml TNFα; B) inducing production of at least about 500 pg/Ml, 1000 pg/Ml, or 2000 pg/Ml IFNγ; or C) inducing production of at least about 50 pg/Ml, 1000 pg/Ml, or 150 pg/Ml IL-2.

Embodiment 115. The antibody construct of any one of embodiments 82-114, wherein the antibody construct has a binding affinity ($K_D$) for MSLN of about 0.7 Nm, 0.8 Nm, 0.9 Nm, 1 Nm or about 1.1 Nm as measured by SPR.

Embodiment 116. The antibody construct of any one of embodiments 82-115, wherein the antibody construct has a binding affinity ($K_D$) for CD3 of about 30 Nm, 40 Nm, 50 Nm, or about 60 Nm as measured by SPR.

Embodiment 117. The antibody construct of any one of embodiments 82-116, wherein the antibody construct has a purity of at least about 95%, 96%, 97%, 98%, or at least about 99% after incubation in a buffer solution for 14 days at 40° C., as measured by size-exclusion chromatography and relative to other high molecular weight species (HMWS) present in the buffer solution following the incubation period.

Embodiment 118. A pharmaceutical composition comprising the antibody construct of any one of embodiments 82-117, and a pharmaceutically acceptable carrier, excipient, diluent, or combination thereof.

Embodiment 119. A nucleic acid molecule or a set of nucleic acid molecules encoding one or more, two or more, or three or more polypeptide chains that form the antibody construct of any one of embodiments 82-117.

Embodiment 120. A vector or a set of vectors comprising the nucleic acid molecule or the set of nucleic acid molecules of embodiment 119.

Embodiment 121. A cell comprising the nucleic acid molecule or the set of nucleic acid molecules of embodiment 119 or the vector or set of vectors of embodiment 120.

Embodiment 122. A method of producing an antibody construct of any one of embodiments 82-117, the method comprising: (a) obtaining a host cell culture comprising at least one host cell comprising one or more nucleic acid molecules encoding one or more, two or more, three or more, or all of the polypeptide chains that form the antibody construct; and (b) recovering the antibody construct from the host cell culture.

Embodiment 123. An antibody construct of any one of embodiments 82-117 for use in the treatment of cancer.

Embodiment 124. Use of an antibody construct of any one of embodiments 82-117 in the manufacture of a medicament for the treatment of cancer.

EXAMPLES

The following Examples are provided for illustrative purposes and are not intended to limit the scope of the disclosure in any way.

The practice of the present disclosure can include and employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Design and Preparation of Bi- and Trivalent MSLN×CD3 Bispecific Antibody Constructs Several bi- or trivalent and bispecific MSLN×CD3 antibody constructs were produced as described below. The antibody constructs and controls were prepared in different formats and geometries, as shown, e.g., in FIGS. 1A-1D. Such antibody constructs were prepared to examine the impact of antibody format and geometry and anti-MSLN paratope affinity on the potency of these T cell engager conrstructs capable of targeting and killing MSLN-expressing tumor cells.

Design of Trivalent and Bispecific Antibody Constructs Targeting MSLN and CD3

Initially, bispecific antibody constructs were prepared in a format in which the MSLN antigen-binding domain was either an scFv domain or Fab domain and the CD3 antigen-binding domain was either a Fab domain or scFv domain. These constructs, including controls, further comprised an IgG1 Fc domain, unless otherwise indicated (see, e.g., TABLE 6). The bispecific antibody constructs that comprise a human IgG1 heterodimeric Fc domain comprised sets of CH3 domain amino acid substitutions promoting the formation of a heterodimeric Fc domain. These sets of amino acid substitutions are referred to herein as (i) Het FcA having the amino acid substitutions T350V/L351Y/F405A/Y407V in the first Fc polypeptide chain (A) and (ii) Het FcB having the amino acid substitutions T350V/T366L/K392L/T394W in the second Fc polypeptide chain (B). Those antibody construct variants in TABLE 6 noted as having "FcKO" comprised the following CH2 amino acid substitutions which knock out, e.g., measurably reduce or ablate, FcTR binding: L234A, L235A and D265S. Amino acid residues in the Fc domain are identified according to the EU index. In addition, several antibody construct formats utilized heterodimeric Fab domains constructed using previously described mutations in the $C_{H1}$ and $C_L$ domains that promote selective and preferential pairing of correct heavy chains and light chains (see, e.g., WO 2014/082179; WO2015/181805; WO 2017/059551).

Bispecific antibody constructs against CD3 and MSLN were designed, expressed, and characterized as described in WO2015109131. Briefly, the genes encoding the antibody constructs' heavy and light chains were constructed via gene synthesis using codons optimized for human/mammalian expression. The anti-CD3 scFv domain and Fab domain sequences were generated from the anti-CD3 monoclonal antibody C3E6 (see, e.g., U.S. Pat. Publ. No. 2019/0359712). The anti-MSLN scFv domain and Fab domain sequences were generated from the $V_H$ and $V_L$ sequences of the mouse anti-MSLN SS antibody (Chowdhury et al., 1998, PNAS, 95: 669-674) with additional humanizing mutations included (see, e.g., U.S. Pat. No. 9,388,222).

Figure 1A:
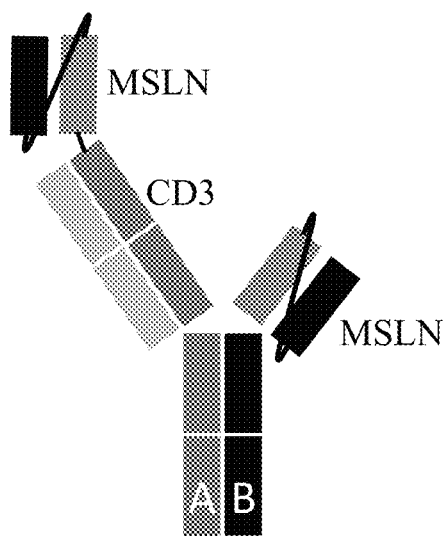
FIG. 1A-1D shows a schematic representation of the geometry (e.g., relative orientation, relative spatial localization, and/or connectivity of binding domains, Fc domains, etc.) and format (e.g., antigen valency; type of binding domains, e.g., scFv, Fab, etc.; presence/absence/type of Fc domain, etc.) of antibody constructs according to certain embodiments of the present disclosure.
Figure 1B:
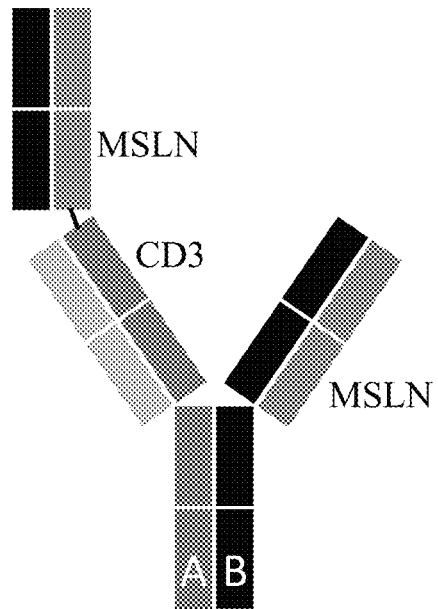
Figure 1C:
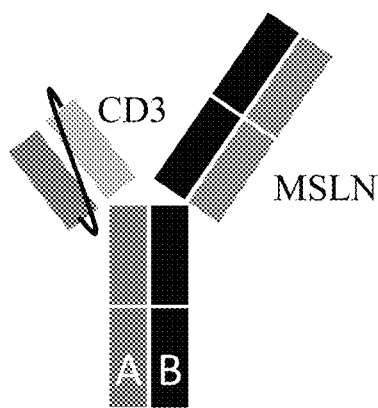
Figure 1D:
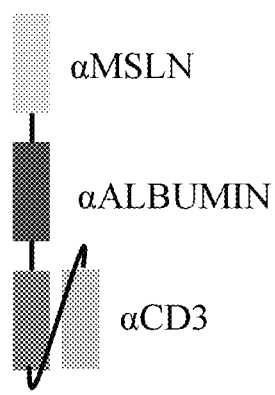

In certain bivalent and bispecific antibody constructs of this disclosure containing a C3E6 Fab domain (e.g., v21815 comprising one anti-CD3 Fab domain and one anti-MSLN scFv domain, see, e.g., FIG. 1C), the $V_H$ and $V_L$ sequences were fused to human IgG1 $C_H$ and $C_L$ sequences, respectively. In other bivalent constructs of this disclosure, C3E6 scFv domains were fused to one chain of the heterodimeric Fc domain. In bivalent constructs containing a SS Fab domain, the SS $V_H$ and $V_L$ domain sequences (Chowdhury et al., 1998, PNAS, 95: 669-674) which included additional humanizing mutations (see, e.g., U.S. Pat. No. 9,388,222) were fused to human IgG1 $C_H$ and $C_L$ sequences, respectively. In other bivalent constructs, SS scFv domains were fused to one chain (e.g., the first or second Fc polypeptide) of the heterodimeric Fc domain. In all embodiments, the scFv domains were fused to one chain of the heterodimeric Fc domain and the VH-CH domains of the Fabs were fused to the second chain of the heterodimeric Fc domain.

In trivalent and bispecific antibody constructs of the present disclosure, which comprised two scFv domains targeting MSLN and one Fab domain targeting CD3 (e.g., v21812 and v32523), the anti-CD3 C3E6 Fab domain was generated by fusing the $V_H$ and $V_L$ sequences to human IgG1 $C_H$ and $C_L$ sequences, respectively. Anti-MSLN scFv domains containing the $V_H$ and $V_L$ sequences of SS (Chowdhury et al., 1998, PNAS, 95: 669-674) with additional humanizing mutations (see, e.g., U.S. Pat. No. 9,388,222) were fused either (i) to the N-terminus of the heterodimeric Fc domain (i.e., to the N-terminus of either the first or second Fc polypeptide) or (ii) the N-terminus of the anti-CD3 C3E6 Fab domain.

In trivalent and bispecific antibody constructs of the present disclosure, comprising two Fab domains targeting MSLN and one Fab targeting CD3 (e.g., v21791 and 2+1 Fab³ TCB), preferential pairing of light chains to specific heavy chains was used. The approach is further described in WO2014082179 and WO2015181805 was used to design heavy chain-light chain heterodimer pairs (i.e., H1-L1 and H2-L2) that exhibit selective and preferential pairing of the respective heavy and light to generate the desired heterodimers. The heterodimers were designed in pairs and included a set of modifications to the $C_L$ domains of the light chains as well as the $C_{H1}$ domains of the two heavy chains. These modifications ensured preferential pairing of the MSLN light chain to MSLN $V_H$-$C_{H1}$ and the CD3 light chain to CD3 VH-CH1 when the immunoglobulin heavy chains were co-expressed with both immunoglobulin light chains. The anti-CD3 C3E6 Fab domains were generated by fusing the $V_H$ and $V_L$ sequences to human IgG1 $C_H$ and $C_L$ sequences, respectively. MSLN $V_H$-$C_{H1}$ domains were fused either (i) to the N-terminus of the heterodimeric Fc domain (i.e., to the N-terminus of either the first or second Fc polypeptide), or (ii) the N-terminus of the anti-CD3 C3E6 Fab $V_H$ domain.

Heavy chain domain structures and formats that were used to generate certain antibody constructs of the present disclosure, e.g., the trivalent and bispecific constructs, as well as other constructs for studying the impact of overall construct format and geometry, are shown below in TABLE 5, from N-terminus to C-terminus.

TABLE 5

Heavy Chain Domain Structures Used in Antibody Constructs Herein

| Heavy chain domain structure: | Exemplary antibody constructs that can comprise the chain format: |
|---|---|
| $V_H$-$V_L$-$V_H$-$C_{H1}$-hinge-CH2—CH3 | v21812 |
| $V_H$-$C_{H1}$-hinge-CH2—CH3 | v18490, v21791, 2 + 1 Fab³ TCB (v29191) |
| $V_H$-$V_L$-hinge-CH2—CH3 | v21812 |
| $V_H$-$C_{H1}$-$V_H$-$C_{H1}$-hinge-CH2—CH3 | v21791, v29191 (2 + 1 Fab³ benchmark) |
| $V_L$-$V_H$-$V_H$-$C_{H1}$-hinge-CH2—CH3 | v32523 |
| $V_L$-$V_H$-hinge-CH2—CH3 | v32523 |
| $V_{HH}$-$V_{HH}$-$V_H$-$V_L$ | v31805 (MH6T-TriTAC benchmark) |

TABLE 6 provides a description of the bi- and trivalent MSLN×CD3 bispecific antibody constructs that were prepared herein with varying valencies and geometry. The respective numbers of MSLN-targeting domains and CD3-targeting domains for each construct are indicated in the "Format" column.

TABLE 6

Description of Certain Antibody Constructs of the Present Disclosure

| Construct # | Format | Heavy Chain A | Heavy Chain B | Fc Description |
|---|---|---|---|---|
| 18490 | mAb | MSLN (SS) Fab | MSLN (SS) Fab | Het Fc, FcKO |
| 31926 | 2 × 1 | N-terminus HA (CR8071 VH/VL) scFv, CD3 C3E6 Fab | HA (CR8071 VH/VL) scFv | Het Fc, FcKO |
| 21815 | 1 × 1 | CD3 C3E6 scFv | MSLN (SS) Fab | Het Fc, FcKO |
| 21791 | 2 × 1 | N-terminus MSLN (SS) Fab, CD3 C3E6 Fab | MSLN (SS) Fab | Het Fc, FcKO |
| 21812 | 2 × 1 | N-terminus MSLN (SS VH/VL) scFv, CD3 C3E6 Fab | MSLN (SS VH/VL) scFv | Het Fc, FcKO |
| 29045 | 2 × 1 | N-terminus MSLN (SS VH1/Vk3_v1) scFv, CD3 C3E6 Fab | MSLN (SS VH1/Vk3_v1) scFv | Het Fc, FcKO |
| 29048 | 2 × 1 | N-terminus MSLN (SS1 VH3/Vk1 v2) scFv, CD3 C3E6 Fab | MSLN (RG7787 VH3/Vk1 v2) scFv | Het Fc, FcKO |
| 32523 | 2 × 1 | N-terminus MSLN (SS VL/VH) scFv, CD3 C3E6 Fab | N-terminus MSLN (SS VL/VH) scFv | Het Fc, FcKO |
| 29191 | 2 × 1 | N-terminus MSLN (RG7787) Fab, CD3 (CH2527) | MSLN (RG7787) Fab | Het Fc, FcKO |
| 31805 | 1 × 1 × 1 | MSLN VHH, Alb VHH, CD3 scFv | n/a | n/a |

By way of example, in TABLE 6, 1×1 indicates that the bispecific antibody construct is bivalent and comprised one MSLN binding domain and one CD3 binding domain, 2×1 indicates that the bispecific antibody construct is trivalent and comprised two MSLN binding domains and one CD3 binding domain, etc. The formats (e.g., 1×1, 2×1, etc.) and geometries (e.g., relative positioning of binding domains) of certain antibody constructs described herein are also illustrated in FIGS. 1A-1D.

Production of MSLN×CD3 Bispecific Antibody Constructs

Generally, the final gene products were sub-cloned into the mammalian expression vector Ptt5 (NRC-BRI, Canada) and expressed in CHO cells (Durocher, Y., Perret, S. & Kamen, A. High-level and high-throughput recombinant protein production by transient transfection of suspension-growing CHO cells. See, e.g., *Nucleic acids research* 30, E9 (2002)).

The CHO cells were transfected in exponential growth phase (1.5 to 2 million cells/Ml) with aqueous 1 mg/Ml 25 kDa polyethylenimine (PEI, Polysciences) using an EI:DNA ratio of 2.5:1 (see, e.g., Raymond C. et al. A simplified polyethylenimine-mediated transfection process for large-scale and high-throughput applications. *Methods*. 55(1):44-51 (2011)). In order to determine the optimal concentration range for forming heterodimers, the DNA was transfected in optimal DNA ratios of the heavy chain A (HC-A), heavy chain B (HC-B), and light chain(s) (LC, LC-A, LC-B)) that allow for heterodimer formation (e.g. HC-A/HC-B/LC ratios=40:40:20; HC-A/HC-B/LC-A/LC-B) ratios=12.5:12.5:25:50). Transfected cells were harvested after 5-6 days with the culture medium collected after centrifugation at 4000 rpm and clarified using a 0.45 m filter.

The clarified culture medium was loaded onto a MabSelect SuRe (GE Healthcare) protein-A column and washed with 10 column volumes of PBS buffer at Ph 7.2. The antibody construct was eluted with 10 column volumes of citrate buffer at Ph 3.6 with the pooled fractions containing the antibody construct neutralized with TRIS at Ph 11. Antibody construct was then quantified based on A280 nm (NanoDrop™).

The antibody construct was further purified by gel filtration using a Superdex 200 HiLoad 16/600 200 pg column (GE Healthcare) via an AKTA Express FPLC at a flowrate of 1 Ml/min. PBS buffer at Ph 7.4 or A5-NaCl (50 Mm sodium acetate, 150 Mm sodium chloride, Ph 5.0) buffer was used at a flow-rate of 1 Ml/min. Fractions of eluted antibody construct were collected based on A280 nm and the fractions were assessed by non-reducing and reducing High Throughput Protein Express assay using Caliper LabChip GXII (Perkin Elmer, Waltham, MA). Procedures were carried out according to HT Protein Express LabChip User Guide version2 LabChip GXII User Manual, with the following modifications. Antibody construct samples, at either 2 μl or 5 μl (concentration range 5-2000 ng/μl), were added to separate wells in 96 well plates (BioRad, Hercules, CA) along with 7 μl of HT Protein Express Sample Buffer (Perkin Elmer #760328). Antibody construct samples were then denatured at 70° C. for 15 mins. The LabChip instrument was operated using the HT Protein Express Chip (Perkin Elmer, Waltham, MA) and the Ab-200 assay setting. Fractions corresponding to the purified Antibody construct were collected, buffer-exchanged into A5Su (50 Mm sodium acetate, 9% sucrose, Ph 5.0) using a Zeba Spin desalting column (Thermo Scientific), concentrated to ~1 mg/Ml, and stored at −80° C.

Endotoxin levels were determined by the LAL (limulus amebocyte lysate) assay using the Endosafe® Portable Test System (PTS, Charles River, Wilmington, MA). Antibody construct was quantified based on A280 nm (Nanodrop) post protein-A and SEC.

UPLC-SEC was performed using a Waters Acquity BEH200 SEC column (2.5 Ml, 4.6×150 mm, stainless steel, 1.7 m particles) (Waters LTD, Mississauga, ON) set to 30° C. and mounted on a Waters Acquity UPLC H-Class Bio system with a PDA detector. Run times consisted of 7 min and a total volume per injection of 2.8 μL with a running buffer of DPBS or DPBS with 0.02% Tween 20 Ph 7.4 at 0.4 Ml/min. Elution was monitored by UV absorbance in the range 210-500 nm, and chromatograms were extracted at 280 nm. Peak integration was performed using Empower 3 software.

The apparent purity and yield of the final antibody construct was estimated by UPLC-SEC and LC/MS as described in detail in, e.g., WO2015109131. All antibody constructs were expressed and purified to >90% heterodimer purity without contaminating homodimers.

Example 2: Thermal Stability of MSLN×CD3 Bispecific Antibody Constructs

The thermal stability of the engineered full-sized bi-/trivalent and bispecific anti-MSLN/anti-CD3 antibody constructs was assessed by differential scanning calorimetry (DSC).

All DSC experiments were carried out using a GE VP-Capillary instrument. The proteins were buffer exchanged into PBS (Ph 7.4) and diluted to 0.3 to 0.7 mg/Ml with 0.137 Ml loaded into the sample cell and measured with a scan rate of 1° C./min from 20 to 100° C. Data was analyzed using the Origin software (GE Healthcare) with the PBS buffer background subtracted.

TABLE 7 shows the maximum melting temperatures (Tm) for each of the peaks in the thermograms of the bivalent and trivalent bispecific anti-MSLN/anti-CD3 antibody constructs.

TABLE 7

Thermostability Data of Tested Antibody Constructs

| Antibody Construct | Targeting Domains | Tm1 (° C.) | Tm2 (° C.) | Tm3 (° C.) | Tm4 (° C.) |
|---|---|---|---|---|---|
| v21815 | scFv, Fab | 62.36 | 66.67 | 77.44 | 82.01 |
| v21812 | scFv$^2$, Fab | 61.21 | 66.90 | 75.58 | 81.87 |
| v21791 | Fab$^3$ | 59.61 | 76.05 | 81.70 | |
| v29045 | scFv$^2$, Fab | 66.72 | 76.34 | | |
| v29048 | scFv$^2$, Fab | 66.08 | 76.19 | | |
| v29191 | Fab$^3$ | 75.46 | | | |

The results in TABLE 7 show that the constructs containing one or more scFv domains can exhibit lower thermostability compared to Fab-based trivalent bispecific constructs, e.g., v21791 and 2+1 Fab$^3$ TCB, which have Fab thermal melting temperatures of over 72° C., comparable to Fabs of commercial IgG antibodies.

Example 3: Determination of Mesothelin Density on Cell Surface of Target Cell Lines As described in various experiments herein, target cell lines with differing levels of plasma membranous mesothelin expression were used to assess how bispecific format and affinity towards mesothelin may impact binding to target and T cells as well as T cell-mediating killing of target cells.

Therefore, plasma membranous mesothelin expression was quantified on those different cell lines as described below.

The Antibody Binding Capacity on cancer cell lines expressing different levels of mesothelin was assessed by flow cytometry using Quantum Simply Cellular anti-human IgG kit (Bangs Laboratories, Inc.). Briefly, Alexa Fluor 647-labelled anti-MSLN antibody, v18490, was used to stain beads and test samples according to the manufacturer's instructions and were run on the same day and at the same photomultiplier tube settings. To calculate the cell surface Antibody Binding Capacity values, the geometric means for the four Quantum Simply Cellular beads and test samples were uploaded to the QuickCal v2.3 Excel spreadsheet-based analysis template (Bangs Laboratories, Inc.).

Plasma membranous mesothelin densities of several cancer cell lines are shown in TABLE 8 below. OVCAR-3 cells showed the highest expression levels followed by H292, HCT116, and BxPC3. MCF7 cells expressed the lowest levels of mesothelin.

TABLE 8

Mesothelin Density on used Cancer Cells Represented as the Average Antibody Binding Capacity

| Cell line | Mesothelin Density (antibody binding capacity) |
|---|---|
| H226 | N/D |
| OVCAR-3 | 768,926 |
| H292 | 152,986 |
| OVCAR-8 | ~85,000 |
| HCT116 | 35,963 |
| BxPC3 | 17,921 |
| A375 | 12,142 |
| H2452 | 10,923 |
| A549 | 10,808 |
| MCF7 | 547 |

Example 4: Assessment of Native Antigen Binding of Antibody Constructs Using Cell ELISA and Flow Cytometry This example describes experiments testing the impact of the bispecific antibody construct's format on its ability to bind to MSLN and CD3 antigens, wherein the binding affinity to native MSLN and CD3 antigens was measured by whole cell ELISA and flow cytometry as described below.

Figure 2A:
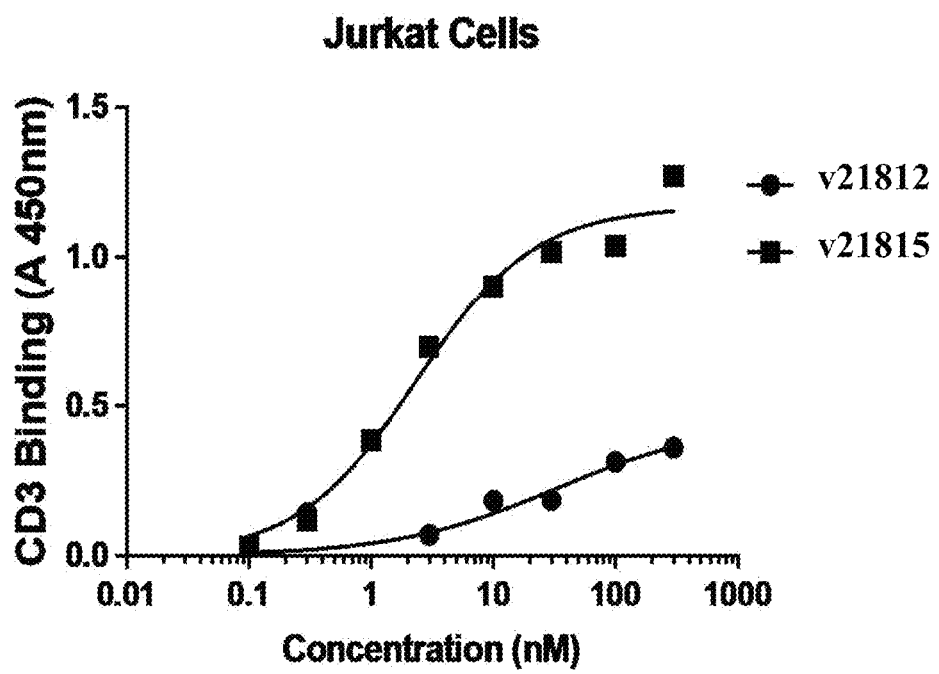
FIG. 2A and FIG. 2B show binding of the trivalent and bispecific anti-(MSLN (scFv$^2$)×CD3 (Fab)) antibody construct v21812 to CD3 on CD3$^+$ Jurkat cells, as assessed by ELISA, and compared to the bivalent and bispecific construct v21815 (FIG. 2A) and the trivalent and bispecific anti-(MSLN×CD3) Fab$^3$ antibody construct v21791 (FIG. 2B).
Figure 2B:
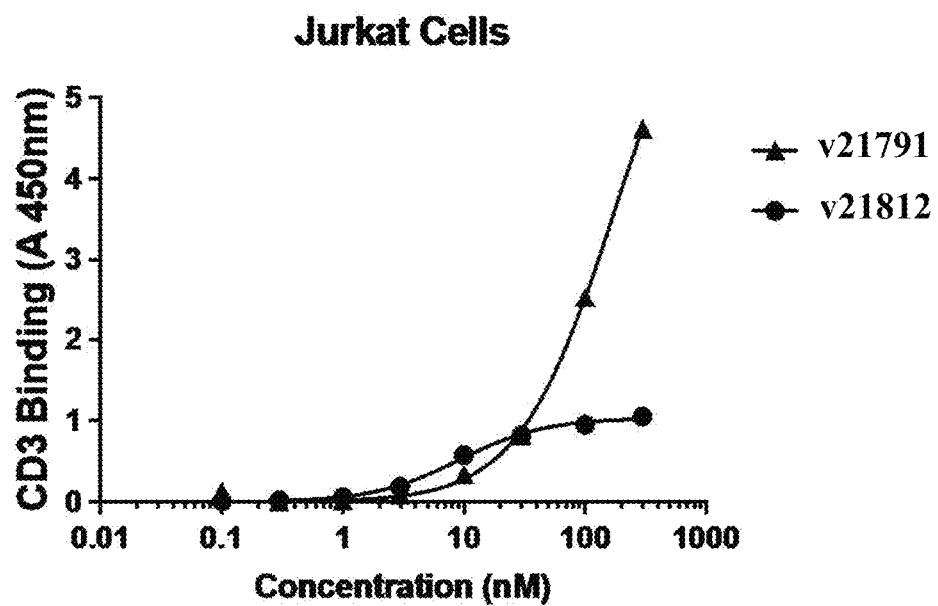

Whole cell binding to CD3$^+$ Jurkat cells (see, e.g., Weiss, J Immunol 1984) of antibody constructs was assessed via Cell ELISA. Cells were centrifuged and seeded in a 96-well filter plate in 50% complete culture medium 50% Blocking buffer. Equal volumes of antibody constructs v21812, v21815 and v21791 or controls were added to cells and incubated for 1 hour. The plate was washed 4 times using vacuum filtration. Subsequently, an HRP-conjugated anti-human IgG Fc gamma specific secondary antibody was added to the wells and further incubated for 1 hour. The plate was washed 7 times by vacuum filtration followed by the addition of TMB substrate at room temperature. The reaction was stopped by adding 1 M sulfuric acid and supernatant was transferred into a clear 96-well plate. Absorbance (450 nm) was read on a Spectramax 340PC plate reader with path-check correction. Binding of the different constructs v21812, v21815 and v21791 to Jurkat cells and the apparent binding affinities are shown in FIGS. 2A-2B and TABLE 9, respectively. The data show that the trivalent and bispecific MSLN×CD3 (2×1) antibody construct v21812 (comprising 2 anti-MSLN scFv domains and 1 anti-CD3 Fab domain, see FIG. 1A) showed, at least in the absence of tumor cells, a slightly less potent binding to CD3$^+$ Jurkat cells compared to both the bivalent and bispecific MSLN×CD3 (1×1) antibody construct v21815 (comprising 1 anti-MSLN Fab domain and 1 anti-CD3 scFv domain, see, e.g., FIG. 1C) as well as the trivalent and bispecific MSLN×CD3 (2×1) antibody construct v21791 (comprising 2 anti-MSLN Fab domains and 1 anti-CD3 Fab domain, see, e.g., FIG. 1B). These data demonstrate the measurable impact a construct's format and geometry can have on antigen binding, but they also show that CD3$^+$ cell binding (and activation) of the antibody construct v21812 may be more dependent on the presence of a tumor-associated antigen such as MSLN, potentially providing initial evidence of a more TAA-dependent T cell activation of antibody construct having the format of v21812, also illustrated in FIG. 1A.

Figure 3A:
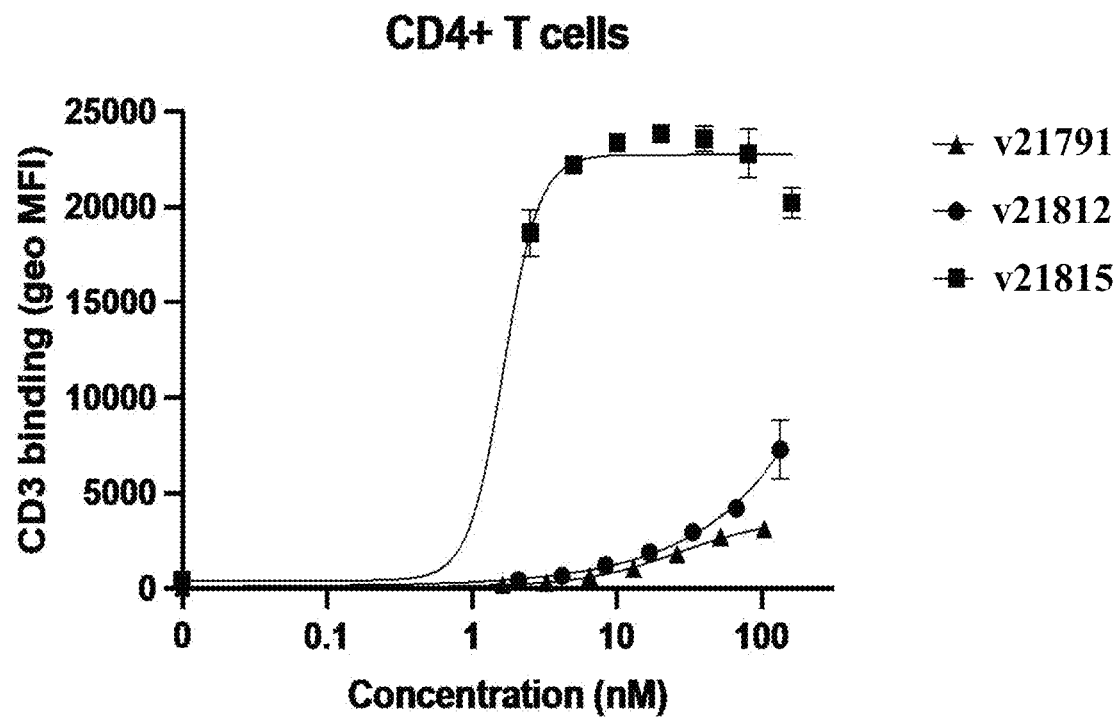
FIG. 3A and FIG. 3B show binding of the trivalent and bispecific anti-(MSLN×CD3) antibody construct v21812, the bivalent and bispecific construct v21815, and the trivalent and bispecific anti-(MSLN×CD3) Fab$^3$ antibody construct v21791, to CD3 on CD4$^+$ (FIG. 3A) and CD8$^+$ (FIG. 3B) T cells, as assessed by flow cytometry.
Figure 3B:
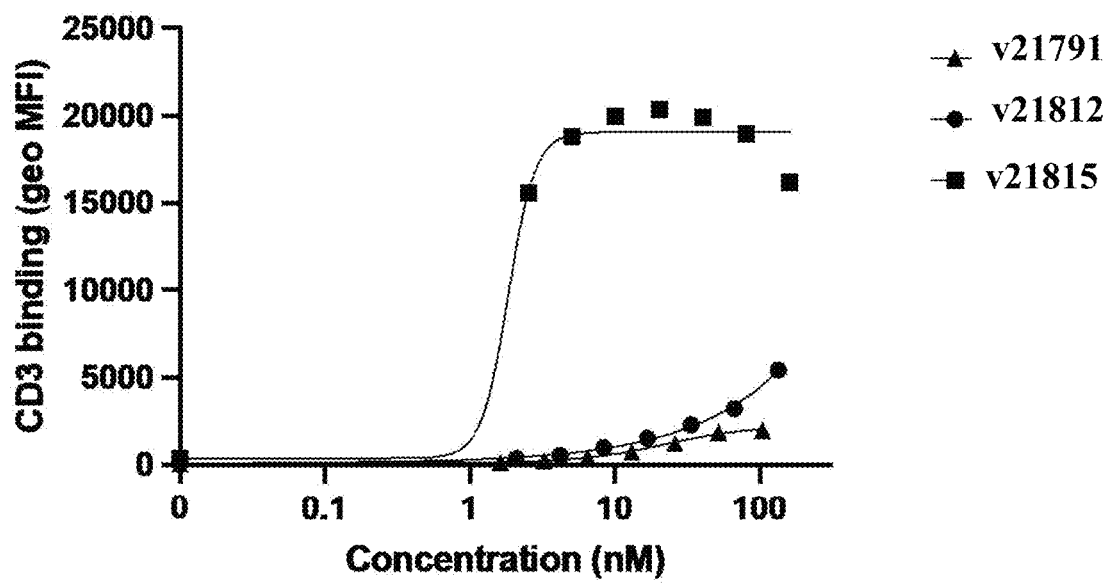

To assess binding of antibody constructs to primary human T cells, frozen human pan T cells or PBMCs were thawed and incubated with either media or serial dilutions of the antibody construct for one hour at 4° C. Commercially available SP34-2 antibody was used as positive control while untreated cultures were used as negative controls. Following incubation with the antibody constructs, the cells were washed and stained with a panel of conjugated antibodies specific for CD4, CD8, and IgG-Fc. The samples were acquired on a flow cytometer and analyzed using FlowJo version 10.1 software. Binding of the different antibody constructs to primary human CD4+ and CD8+ T cells and the apparent binding affinities are shown in FIGS. 3A-3B and TABLE 9, respectively. The data show that the trivalent and bispecific MSLN×CD3 (2×1) antibody construct v21812 exhibited anti-CD3 binding on CD4+ and CD8+ T cells that was comparable to that of the other trivalent and bispecific MSLN×CD3 (2×1, Fab$^3$) antibody construct v21791, and significantly lower than that of the bivalent and bispecific MSLN×CD3 (1×1) antibody construct v21815, further demonstrating the potential impact of construct format on antigen binding.

Figure 4A:
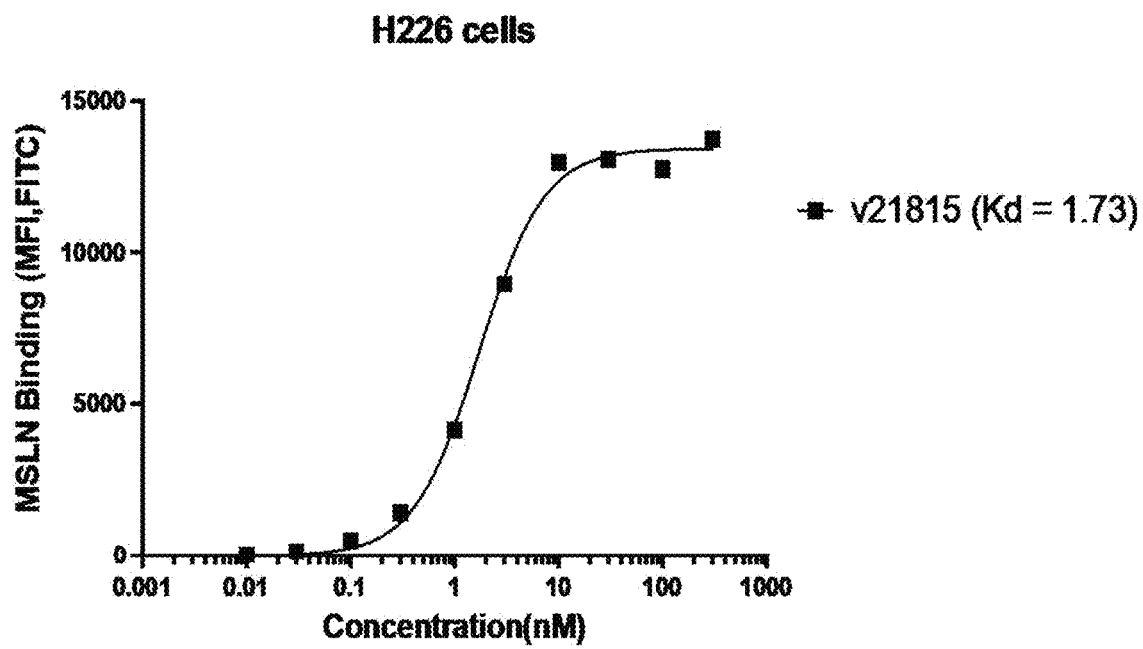
FIG. 4A and FIG. 4B show binding of the bivalent and bispecific construct v21815 to MSLN on MSLN$^+$ H226 cells as measured by flow cytometry (FIG. 4A), with a measured $K_D$ value of about 1.73 nM, as well as binding of the trivalent and bispecific anti-(MSLN×CD3) antibody construct v21812 (i.e., comprising 2 anti-MSLN scFvs+1 anti-CD3 Fab) and the Fab$^3$ antibody constructs v21791 to MSLN on MSLN$^+$ H226 cells as measured by flow cytometry (FIG. 4B), with measured $K_D$ values of about 0.47 nM (v21812) and 0.74 nM (v21791), respectively.
Figure 4B:
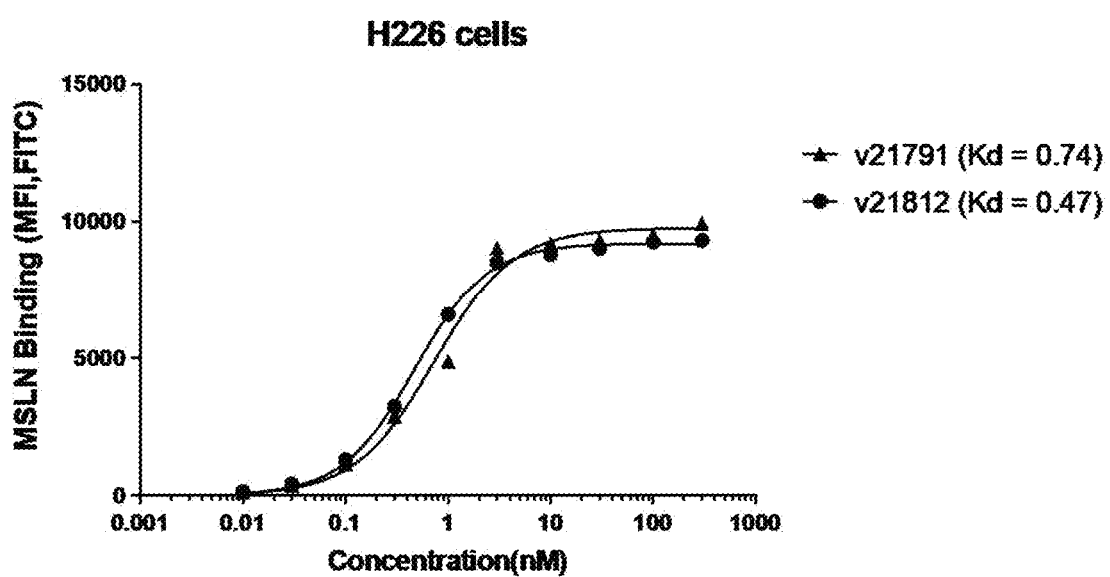

The ability of the tested antibody constructs to bind MSLN-expressing H226 cells was assessed via whole cell FACS binding analysis as described previously (see, e.g., WO2015109131). The binding of the tested antibody constructs to MSLN+ H226 cells (ATCC: CRL-5826; Gazdar, Cancer Res 1990) and apparent binding affinities of the constructs are shown in FIG. 4A-4B and TABLE 9, respectively.

TABLE 9

Apparent Cell Binding Affinities of Tested Constructs

| Antibody Construct | Apparent Affinity (EC$_{50}$, nM) | | |
|---|---|---|---|
| | Jurkat cells | Human T cells | H226/OVCAR-3 cells |
| 18490 | N/A | N/A | 1.6 |
| 21815 | 2.4 | 0.2 | 1.7 |
| 21791 | 402 | 7.4 | 1.9 |
| 21812 | 17.7 | 58.8 | 0.4 |
| 29045 | 1.3 | IND | 0.4 |
| 29048 | 5.5 (15.8) | 183.3 | 0.5 |

The bispecific anti-MSLN/anti-CD3 constructs bound human MSLN+ cells with high affinity (apparent affinity of 0.45-1.93 nM). Unlike the bispecific constructs that were monovalent for MSLN and CD3, the trivalent constructs, e.g., v21812, appear to exhibit bimodal binding to MSLN, indicating single arm followed by two arm binding to the antigen. The observation of bimodal binding suggests that the trivalent formats that are bivalent for MSLN may have an improved ability to differentiate between normal cells expressing low levels of MSLN and tumors expressing high levels of MSLN through increased avidity to MSLN rather than through modifications to affinity, when compared to constructs that are monovalent for MSLN.

The trivalent and bispecific antibody constructs, v21812, v21791, v29045, and v29048, which are bivalent for MSLN and monovalent for CD3 exhibited a reduced binding to CD3+ Jurkat T cells and primary human T cells compared to the bivalent bispecific construct, v21815, which is monovalent for both CD3 and MSLN. These differences in apparent binding affinity between the bivalent and trivalent constructs suggest that binding to target antigens may be format dependent. For example, addition of a second MSLN binding arm to specific sites on the immunoglobulin molecule may result in steric hindrance, thereby decreasing CD3 binding of the construct.

Example 5: Impact of Format of Bispecific Constructs on their In Vitro Activity

To determine the impact of a construct's format on its in vitro activity and preferential killing of tumor cells overexpressing MSLN, selected constructs were tested in primary blood cultures with allogeneic tumor cell lines having varying levels of MSLN expression. The assay was performed in triplicate (n=3) using the experimental set-up as described below.

Frozen human PBMCs were mixed with OVCAR-3 cells (~768,000 MSLN/cell), BxPC3 cells (~17,000 MSLN/cell), or MCF-7 cells (~500 MSLN/cell) such that the ratio of PBMCs to allogeneic tumor cells was adjusted to an E:T ratio of 10:1. The mixtures were incubated together with the selected antibody constructs for 48 hours, after which Vybrant™ DyeCycle™ Violet Stain (ThermoFisher Scientific; V35003) was added to the cells. After a 30-minute incubation period, tumor cell viability was assessed through live tumor cell counts using the CellInsight High Content Screening Platform (ThermoFisher Scientific; CX51110).

Figure 5A:
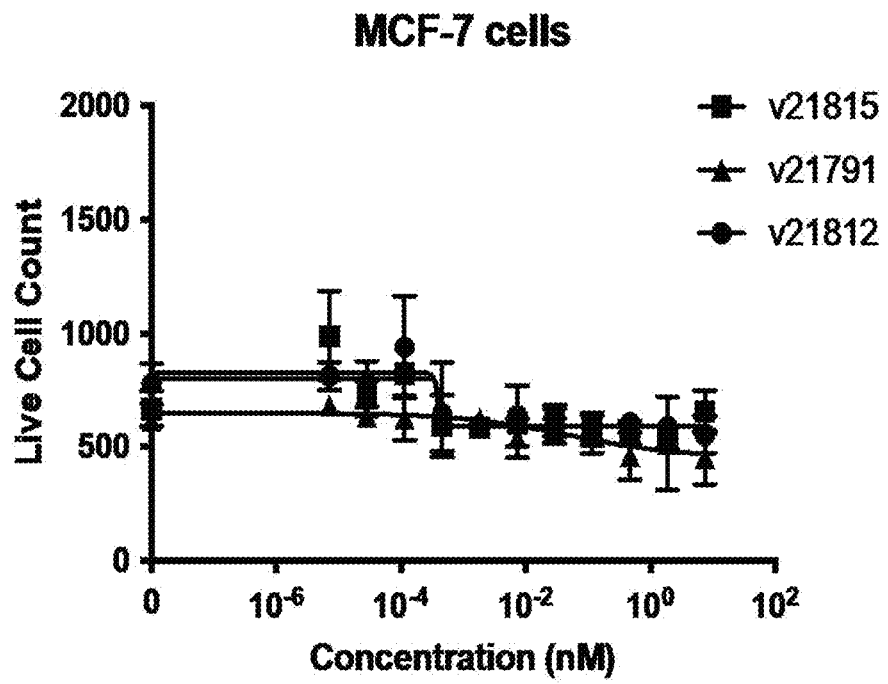
FIGS. 5A-5D show that the trivalent and bispecific anti-(MSLN×CD3) antibody construct v21812 as well as the constructs v21815 and v21791 directed T cells from healthy donors to kill MSLN+ target tumor cells expressing different levels of MSLN: MCF-7 cells (~500 MSLN/cell, FIG. 5A), BxPC3 (~17,000 MSLN/cell, FIG. 5B), and OVCAR-3 (~768,000 MSLN/cell, FIG. 5C). The data show that construct v21812 demonstrated the most potent killing of medium and high MSLN-expressing tumor cells as shown in FIG. 5B and FIG. 5C for BxPC3 and OVCAR-3 cells, respectively.
Figure 5B:
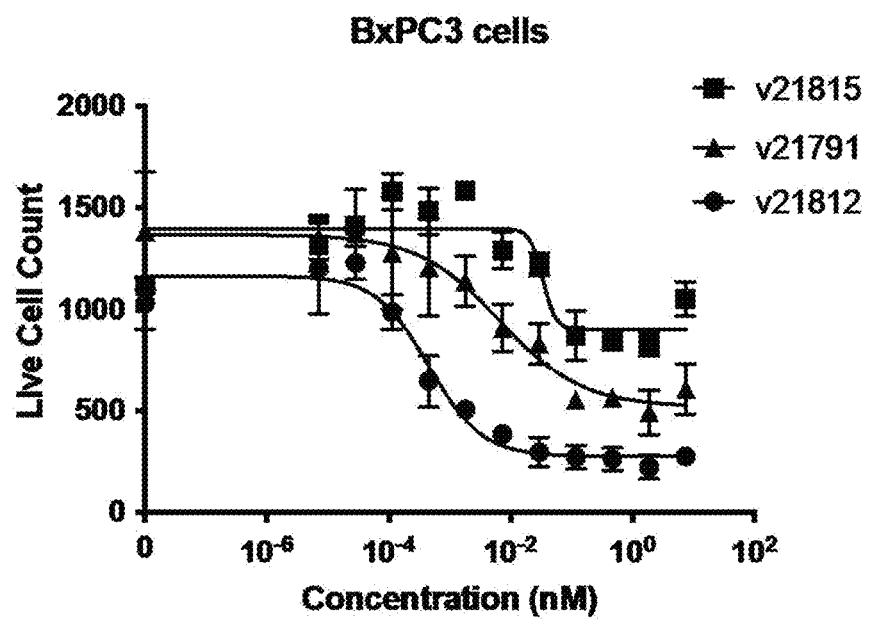
Figure 5C:
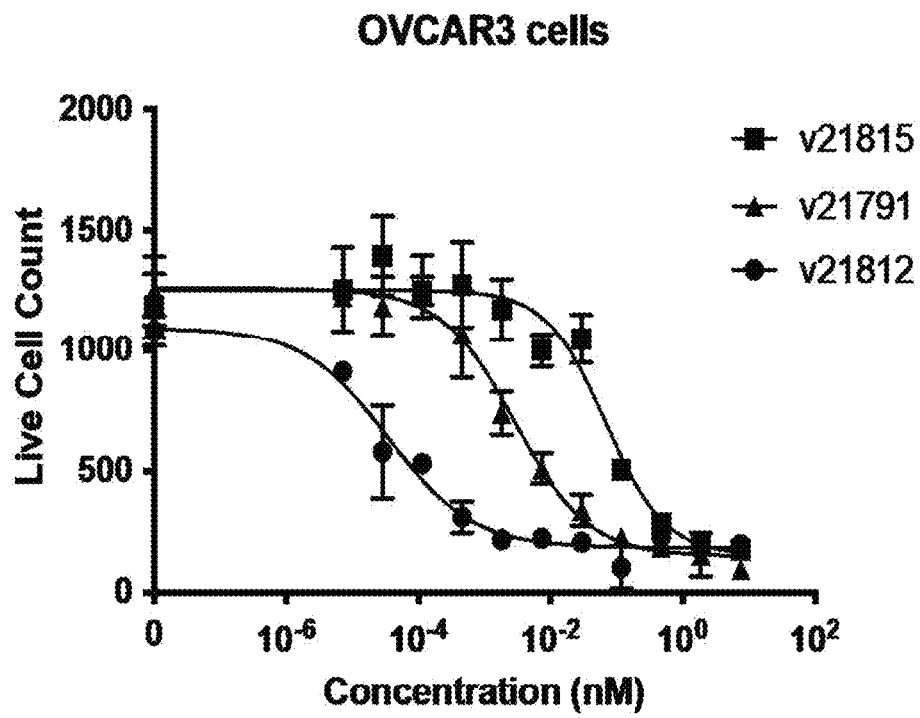

As illustrated in FIGS. 5A-5C and TABLE 10, the potency of the different anti-MSLN/anti-CD3 constructs largely correlated with the level of MSLN expressed by the cell lines, with the highest potency observed towards OVCAR-3 cells (~768,000 MSLN/cell) and the lowest towards MCF-7 cells (~500 MSLN/cell).

TABLE 10

Cytotoxic Activity of Bivalent and Trivalent Bispecific Constructs Towards MSLN+ Tumor Cells with Varying MSLN Expression Levels.

| Construct | OVCAR-3 (Ic$_{50}$ pM) | BxPC3 (Ic$_{50}$ pM) | MCF-7 (Ic$_{50}$ pM) |
| --- | --- | --- | --- |
| 21791 (trivalent) | 2.9 | 6.7 | ND |
| 21812 (trivalent) | 0.03 | 0.5 | ND |
| 21815 (bivalent) | 67.5 | 33.9 | ND |

Figure 5D:
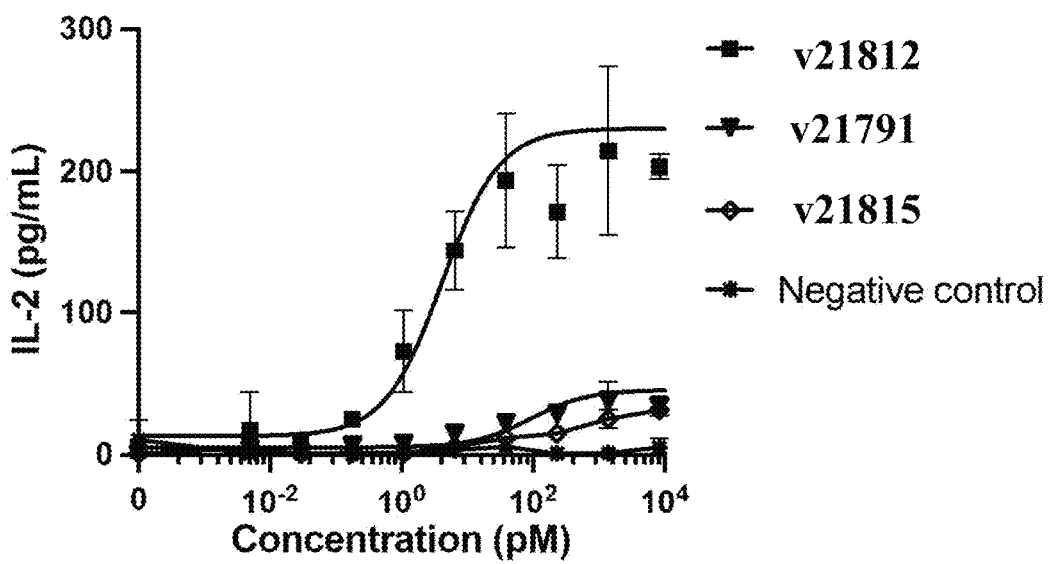

FIG. 5D further shows that the trivalent and bispecific construct v21812 induced significantly higher IL-2 release when compared to both the triple-Fab (Fab$^3$; anti-CD3 Fab×anti-MSLN Fab$^2$) construct v21791 as well as the 1+1 anti-CD3 scFv×anti-MSLN Fab construct v21815. Cytokine release was assessed by co-culturing OVCAR3 tumor cells with human pan-T cells and treating with the test articles for 3 days.

The trivalent and bispecific antibody constructs comprising two anti-MSLN scFv domains and one anti-CD3 Fab domain, e.g., v21812, exhibited the greatest cytotoxic activity towards two of the cell lines overexpressing MSLN, i.e., OVCAR-3 and BxPC3, with low picomolAR (pM) IC$_{50}$ values, and were surprisingly more potent than even the trivalent and bispecific construct v21791 comprising two anti-MSLN Fab domains and one anti-CD3 Fab domain (the latter one showed higher CD3 binding, see, e.g., EXAMPLE 4). This finding demonstrates the impact a construct's format can have of its T cell engaging and activating properties. Indeed, the "triple-Fab" or "Fab$^3$" construct v21791 exhibited approximately 10 to 100 fold lower potency towards OVCAR-3 and BxPC3 compared to the dual scFv trivalent variant, v21812. Maximum killing of the MSLN$^{mid-lo}$ cell line, BxPC3, was also affected by THE MSLN-CD3 bispecific format of the constructs. The maximum killing of BxPC3 induced by the dual scFv format, v21812, was 75%, while the triple-Fab format, v21791, induced 60%, and the bivalent bispecific construct only induced 35%. As expected, no relevant killing of MSLN$^{low/neg}$ cell line, MCF-7, was induced by the three constructs tested. However, both trivalent constructs tested, v21791 and v21812, exhibited greater cytotoxic activity than the bivalent bispecific, v21815.

These results further demonstrate that the cytotoxic activity towards the allogeneic target tumor cells can be modulated through modification of both a construct's valency and format, with the trivalent and bispecific consisting of two anti-MSLN scFv domains and one anti-CD3 Fab domain, v21812, being the most active of all tested construct. In addition, these results suggest that modifying format and valency of a T cell engaging antibody construct can promote preferential killing of tumor cells overexpressing MSLN over cells that have low MSLN expression, as little killing of the MSLN$^{low/neg}$ cell line, MCF-7, was observed.

Example 6: Impact of Bispecific Construct Format on In Vivo Anti-Tumor Activity

This example assessed the impact of the trivalent and bispecific antibody construct's (v21812) format on its in vivo anti-tumor activity using a tumor growth inhibition xenograft study in humanized NOG mice bearing subcutaneous human ovarian NIH:OVCAR-3 tumors. The performance of the trivalent and bispecific construct v21812 was compared to the corresponding Fab$^3$ construct v21791 which contained the same anti-CD3 and anti-MSLN paratope sequences and thus only varied in its format Fab$^3$ (anti-CD3 Fab×anti-MSLN Fab$^2$) vs. Fab (anti-CD3)×scFv$^2$ (anti-MSLN) for v21812.

In Vivo Amplification of Subcutaneous NIH:OVCAR-3 Tumors in Nude Mice

Frozen NIH:OVCAR-3 ascitic cells, obtained from previous in vivo amplification after intraperitoneal (IP) injection of NIH:OVCAR-3 cells, were thawed and subsequently subcutaneously (SC) implanted into Balb/C nu/nu mice (Charles River Laboratories). The NIH:OVCAR-3 ascitic tumor cell implantation was performed 24 to 72 hours after whole body irradiation with a J-source (1.44 Gy, 60Co, BioMEP S.A.RL., Dijon, France). Tumors were fragmented when they reached 500-1500 mm$^3$.

NIH:OVCAR-3 Tumor Induction in NOG Mice for Anti-Tumor Activity Study

Ninety-three (93) irradiated NOG female mice (Taconic), were subcutaneously implanted with the NIH:OVCAR-3 tumor fragments, 24 to 72 hours after irradiation (1.44 Gy, 60Co, BioMep, Bretenieres, France). PBMCs were injected when tumors reached 100-200 mm$^3$. The 93 mice were then split in 3 sub-groups of 31 mice (one sub-group for each donor A, B or C). The three sub-groups had equivalent mean tumor volumes. Each one of the three PBMCs donors was injected in one sub-group of 31 tumor bearing mice on the same day. Each mouse received one single intravenous (IV) injection of 10$^7$ PBMCs (200 μL in PBS).

Two to three days post PBMCs injection, 20 mice from each of the three sub-groups were randomized according to their individual tumor volume using Vivo Manager® software (Biosystemes, Couternon, France). These 20 mice per donor were randomized to form 3 groups of 6 mice (for example, groups 1A, 2A and 3A with mice from donor A) and 2 mice were put in group 4. A statistical test (analysis of variance, ANOVA) was performed to test for homogeneity between groups for each donor. Mice were dosed intravenously with test articles on the day of randomization (DR) then every four days, according to the treatment schedule shown below in TABLE 11.

TABLE 11

Treatment Schedule for In Vivo Study

| Group | Test Article | Dose (IV) | Treatment Schedule |
|---|---|---|---|
| 1A (6 mice-donor A) | Vehicle | N/A | BIWx3W |
| 1B (6 mice-donor B) | | | |
| 1C (6 mice-donor C) | | | |
| 2A (6 mice-donor A) | v21791 | 1.5 mg/kg | BIWx3W |
| 2B (6 mice-donor B) | (Fab$^3$) | | |
| 2C (6 mice-donor C) | | | |
| 3A (6 mice-donor A) | v21812 | 1.5 mg/kg | BIWx3W |
| 3B (6 mice-donor B) | (Fab × scFv$^2$) | | |
| 3C (6 mice-donor C) | | | |

Animals were monitored at regular intervals for tumor growth using caliper measurements and for weight loss. Animals were euthanized and necropsied when (i) tumor volume reached a maximal tumor volume of 2,000 mm$^3$, (ii) when tumor exceeded 10% of normal body weight, (iii) when body weight loss was greater that 20%, or (iv) after a maximum of 12 weeks post tumor injection. Animal housing and experimental procedures were realized according to the French and European Regulations and NRC Guide for the Care and Use of Laboratory Animals.

Results

Figure 6A:
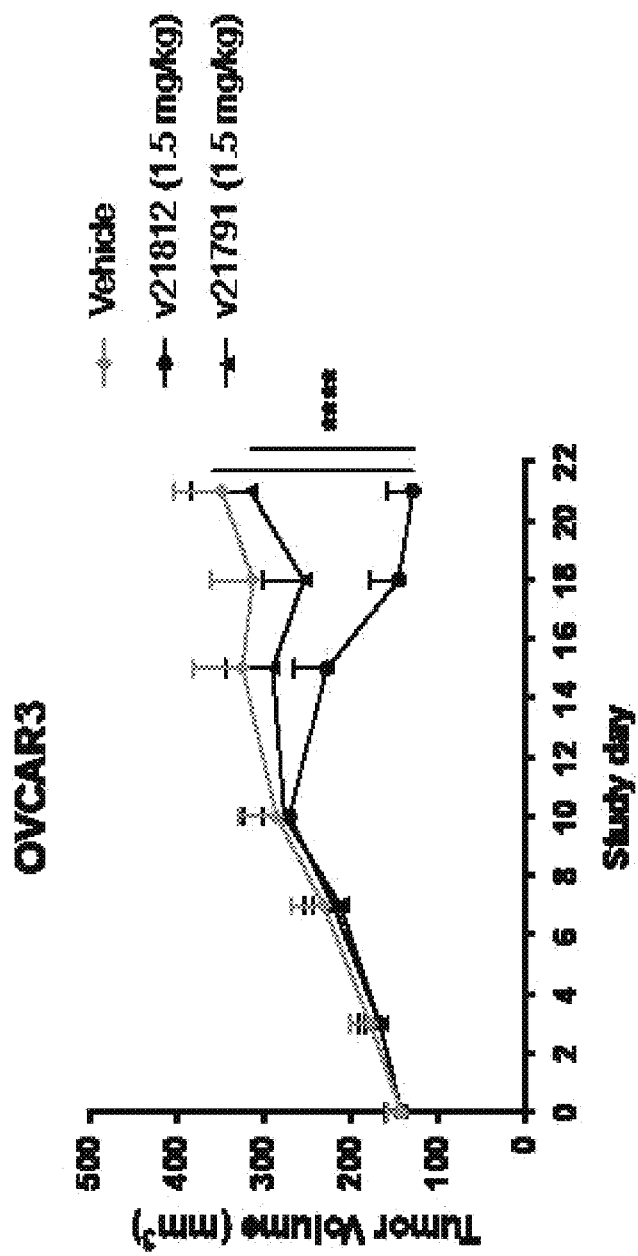
FIG. 6A shows that the trivalent and bispecific antibody construct v21812 inhibited tumor growth, and, over the course of the experiment, even reduced tumor volume, in OVCAR-3-tumor bearing NOG mice, engrafted with human PBMCs. The significant difference in tumor inhibition that the antibody construct v21812 ((MSLN)-scFv$^2$×(CD3)-Fab, see, FIG. 1A) with a specifically designed format and geometry provided in comparison to the corresponding trivalent and bispecific Fab$^3$ construct v21791 (see, e.g., FIG. 1B), which contained identical anti-CD3 and anti-MSLN paratope sequences, was unexpected and surprising, and demonstrates not only the superior in vivo performance of the scFv$^2$×Fab constructs described herein over conventional constructs, but also shows the impact that a construct's format (e.g., use of anti-MSLN scFv domains vs. Fab domains) can have on its properties.
Figure 6B:
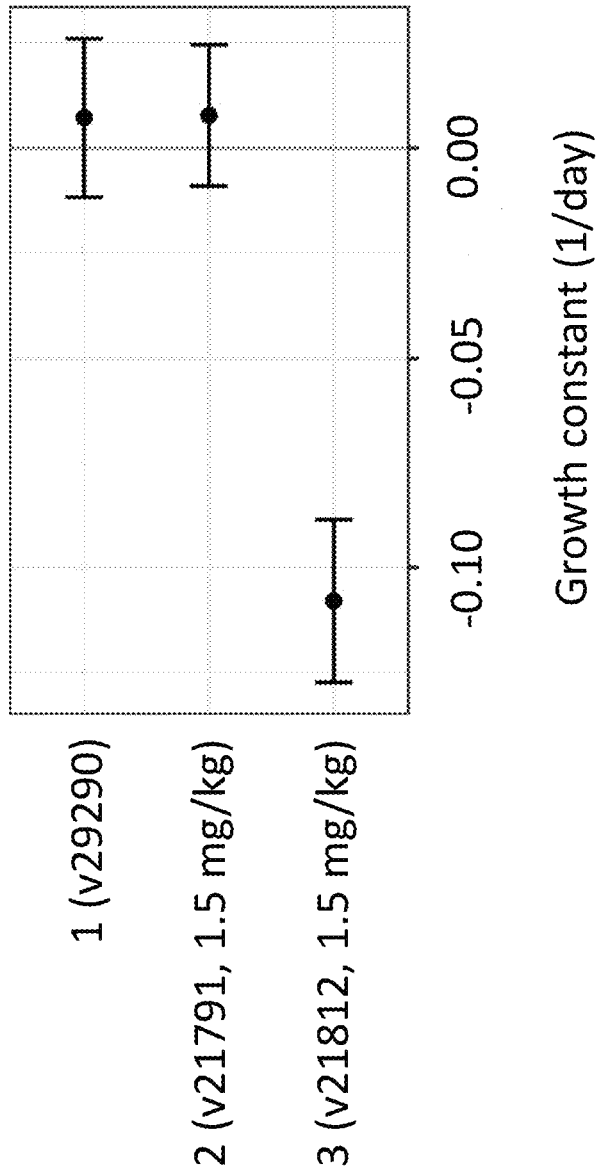
FIG. 6B shows results of the statistical analysis of the experimental data obtained from this in vivo study and further demonstrates that the construct v21812 achieved a significantly lower tumor growth constant compared to the Fab$^3$ construct v21791 which comprised the same anti-CD3 and anti-MSLN paratopes as v21812. The vehicle control was used as a negative control in this study.

OVCAR-3 cells expressed high levels of MSLN (~768,000 MSLN/cell) and were established from progressive ovarian adenocarcinoma. As shown in FIG. 6A, including statistical data in FIG. 6B, tumor outgrowth was observed in vehicle-treated animals and only marginally inhibited by the Fab$^3$ construct, v21791. Treatment with v21812 using a dose of 1.5 mg/kg, however, resulted in significant tumor growth inhibition and a reduction in tumor size relative to the vehicle- and v21791-treated animals. Animal body weight remained stable under all treatment conditions for the duration of the study.

Taken together, these data provide evidence that the Fab (anti-CD3)×scFv$^2$ (anti-MSLN) format of the trivalent and bispecific antibody construct, v21812, may be superior to other conventional formats (e.g., Fab$^3$) in eliciting anti-tumor responses in vivo, and thus this format may produce promising T cell engaging construct candidates (e.g., v21812, v32523) for cancer immunotherapy, that may be able to provide enhanced anti-tumor activity and reduced off-target effects compared to conventional approaches.

Example 7: Impact of Format and Anti-MSLN Paratope Affinity on a Construct's In Vitro Anti-Tumor Activity This example assessed the impact of a construct's format and its anti-MSLN paratope affinity on its cytotoxic anti-tumor activity in vitro. To that end, selected constructs, including the trivalent and bispecific T cell engager v21812, were tested in T cell-dependent cytotoxicity assays with tumor cell lines expressing varying levels of MSLN. Two additional molecules with the same format as v21812 but with reduced affinity to MSLN, v29045 and v29048, were included in this study, as were two benchmark control constructs, the trivalent and bispecific 2+1 Fab$^3$ TCB (v29191) (see, e.g., WO2017055391) and MH6T-triTAC (v31805) (see, e.g., US20180327508) for direct comparison of v21812 against preclinical and clinical benchmarks, respectively.

Experimental Procedure

Antibody constructs to be tested were diluted in RPMI1640 (Gibco)+10% FBS (ThermoFisher) and added to appropriate wells of the 384-well black flat bottom assay plates (ThermoFisher, Watham, MA). Human pan T cells were thawed and mixed with OVCAR-3 (high MSLN density), H292 (mid MSLN density), or IGROV1 (MSLN density) cells at an E:T ratio of 5:1. Plates were incubated for 72 hr at 37° C. and 5% carbon dioxide, after which Vybrant™ DyeCycle™ Violet Stain (ThermoFisher Scientific; V35003) was added to the cells. After a 30-minute incubation period with the stain, tumor cell viability was assessed through live tumor cell counts using the CellInsight High Content Screening Platform (ThermoFisher Scientific; CX51110). The assay was performed with n=3 primary blood donors.

Results

Figure 7A:
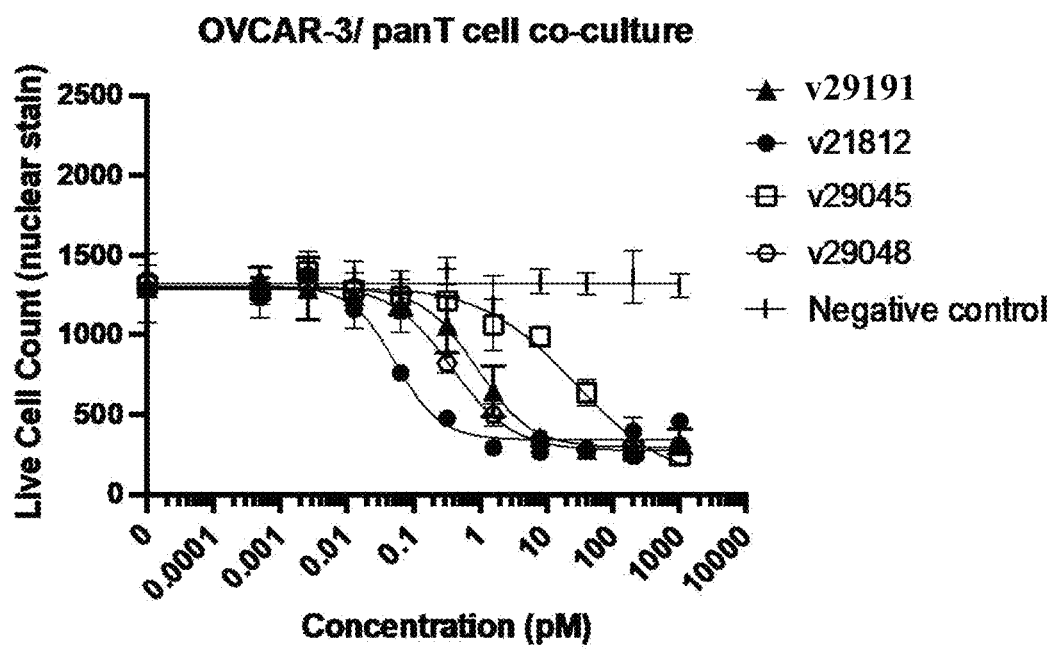
FIGS. 7A-7C show the tumor cell killing activity of the trivalent and bispecific anti-(MSLN×CD3) antibody construct v21812 as well as that of the other MSLN-targeting constructs with lower affinity anti-MSLN paratopes, v29045 and v29048, in three different cell lines having varying levels of MSLN expression and surface presentation: OVCAR-3 (FIG. 7A, ~700,000 MSLN/cell), H292 (FIG. 7B, ~170,000 MSLN/cell) and IGROV-1 (FIG. 7C), which was used as a MSLN-negative control cell line.
Figure 7B:
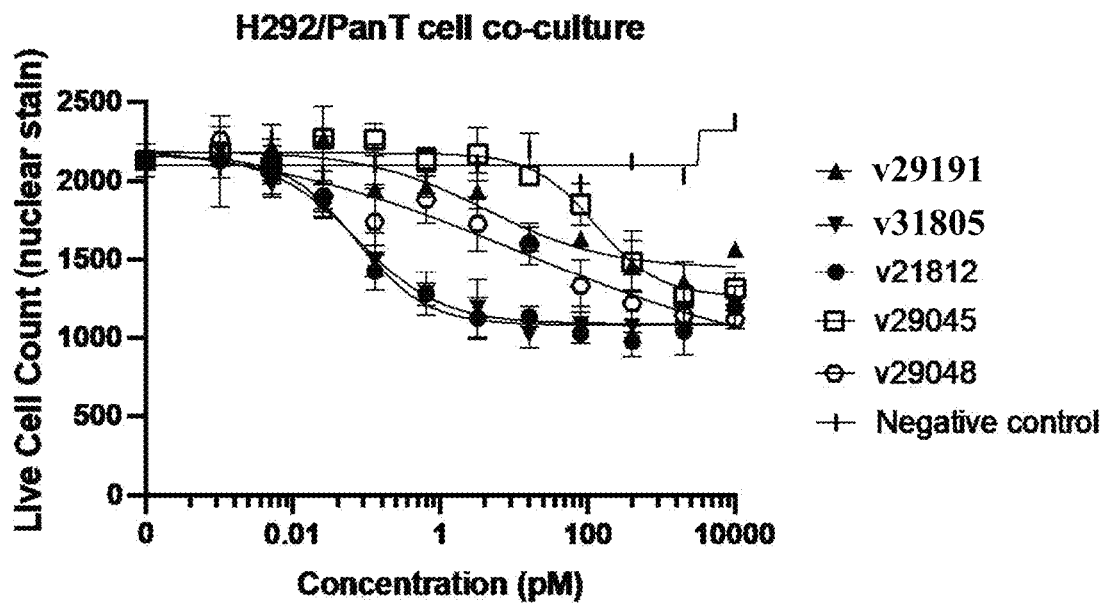
Figure 7C:
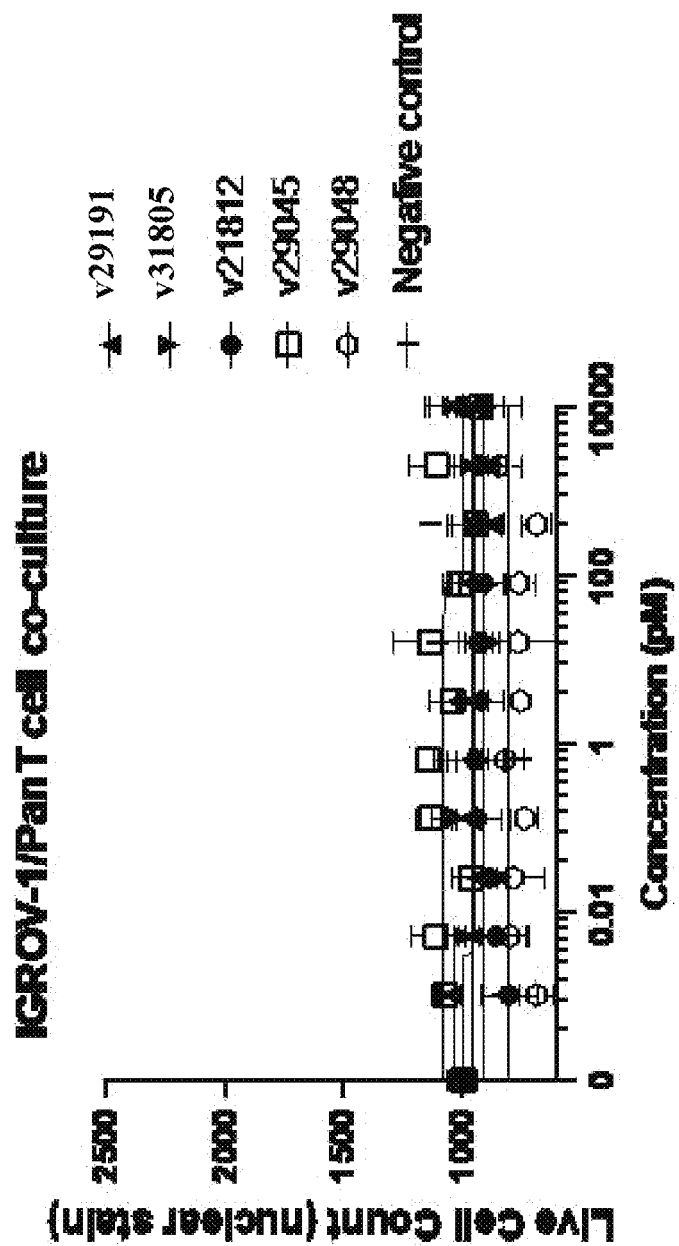

As illustrated in FIGS. 7A-7C and TABLE 12, the potency of the different anti-MSLN-CD3 constructs were positively correlated with the relative affinity towards MSLN as well as the MSLN density on the target cell surface.

TABLE 12

Cytotoxic Activity of Constructs with Engineered Format versus Benchmark Constructs Towards MSLN+ Tumor Cells Grown in Culture with Human Pan T cells

| | Affinity to MSln (nM) | OVCAR-3 (Ic$_{50}$ PM) | H292 (Ic$_{50}$ PM) | IGROV1 (Ic$_{50}$ PM) |
|---|---|---|---|---|
| Antibody Construct | | | | |
| v21812 | 0.9 | 0.05 | 0.07 | ND |
| v29048 | 9.8 | 0.4 | 14.5 | ND |
| v29045 | 62.6 | 27.2 | 129.8 | ND |
| Benchmarks: | | | | |
| v29191 | 0.02 | 0.89 | 4.3 | ND |
| v31805 | 0.04 | — | 0.07 | ND |

Generally, the data demonstrate that all tested constructs with varying valency, format, and geometry showed activity against the MSLN$^{high}$ OVCAR-3 cells and the MSLN$^{mid}$ H292 cells but no significant activity against IGROV-1 cells. The cytotoxic potencies of the three trivalent and bispecific constructs that comprised two anti-MSLN scFv domains and one anti-CD3 Fab domain, v21812, v29048, and v29045, were positively correlated with their binding affinity to MSLN. The construct with the highest anti-tumor cytotoxicity out of those three, v21812, was the one with the highest affinity to MSLN, followed by the molecule with the next highest affinity, v29048, then v29045, which had the lowest affinity to MSLN out of the three.

The construct v21812 also exhibited greater cytotoxic activity than the 2+1 Fab$^3$ TCB benchmark, v29191, even though v21812 has an about 45-fold lower binding affinity to MSLN. This surprising finding suggests that in constructs having moderately different binding affinities to MSLN (e.g., equal to or less than 50-fold), general anti-MSLN affinity may have less of an impact on anti-tumor activity than the constructs' formats. Similarly, the constructs v21812 and v31805 (MH6T-TriTAC) had equivalent activity against H292 cells, even though v21812 has an about 20-fold lower affinity to MSLN than the v31805 benchmark construct.

Overall, these results demonstrate that the cytotoxic activity towards allogeneic target tumor cells of the trivalent and bispecific T cell engaging antibody constructs disclosed herein that comprise two anti-MSLN scFv domains and one anti-CD3 Fab domain was increased compared to conventional molecules by modulating the construct's format and geometry. Specifically, it was unexpectedly found that a construct's format, e.g., having scFv domains instead of Fab domains, can have a stronger effect on a construct's anti-tumor activity than antigen affinity, provided that the difference in antigen affinity is not more than 100-fold, or not more than 50-fold. Indeed, the construct, v21812, had equivalent or even greater anti-tumor activity than the two benchmark constructs tested even though both benchmark molecules show higher apparent binding affinity towards MSLN (e.g., up to 50-fold).

Example 8: Impact of Construct Format and MSLN Affinity on Induction of Pro-Inflammatory Cytokine Release This example examined the impact of a construct's format and anti-MSLN affinity on its ability to induce pro-inflammatory cytokine production and release from immune cells.

Generally, the trivalent and bispecific anti-MSLN/anti-CD3 antibody constructs disclosed herein, e.g., v21812, can activate immune cells such as T cells by simultaneously binding to MSLN on cancer cells and CD3ε on T cells which can lead to cross-linking of CD3ε. The resulting signalling cascade can trigger T cell activation, leading to CD69 upregulation and/or cytokine secretion. To assess the impact of modulating a T cell engager's format and affinity for MSLN on T cell activation, the production of TNFα, IFNγ and IL-2 was measured for various antibody constructs as described below.

Experimental Procedure

Antibody constructs to be tested were diluted in RPMI1640 (Gibco)+10% FBS (ThermoFisher) and added to appropriate wells of the 384-well black flat bottom assay plates (ThermoFisher, Watham, MA). Human pan T cells were thawed and mixed with OVCAR-3 (high MSLN density) cells at an E:T ratio of 5:1 and then added to the plates. Plates were incubated for 72 hr at 37° C. and 5% carbon dioxide. Post incubation, 15 μL/well of supernatant was transferred to non-binding 384-well plates (Greiner-Bio-One, Kremsmünster, Austria) and stored at −80° C.

TNFα, IFNγ and IL-2 were quantified using MSD (Mesoscale Discovery, Piscataway, NJ). The night before cytokine quantification, MSD plates were blocked and coated in capture antibodies according to the manufacturers' instructions. The following day, plates were washed in PBS-T and 5 μl of assay diluent was added to each plate. The supplied TNFα, IFNγ and IL-2 standard (calibrator 1) was titrated as per manufacturer's instructions. Supernatants were thawed at room temperature and 5 μL of samples or standards were transferred to MSD plates. Detection antibodies were prepared at appropriate dilutions and 10 μL was added to each sample and standard well in MSD plates. The plates were sealed with aluminum foil and incubated away from light at room temperature for two hours. Plates were washed 3× in PBS-T and 40 μL MSD Gold read buffer T was added to each well. Plates were read on the MESO SECTOR 6000, and cytokine concentration was determined using MSD software. Data from a standard curve and samples were used to perform a nonlinear curve-fit with x-interpolation to obtain TNFα, IFNγ and IL-2 concentrations in Pg/mL. Three independent experiments were conducted and data from each was analyzed in a nonlinear mixed effect model to generate curve fit and 95% confidence intervals.

Results

Figure 8A:
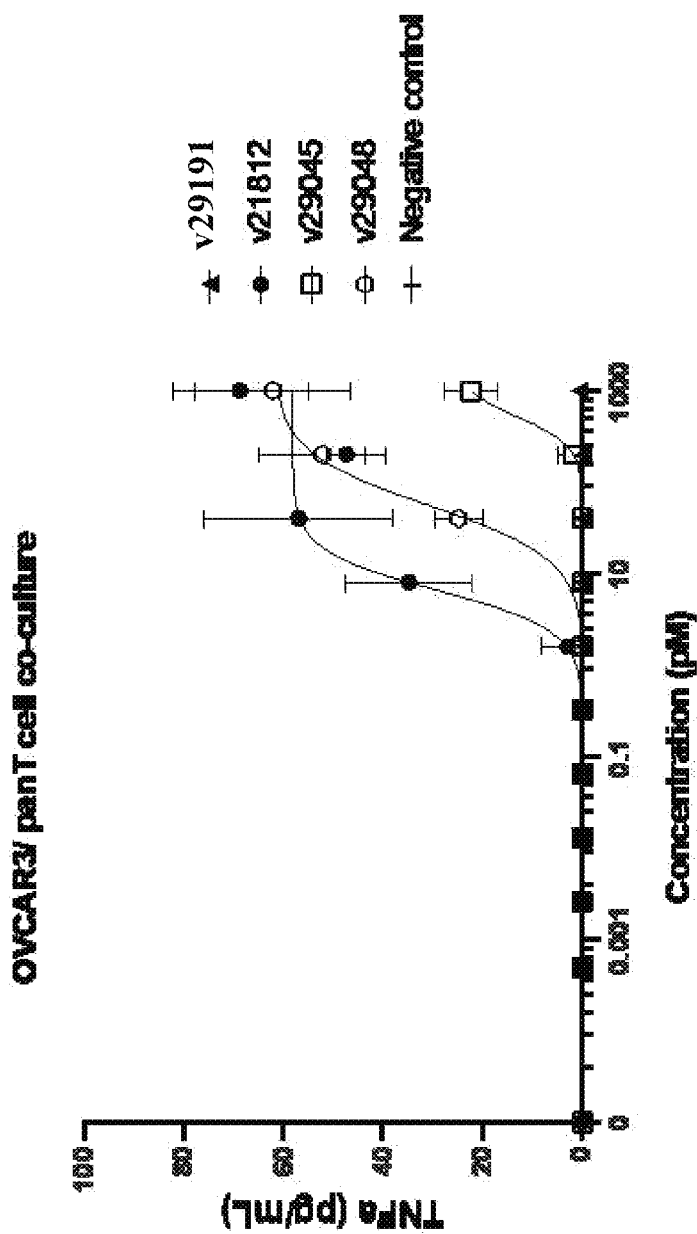
FIGS. 8A-8C show that particularly the trivalent and bispecific antibody construct v21812, and to a lower extent constructs v29045 and v29048 having lower anti-MSLN affinity paratopes, induced production of the pro-inflammatory cytokines tumor-necrosis factor α (TNFα, FIG. 8A), interferon-γ (IFNγ or IFNg, FIG. 8B) and interleukin-2 (IL-2, FIG. 8C) from T cells co-incubated with MSLN+ OVCAR-3 cells (effector cell (E):tumor cell (T) ratio of 5:1) for 48 hours, and when further compared to the 2+1 Fab$^3$ TCB benchmark construct v29191 (same format but different paratope sequences compared to Fab$^3$ construct v21791).
Figure 8B:
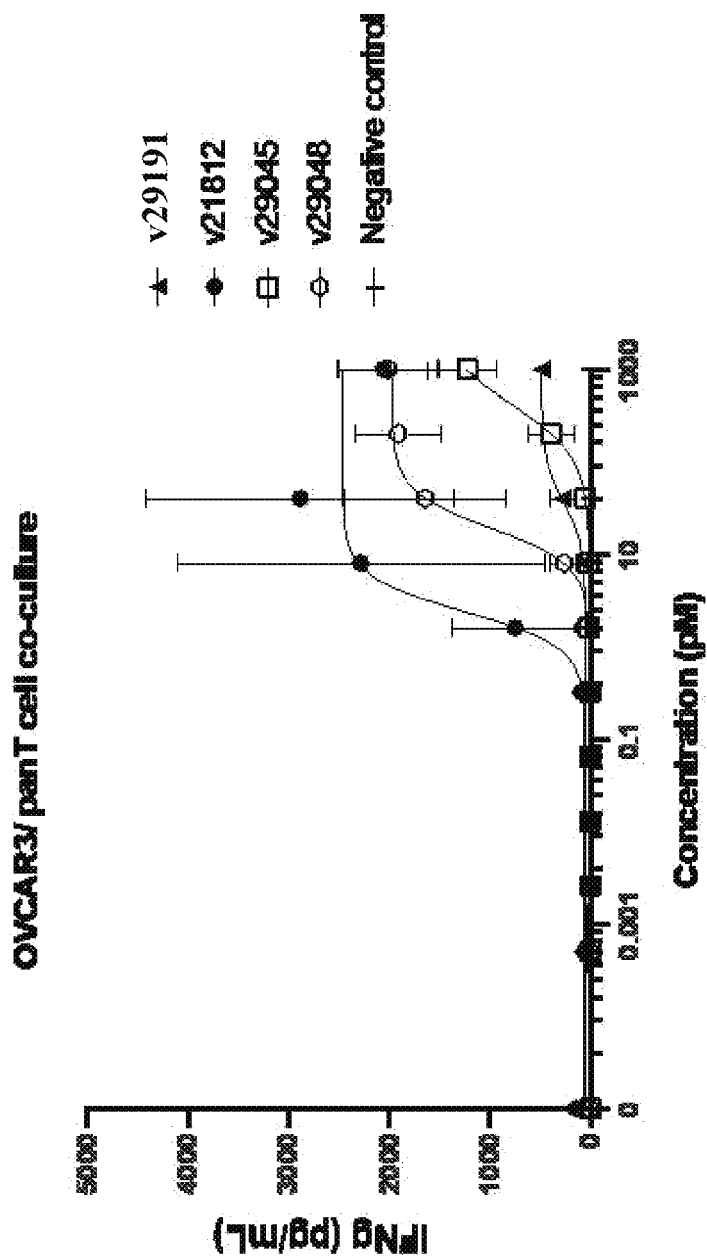
Figure 8C:
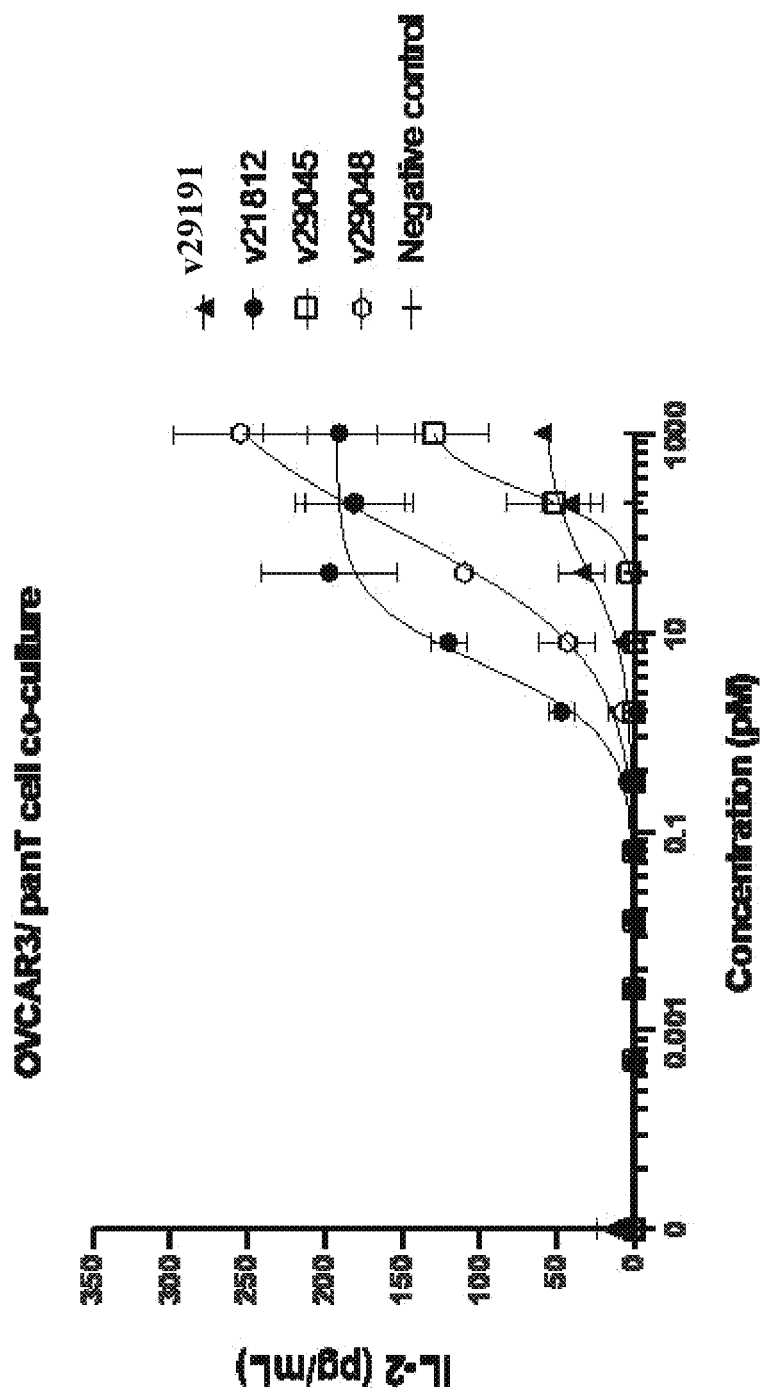

The results of this study are shown in FIGS. 8A-8C for Pan T cell release of TNFα (FIG. 8A), IFNγ (FIG. 8B) and IL-2 (FIG. 8C) after incubation in the presence of the trivalent and bispecific (anti-CD3 Fab/anti-MSLN scFv$^2$) antibody construct v21812, and its lower MSLN affinity versions, v29045 and v29048, all of which were compared to the 2+1 Fab$^3$ TCB benchmark construct (v29191) for comparison to a conventional molecule with conventional format.

Across three independent experiments, the affinity of all tested antibody constructs for MSLN appeared to positively correlate with their ability to induce cytokine induction. The highest affinity molecule, v21812, was the most potent inducer of TNFα, IFNγ and IL-2, followed by v29048, and then v29045. The antibody construct, v21812, also showed significantly higher potency for cytokine induction when compared to the tested 2+1 Fab$^3$ TCB benchmark construct (v29191). It is noted again here that antibody construct v21812 was also the most potent molecule in the T cell-dependent cytotoxicity assays (see, EXAMPLE 6). Taken together, these results suggest that the combination of an increased affinity for MSLN (e.g., v21812 compared to v29048 and v29045) with improved format (e.g., v21812 compared to the v29191 benchmark) can lead to an enhanced activation of T cells, as measured by cytokine production.

Example 9: Impact of Construct Format and Affinity to MSLN on In Vivo Tumor Growth Inhibition This example evaluates the impact of a construct's format and anti-MSLN affinity on its ability to elicit T cell mediated anti-tumor activity in vivo using a tumor growth inhibition xenograft study performed with humanized NOG mice bearing subcutaneous human ovarian NIH:OVCAR-3 tumors.

In-Vivo Amplification of Subcutaneous (SC) NIH:OVCAR-3 Tumors in Nude Mice

Frozen NIH:OVCAR-3 ascitic cells, obtained from previous in vivo amplification after IP injection of NIH:OVCAR-3 cells, were thawed and subsequently SC implanted into BALB/c-nude J mice (Charles River Laboratories). The NIH:OVCAR-3 ascitic tumor cell implantation was performed 24 hours after whole body irradiation with a γ-source (1.44 Gy, 60Co, BioMEP S.A.RL., Dijon, France). Tumors were fragmented when they reached 500-1500 mm³.

NIH:OVCAR-3 Tumor Induction in NOG Mice for Anti-Tumor Activity Study

One hundred and fifty (150) irradiated NOG female mice (Taconic), were subcutaneously implanted with the NIH:OVCAR-3 tumor fragments, 48 hours after irradiation (1.44 Gy, 60Co, BioMep, Bretenieres, France). PBMCs were injected when tumors reach 100-200 mm³. The 150 mice were then split in 3 sub-groups of 50 mice (one sub-group for each donor A, B or C). The three sub-groups had equivalent mean tumor volumes. Each one of the three PBMCs donors was injected in one sub-group of 50 tumor bearing mice on the same day. Each mouse received one single intravenous (IV) injection of $10^7$ PBMCs (200 µL in PBS).

Two to three days post PBMCs injection, 34 mice from each of the three sub-groups were randomized according to their individual tumor volume using Vivo Manager® software (Biosystemes, Couternon, France). These 34 mice per donor were randomized to form 5 groups of 6 mice (for example groups 1A, 2A and 3A with mice from donor A) and 4 mice were put in group 6. A statistical test (analysis of variance, ANOVA) was performed to test for homogeneity between groups for each donor. Mice were dosed intravenously with antibody constructs on the day of randomization (DR) then every four days, according to the treatment schedule shown below in TABLE 13. Briefly, the trivalent and bispecific antibody construct v21812 as well as its lower MSLN affinity versions, v29045 and v29048, each comprising an anti-CD3 Fab domain and two anti-MSLN scFv domains, were compared against the Fab³ construct (1 anti-CD3 Fab and 2 anti-MSLN Fabs) v29191 (also referred to as "2+1 Fab³ TCB benchmark"), and a negative control.

TABLE 13

In Vivo Study Groups and Dosing Regiment

| Group | Test Article | Dose (IV) | Treatment Schedule |
|---|---|---|---|
| 1A (6 mice-donor A) | Negative control | 5.0 mg/kg | BIWx3W |
| 1B (6 mice-donor B) | | | |
| 1C (6 mice-donor C) | | | |
| 2A (6 mice-donor A) | v21812 | 1.5 mg/kg | BIWx3W |
| 2B (6 mice-donor B) | | | |
| 2C (6 mice-donor C) | | | |
| 3A (6 mice-donor A) | v29191 | 5.0 mg/kg | BIWx3W |
| 3B (6 mice-donor B) | | | |
| 3C (6 mice-donor C) | | | |
| 4A (6 mice-donor A) | v29045 | 3.0 mg/kg | BIWx3W |
| 4B (6 mice-donor B) | | | |
| 4C (6 mice-donor C) | | | |
| 5A (6 mice-donor A) | v29048 | 3.0 mg/kg | BIWx3W |
| 5B (6 mice-donor B) | | | |
| 5C (6 mice-donor C) | | | |

Animals were monitored at regular intervals for tumor growth using caliper measurements and for weight loss. Animals were euthanized and necropsied when (i) tumor volume reached a maximal tumor volume of 2 000 mm³, (ii) when tumor exceeds 10% of normal body weight, (iii) at a body weight loss of greater that 20%, or (iv) after a maximum of 12 weeks post tumor injection. Animal housing and experimental procedures were realized according to the French and European Regulations and NRC Guide for the Care and Use of Laboratory Animals.

Results

Figure 9:
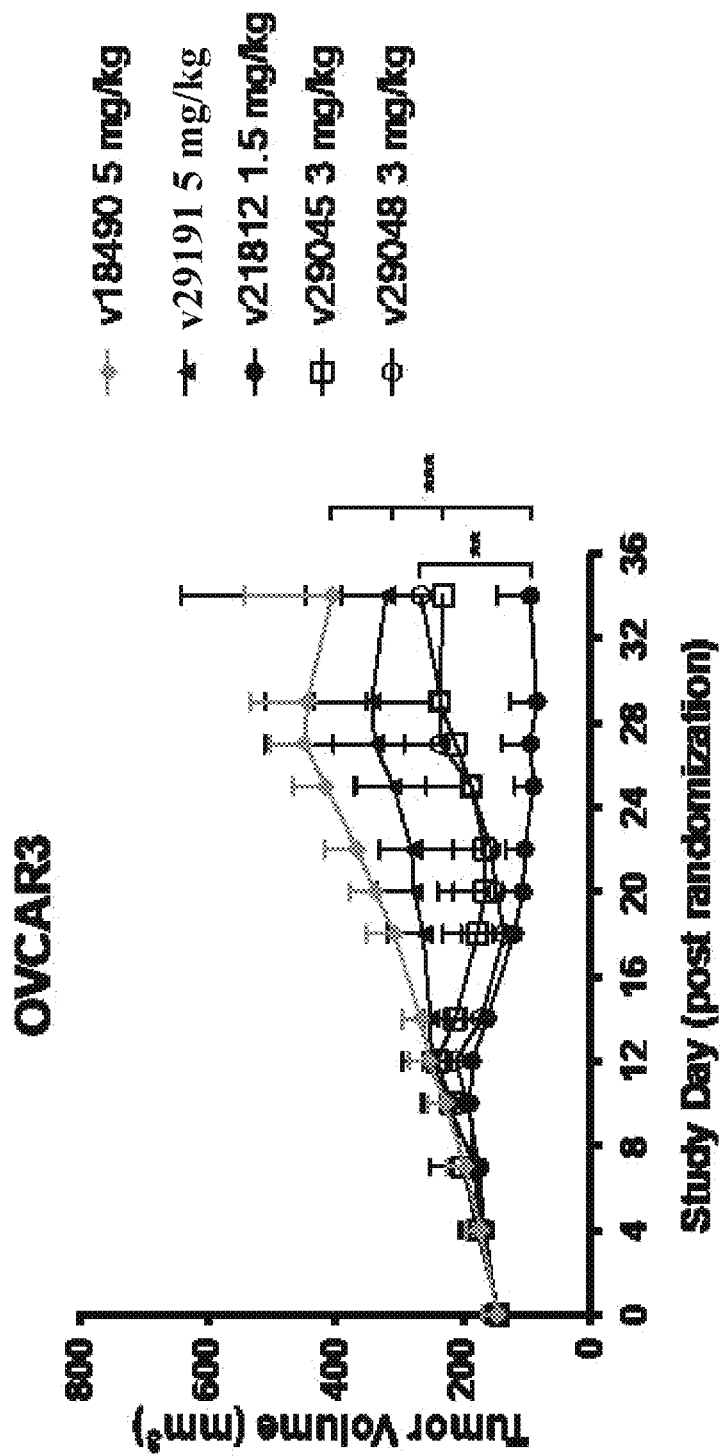
FIG. 9 shows that the trivalent and bispecific anti-(MSLN×CD3) antibody construct of the present disclosure, v21812, significantly inhibited tumor growth and reduced tumor volume over the course of the study in OVCAR-3-tumor bearing NOG mice, engrafted with human PBMCs. The construct v21812 inhibited tumor growth significantly more than the other constructs tested, including the 2+1 Fab$^3$ TCB benchmark construct (v29191, see, FIG. 1B for construct format).  indicates p-value is <0.01, and * indicates p-value is <0.001.

OVCAR-3 cells expressed high levels of MSLN (~768,000 MSLN/cell) and were established from progressive ovarian adenocarcinoma. As shown in FIG. 9, tumor outgrowth was observed in control-treated animals, as well as, although to a lesser degree, in animals that were treated with the 2+1 Fab³ TCB benchmark construct. Treatment of animals with the herein disclosed trivalent and bispecific antibody construct v21812 at a dose of 1.5 mg/kg, however, resulted in significant tumor growth inhibition and a reduction in tumor size relative to all other treatment groups, particularly compared to the 2+1 Fab³ TCB benchmark construct. The lower anti-MSLN affinity versions of v21812, v29045 and v29048, were capable of inhibiting tumor growth, specifically when compared to the 2+1 Fab³ TCB benchmark construct but were not as effective in reducing the tumor size as observed with the higher affinity construct v21812. Furthermore, animal body weight remained stable under all conditions for the duration of the study.

Taken together, these data are in line with the results shown in the other EXAMPLES described herein and further demonstrate that the trivalent and bispecific antibody construct, v21812, may possess a superior format compared to conventional constructs (e.g., v29191) and may possess an optimized affinity for MSLN to induce significant tumor growth inhibition and reduction in tumor size, making this T cell engaging antibody construct a promising candidate for cancer immunotherapy.

Example 10: Engineering of V21812 to Improve Developability and Generation of Antibody Construct V32523

This example describes the engineering and production of a trivalent and bispecific antibody construct, v32523, which is based on variant v21812, comprises the same anti-CD3 and anti-MSLN paratope sequences like v21812, but possesses an enhanced thermostability and developability when compared v21812.

Engineering

To that end, and in order to improve the production quality and thermal stability of v21812, the anti-MSLN scFv domain orientation and linker length was modified and led to the construction of the trivalent and bispecific antibody construct v32523. The anti-MSLN scFv domain order was changed to $V_L$-$V_H$ (from N- to C-terminus), and from $V_H$—$V_L$ in the parent construct v21812, and the Gly-Ser peptide linker connecting the $V_L$ and $V_H$ domains was lengthened to $(G_4S)_4$ (SEQ ID NO:102)(from $(G_4S)_3$ (SEQ ID NO:118) in v21812). The resulting trivalent and bispecific antibody construct v32523 contains the polypeptide chains H1 (SEQ ID NO: 100), H2 (SEQ ID NO: 110), and L1 (SEQ ID NO: 114).

Cloning and Production of v32523

The polypeptide chains H1 (SEQ ID NO: 100), H2 (SEQ ID NO: 110), and L1 (SEQ ID NO: 114) that incorporate the modified anti-MSLN scFv domain structure were subcloned into the mammalian expression vector pTT5 (NRC-BRI, Canada). Production of construct v32523 in CHO cells was performed as described in EXAMPLE 1, with the following modifications. Transfection ratios of the chains H1/H2/L1 were either 1:1:1, 1:1:1.5, or 2:1:3. Material was purified from cell culture supernatants by Protein A, and pooled fractions were neutralized with 1 M sodium acetate, pH 8.8. Protein A-purified material was further purified by SEC (Superdex 200 16/60 or Superdex 200 Increase 10/300) using running buffer A5-NaCl (50 mM sodium acetate, 150 mM NaCl, pH 5.0) or by ion-exchange chromatography (Capto SP ImpRes) with binding in sodium acetate pH 6.0, eluting the desired species at 210 mM NaCl. Final material was typically buffer-exchanged into either PBS, A5Su (50 mM sodium acetate, 9% sucrose, pH 5.0), or H6Su (50 mM histidine, 6% sucrose, pH 6.0).

UPLC-SEC and Thermal Melt Analysis of v32523

Production quality of the engineered construct v32523 was assessed by UPLC-SEC analysis after the protein A purification step describe above and compared to the parental construct v21812. Protein-A purified material was analyzed using a Waters Acquity BEH200 SEC column (2.5 mL, 4.6×150 mm, stainless steel, 1.7 m particles) (Waters LTD, Mississauga, ON) set to 30° C. and mounted on a Waters Acquity UPLC H-Class Bio system with a PDA detector. Run times consisted of 7 min and a total volume per injection of 2.8 µL with a running buffer of A5-NaCl at 0.4 mL/min. Elution was monitored by UV absorbance in the range 210-500 nm, and chromatograms were extracted at 280 nm. Peak integration was performed using Empower 3 software. UPLC-SEC analysis showed that the high-molecular weight species (HMWS) peaks decreased with the new construct v32523 compared to v21812, from 31% HMWS for v21812 to 19% for v32523, consistent with an improvement in production quality for v32523.

Thermal stability was assessed for final SEC-purified samples of v32523 and v21812 by differential scanning calorimetry (DSC) using a GE VP-Capillary instrument. The antibody constructs were buffer exchanged into A5Su buffer and diluted to 0.3 to 0.7 mg/mL in A5Su, with 0.137 mL loaded into the sample cell and measured with a scan rate of 1° C./min from 20 to 100° C. Data was analyzed using the Origin software (GE Healthcare) with the A5Su buffer background subtracted.

TABLE 14A shows the maximum melting temperatures (Tm) for each of the peaks in the thermograms of the bispecific and trivalent anti-MSLN/anti-CD3 antibody constructs v32523 and v21812.

TABLE 14A

Thermostability Data of v32523 and v21812 in A5Su Buffer

| Antibody Construct | Tm onset (° C.) | Tm1 (° C.) | Tm2 (° C.) |
| --- | --- | --- | --- |
| v21812 | 57.37 | 63.18 | 75.87 |
| v32523 | 58.68 | 65.83 | 75.68 |

The results in TABLE 14A show that the engineered variant v32523 has an improved thermal stability compared to the parental construct v21812. Tm onset was increased by 1.31° C., and Tm1 (e.g., attributed to scFv+Fab melting) was increased by 2.65° C.

The trivalent and bispecific antibody construct v32523 was further tested for long-term stability at elevated temperatures, and good stability and developability properties were demonstrated. FIGS. 24A-24B show that the trivalent and bispecific antibody construct v32523 maintains monodispersity after incubation in A5Su at 40° C. for 14 days, as shown by size-exclusion chromatography (SEC, FIG. 24A) dynamic light scatter (DLS, FIG. 24B) analysis, demonstrating a purity of v32523 of at least about 99%, with less than about 1% of other high molecular weight species (HMWS).

For long-term stability measurements, protein samples were prepared in formulation buffer and adjusted to a final concentration of 1 mg/mL. An initial analysis of the samples was performed to establish "t=0" concentration, purity, and dispersity characteristics. For extended incubation testing, samples were split into two aliquots and incubated at 4° C. and 40° C. for 14 days followed by analytics to assess concentration, purity, and dispersity. Concentration was assessed by A280 (Nanodrop). Purity and dispersity was assessed by UPLC-SEC, DLS, LC-MS intact mass analysis, and CE-SDS (Caliper).

Generally, all measured in vitro developability parameters were within normal ranges, as shown and summarised below in in TABLE 14B.

TABLE 14B

| | In Vitro Developability Analytics | | | | | | |
| --- | --- | --- | --- | --- | --- | --- | --- |
| | cIEF | AC-SINS | Nonspecific binding ELISA | | | | |
| Sample | pI | dlambda | 1 | 2 | 3 | 4 | 5 |
| v32523 | 8.97 | 3.00 | 3.21 | 2.78 | 1.50 | 2.26 | 1.93 |

Furthermore, the stability of v32523 was tested in mouse plasma, which demonstrated good plasma stability with no evidence of scFv clipping after incubation of 14 days at 37° C.

For mouse plasma stability studies, protein samples were buffer-exchanged into PBS followed by dilution into mouse plasma or PBS as a control condition. A small aliquot was reserved for "t=0" and stored frozen until assay completion. Samples in mouse plasma or PBS were incubated at 37° C. for up to 14 days and analyzed by LC-MS peptide mass mapping and by SPR binding with MSLN or CD3.

Example 11: Ability of Stability Engineered Construct V32523 to Bind MSLN and CD3 as Assessed by Surface Plasmon Resonance (SPR)

This example demonstrates the ability of the stability engineered trivalent and bispecific (MSLN×CD3) antibody construct, v32523, as well as that of the benchmark construct MH6T-TriTAC (v31805), to bind MSLN on tumor cells and CD3 on immune cells, as assessed by SPR.

Binding of Antibody Constructs to MSLN by SPR

All SPR binding experiments were carried out using a BioRad ProteOn XPR36 instrument at 25° C. with 10 mM HEPES, 150 mM NaCl, 3.4 mM EDTA, and 0.05% Tween 20 at pH 7.4. Recombinant MSLN Fc fusion protein (R&D: 3265-MS) was captured on anti-Fc capture sensorchips. Purified antibody constructs to be tested were indirectly captured on the sensorchip by binding to the recombinant MSLN fusion protein when injected at 25 L/min for 240 s (resulting in approx. 500 RUs), following a buffer injection to establish a stable baseline. Resultant $K_D$ values were determined from binding isotherms using the Equilibrium Fit model with reported values as the mean of three independent runs.

Binding of Antibodies to CD3 by SPR

All SPR binding experiments were carried out using a BioRad ProteOn XPR36 instrument at 25° C. with 10 mM HEPES, 150 mM NaCl, 3.4 mM EDTA, and 0.05% Tween 20 at pH 7.4. Recombinant CD3epsilon/delta Fc fusion protein (Sino Biological; http://www.sinobiological.com/CD3D-CD3-Delta-Protein-g-10182.html) was captured on anti-Fc capture sensorchips. Purified antibody constructs to be tested were indirectly captured on the sensorchip by binding to the recombinant CD3 fusion protein when injected at 25 µL/min for 240 s (resulting in approx. 500 RUs), following a buffer injection to establish a stable baseline. Resultant $K_D$ values were determined from binding isotherms using the Equilibrium Fit model with reported values as the mean of three independent runs.

Results

TABLE 15 below shows that the stability engineered trivalent and bispecific anti-MSLN/anti-CD3 antibody construct, v32523, maintained the binding profile observed for its parental version, v21812. Variant v32523 (as did v21812) had lower affinity to MSLN (32-fold lower) and CD3 (53-fold lower) compared to the benchmark, v31805 (MH6T-TriTAC), which comprised one MSLN-targeting $V_{HH}$ domain and one CD3-targeting scFv, as further described herein.

TABLE 15

Binding of Construct v32523 and Benchmark Control to MSLN and CD3

| | MSLN | | | CD3 | | |
|---|---|---|---|---|---|---|
| Construct | $k_a$ (1/Ms) | $k_d$ (1/s) | $K_D$ (nM) | $k_a$ (1/Ms) | $k_d$ (1/s) | $K_D$ (nM) |
| v32523 | 7.14E+05 | 7.19E-04 | 1.01 | 2.79E+05 | 1.12E-02 | 40.1 |
| v31805 | 5.33E+07 | 1.67E-03 | 0.03 | 7.52E-10 | 3.79E-03 | 0.75 |

Example 12: Binding of Construct V32523 to Human Pan T Cells and MSLN-Expressing Cell Lines This example demonstrates the ability of the stability engineered trivalent and bispecific antibody construct, v32523, and that of the benchmarks, 2+1 Fab³ TCB (v29191) and MH6T-TriTAC (v31805), to bind to CD3- and MSLN-expressing cells, as assessed via whole cell FACS binding analysis as described previously (WO2015109131).

Experimental Procedure

Primary human T cells and MSLN-expressing OVCAR-3 cells were incubated with either media or serial dilutions of the antibody constructs for one hour at 4° C. Following incubation with the antibody constructs, the cells were washed and stained with Alexa fluor 647-conjugated anti-IgG-Fc. The pan T cells were also stained with fluorophore-conjugated antibodies specific for CD4 and CD8. The samples were acquired on a flow cytometer and analyzed using FlowJo version 10.1 software.

Results

Figure 10:
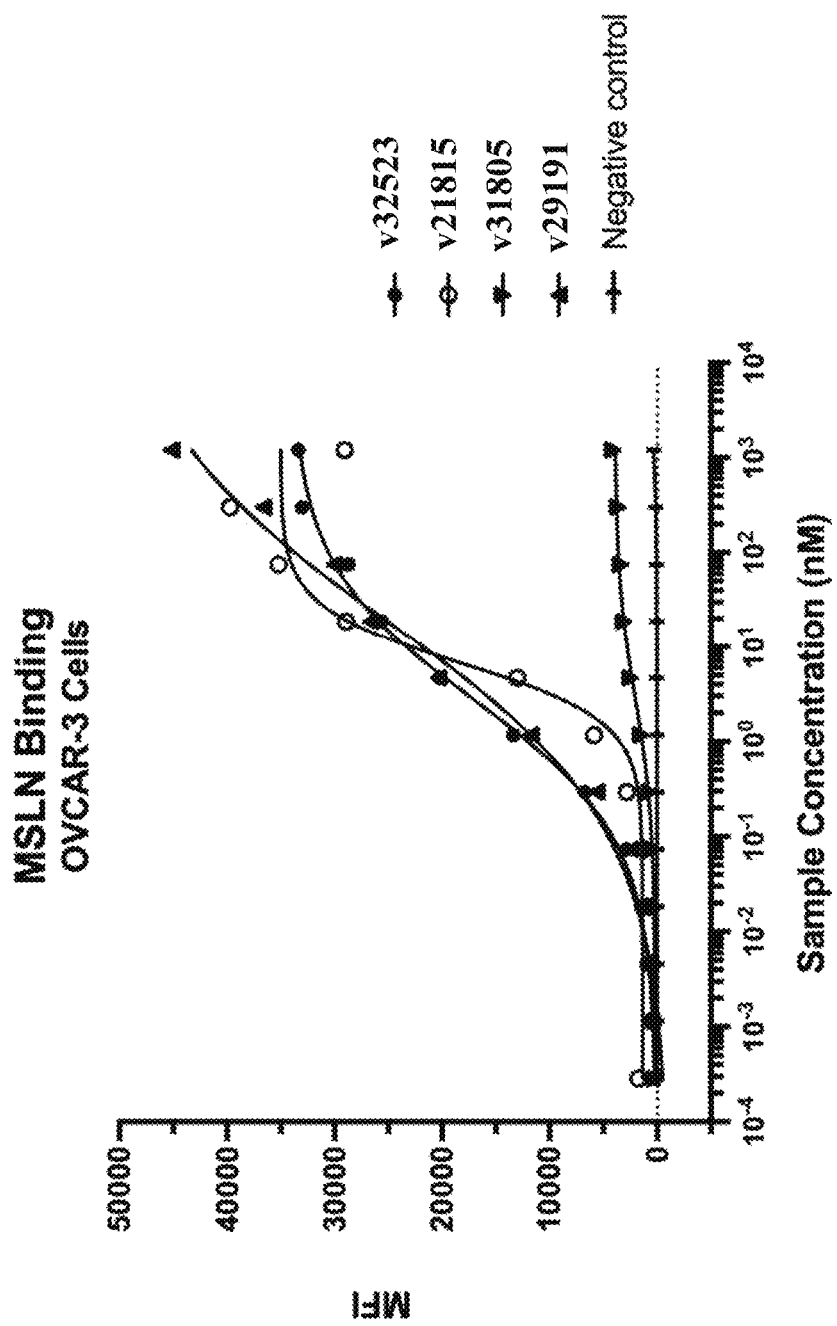
FIG. 10 shows binding of the stability-improved (compared to v21812) trivalent and bispecific antibody construct v32523 (identical domain sequences as v21812, however, both anti-MSLN scFv domains have the domain structure, from N- to C-term, of: $V_L$-Linker$^{scFv}$-$V_H$, compared to: $V_H$-Linker$^{scFv}$-$V_L$ in v21812, and Linker$^{scFv}$ has the sequence of $(G_4S)_4$ (SEQ ID NO:102) in v32523 compared to $(G_4S)_3$ (SEQ ID NO:118) in v21812), to MSLN+ OVCAR-3 cells, as measured by flow cytometry, and compared to the benchmark control constructs v29191 and v31805.
Figure 11A:
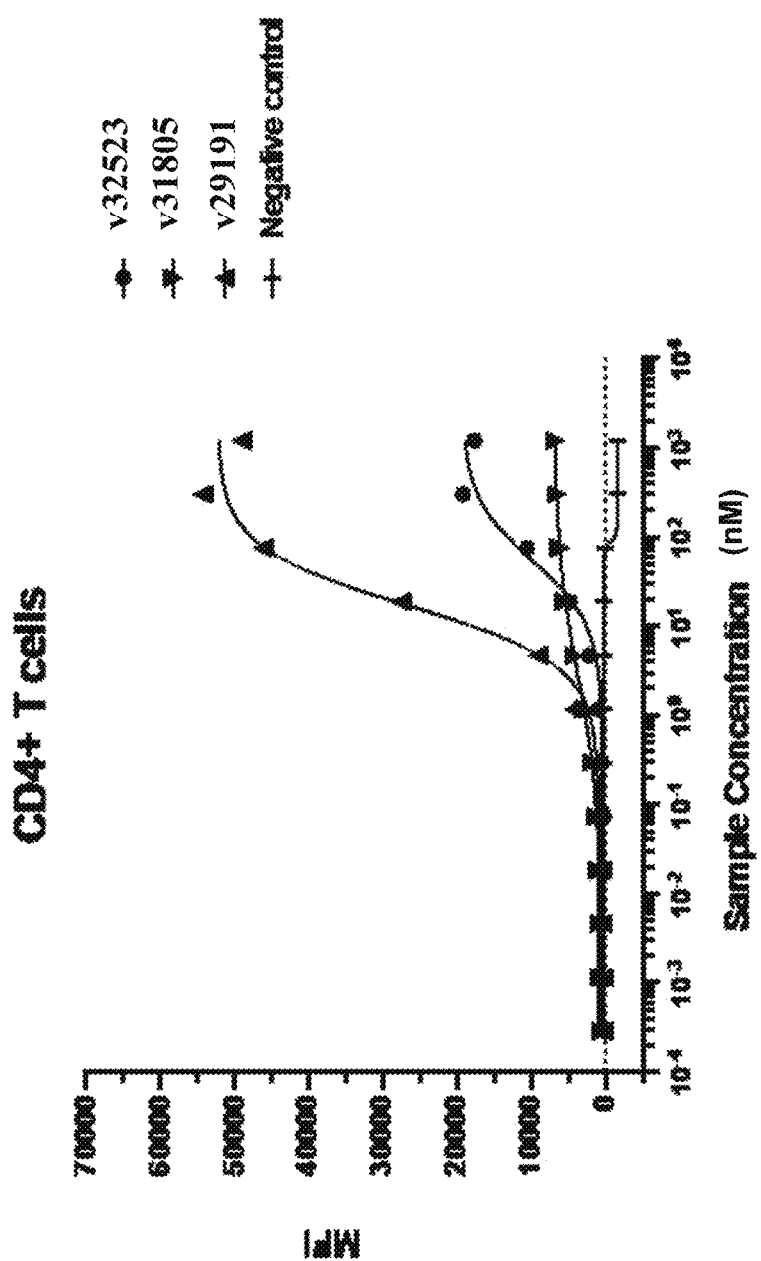
FIGS. 11A-11C show binding of the trivalent and bispecific antibody construct v32523 as well as binding of the benchmark control constructs v29191 and v31805, to CD3$^+$ human Pan T cells in cell cultures comprising CD4$^+$ cells (FIG. 11A), CD8$^+$ cells (FIG. 11B) and a mixture of CD4$^+$ and CD8$^+$ cells (FIG. 11C), as measured by flow cytometry.
Figure 11B:
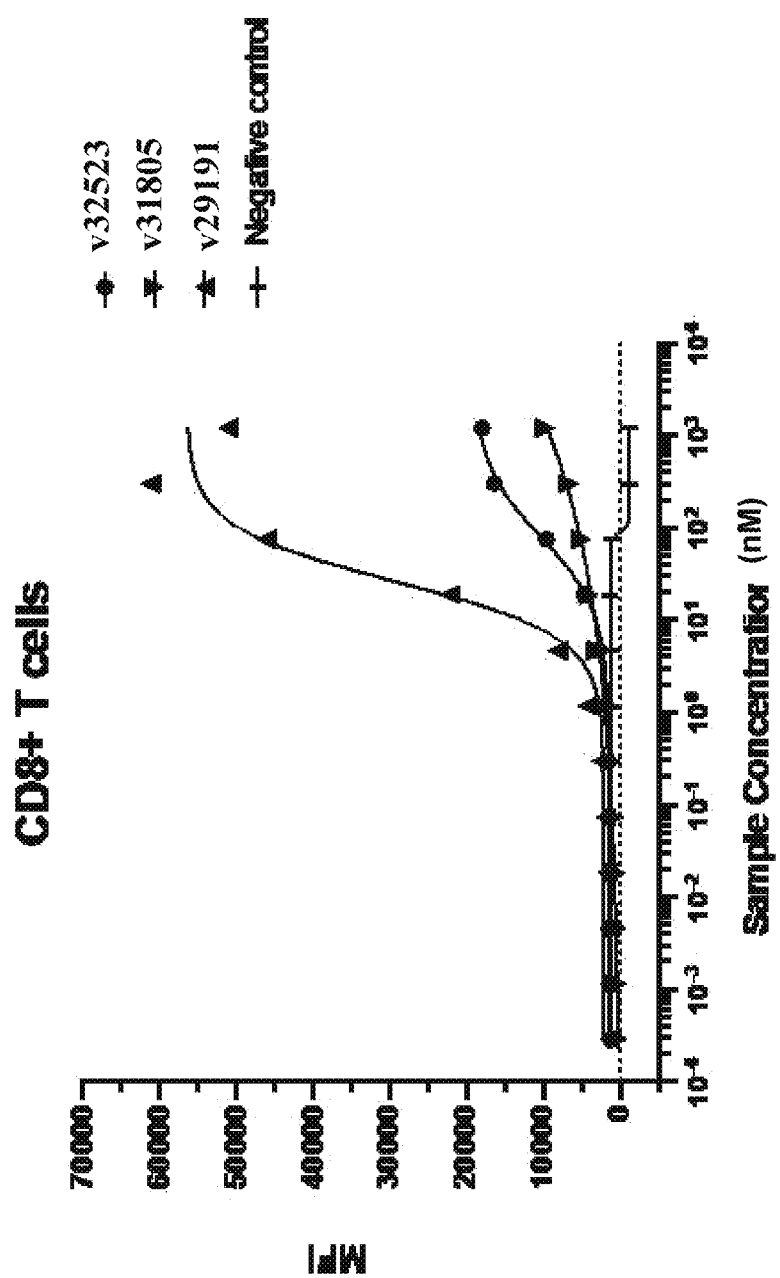
Figure 11C:
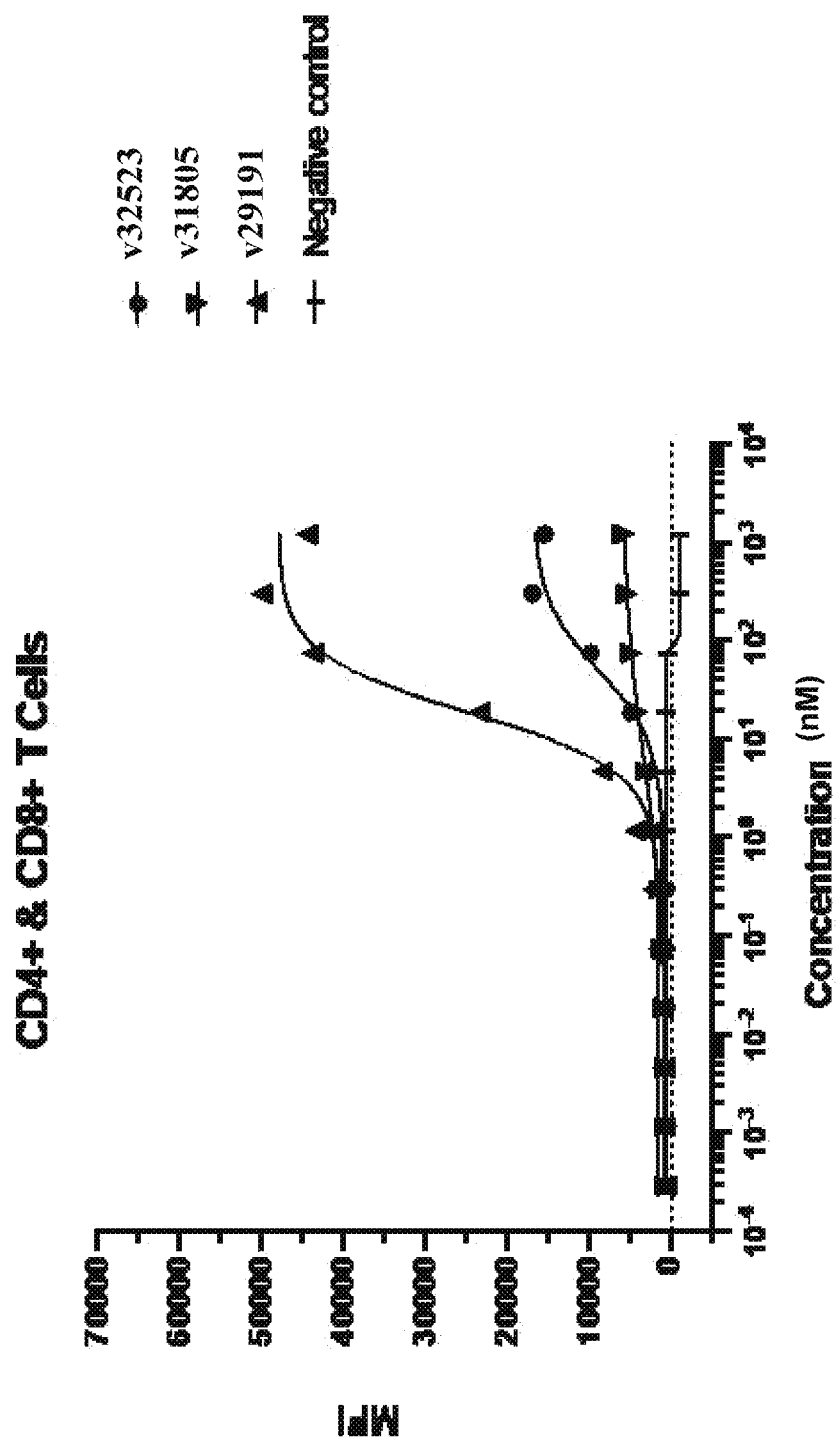

The apparent binding affinities of the tested constructs are shown in FIG. 10 for MSLN and FIGS. 11A-11C for CD3, as well as in TABLE 16 below.

TABLE 16

Whole Cell Binding of Antibody Constructs to Native CD3 and MSLN

| | Apparent Affinity ($EC_{50}$, nM) | |
|---|---|---|
| Construct | human T cells | OVCAR-3 cells |
| Negative control | 102.4 | LOD |
| v32523 | 50.5 | 2.8 |
| v21815 | ND | 6.7 |
| v29191 | 18.7 | 0.4 |
| v31805 | 5.9 | 3.0 |

Overall, the tested antibody constructs bound human MSLN+ cells with high affinity (apparent affinity of 0.4-6.7 nM). Furthermore, and similar to it's parental construct, v21812, the trivalent and bispecific stability engineered antibody construct, v32523, appeared to exhibit bimodal binding to MSLN, indicating single arm followed by two arm binding to the MSLN antigen. This was not observed for the bispecific constructs that were monovalent for MSLN, v21815 and v31805 (MH6T-TriTAC). Hence, the trivalent construct format described herein, e.g., as used in the constructs v21812 and v32523, may provide an enhanced differentiation between normal cells, e.g., those expressing low levels of MSLN, and tumors expressing high levels of MSLN, through increased avidity to MSLN rather than through high affinity interactions.

Additionally, for CD3, the antibody construct v32523, and its parental version, v21812, exhibited similar binding profiles on primary human T cells, with relative affinities around 50 nM. The lower apparent affinity of v32523 to CD3 compared to the benchmark molecules was intentionally designed and appeared in this study to be about 2.7-fold lower compared to the 2+1 Fab³ TCB benchmark and about 8.6-fold lower compared to the v31805 (MH6T-TriTAC) benchmark construct.

Example 13: Induction of T-Cell Mediated Cytotoxcity in an Antigen-Dependent Manner This example demonstrates the ability of the stability engineered trivalent and bispecific antibody construct, v32523, to induce T-cell mediated cytotoxicity in an antigen (e.g., MSLN) dependent manner using cell lines with varying degrees of MSLN expression, and in comparison, to the benchmark construct, v31805, which is currently in clinical trials (see, e.g., NCT03872206).

Experimental Procedure

For the initial assessment of a therapeutic index, construct v32523 was diluted in RPMI1640 (Gibco)+10% FBS (ThermoFisher) and added to appropriate wells of the 384-well black flat bottom assay plates (ThermoFisher, Watham, MA). Human pan T cells were thawed and mixed with H292 cells (~152,000 MSLN/cell), OVTOKO cells (~9,000 MSLN/cell), or MCF7 cells (~500 MSLN/cell) at an E:T ratio of 2:1. Plates were incubated for 72 hours at 37° C. and 5% carbon dioxide, after which Vybrant™ DyeCycle™ Violet Stain (ThermoFisher Scientific) was added to the cells. After a 30-minute incubation period with the stain, tumor cell viability was assessed through live tumor cell counts using the Operetta CLS High Content Analysis System (PerkinElmer). The assay was repeated with two primary blood donors.

To compare the therapeutic index of v32523 to that of the MH6T-triTAC benchmark (v31805) in vitro, additional T cell-dependent cytotoxicity assays were run using the $MSLN^{high}$ cell line H292 and $MSLN^{low/neg}$ cell line, A375 (~12,000 MSLN/cell). The assay was set up as described above at a 5:1 E:T ratio and live tumor cell counts were measured using the CellInsight High Content Screening Platform (ThermoFisher Scientific; CX51110).

Percent tumor cell killing was calculated using the following formula:

$$\% \text{ tumor cell killing} = \left(1 - \frac{\text{number of tumor cells left in sample}}{\text{total number of tumor cells in untreated condition}}\right) \times 100$$

Figure 12A:
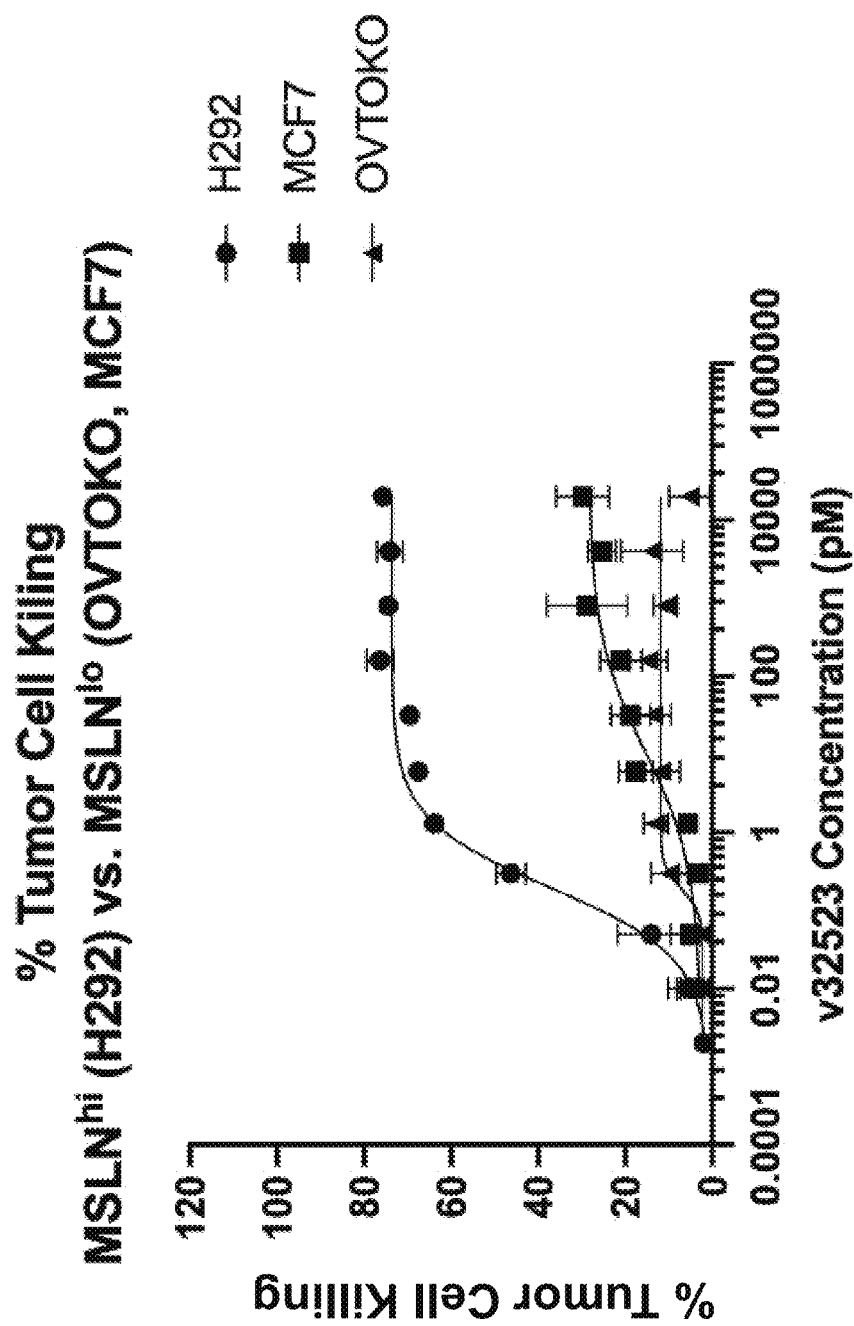
FIGS. 12A-12F show MSLN-dependent T-cell mediated cytotoxicity elicited by the trivalent and bispecific antibody construct v32523 and compared to the benchmark construct, v31805, using cell lines with varying degrees of MSLN expression.
Figure 12B:
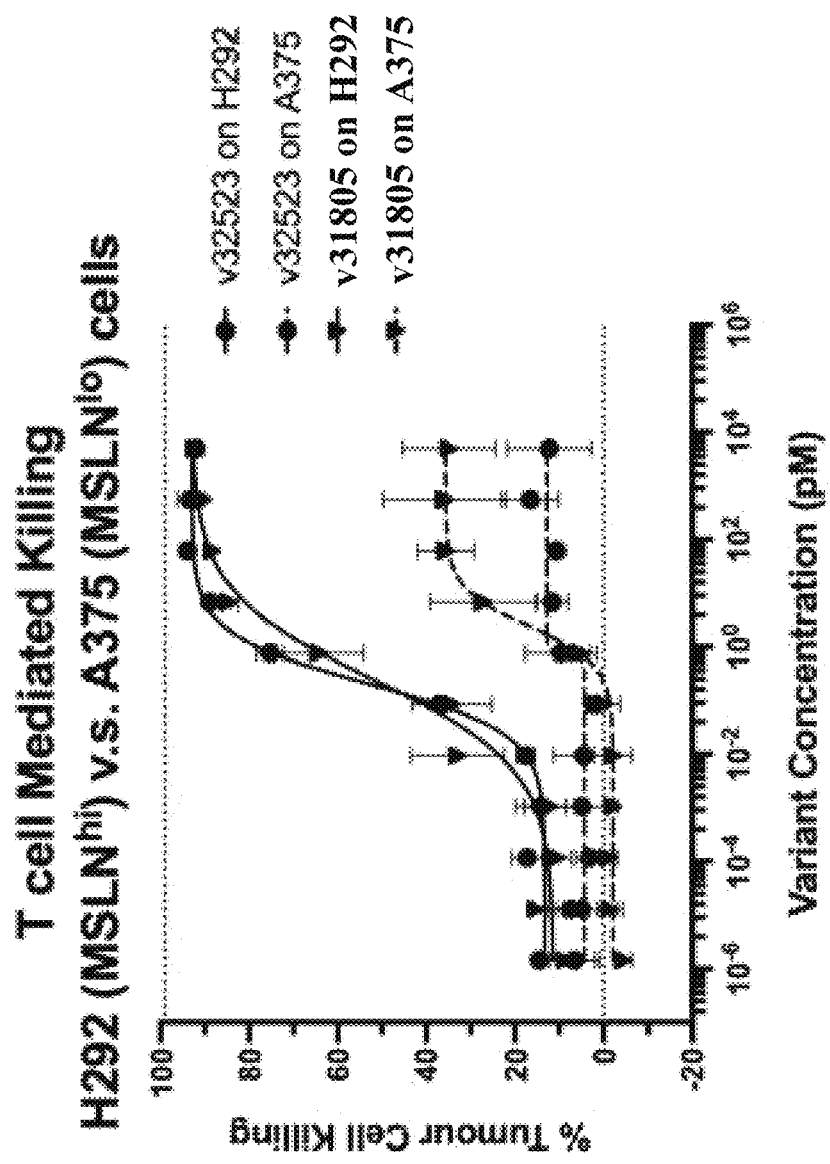

Concentration response curves for the tested constructs are presented in FIGS. 12A-12B and $IC_{50}$ and maximum percent killing values from the T cell-dependent cytotoxicity assay comparing v32523 and v31805 benchmark are shown in TABLE 17.

TABLE 17

Cytotoxic Activity of Constructs v32523 and v31805 benchmark towards MSLN High and Low/Negative Tumor Cells Grown in Culture with Human PanT Cells

| | H292 | | A375 | |
|---|---|---|---|---|
| Construct | $IC_{50}$ (pM) | Max. killing | $IC_{50}$ (pM) | Max. killing |
| v32523 | 0.21 | 92.99 | Ambiguous | 12.83 |
| v31805 | 0.25 | 93.08 | 2.45 | 35.81 |

Figures 12C, 12D:
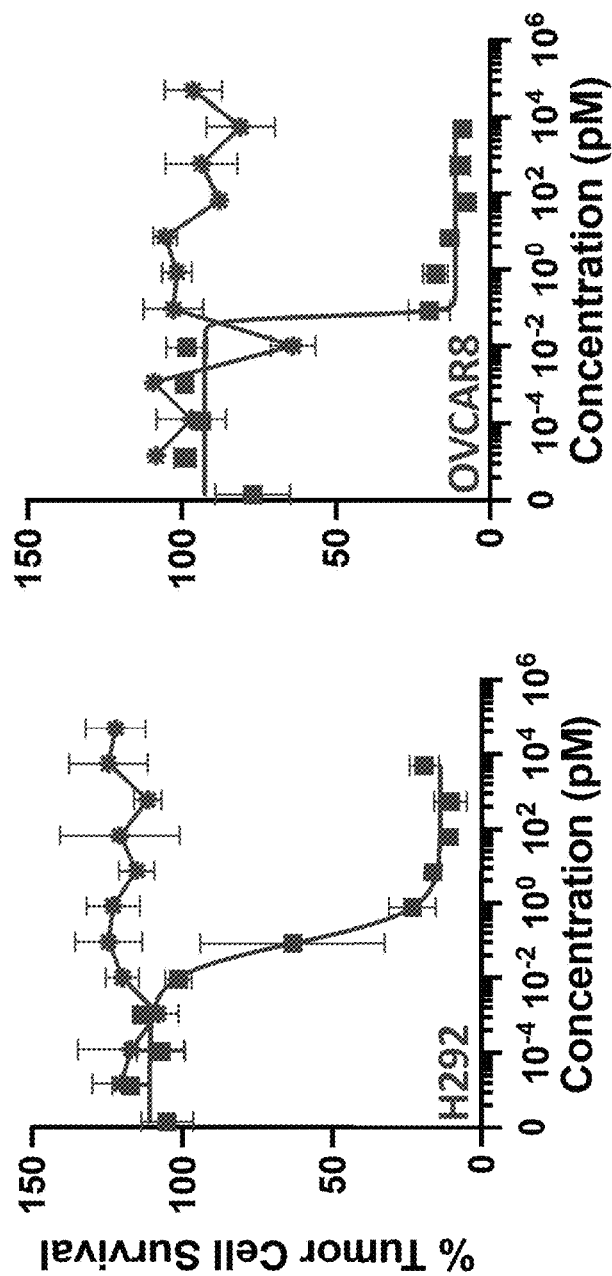
Figures 12E, 12F:
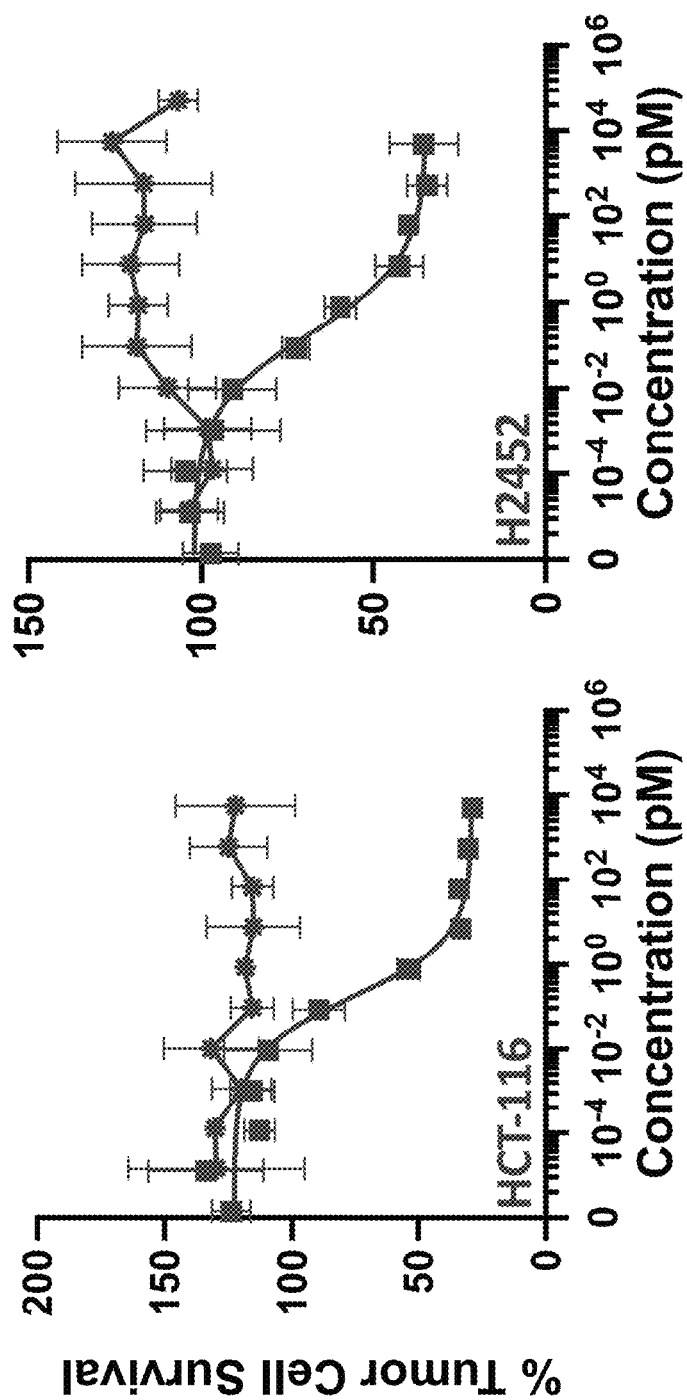
Figure 13A:
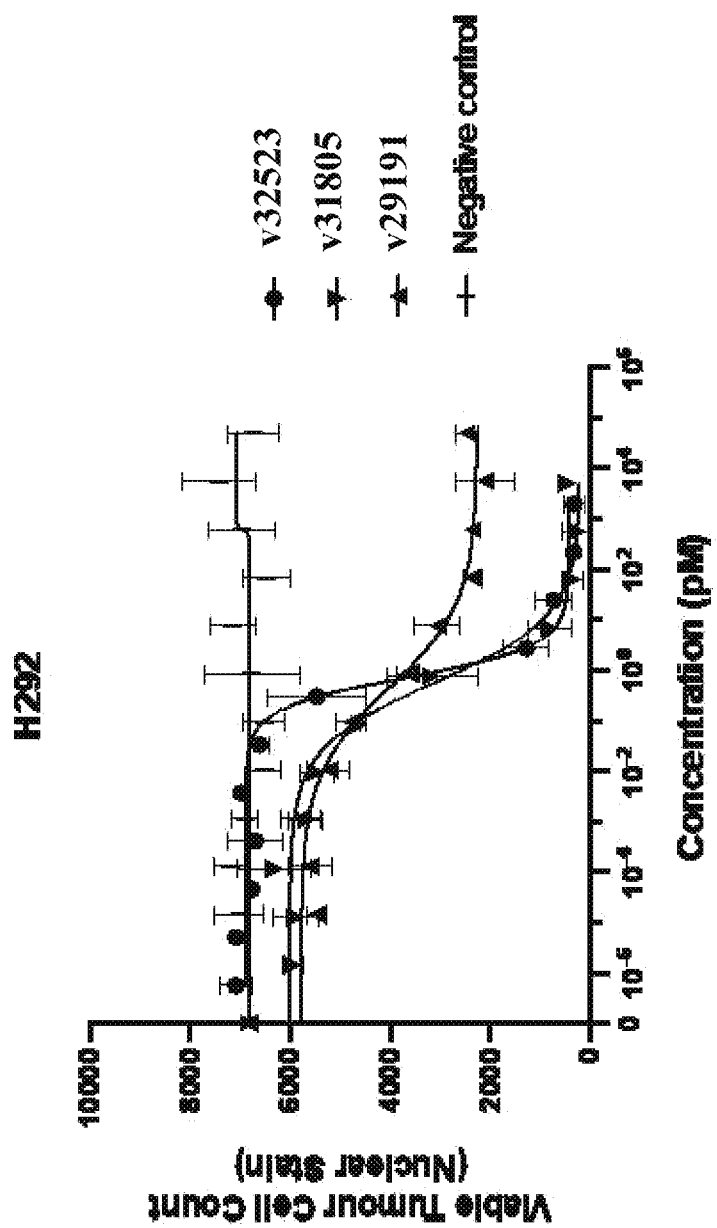
FIGS. 13A-13D show that the trivalent and bispecific antibody construct v32523 directed T cells from healthy donors to kill MSLN+ tumor cells expressing different levels of MSLN: H292 (~152,000 MSLN/cell, FIG. 13A), HCT116 (~35,000 MSLN/cell, FIG. 13B), H2452 (~11,000 MSLN/cell, FIG. 13C), and A549 (~11,000 MSLN/cell, FIG. 13D). In all four tumor cell lines tested, which showed medium to high MSLN expression, the trivalent and bispecific antibody construct v32523 of the present disclosure was at least as potent as, or superior to, the benchmark control constructs v29191 (2+1 Fab$^3$ construct) and v31805 (MH6T-TriTAC).
Figure 13B:
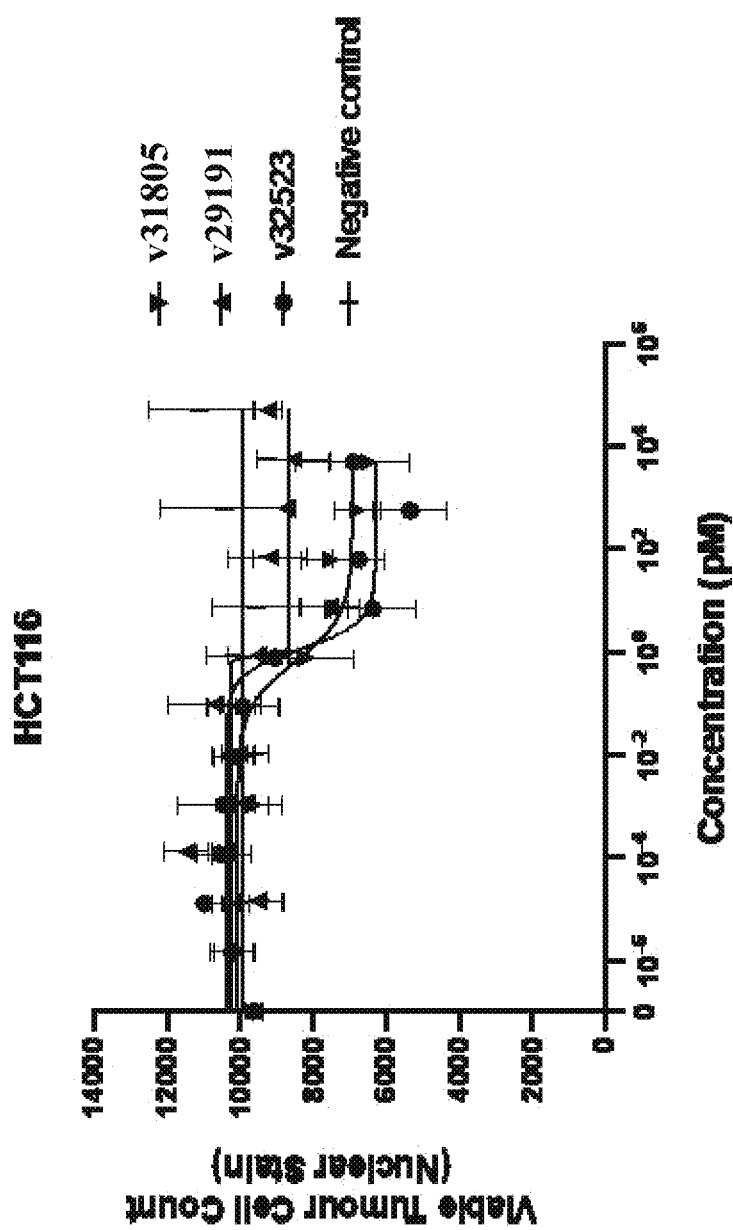
Figure 13C:
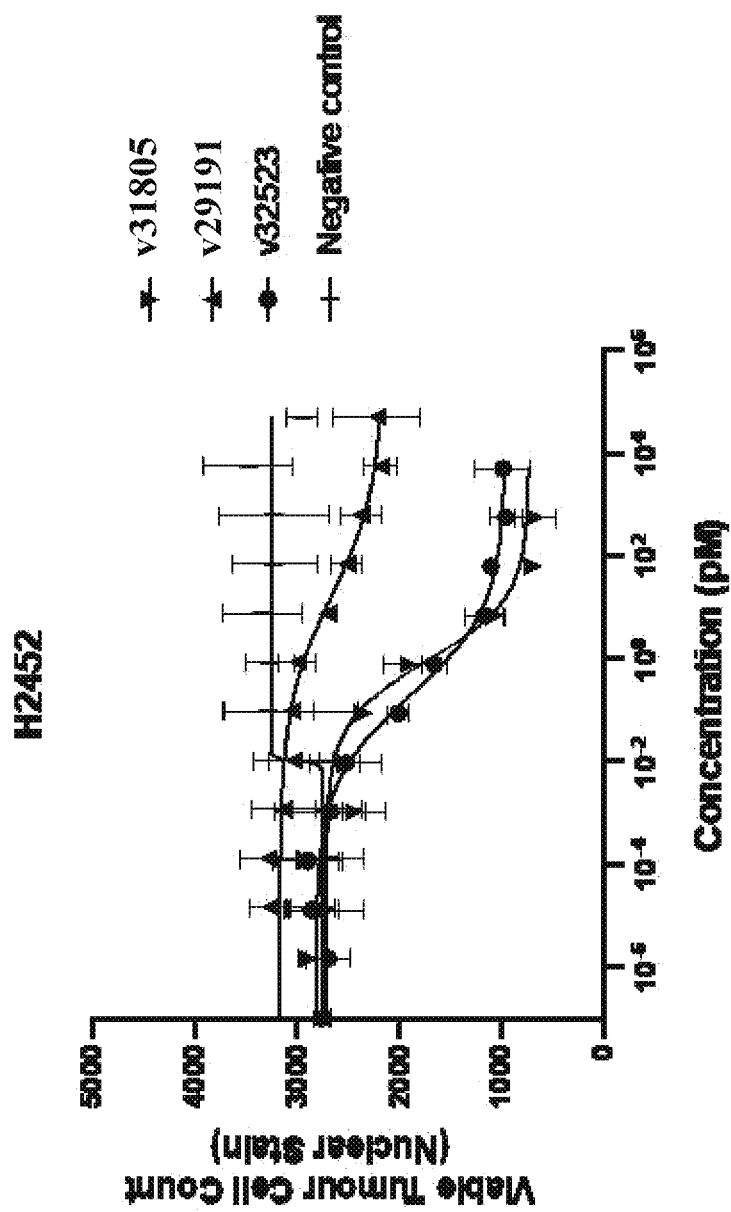
Figure 13D:
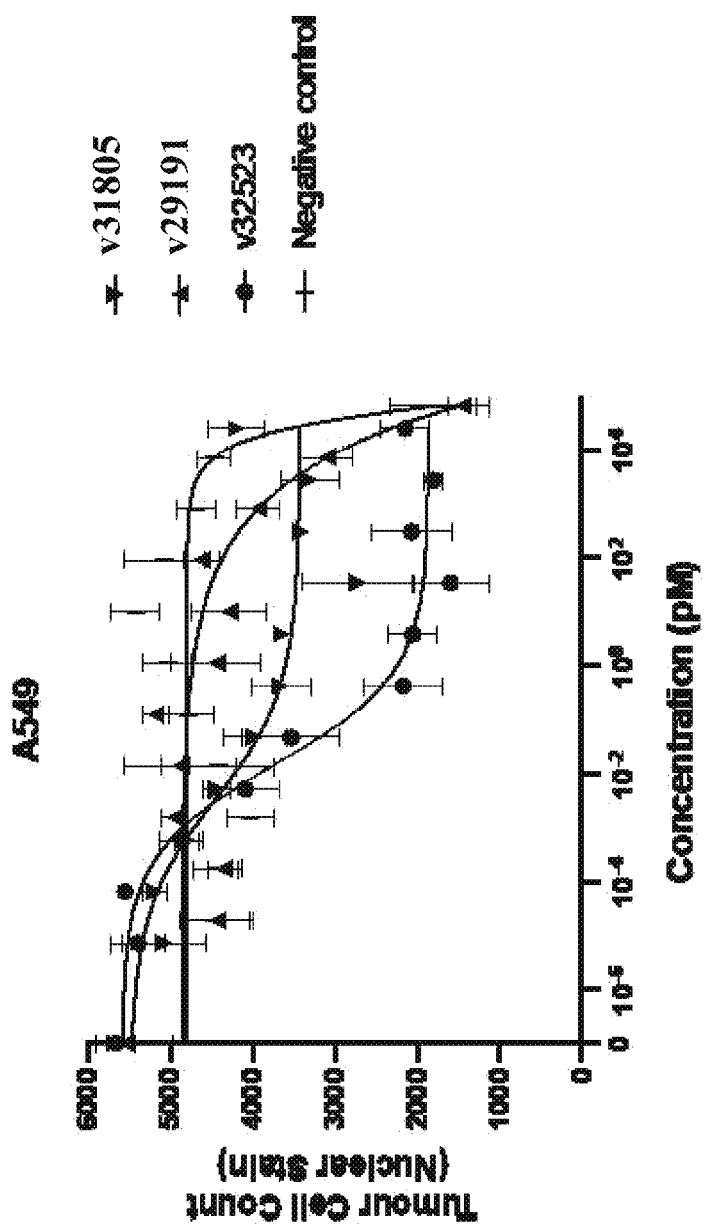
Figure 14A:
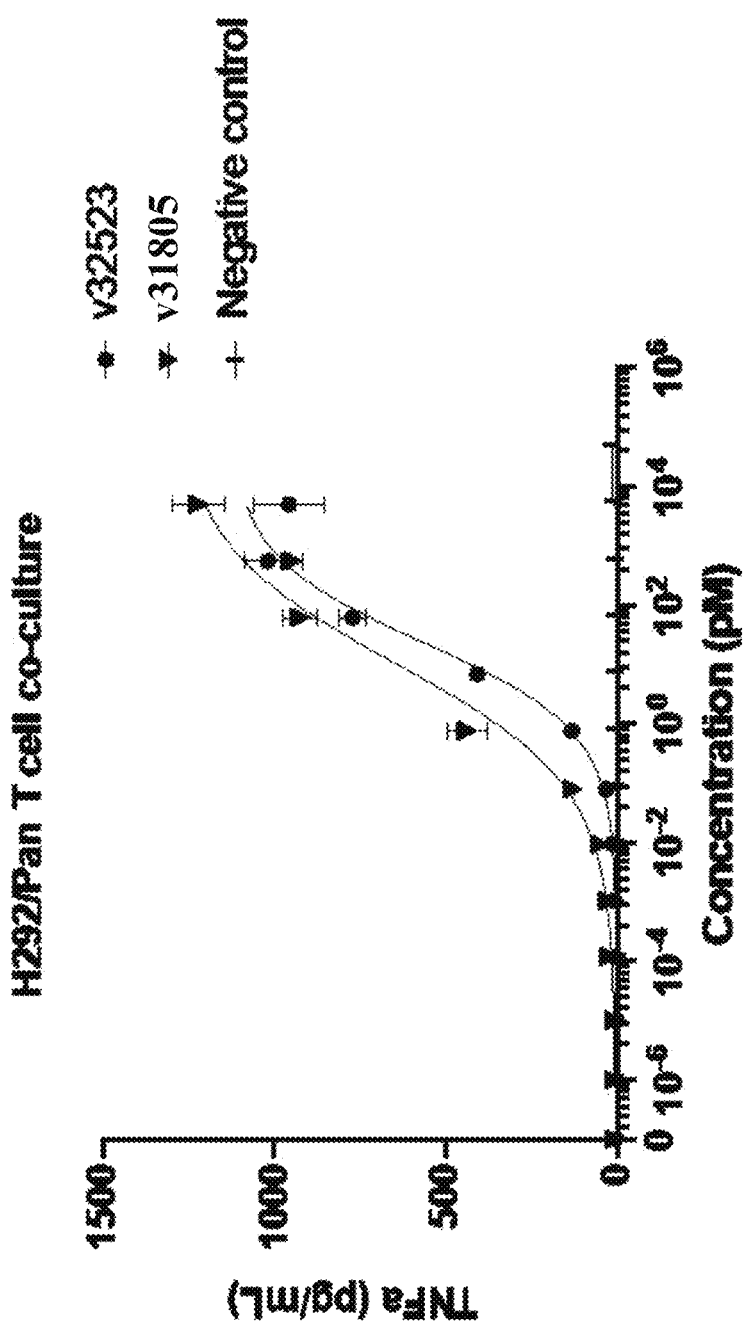
FIGS. 14A-14D show that the trivalent and bispecific antibody construct v32523 as well as the v31805 (MH6T-TriTAC) benchmark control construct induced TNFα (FIG. 14A and FIG. 14C) and IFNγ (FIG. 14B and FIG. 14D)
Figure 14B:
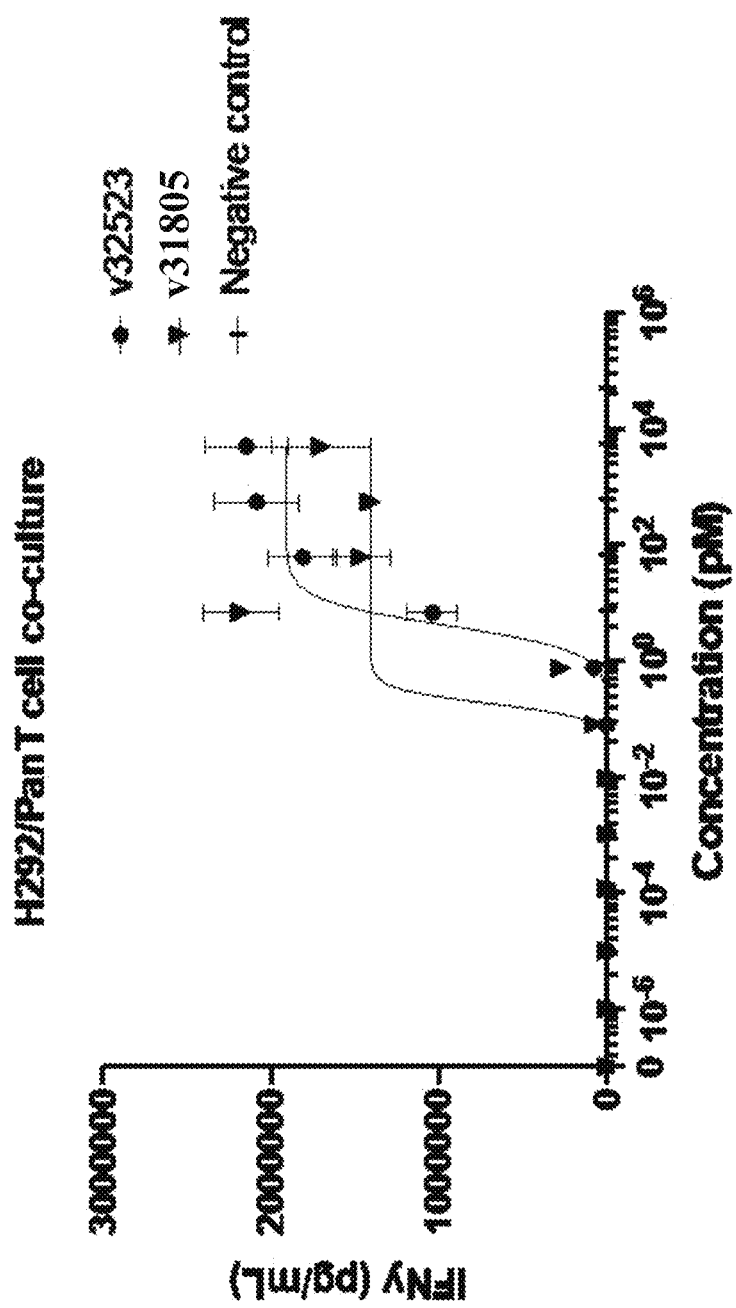
Figure 14C:
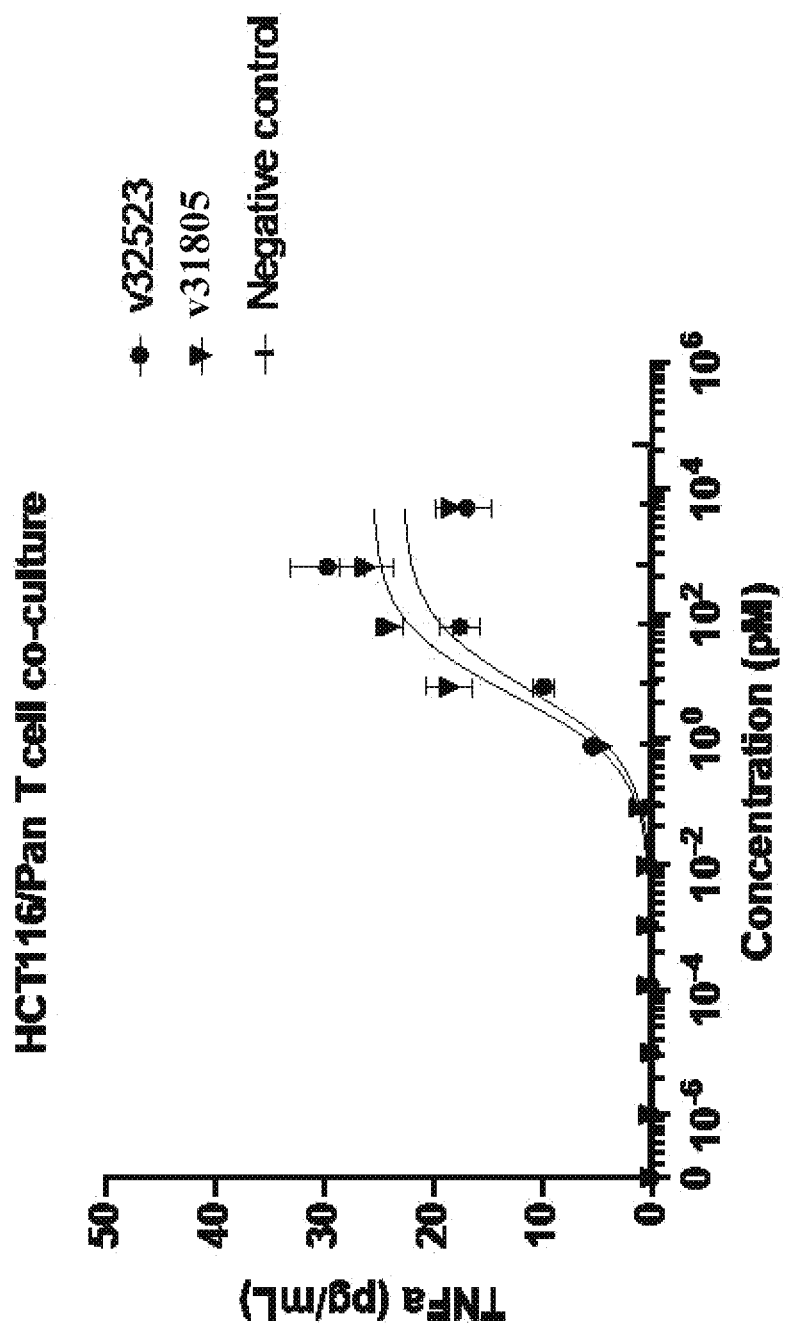
Figure 14D:
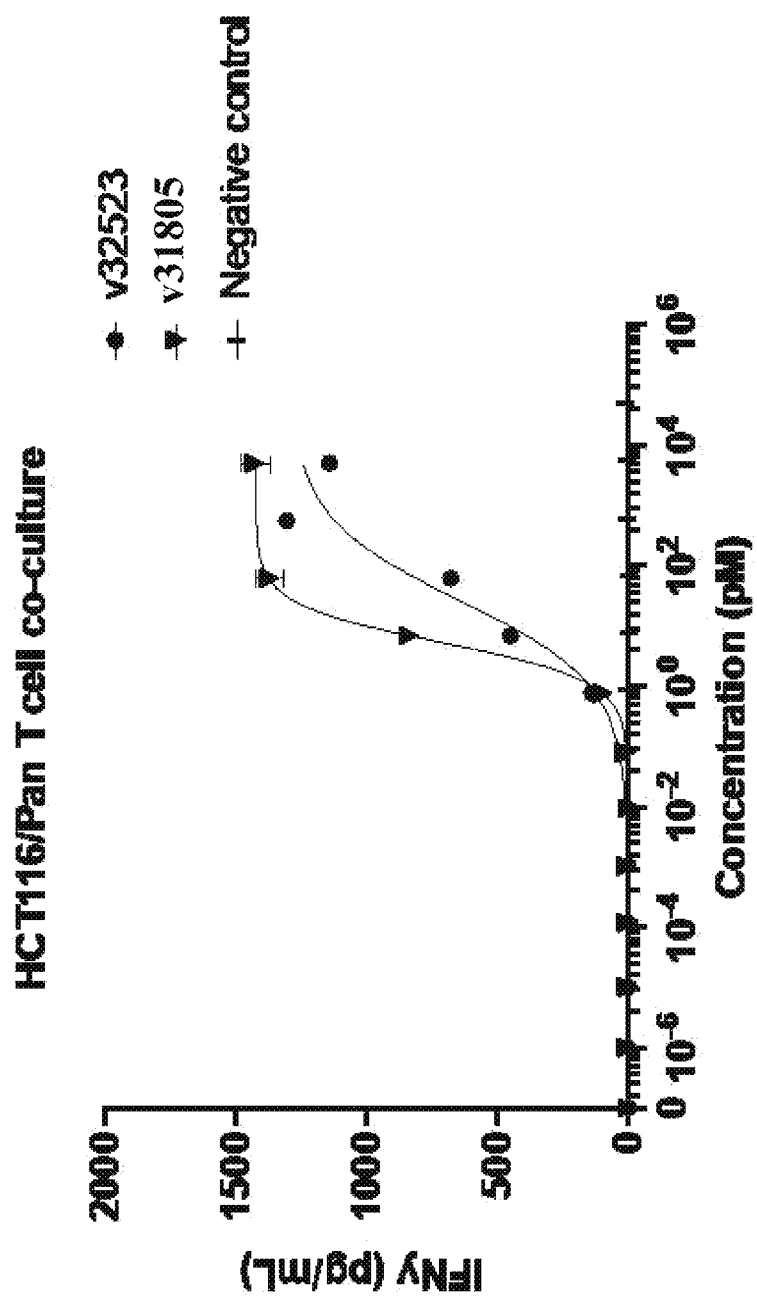

T cell dependent cellular cytotoxicity of the trivalent and bispecific construct v32523 was also tested in the presence of H292 lung cancer cells (FIG. 12C, ~170,000 MSLN/cell), OVCAR8 ovarian cancer cells (FIG. 12D, ~85,000 MSLN/cell), HCT-116 colon cancer cells (FIG. 12E, ~35,000 MSLN/cell) and H2452 mesothelioma cells (FIG. 12F, ~11,000 MSLN/cell), and compared to a negative control. These data further demonstrate the ability of the trivalent and bispecific antibody constructs disclosed herein to distinguish between tumor cells expressing varying amounts of MSLN, whereas the higher the MSLN surface receptor density, the higher the T cell mediated anti-tumor cytotoxicity elicited by the construct (v32523 in this case).

The data show that both tested constructs exhibited similar cytotoxic activity against the MSLN-high cell line, H292, as measured by the $IC_{50}$ value and maximum percent killing (TABLE 17). However, benchmark construct v31805 also exhibited high potency on the MSLN-low/negative cell line, A373, with an $IC_{50}$ value of about 2.45 and 35% maximum killing. On the other hand, the designed construct v32523 was more discriminatory towards antigen expression and hence showed less activity towards A375 when compared to v31805 (MH6T-TriTAC), killing only 12.83% of tumor cells at the highest concentrations tested. Construct v32523 also showed little to no activity on two additional MSLN$^{low}$ cell lines, OVTOKO and MCF7.

In further support of the above, FIGS. 21A-21C show that the trivalent and bispecific antibody construct v32523 induced potent MSLN-dependent cytokine production (IL-2 (FIG. 21A) and TNFα (FIG. 21B)) and T cell proliferation (FIG. 21C). The data demonstrate that no significant induction of cytokine production or T cell proliferation was observed in the absence of MSLN-expressing cells (i.e., presence of T cells only).

Taken together, the results demonstrate that v32523, due to its MSLN-dependent T cell activation, may provide a wider therapeutic index than the benchmark construct, v31805.

Example 14: Induction of Cytokine Release in an Antigen-Dependent Manner

This example shows experiments comparing T cell activation and cytokine release in the presence of tumor cells with varying levels of MSLN expression between the stability engineered trivalent and bispecific antibody construct, v32523, and the two benchmark constructs, Fab$^3$ construct v29191, and v31805. These constructs were tested in T cell-dependent cytotoxicity assays with tumor cell lines expressing varying levels of MSLN as described herein.

The antibody constructs to be tested (i.e., v21812, v29191, v31805) were diluted in RPMI1640 (Gibco)+10% FBS (ThermoFisher) and added to appropriate wells of the 384-well black flat bottom assay plates (ThermoFisher, Watham, MA). Human pan T cells were thawed and mixed with H292 cells (~152,000 MSLN/cell), HCT116 cells (~35,000 MSLN/cell), H2452 cells (~11,000 MSLN/cell), or A549 cells (~11,000 MSLN/cell) at an E:T ratio of 5:1. Plates were incubated for 72 hours at 37° C. and 5% carbon dioxide, after which Vybrant™ DyeCycle™ Violet Stain (ThermoFisher Scientific; V35003) was added to the cells. After a 30-minute incubation period with the stain, tumor cell viability was assessed through live tumor cell counts using the CellInsight High Content Screening Platform (ThermoFisher Scientific; CX51110). The assay was repeated with at least three primary blood donors. Data from the T cell-dependent cytotoxicity assay are presented TABLE 18 below and concentration response curves for the tested antibody constructs are presented in FIGS. 13A-13D.

TABLE 18

Cytotoxic Activity of Tested Antibody Constructs towards MSLN+ Tumor Cells Grown in Culture with Human Pan T Cells

| Construct | H292 [$IC_{50}$ (pM)] | HCT116 [$IC_{50}$ (pM)] | H2452 [$IC_{50}$ (pM)] | A549 [$IC_{50}$ (pM)] |
|---|---|---|---|---|
| v32523 | 0.7 | 1.1 | 0.2 | 0.01 |
| v29191 | 0.4 | Ambiguous | 15.9 | Ambiguous |
| v31805 | 0.7 | 0.6 | 0.9 | 0.003 |

All three antibody constructs tested were highly potent on the MSLN$^{high}$ cell line, H292. On the lower MSLN expressing cell lines, HCT116, H2452 and A549, the Fab$^3$ benchmark constructs v29191 was surprisingly less potent than the herein engineered construct v32523, even though it exhibits 7-fold higher relative affinity to MSLN. And although the construct v32523 showed an about 50-fold lower affinity to CD3 and an about 30-fold lower affinity to MSLN compared to the second benchmark tested, v31805 (MH6T-triTAC), its tumor cell killing activity was within a comparable potency range.

Together, these results further demonstrate that the herein disclosed format of construct v32523 had an unexpected and surprising impact on the construct's ability to provide superior T cell mediated anti-tumor activity and enable a more TAA (i.e., MSLN)-dependent cell killing profile, when compared to the two benchmark constructs tested, v31805 (MH6T-triTAC) and v29191 (2+1 Fab$^3$ TCB), and especially given the fact that the relative antigen affinity (for both CD3 and MSLN) of construct v32523 was lower compared to the two benchmarks.

Example 15: Msln Expression-Dependent Cytokine Induction

This example assessed the ability of the stability engineered trivalent and bispecific antibody construct, v32523, and the benchmark construct v31805 to activate T cells and production of the cytokines TNFα and IFNγ in the presence of the MSLN expressing cell lines H292 (~152,000 MSLN/cell) and HCT116 (~35,000 MSLN/cell).

The antibody constructs to be tested (i.e., v21812 and v31805) were diluted in RPMI1640 (Gibco)+10% FBS (ThermoFisher) and added to appropriate wells of the 384-well black flat bottom assay plates (ThermoFisher, Watham, MA). Human pan T cells were thawed and mixed with H292 or HCT116 cells, respectively, at an E:T ratio of 5:1 and then added to the plates. Plates were incubated for 72 hours at 37° C. and 5% carbon dioxide. Post incubation, 15 L/well of supernatant was transferred to non-binding 384-well plates (Greiner-Bio-One, Kremsmünster, Austria) and stored at −80° C.

The cytokines TNFα and IFNγ were quantified using MSD (Mesoscale Discovery, Piscataway, NJ). The night before cytokine quantification, MSD plates were blocked and coated in capture antibodies according to the manufacturers' instructions. The following day, plates were washed in PBS-T and 5 μl of assay diluent was added to each plate. The supplied TNFα and IFNγ standard (calibrator 1) was titrated as per manufacturer's instructions. Supernatants were thawed at room temperature and 5 μL of samples or standards were transferred to MSD plates. Detection antibodies were prepared at appropriate dilutions and 10 μL was added to each sample and standard well in MSD plates. The plates were sealed with aluminum foil and incubated away from light at room temperature for two hours. Plates were washed 3× in PBS-T and 40 μL MSD Gold read buffer T was added to each well. Plates were read on the MESO SECTOR 6000, and cytokine concentration was determined using MSD software. Data from a standard curve and samples were used to perform a nonlinear curve-fit with x-interpolation to obtain TNFα and IFNγ concentrations in pg/mL. Three independent experiments were conducted for each target cell line and data from each was analyzed in a nonlinear mixed effect model to generate curve fit and 95% confidence intervals.

The data for induction of TNFα and IFNγ by pan T cells after co-incubation with either H292 or HCT116 cells, and in the presence of either construct v32523 or benchmark v31805, are summarized in FIGS. 14A-14D, respectively.

The data show that, across the three independent experiments, the construct v32523 as well as the benchmark v31805 were equivalently potent inducers of TNFα and IFNγ release by T cells co-incubated with H292 or HCT116 cells. Furthermore, it is noted that both constructs showed a cytokine induction profile that appeared to be dependent on MSLN expression of the tumor cells, e.g., as indicated by the significantly increased amounts (in pg/mL) of released cytokine in the H292 setting (approx. 50-fold increase for TNFα and 1000-fold increase for IFNγ, top of curve comparison) compared to the HCT116 setting.

Example 16: Antibody Construct Mediated T Cell Proliferation in the Presence of MSLN Expressing Target Cells This example describes the activation and proliferation of T cells through cross-linking of CD3ε following binding of tested antibody constructs to CD3 and MSLN. Induction of target (i.e., MSLN)-dependent T cell proliferation using the stability engineered trivalent and bispecific antibody construct, v32523, as well as the benchmark construct v31805, was assessed as described below.

The antibody constructs to be tested were diluted in RPMI1640 (Gibco)+10% FBS (Thermofisher Scientific)+1% Pen/Strep (Gibco) and titrated 1:5 in appropriate wells of the 96-well flat bottom assay plates (ThermoFisher, Watham, MA). Human pan T cells were thawed and incubated with 2 μM CellTrace CFSE staining solution (ThermoFisher Scientific) for 15 minutes in a 37° C. 5% carbon dioxide. Following incubation with CellTrace CFSE staining solution, T cells were washed and mixed with OVCAR-3 cells (~768,000 MSLN/cell) at an E:T ratio of 10:1. Plates were incubated at 37° C. and 5% carbon dioxide for 5 days, after which cells were transferred to the wells of a V-bottom 96 well plate and washed with 1×PBS (Gibco)+2% FBS (ThermoFisher Scientific). Cells were then stained with APC-conjugated anti-human CD3, OKT3, and Zombie Violet live/dead stain (Biolegend) and incubated at room temperature (RT) for 60 minutes. Following staining of cells, plates were washed three times with 1×PBS (Gibco)+2% FBS (ThermoFisher Scientific). CFSE, APC and BV421 signals of up to 100,000 events per well were measured by flow cytometry using BD LSRFortessa Cell Analyzer (BD Biosciences). Data analysis and T cell proliferation modeling was completed using FlowJo software (BD Biosciences).

Concentration response curves for the tested antibody constructs v32523 and v31805 (MH6T-triTAC) are shown in FIG. 15. The data show that both CD3×MSLN bispecific antibody construct induced comparable levels of T cell proliferation, with about 40% of T cells having proliferated at antibody construct concentrations equal to or higher than about 8 pM.

Furthermore, the two constructs v32523 and v31805 were tested in high (5:1, FIG. 22A) and low (1:5, FIG. 22B) E:T ratio environments, and the trivalent and bispecific construct v32523 exhibited greater anti-tumor activity in both scenarios when compared to the clinical benchmark construct v31805. T cell dependent cellular cytotoxicity was assessed by co-culturing human PBMCs with OVCAR3 tumor cells at 5:1 (FIG. 22A) or 1:5 (FIG. 22B) E:T ratio then treating with v32523 or v31805 for 3 days. Cell killing was measured by high content imaging.

Example 17: In Vivo Tumor Growth Inhibition Using a Trivalent and Bispecific Antibody Construct This example describes two in vivo dose-range finding xenograft studies for the stability engineered trivalent and bispecific antibody construct, v32523, using two different MSLN-expressing tumor cell lines, OVCAR-3 and HCT116. This study was further set out to determine the ability of construct v32523 to inhibit tumor growth and/or reduce tumor size relative to control animals.

Human Ovarian Cancer Model: NIH:OVCAR-3
In-Vivo Amplification of Subcutaneous (SC) NIH:OVCAR-3 Tumors in Nude Mice Frozen NIH:OVCAR-3 ascitic cells, obtained from previous in vivo amplification after intraperitoneal (IP) injection of NIH:OVCAR-3 cell line, were thawed and subsequently SC implanted into BALB/c-nude J mice (Charles River Laboratories). The NIH:OVCAR-3 ascitic tumor cell implantation was performed 24 hours after whole body irradiation with a γ-source (1.44 Gy, 60Co, BioMEP S.A.RL., Dijon, France). Tumors were fragmented when they reached 500-1500 mm$^3$.

NIH:OVCAR-3 Tumor Induction in NOG Mice for Anti-Tumor Activity Study

Irradiated NOG female mice (Taconic) were subcutaneously implanted with the NIH:OVCAR-3 tumor fragments, 48 hours after irradiation (1.44 Gy, 60 Co, BioMep, Bretenieres, France). PBMCs were injected when tumors reach 100-200 mm³. The mice were then split in 3 sub-groups (one sub-group for each donor A, B or C). The three sub-groups had equivalent mean tumor volumes. Each one of the three PBMCs donors was injected in one sub-group on the same day. Each mouse received one single intravenous (IV) injection of $10^7$ PBMCs (200 µL in PBS).

Two to three days post PBMCs injection, mice from each of the three sub-groups were randomized according to their individual tumor volume using Vivo Manager® software (Biosystemes, Couternon, France). These mice were randomized to form 5 groups of 7 mice (for example groups 1A, 2A and 3A with mice from donor A).

TABLE 19

Study Groups and Dosing Regiment for NIH: OVCAR-3 Study

| Group | Test Article | Dose (IV) | Treatment Schedule |
|---|---|---|---|
| 1A (7 mice-donor A) | Negative control | 3.0 mg/kg | Q7Dx4 |
| 1B (7 mice-donor B) | | | |
| 1C (7 mice-donor C) | | | |
| 2A (7 mice-donor A) | v32523 | 3.0 mg/kg | Q7Dx4 |
| 2B (7 mice-donor B) | | | |
| 2C (7 mice-donor C) | | | |
| 3A (7 mice-donor A) | v32523 | 1.0 mg/kg | Q7Dx4 |
| 3B (7 mice-donor B) | | | |
| 3C (7 mice-donor C) | | | |
| 4A (7 mice-donor A) | v32523 | 0.1 mg/kg | Q7Dx4 |
| 4B (7 mice-donor B) | | | |
| 4C (7 mice-donor C) | | | |
| 5A (7 mice-donor A) | v32523 | 0.01 mg/kg | Q7Dx4 |
| 5B (7 mice-donor B) | | | |
| 5C (7 mice-donor C) | | | |

A statistical test (analysis of variance, ANOVA) was performed to test for homogeneity between groups for each donor. Mice were dosed intravenously with the antibody construct on the day of randomization (DR) then every four days, according to the treatment schedule shown in TABLE 19.

Animals were monitored at regular intervals for tumor growth using caliper measurements and for weight loss. Animals were euthanized and necropsied when (i) tumor volume reached a maximal tumor volume of 2 000 mm³, (ii) when tumor exceeds 10% of normal body weight, (iii) at a body weight loss of greater than 20%, or (iv) after a maximum of 12 weeks post tumor injection. Animal housing and experimental procedures were realized according to the French and European Regulations and NRC Guide for the Care and Use of Laboratory Animals.

As shown in FIG. 16A, tumor outgrowth was observed in control-treated animals. Treatment with v32523 at doses of 1.0 and 3.0 mg/kg resulted in significant tumor growth inhibition, and, particularly for the 3.0 mg/kg group, a significant reduction in tumor size was achieved, relative to the control-treated animals. Animal body weight remained stable under all conditions for the duration of the study.

Taken together, these data further demonstrate that the trivalent and bispecific antibody construct, v32523, may possess a superior format combined with a tailored affinity profile for MSLN, that can enable such constructs (e.g., v21812, v32523) to induce significant tumor growth inhibition in vivo.

Human Colorectal Cancer Model: HCT116
HCT116 Tumor Induction and PBMC Engraftment in NPG Mice for Anti-Tumor Activity NOG female mice (Beijing Vital Star Biotechnology Co, Ltd.) were inoculated subcutaneously in the right front flank region with HCT116 tumor cells ($5 \times 10^6$) in 0.1 ml of PBS for tumor development. On the same day, each mouse was also inoculated intraperitoneally with $5 \times 10^6$ human PBMC for human immune system construction. The date of inoculation is denoted as day 0.

Animals with a single tumor of a volume of 80-250 mm³ were distributed in experimental study groups according to the study protocol. At randomization, the mean tumor volume for all groups was between 125-200 mm³ with an intergroup variability of less than 4 mm³. Animals inoculated with donor 1 and donor 2 were enrolled and randomly allocated to 6 study groups. Randomization was performed based on "Matched distribution" method (StudyDirector™ software, version 3.1.399.19). Animals not randomized were maintained until sponsor authorization.

The treatment was initiated immediately post randomization per study design. The test article administration and the animal numbers for each study group are shown in TABLE 20.

TABLE 20

Study Groups and Dosing Regiment for HCT116 Study

| Group | Test Article | Dose (IV) | Treatment Schedule |
|---|---|---|---|
| 1A (6 mice-donor A) | Negative control | 3.0 mg/kg | Q7Dx4 |
| 1B (6 mice-donor B) | | | |
| 2A (6 mice-donor A) | v32523 | 3.0 mg/kg | Q7Dx4 |
| 2B (6 mice-donor B) | | | |
| 3A (6 mice-donor A) | v32523 | 1.0 mg/kg | Q7Dx4 |
| 3B (6 mice-donor B) | | | |
| 4A (6 mice-donor A) | v32523 | 0.5 mg/kg | Q7Dx4 |
| 4B (6 mice-donor B) | | | |
| 5A (6 mice-donor A) | v32523 | 0.1 mg/kg | Q7Dx4 |
| 5B (6 mice-donor B) | | | |
| 6A (6 mice-donor A) | N/A | N/A | N/A |
| 6B (6 mice-donor B) | | | |

After tumor cells inoculation, tumor volumes were measured twice per week after randomization in two dimensions using a caliper. The animals were checked daily for morbidity and mortality. During routine monitoring, the animals were checked for any effects of tumor growth and treatments on behavior such as mobility, food and water consumption, body weight gain/loss (body weights were measured twice per week after randomization or based on sponsor's request after randomization), eye/hair matting and any other abnormalities. Mortality and observed clinical signs were recorded for individual animals in detail. Animals were euthanized and necropsied when (i) tumor volume reached a maximal tumor volume of 2,000 mm³, (ii) when tumor exceeds 10% of normal body weight, (iii) at a body weight loss greater that 20%, or (iv) after a maximum of 35 days post tumor injection.

As shown in FIG. 16B, tumor outgrowth was observed in vehicle and negative control-treated animals. All doses of v32523 resulted in significant tumor growth inhibition relative to the control-treated animals. Furthermore, the construct v32523 achieved measurable reduction in tumor size at doses of 3.0 mg/kg and even as low as 1.0 mg/kg. Animal body weight remained stable under all conditions for the duration of the study.

Taken together, these data demonstrate that the trivalent and bispecific antibody construct, v32523, can induce significant tumor growth inhibition and/or reduction in tumor growth in multiple xenograft models of different mesothelin expressing indications, highlighting the fact that the trivalent and bispecific antibody constructs described herein may have the ability to serve as an additional treatment option for mesothelin expressing cancers.

Example 18: Pharmacokinetics of Trivalent and Bispecific Antibody Constructs

This example describes in vivo studies using naïve as well as MSLN+ tumor bearing mice to determine pharmacokinetic properties of the trivalent and bispecific antibody construct, v32523.

PK of Construct v32523 in Naïve Mice

NOG female mice (Beijing Vital Star Biotechnology Co, Ltd.) were randomly allocated to four study groups according to body weight. Randomization was performed on Day 0 based on "Matched distribution" method (StudyDirector™ software, version 3.1.399.19). The treatment was initiated immediately post randomization per study design. The test article administration and the animal numbers in each study group are shown in TABLE 21 below.

TABLE 21

PK Study Groups and Dosing Regimen

| Group | Number of Mice | Test Article | Dose (IV) | Treatment Schedule |
|---|---|---|---|---|
| 1 | 6 | v32523 | 3.0 mg/kg | Single dose |
| 2 | 6 | v32523 | 1.0 mg/kg | Single dose |
| 3 | 6 | v32523 | 0.5 mg/kg | Single dose |
| 4 | 6 | v32523 | 0.1 mg/kg | Single dose |

The study was performed for 14 days during which, serum was sampled according to the schedule outlined below in TABLE 22.

TABLE 22

Serum Sampling Schedule

| Group | No. of Animal(s) to be Sampled | Time of Sample Collection |
|---|---|---|
| 1 and 2 | 1, 2, 3 | 1 h, 48 h and 7 days |
|  | 4, 5, 6 | 6 h, 72 h and 14 days |
| 3 and 4 | 1, 2, 3 | 1 h, 48 h and 7 days |
|  | 4, 5, 6 | 6 h and 72 h |

The animals were checked daily for morbidity and mortality. During routine monitoring, the animals were checked for any effects of treatments on behavior such as mobility, food and water consumption, body weight gain/loss (body weights were measured twice per week after randomization), eye/hair matting and any other abnormalities. Mortality and observed clinical signs were recorded for individual animals.

A colorimetric ELISA method was used to measure the presence and amount of v32523 in the mouse serum samples. Plates coated with recombinant mesothelin-Fc fusion protein were used to capture v32523, which was then detected with HRP-conjugated goat anti-human IgG F(ab)$_2$ antibody. Color development was achieved using TBM substrate solution followed by HCL to stop the reaction.

Serum concentrations of v32523 were accurately determined for all timepoints tested and are shown in FIG. 17B and summarized in TABLE 23. Calculated values of serum half-life and clearance were similar between the doses of 3.0, 1.0, and 0.1 mg/kg. The serum half-life of v32523 was consistent with the expected half-life of an antibody and was calculated to be between 5-18 days in naive mice. Clearance appeared to be linear at doses of 1.0 mg/kg and above but may be nonlinear at lower doses.

TABLE 23

Single-Dose PK Parameters Obtained from Naïve Mice

| Test article | Dose (mg/kg) | Half-life (hr) | Cmax (ng/mL) | AUC$_{INF}$ (hr*ng/mL) | CL (mL/hr/kg) | Vz (mL/kg) |
|---|---|---|---|---|---|---|
| v32523 | 3.0 | 455.1 | 75 545.6 | 27,719,202.7 | 0.11 | 71.1 |
|  | 1.0 | 355.4 | 22 485.2 | 5,520,738.0 | 0.18 | 92.9 |
|  | 0.5 | 122.9 | 10 579.5 | 1,342,531.8 | 0.37 | 66.0 |
|  | 0.1 | 318.5 | 2 252.9 | 636,768.3 | 0.16 | 72.2 |

PK of Construct v32523 in PBMC-Engrafted, OVCAR3 Tumor-Bearing Mice

Serum was collected from mice in the NIH:OVCAR-3 in vivo efficacy study described in EXAMPLE 17 according to the schedule shown below in TABLE 24.

TABLE 24

Serum Sampling Schedule

| Group | Animals per Timepoint | Time of Sample Collection |
|---|---|---|
| Negative control (3.0 mg/kg) | 2 (x3 donors) | 1 h, 24 h, 72 h |
|  | 3 (x3 donors) | 6 h, 168 h |
| v32523 (3.0 mg/kg) | 2 (x3 donors) | 1 h, 24 h, 72 h |
|  | 3 (x3 donors) | 6 h, 168 h |
| v32523 (1.0 mg/kg) | 2 (x3 donors) | 1 h, 24 h, 72 h |
|  | 3 (x3 donors) | 6 h, 168 h |
| v32523 (0.1 mg/kg) | 2 (x3 donors) | 1 h, 24 h, 72 h |
|  | 3 (x3 donors) | 6 h, 168 h |

A colorimetric ELISA method was used to measure presence and amount of v32523 in the mouse serum samples. Plates coated with recombinant mesothelin-Fc fusion protein were used to capture v32523. To capture the Negative control antibody in the mouse serum samples, plates coated were coated with goat anti-human IgG Fc (Jackson Laboratories, Catalog #109-005-098). Both test articles were detected with HRP-conjugated goat anti-human IgG F(ab)2 antibody. Color development was achieved using TBM substrate solution followed by HCL to stop the reaction.

Serum concentrations of v32523 were accurately determined for the 3.0 and 1.0 mg/kg doses at all timepoints tested and are presented in FIG. 17A and summarized below in TABLE 25. Measured serum concentrations of the negative control, dosed at 3 mg/kg, were higher than concentrations of v32523 at the same dose. Single-dose PK parameters were calculated for v32523 at 3.0 and 1.0 mg/kg and the negative control at 3.0 mg/kg. Clearance of v32523 appeared to be linear at doses of 1.0 mg/kg and higher, and serum half-life was approximately 4.5-5.5 days at these doses. A follow-up analysis confirmed that serum exposure of the negative control molecule was equivalent to or greater than exposure to the highest dose of v32523 tested.

TABLE 25

Single-Dose PK Parameters Obtained from
PBMC-Engrafted, OVCAR3 Tumor-Bearing Mice

| Test article | Dose (mg/kg) | Half-life (hr) | Cmax (ng/mL) | $AUC_{INF}$ (hr*ng/mL) | CL (mL/hr/kg) | Vz (mL/kg) |
|---|---|---|---|---|---|---|
| Negative control | 3.0 | 221.5 | 168.5 | 34,338.4 | 0.09 | 27.9 |
| v32523 | 3.0 | 106.9 | 73.4 | 5,425.2 | 0.55 | 85.3 |
|  | 1.0 | 134.5 | 27.6 | 2,212.9 | 0.45 | 87.7 |

Example 19: In Vivo Studies Comparing a Trivalent and Bispecific Antibody Constructs to Clinical Benchmark Constructs This example describes three in vivo head-to-head comparison studies evaluating the in vivo anti-tumor activity of the trivalent and bispecific antibody construct, v32523, relative to the benchmark constructs (i) Fab$^3$ trivalent and bispecific v29191, and (ii) clinical benchmark v31805. This study was conducted using exposure-matched doses of the construct v31805 due to its difference in molecular weight and overall format (see, e.g., FIG. 1D) compared to the other two tested constructs.

Study 1: Human Colorectal Cancer Model, HCT116, with Constructs v32523 and v31805

NOG female mice (Beijing Vital Star Biotechnology Co, Ltd.) were inoculated subcutaneously in the right front flank region with HCT116 tumor cells (5×10$^6$) in 0.1 ml of PBS for tumor development. On the same day, each mouse was also inoculated intraperitoneally with 5×10$^6$ human PBMC for human immune system construction. The date of inoculation was be denoted as day 0.

Animals with a single tumor of a volume of 80-250 mm$^3$ were distributed in experimental groups according to the study protocol. At randomization the mean tumor volume for all groups was between 125-200 mm$^3$ with an intergroup variability of less than 4 mm$^3$. Animals inoculated with donor 1 and donor 2 were enrolled and randomly allocated to 7 study groups. Randomization was performed based on "Matched distribution" method (StudyDirector™ software, version 3.1.399.19). Animals not randomized were maintained until sponsor authorization.

The treatment was initiated immediately post randomization per study design. The test article administration and the animal numbers in each study group are shown below in TABLE 26.

TABLE 26

Study Groups and Dosing Regiment
Comparing v32523 against v31805

| Group | Test Article | Dose | Treatment Schedule |
|---|---|---|---|
| 1A (6 mice-donor A) 1B (6 mice-donor B) | Negative control | 3.0 mg/kg (IV) | Qwx4 |
| 2A (6 mice-donor A) 2B (6 mice-donor B) | v32523 | 3.0 mg/kg (IV) | Qwx4 |
| 3A (6 mice-donor A) 3B (6 mice-donor B) | v32523 | 1.0 mg/kg (IV) | Qwx4 |
| 4A (6 mice-donor A) 4B (6 mice-donor B) | v31805 | 0.81 mg/kg (IV) | Qdx25 |
| 5A (6 mice-donor A) 5B (6 mice-donor B) | v31805 | 0.43 mg/kg (IP) | Qdx25 |
| 6A (6 mice-donor A) 6B (6 mice-donor B) | v31805 | 0.14 mg/kg (IP) | Qdx25 |
| 7A (6 mice-donor A) 7B (6 mice-donor B) | v31805 | 0.007 mg/kg (IP) | Qdx25 |

Study 2: Human Colorectal Cancer Model, HCT116, with Constructs v32523, v29191 and v31805

Tumor inoculation and animal randomization was carried out as described for the first HCT116 study described above using constructs v32523 and v31805. Similarly, the treatment was initiated immediately post randomization per study design. The test article administration and the animal numbers in each study group are shown below in TABLE 27.

TABLE 27

Study Groups and Dosing Regiment Comparing
v32523 against v31805 and v29191

| Group | Test Article | Dose | Treatment Schedule |
|---|---|---|---|
| 1A (6 mice-donor A) 1B (6 mice-donor B) | Negative control | 3.0 mg/kg (IV) | Qwx4 |
| 2A (6 mice-donor A) 2B (6 mice-donor B) | v32523 | 3.0 mg/kg (IV) | Qwx4 |
| 3A (6 mice-donor A) 3B (6 mice-donor B) | v29191 | 3.0 mg/kg (IV) | Qwx4 |
| 4A (6 mice-donor A) 4B (6 mice-donor B) | v29191 | 1.0 mg/kg (IV) | Qwx4 |
| 5A (6 mice-donor A) 5B (6 mice-donor B) | v31805 | 0.81 mg/kg (IP) | Qdx25 |
| 6A (6 mice-donor A) 6B (6 mice-donor B) | v31805 | 0.43 mg/kg (IP) | Qdx25 |

After tumor cell inoculation, tumor volumes were measured twice per week after randomization in two dimensions using a caliper. The animals were checked daily for morbidity and mortality. During routine monitoring, the animals were checked for any effects of tumor growth and treatments on behavior such as mobility, food and water consumption, body weight gain/loss (body weights were measured twice per week after randomization or based on sponsor's request after randomization), eye/hair matting and any other abnormalities. Mortality and observed clinical signs were recorded for individual animals in detail. Animals were euthanized and necropsied when (i) tumor volume reached a maximal tumor volume of 2,000 mm$^3$, (ii) when tumor exceeds 10% of normal body weight, (iii) at a body weight loss greater that 20%, or (iv) after a maximum of 35 days post tumor injection.

The data shown in FIGS. 18-19 for the first HCT116 study (v32523 vs. v31805) and the second HCT116 study (v32523 vs. v31805 and v29191), respectively, indicated tumor outgrowth in the negative control-treated animals of both studies. The data also clearly show that the 1 mg/kg and 3 mg/kg doses of construct v32523 resulted in significant tumor growth inhibition relative to both the control-treated animals as well as those animals that were treated with either one of the two benchmark constructs. Specifically, the 1 mg/kg and 3 mg/kg doses of v32523 resulted in significantly greater tumor growth inhibition compared to the exposure matched v31805 doses of 0.14 mg/kg and 0.43 mg/kg, respectively. In the second HCT116 study, it is also noted that construct v32523 at 3 mg/kg also showed greater anti-tumor activity than the Fab[3] benchmark (v29191) at both doses tested, 1 mg/kg and 3 mg/kg.

Study 3: Human Ovarian Cancer Model, NIH:OVCAR-3 with v32523 and MH6T-triTAC

Frozen NIH:OVCAR-3 ascitic cells, obtained from previous in vivo amplification after IP injection of NIH:OVCAR-3 cell line, were thawed and subsequently SC implanted into BALB/c-nude J mice (Charles River Laboratories). The NIH:OVCAR-3 ascitic tumor cell implantation was performed 24 hours after whole body irradiation with a γ-source (1.44 Gy, 60Co, BioMEP S.A.RL., Dijon, France). Tumors were fragmented when they reached 500-1500 mm$^3$.

Irradiated NOG female mice (Taconic) were subcutaneously implanted with the NIH:OVCAR-3 tumor fragments, 48 hours after irradiation (1.44 Gy, 60Co, BioMep, Bretenieres, France). PBMCs were injected when tumors reached 100-200 mm$^3$. The mice were then split into 3 sub-groups (one sub-group for each donor A, B or C). The three sub-groups had equivalent mean tumor volumes. Each one of the three PBMCs donors was injected in one sub-group of tumor bearing mice on the same day. Each mouse received one single intravenous (IV) injection of 107 PBMCs (200 μL in PBS).

Two to three days post PBMCs injection, mice from each of the three sub-groups were randomized according to their individual tumor volume using Vivo Manager® software (Biosystemes, Couternon, France). These mice were randomized to form 3 groups of 7 mice (for example, groups 1A, 2A and 3A with mice from donor A). A statistical test (analysis of variance, ANOVA) was performed to test for homogeneity between groups for each donor. Mice were dosed intravenously with test articles on the day of randomization then every four days, according to the treatment schedule shown below in TABLE 28.

TABLE 28

Study Groups and Dosing Regiment Comparing v32523 against v31805

| Group | Test Article | Dose | Treatment Schedule |
|---|---|---|---|
| 1A (7 mice-donor A) | Negative control | 3.0 mg/kg (IV) | Q7Dx4 |
| 1B (7 mice-donor B) | | | |
| 1C (7 mice-donor C) | | | |
| 2A (7 mice-donor A) | v32523 | 3.0 mg/kg (IV) | Q7Dx4 |
| 2B (7 mice-donor B) | | | |
| 2C (7 mice-donor C) | | | |
| 3A (7 mice-donor A) | v31805 | 0.8 mg/kg (IP) | Qdx25 |
| 3B (7 mice-donor B) | | | |
| 3C (7 mice-donor C) | | | |

Animals were monitored at regular intervals for tumor growth using caliper measurements and for weight loss. Animals were euthanized and necropsied when (i) tumor volume reached a maximal tumor volume of 2 000 mm$^3$, (ii) when tumor exceeds 10% of normal body weight, (iii) at greater than 20% body weight loss, or (iv) after a maximum of 12 weeks post tumor injection. Animal housing and experimental procedures were realized according to the French and European Regulations and NRC Guide for the Care and Use of Laboratory Animals. Animal body weight remained stable under all conditions for the duration of this study.

As shown in FIG. 20, tumor outgrowth was observed in control-treated animals, and, although to a lesser extent, in the treatment group that used the clinical benchmark construct v31805 (MH6T-triTAC). Treatment with the trivalent and bispecific construct v32523, on the other hand, resulted in significant tumor growth inhibition and reduction in tumor size relative to the control- and v31805-treated animals.

Taken together, the data obtained from these three in vivo studies using different tumor models further demonstrate the superior in vivo anti-tumor activity of the engineered trivalent and bispecific antibody constructs of the present disclosure over conventional constructs, including construct v31805, which is currently evaluated in clinical trials.

Example 20: Non-Human Primate Toxicology Study

This example describes a toxicology study that was conducted in cynomolgus monkeys using the trivalent and bispecific antibody construct v38490. As further described herein, the construct v38490 is essentially identical to v32523, except that the two heavy chains each contained an additional C-terminal lysine residue and was used in this study solely for production purposes. It is assumed that the C-terminal lysine residues are cleaved shortly after expression.

Cynomolgus monkeys were given a single i.v. dose of 1, 10, or 30 mg/kg v38490. Serum levels of fibrinogen were elevated compared to baseline in animals treated with v38490 (FIG. 23A). Transient increases in IL-6 (FIG. 23B), MCP-1 and GM-CSF were observed. Hyperplasia/hypertrophy and mild inflammation in mesothelium of multiple tissues was observed 1 week after dosing with v38490. Observations were similar at all doses tested, i.e., using 1, 10, and 30 mg/kg doses of v38490.

Following dosing, serum was collected over 14 days and v38490 serum concentrations were measured by ELISA. The serum half-life of v38490 in cynomolgus monkeys was calculated to about 3 days (FIG. 23C).

The description, for purposes of explanation, has been described with reference to specific implementations. However, the illustrative discussions above are not intended to be exhaustive or to limit the implementations to the precise forms disclosed. Many modifications and variations are possible in view of the embodiments described herein. The implementations were chosen and described in order to best explain the principles and their practical applications, to thereby enable others skilled in the art to best utilize the implementations and various implementations with various modifications as are suited to the particular use contemplated.

All publications, patents, and patent applications mentioned in this specification are herein incorporated by reference in their entireties to the same extent as if each individual publication, patent, or patent application was specifically and individually indicated to be incorporated by reference. In the event of a conflict between a term herein and a term in an incorporated reference, the term herein controls.

Sequence Table

Selected embodiments and amino acid sequences of antibody constructs and portions or fragments thereof (e.g., amino acid chains, scFv, Fab or Fc domains, linker, etc.) that are disclosed and described herein are shown in TABLE 29.

Unless otherwise defined herein, antibody construct polypeptide chains labeled with an "H" refer to an Ig heavy chain, and polypeptide chains labeled with an "L" refer to an Ig light chain.

TABLE 29

Amino Acid Sequences of Antibody Constructs and Domains thereof

| Domain # Description/ Variant #/ Target | Chain/ Type | SEQ ID NO | SEQUENCE |
|---|---|---|---|
| v32523 = Trivalent and Bispecific Antibody Construct [MSLN (2 scFv) x CD3 (1 Fab)] | | | |
| 23866 | H | 100 | DIQMTQSPSSLSASVGDRVTITCSASSSVSYMHWYQQKS GKAPKLLIYDTSKLASGVPSRFSGSGSGTDFTLTISSLQ PEDFATYYCQQWSGYPLTFGQGTKLEIKGGGGSGGGGSG GGGSGGGGSQVQLVQSGAEVKKPGASVKVSCKASGYSFT GYTMNWVRQAPGQGLEWMGLITPYNGASSYNQKFRGKAT MTVDTSTSTVYMELSSLRSEDTAVYYCARGGYDGRGFDY WGQGTLVTVSSGGGGSEVQLVESGGGLVQPGGSLRLSCA ASGVTFNYYGMSWIRQAPGKGLEWVASITSSGGRIYYPD SVKGRFTISRENTQKTLYLQMNSLRAEDTAVYYCTLDGR DGWVAYWGQGTLVTVSSASTKGPSVFPLAPSSKSTSGGT AALGCLVKDYFPEPVTVSWNSGALTSGVHTFPAVLQSSG LYSLSSVVTVPSSSLGTQTYICNVNHKPSNTKVDKKVEP KSCDKTHTCPPCPAPEAAGGPSVFLFPPKPKDTLMISRT PEVTCVVVSVSHEDPEVKFNWYVDGVEVHNAKTKPREEQ YNSTYRVVSVLTVLHQDWLNGKEYKCKVSNKALPAPIEK TISKAKGQPREPQVYVYPPSRDELTKNQVSLTCLVKGFY PSDIAVEWESNGQPENNYKTTPPVLDSDGSFALVSKLTV DKSRWQQGNVFSCSVMHEALHNHYTQKSLSLSPG |
| 29294 | H + "K" (C-term. Lysine) | 171 | DIQMTQSPSSLSASVGDRVTITCSASSSVSYMHWYQQKS GKAPKLLIYDTSKLASGVPSRFSGSGSGTDFTLTISSLQ PEDFATYYCQQWSGYPLTFGQGTKLEIKGGGGSGGGGSG GGGSGGGGSQVQLVQSGAEVKKPGASVKVSCKASGYSFT GYTMNWVRQAPGQGLEWMGLITPYNGASSYNQKFRGKAT MTVDTSTSTVYMELSSLRSEDTAVYYCARGGYDGRGFDY WGQGTLVTVSSGGGGSEVQLVESGGGLVQPGGSLRLSCA ASGVTFNYYGMSWIRQAPGKGLEWVASITSSGGRIYYPD SVKGRFTISRENTQKTLYLQMNSLRAEDTAVYYCTLDGR DGWVAYWGQGTLVTVSSASTKGPSVFPLAPSSKSTSGGT AALGCLVKDYFPEPVTVSWNSGALTSGVHTFPAVLQSSG LYSLSSVVTVPSSSLGTQTYICNVNHKPSNTKVDKKVEP KSCDKTHTCPPCPAPEAAGGPSVFLFPPKPKDTLMISRT PEVTCVVVSVSHEDPEVKFNWYVDGVEVHNAKTKPREEQ YNSTYRVVSVLTVLHQDWLNGKEYKCKVSNKALPAPIEK TISKAKGQPREPQVYVYPPSRDELTKNQVSLTCLVKGFY PSDIAVEWESNGQPENNYKTTPPVLDSDGSFALVSKLTV DKSRWQQGNVFSCSVMHEALHNHYTQKSLSLSPGK |
| MSLN | $V_L$ | 101 | DIQMTQSPSSLSASVGDRVTITCSASSSVSYMHWYQQKS GKAPKLLIYDTSKLASGVPSRFSGSGSGTDFTLTISSLQ PEDFATYYCQQWSGYPLTFGQGTKLEIK |
| $(G_4S)_4$ | Linker | 102 | GGGGSGGGGSGGGGSGGGGS |
| MSLN | $V_H$ | 103 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SS |
| VL-Linker$^{scFv}$-VH | SCFv1, v32523 scFv2 | 149 | DIQMTQSPSSLSASVGDRVTITCSASSSVSYMHWYQQKS GKAPKLLIYDTSKLASGVPSRFSGSGSGTDFTLTISSLQ PEDFATYYCQQWSGYPLTFGQGTKLEIKGGGGSGGGGSG GGGSGGGGSQVQLVQSGAEVKKPGASVKVSCKASGYSFT GYTMNWVRQAPGQGLEWMGLITPYNGASSYNQKFRGKAT MTVDTSTSTVYMELSSLRSEDTAVYYCARGGYDGRGFDY WGQGTLVTVSS |
| $(G_4S)$ | Linker | 104 | GGGGS |
| CD3 | $V_H$ | 105 | EVQLVESGGGLVQPGGSLRLSCAASGVTFNYYGMSWIRQ APGKGLEWVASITSSGGRIYYPDSVKGRFTISRENTQKT LYLQMNSLRAEDTAVYYCTLDGRDGWVAYWGQGTLV TVSS |

TABLE 29-continued

Amino Acid Sequences of Antibody Constructs and Domains thereof

| Domain #<br>Description/<br>Variant #/<br>Target | Chain/<br>Type | SEQ<br>ID<br>NO | SEQUENCE |
|---|---|---|---|
| IGHG1 | C$_{H1}$ | 106 | ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKV |
| IGHG1 | Hinge | 107 | EPKSCDKTHTCPPCP |
| IGHG1 | CH2 | 108 | APEAAGGPSVFLFPPKPKDTLMISRTPEVTCVVVSVSHE<br>DPEVKFNWYVDGVEVHNAKTKPREEQYNSTYRVVSVLTV<br>LHQDWLNGKEYKCKVSNKALPAPIEKTISKAK |
| IGHG1 | CH3 | 109 | GQPREPQVYVYPPSRDELTKNQVSLTCLVKGFYPSDIAV<br>EWESNGQPENNYKTTPPVLDSDGSFALVSKLTVDKSRWQ<br>QGNVFSCSVMHEALHNHYTQKSLSLSPG |
| 23867 | H | 110 | DIQMTQSPSSLSASVGDRVTITCSASSSVSYMHWYQQKS<br>GKAPKLLIYDTSKLASGVPSRFSGSGSGTDFTLTISSLQ<br>PEDFATYYCQQWSGYPLTFGQGTKLEIKGGGGSGGGGSG<br>GGGSGGGGSQVQLVQSGAEVKKPGASVKVSCKASGYSFT<br>GYTMNWVRQAPGQGLEWMGLITPYNGASSYNQKFRGKAT<br>MTVDTSTSTVYMELSSLRSEDTAVYYCARGGYDGRGFDY<br>WGQGTLVTVSSAAEPKSSDKTHTCPPCPAPEAAGGPSVF<br>LFPPKPKDTLMISRTPEVTCVVVSVSHEDPEVKFNWYVD<br>GVEVHNAKTKPREEQYNSTYRVVSVLTVLHQDWLNGKEY<br>KCKVSNKALPAPIEKTISKAKGQPREPQVYVLPPSRDEL<br>TKNQVSLLCLVKGFYPSDIAVEWESNGQPENNYLTWPPV<br>LDSDGSFFLYSKLTVDKSRWQQGNVFSCSVMHEALHNHY<br>TQKSLSLSPG |
| 29295 | H + "K"<br>(C-term.<br>Lysine) | 172 | DIQMTQSPSSLSASVGDRVTITCSASSSVSYMHWYQQKS<br>GKAPKLLIYDTSKLASGVPSRFSGSGSGTDFTLTISSLQ<br>PEDFATYYCQQWSGYPLTFGQGTKLEIKGGGGSGGGGSG<br>GGGSGGGGSQVQLVQSGAEVKKPGASVKVSCKASGYSFT<br>GYTMNWVRQAPGQGLEWMGLITPYNGASSYNQKFRGKAT<br>MTVDTSTSTVYMELSSLRSEDTAVYYCARGGYDGRGFDY<br>WGQGTLVTVSSAAEPKSSDKTHTCPPCPAPEAAGGPSVF<br>LFPPKPKDTLMISRTPEVTCVVVSVSHEDPEVKFNWYVD<br>GVEVHNAKTKPREEQYNSTYRVVSVLTVLHQDWLNGKEY<br>KCKVSNKALPAPIEKTISKAKGQPREPQVYVLPPSRDEL<br>TKNQVSLLCLVKGFYPSDIAVEWESNGQPENNYLTWPPV<br>LDSDGSFFLYSKLTVDKSRWQQGNVFSCSVMHEALHNHY<br>TQKSLSLSPGK |
| MSLN | V$_L$ | 101 | DIQMTQSPSSLSASVGDRVTITCSASSSVSYMHWYQQKS<br>GKAPKLLIYDTSKLASGVPSRFSGSGSGTDFTLTISSLQ<br>PEDFATYYCQQWSGYPLTFGQGTKLEIK |
| (G$_4$S)$_4$ | Linker | 102 | GGGGSGGGGSGGGGSGGGGS |
| MSLN | V$_H$ | 103 | QVQLVQSGAEVKKPGASVKVSCKASGYSFTGYTMNWVRQ<br>APGQGLEWMGLITPYNGASSYNQKFRGKATMTVDTSTST<br>VYMELSSLRSEDTAVYYCARGGYDGRGFDYWGQGTLVTV<br>SS |
| Fc_hybrid | Linker | 111 | AAEPKSSDKTHTCPPCP |
| IGHG1 | Hinge | 112 | EPKSSDKTHTCPPCP |
| IGHG1 | CH2 | 108 | APEAAGGPSVFLFPPKPKDTLMISRTPEVTCVVVSVSHE<br>DPEVKFNWYVDGVEVHNAKTKPREEQYNSTYRVVSVLTV<br>LHQDWLNGKEYKCKVSNKALPAPIEKTISKAK |
| IGHG1 | CH3 | 113 | GQPREPQVYVLPPSRDELTKNQVSLLCLVKGFYPSDIAV<br>EWESNGQPENNYLTWPPVLDSDGSFFLYSKLTVDKSRWQ<br>QGNVFSCSVMHEALHNHYTQKSLSLSPG |
| 16412 | L | 114 | NFMLTQPHSVSESPGKTVTISCKRNTGNIGSNYVNWYQQ<br>HEGSSPTTIIYRNDKRPDGVSDRFSGSIDRSSKSASLTI<br>SNLKTEDEADYFCQSYSSGFIFGGGTKLTVLGQPKAAPS<br>VTLFPPSSEELQANKATLVCLISDFYPGAVTVAWKADSS<br>PVKAGVETTTPSKQSNNKYAASSYLSLTPEQWKSHRSYS<br>CQVTHEGSTVEKTVAPTECS |

TABLE 29-continued

Amino Acid Sequences of Antibody Constructs and Domains thereof

| Domain # Description/ Variant #/ Target | Chain/ Type | SEQ ID NO | SEQUENCE |
|---|---|---|---|
| CD3 | V_L | 115 | NFMLTQPHSVSESPGKTVTISCKRNTGNIGSNYVNWYQQ HEGSSPTTIIYRNDKRPDGVSDRFSGSIDRSSKSASLTI SNLKTEDEADYFCQSYSSGFIFGGGTKLTVL |
| IGLC2 | C_L | 116 | GQPKAAPSVTLFPPSSEELQANKATLVCLISDFYPGAVT VAWKADSSPVKAGVETTTPSKQSNNKYAASSYLSLTPEQ WKSHRSYSCQVTHEGSTVEKTVAPTECS | v21812 = Trivalent and Bispecific Antibody Construct [MSLN (2 scFv) x CD3 (1 Fab)]

| | | | |
|---|---|---|---|
| 12934 | H | 117 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSGGGGSGGGGSGGGGSDIQMTQSPSSLSASVGDRVTIT CSASSSVSYMHWYQQKSGKAPKLLIYDTSKLASGVPSRF SGSGSGTDFTLTISSLQPEDFATYYCQQWSGYPLTFGQG TKLEIKAAEPKSSDKTHTCPPCPAPEAAGGPSVFLFPPK PKDTLMISRTPEVTCVVVSVSHEDPEVKFNWYVDGVEVH NAKTKPREEQYNSTYRVVSVLTVLHQDWLNGKEYKCKVS NKALPAPIEKTISKAKGQPREPQVYVLPPSRDELTKNQV SLLCLVKGFYPSDIAVEWESNGQPENNYLTWPPVLDSDG SFFLYSKLTVDKSRWQQGNVFSCSVMHEALHNHYTQKSL SLSPG |
| MSLN | V_H | 103 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SS |
| (G_4S)_3 | Linker | 118 | GGGGSGGGGSGGGGS |
| MSLN | V_L | 101 | DIQMTQSPSSLSASVGDRVTITCSASSSVSYMHWYQQKS GKAPKLLIYDTSKLASGVPSRFSGSGSGTDFTLTISSLQ PEDFATYYCQQWSGYPLTFGQGTKLEIK |
| VH-Linker^scFv-VL | v21812 scFv1, scFv2 | 150 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSGGGGSGGGGSGGGGSDIQMTQSPSSLSASVGDRVTIT CSASSSVSYMHWYQQKSGKAPKLLIYDTSKLASGVPSRF SGSGSGTDFTLTISSLQPEDFATYYCQQWSGYPLTFGQG TKLEIK |
| Fc_hybrid | Linker | 111 | AAEPKSSDKTHTCPPCP |
| IGHG1 | Hinge | 112 | EPKSSDKTHTCPPCP |
| IGHG1 | CH2 | 108 | APEAAGGPSVFLFPPKPKDTLMISRTPEVTCVVVSVSHE DPEVKFNWYVDGVEVHNAKTKPREEQYNSTYRVVSVLTV LHQDWLNGKEYKCKVSNKALPAPIEKTISKAK |
| IGHG1 | CH3 | 113 | GQPREPQVYVLPPSRDELTKNQVSLLCLVKGFYPSDIAV EWESNGQPENNYLTWPPVLDSDGSFFLYSKLTVDKSRWQ QGNVFSCSVMHEALHNHYTQKSLSLSPG |
| 16379 | H | 119 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSGGGGSGGGGSGGGGSDIQMTQSPSSLSASVGDRVTIT CSASSSVSYMHWYQQKSGKAPKLLIYDTSKLASGVPSRF SGSGSGTDFTLTISSLQPEDFATYYCQQWSGYPLTFGQG TKLEIKGGGGSEVQLVESGGGLVQPGGSLRLSCAASGVT FNYYGMSWIRQAPGKGLEWVASITSSGGRIYYPDSVKGR FTISRENTQKTLYLQMNSLRAEDTAVYYCTLDGRDGWVA YWGQGTLVTVSSASTKGPSVFPLAPSSKSTSGGTAALGC LVKDYFPEPVTVSWNSGALTSGVHTFPAVLQSSGLYSLS SVVTVPSSSLGTQTYICNVNHKPSNTKVDKKVEPKSCDK THTCPPCPAPEAAGGPSVFLFPPKPKDTLMISRTPEVTC VVVSVSHEDPEVKFNWYVDGVEVHNAKTKPREEQYNSTY RVVSVLTVLHQDWLNGKEYKCKVSNKALPAPIEKTISKA |

TABLE 29-continued

Amino Acid Sequences of Antibody Constructs and Domains thereof

| Domain #<br>Description/<br>Variant #/<br>Target | Chain/<br>Type | SEQ<br>ID<br>NO | SEQUENCE |
|---|---|---|---|
| | | | KGQPREPQVYVYPPSRDELTKNQVSLTCLVKGFYPSDIA<br>VEWESNGQPENNYKTTPPVLDSDGSFALVSKLTVDKSRW<br>QQGNVFSCSVMHEALHNHYTQKSLSLSPG |
| | $V_H$ | 103 | QVQLVQSGAEVKKPGASVKVSCKASGYSFTGYTMNWVRQ<br>APGQGLEWMGLITPYNGASSYNQKFRGKATMTVDTSTST<br>VYMELSSLRSEDTAVYYCARGGYDGRGFDYWGQGTLVTV<br>SS |
| $(G_4S)_3$ | Linker | 118 | GGGGSGGGGSGGGGS |
| | $V_L$ | 101 | DIQMTQSPSSLSASVGDRVTITCSASSSVSYMHWYQQKS<br>GKAPKLLIYDTSKLASGVPSRFSGSGSGTDFTLTISSLQ<br>PEDFATYYCQQWSGYPLTFGQGTKLEIK |
| $(G_4S)$ | Linker | 104 | GGGGS |
| | $V_H$ | 105 | EVQLVESGGGLVQPGGSLRLSCAASGVTFNYYGMSWIRQ<br>APGKGLEWVASITSSGGRIYYPDSVKGRFTISRENTQKT<br>LYLQMNSLRAEDTAVYYCTLDGRDGWVAYWGQGTLV<br>TVSS |
| IGHG1 | $C_{H1}$ | 106 | ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKV |
| IGHG1 | Hinge | 107 | EPKSCDKTHTCPPCP |
| IGHG1 | CH2 | 108 | APEAAGGPSVFLFPPKPKDTLMISRTPEVTCVVVSVSHE<br>DPEVKFNWYVDGVEVHNAKTKPREEQYNSTYRVVSVLTV<br>LHQDWLNGKEYKCKVSNKALPAPIEKTISKAK |
| IGHG1 | CH3 | 109 | GQPREPQVYVYPPSRDELTKNQVSLTCLVKGFYPSDIAV<br>EWESNGQPENNYKTTPPVLDSDGSFALVSKLTVDKSRWQ<br>QGNVFSCSVMHEALHNHYTQKSLSLSPG |
| 16412 | L | 114 | NFMLTQPHSVSESPGKTVTISCKRNTGNIGSNYVNWYQQ<br>HEGSSPTTIIYRNDKRPDGVSDRFSGSIDRSSKSASLTI<br>SNLKTEDEADYFCQSYSSGFIFGGGTKLTVLGQPKAAPS<br>VTLFPPSSEELQANKATLVCLISDFYPGAVTVAWKADSS<br>PVKAGVETTTPSKQSNNKYAASSYLSLTPEQWKSHRSYS<br>CQVTHEGSTVEKTVAPTECS |
| CD3 | $V_L$ | 115 | NFMLTQPHSVSESPGKTVTISCKRNTGNIGSNYVNWYQQ<br>HEGSSPTTIIYRNDKRPDGVSDRFSGSIDRSSKSASLTI<br>SNLKTEDEADYFCQSYSSGFIFGGGTKLTVL |
| IGLC2 | $C_L$ | 116 | GQPKAAPSVTLFPPSSEELQANKATLVCLISDFYPGAVT<br>VAWKADSSPVKAGVETTTPSKQSNNKYAASSYLSLTPEQ<br>WKSHRSYSCQVTHEGSTVEKTVAPTECS |
| MSLN<br>(Kabat) | HCDR1 | 120 | GYTMN |
| MSLN<br>(Kabat) | HCDR2 | 121 | LITPYNGASSYNQKFRG |
| MSLN<br>(Kabat) | HCDR3 | 122 | GGYDGRGFDY |
| MSLN<br>(Kabat) | LCDR1 | 123 | SASSSVSYMH |
| MSLN<br>(Kabat) | LCDR2 | 124 | DTSKLAS |
| MSLN<br>(Kabat) | LCDR3 | 125 | QQWSGYPLT |
| CD3<br>(IMGT) | HCDR1 | 126 | GVTFNYYG |

TABLE 29-continued

Amino Acid Sequences of Antibody Constructs and Domains thereof

| Domain # Description/ Variant #/ Target | Chain/ Type | SEQ ID NO | SEQUENCE |
|---|---|---|---|
| CD3 (IMGT) | HCDR2 | 127 | ITSSGGRI |
| CD3 (IMGT) | HCDR3 | 128 | TLDGRDGWVAY |
| CD3 (IMGT) | LCDR1 | 129 | TGNIGSNY |
| CD3 (IMGT) | LCDR2 | 130 | RND |
| CD3 (IMGT) | LCDR3 | 131 | QSYSSGFI |
| $(G_4S)_n$, | Linker | 132 | $(GGGGS)_n$, n = 1, 2, 3, 4 or 5 |
| $(EAAAK)_n$ | Linker | 133 | $(EAAAK)_n$, n = 1, 2, 3, 4 or 5 |
| | Linker | 134 | EAAAK |
| | Linker | 135 | EAAAKEAAAK |
| $(P)_n$ | Linker | 136 | PPP |
| | Linker | 137 | PPPP |
| | Linker | 138 | GPPPG |
| | Linker | 139 | GGPPPGG |
| | Linker | 140 | GPPPPG |
| | Linker | 141 | GGPPPPGG |
| $(Gly_nSer)_m$ | Linker | 142 | $(Gly_nSer)_m$, n and m independently = 1, 2, 3, 4 or 5 |
| | Linker | 143 | $(Gly_3Ser)_n(Gly_4Ser)_1$, n = 1, 2, 3, 4 or 5 |
| | Linker | 144 | $(Gly_3Ser)_1(Gly_4Ser)_n$, n = 1, 2, 3, 4 or 5 |
| | Linker | 145 | $(Gly_3Ser)_n(Gly_4Ser)_n$, n = 1, 2, 3, 4 or 5 |
| | Linker | 146 | $(G_mS)_n$-GG, m and n are independently integers from 0 to 20 |
| | Linker | 147 | $(SG_n)_m$, m and n are independently integers from 0 to 20 |
| | Linker | 148 | $(SEG_n)_m$, m and n are independently integers from 0 to 20 |
| v19490 = Bivalent and Monospecific Antibody [MSLN (2 Fab)] | | | |
| 12932 | H | 151 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP EAAGGPSVFLFPPKPKDTLMISRTPEVTCVVVSVSHEDP EVKFNWYVDGVEVHNAKTKPREEQYNSTYRVVSVLTVLH QDWLNGKEYKCKVSNKALPAPIEKTISKAKGQPREPQVY VLPPSRDELTKNQVSLLCLVKGFYPSDIAVEWESNGQPE NNYLTWPPVLDSDGSFFLYSKLTVDKSRWQQGNVFSCSV MHEALHNHYTQKSLSLSPG |

TABLE 29-continued

Amino Acid Sequences of Antibody Constructs and Domains thereof

| Domain #<br>Description/<br>Variant #/<br>Target | Chain/<br>Type | SEQ<br>ID<br>NO | SEQUENCE |
|---|---|---|---|
| 12966 | H | 152 | QVQLVQSGAEVKKPGASVKVSCKASGYSFTGYTMNWVRQ<br>APGQGLEWMGLITPYNGASSYNQKFRGKATMTVDTSTST<br>VYMELSSLRSEDTAVYYCARGGYDRGFDYWGQGTLVTV<br>SSASTKGPSVFPLAPSSKSTSGGTAALGCLVKDYFPEPV<br>TVSWNSGALTSGVHTFPAVLQSSGLYSLSSVVTVPSSSL<br>GTQTYICNVNHKPSNTKVDKKVEPKSCDKTHTCPPCPAP<br>EAAGGPSVFLFPPKPKDTLMISRTPEVTCVVVSVSHEDP<br>EVKFNWYVDGVEVHNAKTKPREEQYNSTYRVVSVLTVLH<br>QDWLNGKEYKCKVSNKALPAPIEKTISKAKGQPREPQVY<br>VYPPSRDELTKNQVSLTCLVKGFYPSDIAVEWESNGQPE<br>NNYKTTPPVLDSDGSFALVSKLTVDKSRWQQGNVFSCSV<br>MHEALHNHYTQKSLSLSPG |
| 12933 | L | 153 | DIQMTQSPSSLSASVGDRVTITCSASSSVSYMHWYQQKS<br>GKAPKLLIYDTSKLASGVPSRFSGSGSGTDFTLTISSLQ<br>PEDFATYYCQQWSGYPLTFGQGTKLEIKRTVAAPSVFIF<br>PPSDEQLKSGTASVVCLLNNFYPREAKVQWKVDNALQSG<br>NSQESVTEQDSKDSTYSLSSTLTLSKADYEKHKVYACEV<br>THQGLSSPVTKSFNRGEC |
| v31926 = Negative Control Antibody<br>[Hemagglutinin (HA) (2 scFv) x CD3 (1 Fab)] | | | |
| 23427 | H | 154 | QVQLVQSGAEVKKPGASVRVSCRASGYIFTESGITWVRQ<br>APGQGLEWMGWISGYSGDTKYAQKLQGRVTMTKDTSTTT<br>AYMELRSLRYDDTAVYYCARDVQYSGSYLGAYYFDYWSP<br>GTLVTVSSGGGGSGGGGSGGGGSGGGQSVLTQPPSASGT<br>PGQRVTISCSGSSSNIGTNYVYWYQQFPGTAPKLLIYRS<br>YQRPSGVPDRESGSKSGSSASLAISGLQSEDEADYYCAT<br>WDDSLDGWVFGGGTKLTVLGGGGSEVQLVESGGGLVQPG<br>GSLRLSCAASGVTFNYYGMSWIRQAPGKGLEWVASITSS<br>GGRIYYPDSVKGRFTISRENTQKTLYLQMNSLRAEDTAV<br>YYCTLDGRDGWVAYWGQGTLVTVSSASTKGPSVFPLAPS<br>SKSTSGGTAALGCLVKDYFPEPVTVSWNSGALTSGVHTF<br>PAVLQSSGLYSLSSVVTVPSSSLGTQTYICNVNHKPSNT<br>KVDKKVEPKSCDKTHTCPPCPAPEAAGGPSVFLFPPKPK<br>DTLMISRTPEVTCVVVSVSHEDPEVKFNWYVDGVEVHNA<br>KTKPREEQYNSTYRVVSVLTVLHQDWLNGKEYKCKVSNK<br>ALPAPIEKTISKAKGQPREPQVYVYPPSRDELTKNQVSL<br>TCLVKGFYPSDIAVEWESNGQPENNYKTTPPVLDSDGSF<br>ALVSKLTVDKSRWQQGNVFSCSVMHEALHNHYTQKSLSL<br>SPG |
| 11020 | H | 155 | QVQLVQSGAEVKKPGASVRVSCRASGYIFTESGITWVRQ<br>APGQGLEWMGWISGYSGDTKYAQKLQGRVTMTKDTSTTT<br>AYMELRSLRYDDTAVYYCARDVQYSGSYLGAYYFDYWSP<br>GTLVTVSSGGGGSGGGGSGGGGSGGGQSVLTQPPSASGT<br>PGQRVTISCSGSSSNIGTNYVYWYQQFPGTAPKLLIYRS<br>YQRPSGVPDRFSGSKSGSSASLAISGLQSEDEADYYCAT<br>WDDSLDGWVFGGGTKLTVLAAEPKSSDKTHTCPPCPAPE<br>AAGGPSVFLFPPKPKDTLMISRTPEVTCVVVSVSHEDPE<br>VKFNWYVDGVEVHNAKTKPREEQYNSTYRVVSVLTVLHQ<br>DWLNGKEYKCKVSNKALPAPIEKTISKAKGQPREPQVYV<br>LPPSRDELTKNQVSLLCLVKGFYPSDIAVEWESNGQPEN<br>NYLTWPPVLDSDGSFFLYSKLTVDKSRWQQGNVFSCSVM<br>HEALHNHYTQKSLSLSPG |
| 16412 | L | 114 | NFMLTQPHSVSESPGKTVTISCKRNTGNIGSNYVNWYQQ<br>HEGSSPTTIIYRNDKRPDGVSDRFSGSIDRSSKSASLTI<br>SNLKTEDEADYFCQSYSSGFIFGGGTKLTVLGQPKAAPS<br>VTLFPPSSEELQANKATLVCLISDFYPGAVTVAWKADSS<br>PVKAGVETTTPSKQSNNKYAASSYLSLTPEQWKSHRSYS<br>CQVTHEGSTVEKTVAPTECS |
| v21815 = Bivalent and Bispecific Antibody Construct<br>[MSLN (1 Fab) x CD3 (1 scFv)] | | | |
| 16303 | H | 156 | EVQLVESGGGLVQPGGSLRLSCAASGVTFNYYGMSWIRQ<br>APGKGLEWVASITSSGGRIYYPDSVKGRFTISRENTQKT<br>LYLQMNSLRAEDTAVYYCTLDGRDGWVAYWGQGTLVTVS<br>SGGGGSGGGGSGGGGSNFMLTQPHSVSESPGKTVTISCK<br>RNTGNIGSNYVNWYQQHEGSSPTTIIYRNDKRPDGVSDR |

TABLE 29-continued

Amino Acid Sequences of Antibody Constructs and Domains thereof

| Domain # Description/ Variant #/ Target | Chain/ Type | SEQ ID NO | SEQUENCE |
|---|---|---|---|
| | | | FSGSIDRSSKSASLTISNLKTEDEADYFCQSYSSGFIFG GGTKLTVLAAEPKSSDKTHTCPPCPAPEAAGGPSVFLFP PKPKDTLMISRTPEVTCVVVSVSHEDPEVKFNWYVDGVE VHNAKTKPREEQYNSTYRVVSVLTVLHQDWLNGKEYKCK VSNKALPAPIEKTISKAKGQPREPQVYVYPPSRDELTKN QVSLTCLVKGFYPSDIAVEWESNGQPENNYKTTPPVLDS DGSFALVSKLTVDKSRWQQGNVFSCSVMHEALHNHYTQK SLSLSPG |
| 12932 | H | 151 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP EAAGGPSVFLFPPKPKDTLMISRTPEVTCVVVSVSHEDP EVKFNWYVDGVEVHNAKTKPREEQYNSTYRVVSVLTVLH QDWLNGKEYKCKVSNKALPAPIEKTISKAKGQPREPQVY VLPPSRDELTKNQVSLLCLVKGFYPSDIAVEWESNGQPE NNYLTWPPVLDSDGSFFLYSKLTVDKSRWQQGNVFSCSV MHEALHNHYTQKSLSLSPG |
| 12933 | L | 153 | DIQMTQSPSSLSASVGDRVTITCSASSSVSYMHWYQQKS GKAPKLLIYDTSKLASGVPSRFSGSGSGTDFTLTISSLQ PEDFATYYCQQWSGYPLTFGQGTKLEIKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC |
| v21791 = Trivalent and Bispecific Antibody Construct [MSLN (2 Fab) x CD3 (1 Fab)] | | | |
| 16293 | H | 157 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSASTKGPSVFPRAPSSKSTSGGTAALGCLVKDYFPEPV TVSWNSGALTSGVHTFPAVLQSSGLYKLSSVVTVPSSSL GTQTYICNVNHKPSNTKVDKKVEPKSCDKTHTGGEVQLV ESGGGLVQPGGSLRLSCAASGVTFNYYGMSWIRQAPGKG LEWVASITSSGGRIYYPDSVKGRFTISRENTQKTLYLQM NSLRAEDTAVYYCTLDGRDGWVAYWGQGTLVTVSSASTK GPSVFPLAPSSKSTSGGTAWLGCDVTDYFPEPVTVSWNS GALTSGVHTFPAVLQSSGLYSLSSVVTVPSSSLGTQTYI CNVNHKPSNTKVDKKVEPKSCDKTHTCPPCPAPEAAGGP SVFLFPPKPKDTLMISRTPEVTCVVVSVSHEDPEVKFNW YVDGVEVHNAKTKPREEQYNSTYRVVSVLTVLHQDWLNG KEYKCKVSNKALPAPIEKTISKAKGQPREPQVYVPPSR DELTKNQVSLTCLVKGFYPSDIAVEWESNGQPENNYKTT PPVLDSDGSFALVSKLTVDKSRWQQGNVFSCSVMHEALH NHYTQKSLSLSPG |
| 16288 | H | 158 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSASTKGPSVFPRAPSSKSTSGGTAALGCLVKDYFPEPV TVSWNSGALTSGVHTFPAVLQSSGLYKLSSVVTVPSSSL GTQTYICNVNHKPSNTKVDKKVEPKSCDKTHTCPPCPAP EAAGGPSVFLFPPKPKDTLMISRTPEVTCVVVSVSHEDP EVKFNWYVDGVEVHNAKTKPREEQYNSTYRVVSVLTVLH QDWLNGKEYKCKVSNKALPAPIEKTISKAKGQPREPQVY VLPPSRDELTKNQVSLLCLVKGFYPSDIAVEWESNGQPE NNYLTWPPVLDSDGSFFLYSKLTVDKSRWQQGNVFSCSV MHEALHNHYTQKSLSLSPG |
| 16292 | L | 159 | NFMLTQPHSVSESPGKTVTISCKRNTGNIGSNYVNWYQQ HEGSSPTTIIYRNDKRPDGVSDRFSGSIDRSSKSASLTI SNLKTEDEADYFCQSYSSGFIFGGGTKLTVLGQPKAAPS VTLFPPSSEQLQANKARLVCLISDFYPGAVTVAWKADSS PVKAGVETTTPSKQSNNKYAASSYLSLTPEQWKSHKSYS CQVTHEGSTVEKTVAPAECS |

TABLE 29-continued

Amino Acid Sequences of Antibody Constructs and Domains thereof

| Domain # Description/ Variant #/ Target | Chain/ Type | SEQ ID NO | SEQUENCE |
|---|---|---|---|
| 16284 | L | 160 | DIQMTQSPSSLSASVGDRVTITCSASSSVSYMHWYQQKS GKAPKLLIYDTSKLASGVPSRFSGSGSGTDFTLTISSLQ PEDFATYYCQQWSGYPLTFGQGTKLEIKRTVAAPSVFIF PPSDEQLKSGTASVGCWLNNFYPREAKVQWKVDNALQSG NSQESVTEQDSKDSTYSLDSTLELSKADYEKHKVYACEV THQGLSSPVTKSFNRGEC | v29045 = Trivalent and Bispecific Antibody Construct
[MSLN (2 scFv) x CD3 (1 Fab)]

| 21200 | H | 161 | QVQLVQSGAEVKKPGASVKISCKASGYSFTGYTMNWVRQ APGQGLEWIGLITPYSGASSYAQKFQGRATLTVDKSTST AYMELSSLRSEDTAVYYCARGGYDGRGFDYWGQGTLVTV SSGGGGSGGGGSGGGGSEIVLTQSPATLSLSPGERVTMS CSASSSVSYMHWYQQKPGQAPRLWIYDTSKLASGVPARF SGSGSGTDYTLTISSVEPEDFAVYYCQQWSGYPLTFGQG TKVEIKGGGGSEVQLVESGGGLVQPGGSLRLSCAASGVT FNYYGMSWIRQAPGKGLEWVASITSSGGRIYYPDSVKGR FTISRENTQKTLYLQMNSLRAEDTAVYYCTLDRDGWVA YWGQGTLVTVSSASTKGPSVFPLAPSSKSTSGGTAALGC LVKDYFPEPVTVSWNSGALTSGVHTFPAVLQSSGLYSLS SVVTVPSSSLGTQTYICNVNHKPSNTKVDKKVEPKSCDK THTCPPCPAPEAAGGPSVFLFPPKPKDTLMISRTPEVTC VVVSVSHEDPEVKFNWYVDGVEVHNAKTKPREEQYNSTY RVVSVLTVLHQDWLNGKEYKCKVSNKALPAPIEKTISKA KGQPREPQVYVYPPSRDELTKNQVSLTCLVKGFYPSDIA VEWESNGQPENNYKTTPPVLDSDGSFALVSKLTVDKSRW QQGNVFSCSVMHEALHNHYTQKSLSLSPG |
| 21181 | H | 162 | QVQLVQSGAEVKKPGASVKISCKASGYSFTGYTMNWVRQ APGQGLEWIGLITPYSGASSYAQKFQGRATLTVDKSTST AYMELSSLRSEDTAVYYCARGGYDGRGFDYWGQGTLVTV SSGGGGSGGGGSGGGGSEIVLTQSPATLSLSPGERVTMS CSASSSVSYMHWYQQKPGQAPRLWIYDTSKLASGVPARF SGSGSGTDYTLTISSVEPEDFAVYYCQQWSGYPLTFGQG TKVEIKAAEPKSSDKTHTCPPCPAPEAAGGPSVFLFPPK PKDTLMISRTPEVTCVVVSVSHEDPEVKFNWYVDGVEVH NAKTKPREEQYNSTYRVVSVLTVLHQDWLNGKEYKCKVS NKALPAPIEKTISKAKGQPREPQVYVLPPSRDELTKNQV SLLCLVKGFYPSDIAVEWESNGQPENNYLTWPPVLDSDG SFFLYSKLTVDKSRWQQGNVFSCSVMHEALHNHYTQKSL SLSPG |
| 16412 | L | 114 | NFMLTQPHSVSESPGKTVTISCKRNTGNIGSNYVNWYQQ HEGSSPTTIIYRNDKRPDGVSDRFSGSIDRSSKSASLTI SNLKTEDEADYFCQSYSSGFIFGGGTKLTVLGQPKAAPS VTLFPPSSEELQANKATLVCLISDFYPGAVTVAWKADSS PVKAGVETTTPSKQSNNKYAASSYLSLTPEQWKSHRSYS CQVTHEGSTVEKTVAPTECS | v29048 = Trivalent and Bispecific Antibody Construct
[MSLN (2 scFv) x CD3 (1 Fab)]

| 21203 | H | 163 | EVQLLESGGGLVQPGGSVRISCAASGYSFTGYTMNWVRQ APGKGLEWIGLITPYSGASSYADSFKGRATLSVDNSKNT AYMQLNSLRAEDTAVYYCARGGYDGRGFDYWGQGTLVTV SSGGGGSGGGGSGGGGSDIQLTQSPSSLSASVGDRVTMT CSASSSVSYMHWYQQKPGKAPKLWIYDTSKLASGVPSRF SGSGSGTDYTLTISSVQPEDFATYYCQQWSKHPLTFGQG TKVEIKGGGGSEVQLVESGGGLVQPGGSLRLSCAASGVT FNYYGMSWIRQAPGKGLEWVASITSSGGRIYYPDSVKGR FTISRENTQKTLYLQMNSLRAEDTAVYYCTLDRDGWVA YWGQGTLVTVSSASTKGPSVFPLAPSSKSTSGGTAALGC LVKDYFPEPVTVSWNSGALTSGVHTFPAVLQSSGLYSLS SVVTVPSSSLGTQTYICNVNHKPSNTKVDKKVEPKSCDK THTCPPCPAPEAAGGPSVFLFPPKPKDTLMISRTPEVTC VVVSVSHEDPEVKFNWYVDGVEVHNAKTKPREEQYNSTY RVVSVLTVLHQDWLNGKEYKCKVSNKALPAPIEKTISKA KGQPREPQVYVYPPSRDELTKNQVSLTCLVKGFYPSDIA VEWESNGQPENNYKTTPPVLDSDGSFALVSKLTVDKSRW QQGNVFSCSVMHEALHNHYTQKSLSLSPG |

TABLE 29-continued

Amino Acid Sequences of Antibody Constructs and Domains thereof

| Domain # Description/ Variant #/ Target | Chain/ Type | SEQ ID NO | SEQUENCE |
|---|---|---|---|
| 21184 | H | 164 | EVQLLESGGGLVQPGGSVRISCAASGYSFTGYTMNWVRQ APGKGLEWIGLITPYSGASSYADSFKGRATLSVDNSKNT AYMQLNSLRAEDTAVYYCARGGYDGRGFDYWGQGTLVTV SSGGGGSGGGGSGGGGSDIQLTQSPSSLSASVGDRVTMT CSASSSVSYMHWYQQKPGKAPKLWIYDTSKLASGVPSRF SGSGSGTDYTLTISSVQPEDFATYYCQQWSKHPLTFGQG TKVEIKAAEPKSSDKTHTCPPCPAPEAAGGPSVFLFPPK PKDTLMISRTPEVTCVVVSVSHEDPEVKFNWYVDGVEVH NAKTKPREEQYNSTYRVVSVLTVLHQDWLNGKEYKCKVS NKALPAPIEKTISKAKGQPREPQVYVLPPSRDELTKNQV SLLCLVKGFYPSDIAVEWESNGQPENNYLTWPPVLDSDG SFFLYSKLTVDKSRWQQGNVFSCSVMHEALHNHYTQKSL SLSPG |
| 16412 | L | 114 | NFMLTQPHSVSESPGKTVTISCKRNTGNIGSNYVNWYQQ HEGSSPTTIIYRNDKRPDGVSDRFSGSIDRSSKSASLTI SNLKTEDEADYFCQSYSSGFIFGGGTKLTVLGQPKAAPS VTLFPPSSEELQANKATLVCLISDFYPGAVTVAWKADSS PVKAGVETTTPSKQSNNKYAASSYLSLTPEQWKSHRSYS CQVTHEGSTVEKTVAPTECS | v29191 = 2 + 1 Fab$^3$ TCB Benchmark Construct
[MSLN (2 Fab) x CD3 (1 Fab) = Fab$^3$]

| 21373 | H | 165 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSASTKGPSVFPLAPSSKSTSGGTAALGCLVEDYFPEPV TVSWNSGALTSGVHTFPAVLQSSGLYSLSSVVTVPSSSL GTQTYICNVNHKPSNTKVDEKVEPKSCDGGGGSGGGGSQ AVVTQEPSLTVSPGGTVTLTCGSSTGAVTTSNYANWVQE KPGQAFRGLIGGTNKRAPGTPARFSGSLLGGKAALTLSG AQPEDEAEYYCALWYSNLWVFGGGTKLTVLSSASTKGPS VFPLAPSSKSTSGGTAALGCLVKDYFPEPVTVSWNSGAL TSGVHTFPAVLQSSGLYSLSSVVTVPSSSLGTQTYICNV NHKPSNTKVDKKVEPKSCDKTHTCPPCPAPEAAGGPSVF LFPPKPKDTLMISRTPEVTCVVVDVSHEDPEVKENWYVD GVEVHNAKTKPREEQYNSTYRVVSVLTVLHQDWLNGKEY KCKVSNKALGAPIEKTISKAKGQPREPQVYTLPPCRDEL TKNQVSLWCLVKGFYPSDIAVEWESNGQPENNYKTTPPV LDSDGSFFLYSKLTVDKSRWQQGNVFSCSVMHEALHNHY TQKSLSLSPG |
|---|---|---|---|
| 21372 | H | 166 | QVQLVQSGAEVKKPGASVKVSCKASGYSFTGYTMNWVRQ APGQGLEWMGLITPYNGASSYNQKFRGKATMTVDTSTST VYMELSSLRSEDTAVYYCARGGYDGRGFDYWGQGTLVTV SSASTKGPSVFPLAPSSKSTSGGTAALGCLVEDYFPEPV TVSWNSGALTSGVHTFPAVLQSSGLYSLSSVVTVPSSSL GTQTYICNVNHKPSNTKVDEKVEPKSCDKTHTCPPCPAP EAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALGAPIEKTISKAKGQPREPQVC TLPPSRDELTKNQVSLSCAVKGFYPSDIAVEWESNGQPE NNYKTTPPVLDSDGSFFLVSKLTVDKSRWQQGNVFSCSV MHEALHNHYTQKSLSLSPG |
| 21340 | L | 167 | EVQLLESGGGLVQPGGSLRLSCAASGFTFSTYAMNWVRQ APGKGLEWVSRIRSKYNNYATYYADSVKGRFTISRDDSK NTLYLQMNSLRAEDTAVYYCVRHGNFGNSYVSWFAYWGQ GTLVTVSSASVAAPSVFIFPPSDEQLKSGTASVVCLLNN FYPREAKVQWKVDNALQSGNSQESVTEQDSKDSTYSLSS TLTLSKADYEKHKVYACEVTHQGLSSPVTKSFNRGEC |

TABLE 29-continued

Amino Acid Sequences of Antibody Constructs and Domains thereof

| Domain # Description/ Variant #/ Target | Chain/ Type | SEQ ID NO | SEQUENCE |
|---|---|---|---|
| 21341 | L | 168 | DIQMTQSPSSLSASVGDRVTITCSASSSVSYMHWYQQKS GKAPKLLIYDTSKLASGVPSRFSGSGSGTDFTLTISSLQ PEDFATYYCQQWSKHPLTFGQGTKLEIKRTVAAPSVFIF PPSDRKLKSGTASVVCLLNNFYPREAKVQWKVDNALQSG NSQESVTEQDSKDSTYSLSSTLTLSKADYEKHKVYACEV THQGLSSPVTKSFNRGEC | v31805 = MH6T-TriTAC Benchmark Construct
[MSLN (V$_{HH}$) x Alb (V$_{HH}$) x CD3 (scFv)]

| 23324 | A | 169 | QVQLVESGGGVVQAGGSLTLSCAASGSTFSIRAMRWYRQ APGTERDLVAVIYGSSTYYADAVKGRFTISRDNSKNTLY LQMNSLRAEDTAVYYCNADTIGTARDYWGQGTLVTVSSG GGGSGGGSEVQLVESGGGLVQPGNSLRLSCAASGFTFSK FGMSWVRQAPGKGLEWVSSISGSGRDTLYADSVKGRFTI SRDNAKTTLYLQMNSLRPEDTAVYYCTIGGSLSVSSQGT LVTVSSGGGGSGGGSEVQLVESGGGLVQPGGSLKLSCAA SGFTFNKYAINWVRQAPGKGLEWVARIRSKYNNYATYYA DQVKDRFTISRDDSKNTAYLQMNNLKTEDTAVYYCVRHA NFGNSYISYWAYWGQGTLVTVSSGGGGSGGGGSGGGGSQ TVVTQEPSLTVSPGGTVTLTCASSTGAVTSGNYPNWVQQ KPGQAPRGLIGGTKFLVPGTPARFSGSLLGGKAALTLSG VQPEDEAEYYCTLWYSNRWVFGGGTKLTVLHHHHHH |
| 253 | B | 170 | DAHKSEVAHRFKDLGEENFKALVLIAFAQYLQQCPFEDH VKLVNEVTEFAKTCVADESAENCDKSLHTLFGDKLCTVA TLRETYGEMADCCAKQEPERNECFLQHKDDNPNLPRLVR PEVDVMCTAFHDNEETFLKKYLYEIARRHPYFYAPELLF FAKRYKAAFTECCQAADKAACLLPKLDELRDEGKASSAK QRLKCASLQKFGERAFKAWAVARLSQRFPKAEFAEVSKL VTDLTKVHTECCHGDLLECADDRADLAKYICENQDSISS KLKECCEKPLLEKSHCIAEVENDEMPADLPSLAADFVES KDVCKNYAEAKDVFLGMFLYEYARRHPDYSVVLLLRLAK TYETTLEKCCAAADPHECYAKVFDEFKPLVEEPQNLIKQ NCELFEQLGEYKFQNALLVRYTKKVPQVSTPTLVEVSRN LGKVGSKCCKHPEAKRMPCAEDYLSVVLNQLCVLHEKTP VSDRVTKCCTESLVNRRPCFSALEVDETYVPKEFNAETF TFHADICTLSEKERQIKKQTALVELVKHKPKATKEQLKA VMDDFAAFVEKCCKADDKETCFAEEGKKLVAASQAALGL |

What is claimed is:

1. An antibody construct, comprising:
   (i) a Fab domain that binds to cluster of differentiation 3 (CD3), wherein the Fab domain comprises a Fab heavy chain comprising a heavy chain variable ($V_H$) domain comprising a heavy chain complementarity determining region (HCDR) 1 sequence comprising the amino acid sequence set forth in SEQ ID NO: 126, an HCDR2 sequence comprising the amino acid sequence set forth in SEQ ID NO: 127, and an HCDR3 sequence comprising the amino acid sequence set forth in SEQ ID NO: 128, and a Fab light chain comprising a light chain variable ($V_L$) domain comprising a light chain complementarity determining region (LCDR) 1 sequence comprising the amino acid sequence set forth in SEQ ID NO: 129, an LCDR2 sequence comprising the amino acid sequence set forth in SEQ ID NO: 130, and an LCDR3 sequence comprising the amino acid sequence set forth in SEQ ID NO: 131;
   (ii) a first scFv domain (scFv1) and a second scFv domain (scFv2), wherein the scFv1 and the scFv2 bind to mesothelin (MSLN), and wherein the scFv1 and the scFv2 each comprise a $V_H$ domain comprising an HCDR1 sequence comprising the amino acid sequence set forth in SEQ ID NO: 120, an HCDR2 sequence comprising the amino acid sequence set forth in SEQ ID NO: 121, and an HCDR3 sequence comprising the amino acid sequence set forth in SEQ ID NO: 122, and a $V_L$ domain comprising an LCDR1 sequence comprising the amino acid sequence set forth in SEQ ID NO: 123, an LCDR2 sequence comprising the amino acid sequence set forth in SEQ ID NO: 124, and an LCDR3 sequence comprising the amino acid sequence set forth in SEQ ID NO: 125; and
   (iii) a dimeric Fc domain comprising a first Fc polypeptide and a second Fc polypeptide,
   wherein:
   the antibody construct is trivalent,
   the C-terminus of the Fab heavy chain is coupled to the N-terminus of the first Fc polypeptide,
   the scFv1 is coupled to the N-terminus of the second Fc polypeptide, and
   the scFv2 is coupled to the N-terminus of the Fab heavy chain.

2. The antibody construct of claim 1, wherein the scFv1 and the scFv2 each comprise (i) a $V_H$ domain comprising the amino acid sequence set forth in SEQ ID NO: 103, and (ii) a $V_L$ domain comprising the amino acid sequence set forth in SEQ ID NO: 101.

3. The antibody construct of claim 1, wherein the scFv1 and the scFv2 each comprise (i) a $V_H$ domain consisting of the amino acid sequence set forth in SEQ ID NO: 103, and (ii) a $V_L$ domain consisting of the amino acid sequence set forth in SEQ ID NO: 101.

4. The antibody construct of claim 1, wherein the scFv1 and the scFv2 each further comprise a linker$^{scFv}$ that couples the $V_L$ domain to the $V_H$ domain.

5. The antibody construct of claim 4, wherein the linker$^{scFv}$ comprises the amino acid sequence (G4S) n, and wherein n is 4.

6. The antibody construct of claim 4, wherein the linker$^{scFv}$ comprises the amino acid sequence (G4S) n, and wherein n is 3.

7. The antibody construct of claim 5, wherein the scFv1 and the scFv2 each have the domain structure, from N-terminus to C-terminus, of $V_L$-linker$^{scFv}$-$V_H$.

8. The antibody construct of claim 6, wherein the scFv1 and the scFv2 each have the domain structure, from N-terminus to C-terminus, of $V_H$-linker$^{scFv}$-$V_L$.

9. The antibody construct of claim 1, wherein (i) the Fab heavy chain comprises a $V_H$ domain comprising the amino acid sequence set forth in SEQ ID NO: 105, and (ii) the Fab light chain comprises a $V_L$ domain comprising the amino acid sequence set forth in SEQ ID NO: 115.

10. The antibody construct of claim 1, wherein (i) the Fab heavy chain comprises a $V_H$ domain consisting of the amino acid sequence set forth in SEQ ID NO: 105, and (ii) the Fab light chain comprises a $V_L$ domain consisting of the amino acid sequence set forth in SEQ ID NO: 115.

11. The antibody construct of claim 1, wherein the first Fc polypeptide, the second Fc polypeptide, or both the first and the second Fc polypeptides, is an IgG1-derived Fc polypeptide or human IgG1-derived Fc polypeptide.

12. The antibody construct of claim 1, wherein the Fab heavy chain of the Fab domain is coupled to the first Fc polypeptide via a linker$^{Fab-Fc}$ comprising the amino acid sequence set forth in SEQ ID NO: 107, the scFv1 is coupled to the second Fc polypeptide via a linker$^{scFv-Fc}$ comprising the amino acid sequence set forth in SEQ ID NO: 112, and the scFv2 is coupled to the Fab heavy chain via a linker$^{scFv-Fab}$ comprising the amino acid sequence set forth in SEQ ID NO: 104.

13. The antibody construct of claim 1, wherein the dimeric Fc domain is a heterodimeric Fc domain, wherein the first Fc polypeptide and the second Fc polypeptide each comprise a CH3 domain and a CH2 domain, and wherein the first Fc polypeptide, the second Fc polypeptide, or both the first and the second Fc polypeptides comprise one or more amino acid substitutions in the CH3 domain compared to a corresponding wild-type IgG1 CH3 domain sequence, wherein the one or more amino acid substitutions promote preferential pairing of the first and second Fc polypeptides to form the heterodimeric Fc domain.

14. The antibody construct of claim 13, wherein the first or second Fc polypeptide comprises the amino acid substitutions T350V_L351Y_F405A_Y407V, and the other Fc polypeptide comprises the amino acid substitutions T350V_T366L_K392L_T394W, and wherein the numbering of amino acid residues in the first and second Fc polypeptides is according to the EU numbering system.

15. The antibody construct of claim 13, wherein the first Fc polypeptide, the second Fc polypeptide, or both the first and the second Fc polypeptides comprise one or more amino acid substitutions in the CH2 domain compared to a corresponding wild-type IgG1 CH2 domain sequence, wherein the one or more amino acid substitutions reduce or eliminate binding of the antibody construct to an Fcγ-receptor.

16. The antibody construct of claim 15, wherein the CH2 domain sequences of the first and second Fc polypeptides comprise the amino acid substitutions L234A_L235A_D265S, and wherein the numbering of amino acid residues in the first and second Fc polypeptides is according to the EU numbering system.

17. The antibody construct of claim 1, wherein the antibody construct comprises a first heavy chain (H1) comprising the amino acid sequence set forth in SEQ ID NO: 100, a second heavy chain (H2) comprising the amino acid sequence set forth in SEQ ID NO: 110, and a light chain (L1) comprising the amino acid sequence set forth in SEQ ID NO: 114.

18. The antibody construct of claim 17, wherein one or both of the H1 and H2 further comprise a C-terminal lysine residue.

19. The antibody construct of claim 18, wherein the H1 comprises the amino acid sequence set forth in SEQ ID NO: 171, the H2 comprises the amino acid sequence set forth in SEQ ID NO: 172, and the L1 comprises the amino acid sequence set forth in SEQ ID NO: 114.

20. The antibody construct of claim 1, wherein (a) the scFv1 and the scFv2 each comprise (i) a $V_H$ domain comprising the amino acid sequence set forth in SEQ ID NO: 103, and (ii) a $V_L$ domain comprising the amino acid sequence set forth in SEQ ID NO: 101; (b) the Fab heavy chain comprises a $V_H$ domain comprising the amino acid sequence set forth in SEQ ID NO: 105; and (c) the Fab light chain comprises a $V_L$ domain comprising the amino acid sequence set forth in SEQ ID NO: 115.

21. The antibody construct of claim 20, wherein the scFv1 and the scFv2 each further comprise a linker$^{scFv}$ that couples the $V_L$ domain to the $V_H$ domain, and the scFv1 and the scFv2 each have the domain structure, from N-terminus to C-terminus, of $V_L$-linker$^{scFv}$-$V_H$.

22. The antibody construct of claim 21, wherein the linker$^{scFv}$ comprises the amino acid sequence $(G_4S)_n$, and wherein n is 4.

23. The antibody construct of claim 21, wherein the first Fc polypeptide and the second Fc polypeptides are human IgG1-derived Fc polypeptides.

24. The antibody construct of claim 23, wherein the dimeric Fc domain is a heterodimeric Fc domain, wherein the first Fc polypeptide and the second Fc polypeptide each comprise a CH3 domain and a CH2 domain, and wherein the first Fc polypeptide, the second Fc polypeptide, or both the first and the second Fc polypeptides comprise one or more amino acid substitutions in the CH3 domain compared to a corresponding wild-type IgG1 CH3 domain sequence, wherein the one or more amino acid substitutions promote preferential pairing of the first and second Fc polypeptides to form the heterodimeric Fc domain.

25. The antibody construct of claim 24, wherein the first or second Fc polypeptide comprises the amino acid substitutions T350V_L351Y_F405A_Y407V, and the other Fc polypeptide comprises the amino acid substitutions T350V_T366L_K392L_T394W, and wherein the numbering of amino acid residues in the first and second Fc polypeptides is according to the EU numbering system.

26. The antibody construct of claim 24, wherein the first Fc polypeptide, the second Fc polypeptide, or both the first and the second Fc polypeptides comprise one or more amino acid substitutions in the CH2 domain compared to a corresponding wild-type IgG1 CH2 domain sequence, wherein the one or more amino acid substitutions reduce or eliminate binding of the antibody construct to an Fcγ-receptor.

27. The antibody construct of claim 26, wherein the CH2 domain sequences of the first and second Fc polypeptides comprise the amino acid substitutions L234A_L235A_D265S, and wherein the numbering of amino acid residues in the first and second Fc polypeptides is according to the EU numbering system.

28. An antibody construct comprising: (i) a first heavy chain (H1) comprising the amino acid sequence set forth in SEQ ID NO: 100, (ii) a second heavy chain (H2) comprising the amino acid sequence set forth in SEQ ID NO: 110, and (iii) a light chain (L1) comprising the amino acid sequence set forth in SEQ ID NO: 114, wherein the antibody construct is trivalent.

29. A pharmaceutical composition comprising the antibody construct of claim 1, and a pharmaceutically acceptable carrier, excipient, diluent, or combination thereof.

30. A pharmaceutical composition comprising the antibody construct of claim 28, and a pharmaceutically acceptable carrier, excipient, diluent, or combination thereof.

* * * * *

SEQUENCE LISTING

```
Sequence total quantity: 172
SEQ ID NO: 1              moltype = AA  length = 217
FEATURE                   Location/Qualifiers
source                    1..217
                          mol_type = protein
                          organism = Homo sapiens
SEQUENCE: 1
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLTCLVK GFYPSDIAVE WESNGQPENN YKTTPPVLDS DGSFFLYSKL   180
TVDKSRWQQG NVFSCSVMHE ALHNHYTQKS LSLSPGK                            217

SEQ ID NO: 2              moltype =      length =
SEQUENCE: 2
000

SEQ ID NO: 3              moltype =      length =
SEQUENCE: 3
000

SEQ ID NO: 4              moltype =      length =
SEQUENCE: 4
000

SEQ ID NO: 5              moltype =      length =
```

-continued

```
SEQUENCE: 5
000

SEQ ID NO: 6              moltype =    length =
SEQUENCE: 6
000

SEQ ID NO: 7              moltype =    length =
SEQUENCE: 7
000

SEQ ID NO: 8              moltype =    length =
SEQUENCE: 8
000

SEQ ID NO: 9              moltype =    length =
SEQUENCE: 9
000

SEQ ID NO: 10             moltype =    length =
SEQUENCE: 10
000

SEQ ID NO: 11             moltype =    length =
SEQUENCE: 11
000

SEQ ID NO: 12             moltype =    length =
SEQUENCE: 12
000

SEQ ID NO: 13             moltype =    length =
SEQUENCE: 13
000

SEQ ID NO: 14             moltype =    length =
SEQUENCE: 14
000

SEQ ID NO: 15             moltype =    length =
SEQUENCE: 15
000

SEQ ID NO: 16             moltype =    length =
SEQUENCE: 16
000

SEQ ID NO: 17             moltype =    length =
SEQUENCE: 17
000

SEQ ID NO: 18             moltype =    length =
SEQUENCE: 18
000

SEQ ID NO: 19             moltype =    length =
SEQUENCE: 19
000

SEQ ID NO: 20             moltype =    length =
SEQUENCE: 20
000

SEQ ID NO: 21             moltype =    length =
SEQUENCE: 21
000

SEQ ID NO: 22             moltype =    length =
SEQUENCE: 22
000

SEQ ID NO: 23             moltype =    length =
SEQUENCE: 23
000

SEQ ID NO: 24             moltype =    length =
SEQUENCE: 24
000
```

| | | |
|---|---|---|
| SEQ ID NO: 25<br>SEQUENCE: 25<br>000 | moltype = | length = |
| SEQ ID NO: 26<br>SEQUENCE: 26<br>000 | moltype = | length = |
| SEQ ID NO: 27<br>SEQUENCE: 27<br>000 | moltype = | length = |
| SEQ ID NO: 28<br>SEQUENCE: 28<br>000 | moltype = | length = |
| SEQ ID NO: 29<br>SEQUENCE: 29<br>000 | moltype = | length = |
| SEQ ID NO: 30<br>SEQUENCE: 30<br>000 | moltype = | length = |
| SEQ ID NO: 31<br>SEQUENCE: 31<br>000 | moltype = | length = |
| SEQ ID NO: 32<br>SEQUENCE: 32<br>000 | moltype = | length = |
| SEQ ID NO: 33<br>SEQUENCE: 33<br>000 | moltype = | length = |
| SEQ ID NO: 34<br>SEQUENCE: 34<br>000 | moltype = | length = |
| SEQ ID NO: 35<br>SEQUENCE: 35<br>000 | moltype = | length = |
| SEQ ID NO: 36<br>SEQUENCE: 36<br>000 | moltype = | length = |
| SEQ ID NO: 37<br>SEQUENCE: 37<br>000 | moltype = | length = |
| SEQ ID NO: 38<br>SEQUENCE: 38<br>000 | moltype = | length = |
| SEQ ID NO: 39<br>SEQUENCE: 39<br>000 | moltype = | length = |
| SEQ ID NO: 40<br>SEQUENCE: 40<br>000 | moltype = | length = |
| SEQ ID NO: 41<br>SEQUENCE: 41<br>000 | moltype = | length = |
| SEQ ID NO: 42<br>SEQUENCE: 42<br>000 | moltype = | length = |
| SEQ ID NO: 43<br>SEQUENCE: 43<br>000 | moltype = | length = |
| SEQ ID NO: 44<br>SEQUENCE: 44<br>000 | moltype = | length = |

```
SEQ ID NO: 45          moltype =    length =
SEQUENCE: 45
000

SEQ ID NO: 46          moltype =    length =
SEQUENCE: 46
000

SEQ ID NO: 47          moltype =    length =
SEQUENCE: 47
000

SEQ ID NO: 48          moltype =    length =
SEQUENCE: 48
000

SEQ ID NO: 49          moltype = AA  length = 20
FEATURE                Location/Qualifiers
source                 1..20
                       mol_type = protein
                       organism = synthetic construct
SEQUENCE: 49
METDTLLLWV LLLWVPGSTG                                            20

SEQ ID NO: 50          moltype = AA  length = 23
FEATURE                Location/Qualifiers
source                 1..23
                       mol_type = protein
                       organism = synthetic construct
SEQUENCE: 50
MRPTWAWWLF LVLLLALWAP ARG                                        23

SEQ ID NO: 51          moltype = AA  length = 19
FEATURE                Location/Qualifiers
source                 1..19
                       mol_type = protein
                       organism = synthetic construct
SEQUENCE: 51
MGWSCIILFL VATATGVHS                                             19

SEQ ID NO: 52          moltype =    length =
SEQUENCE: 52
000

SEQ ID NO: 53          moltype =    length =
SEQUENCE: 53
000

SEQ ID NO: 54          moltype =    length =
SEQUENCE: 54
000

SEQ ID NO: 55          moltype =    length =
SEQUENCE: 55
000

SEQ ID NO: 56          moltype =    length =
SEQUENCE: 56
000

SEQ ID NO: 57          moltype =    length =
SEQUENCE: 57
000

SEQ ID NO: 58          moltype =    length =
SEQUENCE: 58
000

SEQ ID NO: 59          moltype =    length =
SEQUENCE: 59
000

SEQ ID NO: 60          moltype =    length =
SEQUENCE: 60
000

SEQ ID NO: 61          moltype =    length =
SEQUENCE: 61
```

000

SEQ ID NO: 62           moltype =    length =
SEQUENCE: 62
000

SEQ ID NO: 63           moltype =    length =
SEQUENCE: 63
000

SEQ ID NO: 64           moltype =    length =
SEQUENCE: 64
000

SEQ ID NO: 65           moltype =    length =
SEQUENCE: 65
000

SEQ ID NO: 66           moltype =    length =
SEQUENCE: 66
000

SEQ ID NO: 67           moltype =    length =
SEQUENCE: 67
000

SEQ ID NO: 68           moltype =    length =
SEQUENCE: 68
000

SEQ ID NO: 69           moltype =    length =
SEQUENCE: 69
000

SEQ ID NO: 70           moltype =    length =
SEQUENCE: 70
000

SEQ ID NO: 71           moltype =    length =
SEQUENCE: 71
000

SEQ ID NO: 72           moltype =    length =
SEQUENCE: 72
000

SEQ ID NO: 73           moltype =    length =
SEQUENCE: 73
000

SEQ ID NO: 74           moltype =    length =
SEQUENCE: 74
000

SEQ ID NO: 75           moltype =    length =
SEQUENCE: 75
000

SEQ ID NO: 76           moltype =    length =
SEQUENCE: 76
000

SEQ ID NO: 77           moltype =    length =
SEQUENCE: 77
000

SEQ ID NO: 78           moltype =    length =
SEQUENCE: 78
000

SEQ ID NO: 79           moltype =    length =
SEQUENCE: 79
000

SEQ ID NO: 80           moltype =    length =
SEQUENCE: 80
000

SEQ ID NO: 81           moltype =    length =

```
SEQUENCE: 81
000

SEQ ID NO: 82         moltype =    length =
SEQUENCE: 82
000

SEQ ID NO: 83         moltype =    length =
SEQUENCE: 83
000

SEQ ID NO: 84         moltype =    length =
SEQUENCE: 84
000

SEQ ID NO: 85         moltype =    length =
SEQUENCE: 85
000

SEQ ID NO: 86         moltype =    length =
SEQUENCE: 86
000

SEQ ID NO: 87         moltype =    length =
SEQUENCE: 87
000

SEQ ID NO: 88         moltype =    length =
SEQUENCE: 88
000

SEQ ID NO: 89         moltype =    length =
SEQUENCE: 89
000

SEQ ID NO: 90         moltype =    length =
SEQUENCE: 90
000

SEQ ID NO: 91         moltype =    length =
SEQUENCE: 91
000

SEQ ID NO: 92         moltype =    length =
SEQUENCE: 92
000

SEQ ID NO: 93         moltype =    length =
SEQUENCE: 93
000

SEQ ID NO: 94         moltype =    length =
SEQUENCE: 94
000

SEQ ID NO: 95         moltype =    length =
SEQUENCE: 95
000

SEQ ID NO: 96         moltype =    length =
SEQUENCE: 96
000

SEQ ID NO: 97         moltype =    length =
SEQUENCE: 97
000

SEQ ID NO: 98         moltype =    length =
SEQUENCE: 98
000

SEQ ID NO: 99         moltype =    length =
SEQUENCE: 99
000

SEQ ID NO: 100        moltype = AA   length = 697
FEATURE               Location/Qualifiers
source                1..697
                      mol_type = protein
```

```
                        organism = synthetic construct
SEQUENCE: 100
DIQMTQSPSS LSASVGDRVT ITCSASSSVS YMHWYQQKSG KAPKLLIYDT SKLASGVPSR    60
FSGSGSGTDF TLTISSLQPE DFATYYCQQW SGYPLTFGQG TKLEIKGGGG SGGGGSGGGG   120
SGGGGSQVQL VQSGAEVKKP GASVKVSCKA SGYSFTGYTM NWVRQAPGQG LEWMGLITPY   180
NGASSYNQKF RGKATMTVDT STSTVYMELS SLRSEDTAVY YCARGGYDGR GFDYWGQGTL   240
VTVSSGGGGS EVQLVESGGG LVQPGGSLRL SCAASGVTFN YYGMSWIRQA PGKGLEWVAS   300
ITSSGGRIYY PDSVKGRFTI SRENTQKTLY LQMNSLRAED TAVYYCTLDG RDGWVAYWGQ   360
GTLVTVSSAS TKGPSVFPLA PSSKSTSGGT AALGCLVKDY FPEPVTVSWN SGALTSGVHT   420
FPAVLQSSGL YSLSSVVTVP SSSLGTQTYI CNVNHKPSNT KVDKKVEPKS CDKTHTCPPC   480
PAPEAAGGPS VFLFPPKPKD TLMISRTPEV TCVVVSVSHE DPEVKFNWYV DGVEVHNAKT   540
KPREEQYNST YRVVSVLTVL HQDWLNGKEY KCKVSNKALP APIEKTISKA KGQPREPQVY   600
VYPPSRDELT KNQVSLTCLV KGFYPSDIAV EWESNGQPEN NYKTTPPVLD SDGSFALVSK   660
LTVDKSRWQQ GNVFSCSVMH EALHNHYTQK SLSLSPG                            697

SEQ ID NO: 101          moltype = AA   length = 106
FEATURE                 Location/Qualifiers
source                  1..106
                        mol_type = protein
                        organism = synthetic construct
SEQUENCE: 101
DIQMTQSPSS LSASVGDRVT ITCSASSSVS YMHWYQQKSG KAPKLLIYDT SKLASGVPSR    60
FSGSGSGTDF TLTISSLQPE DFATYYCQQW SGYPLTFGQG TKLEIK                  106

SEQ ID NO: 102          moltype = AA   length = 20
FEATURE                 Location/Qualifiers
source                  1..20
                        mol_type = protein
                        organism = synthetic construct
SEQUENCE: 102
GGGGSGGGGS GGGGSGGGGS                                                20

SEQ ID NO: 103          moltype = AA   length = 119
FEATURE                 Location/Qualifiers
source                  1..119
                        mol_type = protein
                        organism = synthetic construct
SEQUENCE: 103
QVQLVQSGAE VKKPGASVKV SCKASGYSFT GYTMNWVRQA PGQGLEWMGL ITPYNGASSY    60
NQKFRGKATM TVDTSTSTVY MELSSLRSED TAVYYCARGG YDGRGFDYWG QGTLVTVSS    119

SEQ ID NO: 104          moltype = AA   length = 5
FEATURE                 Location/Qualifiers
source                  1..5
                        mol_type = protein
                        organism = synthetic construct
SEQUENCE: 104
GGGGS                                                                 5

SEQ ID NO: 105          moltype = AA   length = 118
FEATURE                 Location/Qualifiers
source                  1..118
                        mol_type = protein
                        organism = synthetic construct
SEQUENCE: 105
EVQLVESGGG LVQPGGSLRL SCAASGVTFN YYGMSWIRQA PGKGLEWVAS ITSSGGRIYY    60
PDSVKGRFTI SRENTQKTLY LQMNSLRAED TAVYYCTLDG RDGWVAYWGQ GTLVTVSS     118

SEQ ID NO: 106          moltype = AA   length = 98
FEATURE                 Location/Qualifiers
source                  1..98
                        mol_type = protein
                        organism = synthetic construct
SEQUENCE: 106
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKV                            98

SEQ ID NO: 107          moltype = AA   length = 15
FEATURE                 Location/Qualifiers
source                  1..15
                        mol_type = protein
                        organism = synthetic construct
SEQUENCE: 107
EPKSCDKTHT CPPCP                                                     15

SEQ ID NO: 108          moltype = AA   length = 110
FEATURE                 Location/Qualifiers
source                  1..110
                        mol_type = protein
```

```
                       organism = synthetic construct
SEQUENCE: 108
APEAAGGPSV FLFPPKPKDT LMISRTPEVT CVVVSVSHED PEVKFNWYVD GVEVHNAKTK          60
PREEQYNSTY RVVSVLTVLH QDWLNGKEYK CKVSNKALPA PIEKTISKAK                    110

SEQ ID NO: 109          moltype = AA   length = 106
FEATURE                 Location/Qualifiers
source                  1..106
                        mol_type = protein
                        organism = synthetic construct
SEQUENCE: 109
GQPREPQVYV YPPSRDELTK NQVSLTCLVK GFYPSDIAVE WESNGQPENN YKTTPPVLDS          60
DGSFALVSKL TVDKSRWQQG NVFSCSVMHE ALHNHYTQKS LSLSPG                        106

SEQ ID NO: 110          moltype = AA   length = 478
FEATURE                 Location/Qualifiers
source                  1..478
                        mol_type = protein
                        organism = synthetic construct
SEQUENCE: 110
DIQMTQSPSS LSASVGDRVT ITCSASSSVS YMHWYQQKSG KAPKLLIYDT SKLASGVPSR          60
FSGSGSGTDF TLTISSLQPE DFATYYCQQW SGYPLTFGQG TKLEIKGGGG SGGGGSGGGG         120
SGGGGSQVQL VQSGAEVKKP GASVKVSCKA SGYSFTGYTM NWVRQAPGQG LEWMGLITPY         180
NGASSYNQKF RGKATMTVDT STSTVYMELS SLRSEDTAVY YCARGGYDGR GFDYWGQGTL         240
VTVSSAAEPK SSDKTHTCPP CPAPEAAGGP SVFLFPPKPK DTLMISRTPE VTCVVVSVSH         300
EDPEVKFNWY VDGVEVHNAK TKPREEQYNS TYRVVSVLTV LHQDWLNGKE YKCKVSNKAL         360
PAPIEKTISK AKGQPREPQV YVLPPSRDEL TKNQVSLLCL VKGFYPSDIA VEWESNGQPE         420
NNYLTWPPVL DSDGSFFLYS KLTVDKSRWQ QGNVFSCSVM HEALHNHYTQ KSLSLSPG          478

SEQ ID NO: 111          moltype = AA   length = 17
FEATURE                 Location/Qualifiers
source                  1..17
                        mol_type = protein
                        organism = synthetic construct
SEQUENCE: 111
AAEPKSSDKT HTCPPCP                                                         17

SEQ ID NO: 112          moltype = AA   length = 15
FEATURE                 Location/Qualifiers
source                  1..15
                        mol_type = protein
                        organism = synthetic construct
SEQUENCE: 112
EPKSSDKTHT CPPCP                                                           15

SEQ ID NO: 113          moltype = AA   length = 106
FEATURE                 Location/Qualifiers
source                  1..106
                        mol_type = protein
                        organism = synthetic construct
SEQUENCE: 113
GQPREPQVYV LPPSRDELTK NQVSLLCLVK GFYPSDIAVE WESNGQPENN YLTWPPVLDS          60
DGSFFLYSKL TVDKSRWQQG NVFSCSVMHE ALHNHYTQKS LSLSPG                        106

SEQ ID NO: 114          moltype = AA   length = 215
FEATURE                 Location/Qualifiers
source                  1..215
                        mol_type = protein
                        organism = synthetic construct
SEQUENCE: 114
NFMLTQPHSV SESPGKTVTI SCKRNTGNIG SNYVNWYQQH EGSSPTTIIY RNDKRPDGVS          60
DRFSGSIDRS SKSASLTISN LKTEDEADYF CQSYSSGFIF GGGTKLTVLG QPKAAPSVTL        120
FPPSSEELQA NKATLVCLIS DFYPGAVTVA WKADSSPVKA GVETTTPSKQ SNNKYAASSY        180
LSLTPEQWKS HRSYSCQVTH EGSTVEKTVA PTECS                                   215

SEQ ID NO: 115          moltype = AA   length = 109
FEATURE                 Location/Qualifiers
source                  1..109
                        mol_type = protein
                        organism = synthetic construct
SEQUENCE: 115
NFMLTQPHSV SESPGKTVTI SCKRNTGNIG SNYVNWYQQH EGSSPTTIIY RNDKRPDGVS          60
DRFSGSIDRS SKSASLTISN LKTEDEADYF CQSYSSGFIF GGGTKLTVL                    109

SEQ ID NO: 116          moltype = AA   length = 106
FEATURE                 Location/Qualifiers
source                  1..106
                        mol_type = protein
                        organism = synthetic construct
```

-continued

```
SEQUENCE: 116
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 117          moltype = AA   length = 473
FEATURE                 Location/Qualifiers
source                  1..473
                        mol_type = protein
                        organism = synthetic construct
SEQUENCE: 117
QVQLVQSGAE VKKPGASVKV SCKASGYSFT GYTMNWVRQA PGQGLEWMGL ITPYNGASSY    60
NQKFRGKATM TVDTSTSTVY MELSSLRSED TAVYYCARGG YDGRGFDYWG QGTLVTVSSG   120
GGGSGGGGSG GGGSDIQMTQ SPSSLSASVG DRVTITCSAS SSVSYMHWYQ QKSGKAPKLL   180
IYDTSKLASG VPSRFSGSGS GTDFTLTISS LQPEDFATYY CQQWSGYPLT FGQGTKLEIK   240
AAEPKSSDKT HTCPPCPAPE AAGGPSVFLF PPKPKDTLMI SRTPEVTCVV VSVSHEDPEV   300
KFNWYVDGVE VHNAKTKPRE EQYNSTYRVV SVLTVLHQDW LNGKEYKCKV SNKALPAPIE   360
KTISKAKGQP REPQVYVLPP SRDELTKNQV SLLCLVKGFY PSDIAVEWES NGQPENNYLT   420
WPPVLDSDGS FFLYSKLTVD KSRWQQGNVF SCSVMHEALH NHYTQKSLSL SPG          473

SEQ ID NO: 118          moltype = AA   length = 15
FEATURE                 Location/Qualifiers
source                  1..15
                        mol_type = protein
                        organism = synthetic construct
SEQUENCE: 118
GGGGSGGGGS GGGGS                                                     15

SEQ ID NO: 119          moltype = AA   length = 692
FEATURE                 Location/Qualifiers
source                  1..692
                        mol_type = protein
                        organism = synthetic construct
SEQUENCE: 119
QVQLVQSGAE VKKPGASVKV SCKASGYSFT GYTMNWVRQA PGQGLEWMGL ITPYNGASSY    60
NQKFRGKATM TVDTSTSTVY MELSSLRSED TAVYYCARGG YDGRGFDYWG QGTLVTVSSG   120
GGGSGGGGSG GGGSDIQMTQ SPSSLSASVG DRVTITCSAS SSVSYMHWYQ QKSGKAPKLL   180
IYDTSKLASG VPSRFSGSGS GTDFTLTISS LQPEDFATYY CQQWSGYPLT FGQGTKLEIK   240
GGGGSEVQLV ESGGGLVQPG GSLRLSCAAS GVTFNYYGMS WIRQAPGKGL EWVASITSSG   300
GRIYYPDSVK GRFTISRENT QKTLYLQMNS LRAEDTAVYY CTLDGRDGWV AYWGQGTLVT   360
VSSASTKGPS VFPLAPSSKS TSGGTAALGC LVKDYFPEPV TVSWNSGALT SGVHTFPAVL   420
QSSGLYSLSS VVTVPSSSLG TQTYICNVNH KPSNTKVDKK VEPKSCDKTH TCPPCPAPEA   480
AGGPSVFLFP PKPKDTLMIS RTPEVTCVVV SVSHEDPEVK FNWYVDGVEV HNAKTKPREE   540
QYNSTYRVVS VLTVLHQDWL NGKEYKCKVS NKALPAPIEK TISKAKGQPR EPQVYVYPPS   600
RDELTKNQVS LTCLVKGFYP SDIAVEWESN GQPENNYKTT PPVLDSDGSF ALVSKLTVDK   660
SRWQQGNVFS CSVMHEALHN HYTQKSLSLS PG                                 692

SEQ ID NO: 120          moltype = AA   length = 5
FEATURE                 Location/Qualifiers
source                  1..5
                        mol_type = protein
                        organism = synthetic construct
SEQUENCE: 120
GYTMN                                                                5

SEQ ID NO: 121          moltype = AA   length = 17
FEATURE                 Location/Qualifiers
source                  1..17
                        mol_type = protein
                        organism = synthetic construct
SEQUENCE: 121
LITPYNGASS YNQKFRG                                                   17

SEQ ID NO: 122          moltype = AA   length = 10
FEATURE                 Location/Qualifiers
source                  1..10
                        mol_type = protein
                        organism = synthetic construct
SEQUENCE: 122
GGYDGRGFDY                                                           10

SEQ ID NO: 123          moltype = AA   length = 10
FEATURE                 Location/Qualifiers
source                  1..10
                        mol_type = protein
                        organism = synthetic construct
SEQUENCE: 123
SASSSVSYMH                                                           10

SEQ ID NO: 124          moltype = AA   length = 7
```

```
FEATURE                 Location/Qualifiers
source                  1..7
                        mol_type = protein
                        organism = synthetic construct
SEQUENCE: 124
DTSKLAS                                                                 7

SEQ ID NO: 125          moltype = AA  length = 9
FEATURE                 Location/Qualifiers
source                  1..9
                        mol_type = protein
                        organism = synthetic construct
SEQUENCE: 125
QQWSGYPLT                                                               9

SEQ ID NO: 126          moltype = AA  length = 8
FEATURE                 Location/Qualifiers
source                  1..8
                        mol_type = protein
                        organism = synthetic construct
SEQUENCE: 126
GVTFNYYG                                                                8

SEQ ID NO: 127          moltype = AA  length = 8
FEATURE                 Location/Qualifiers
source                  1..8
                        mol_type = protein
                        organism = synthetic construct
SEQUENCE: 127
ITSSGGRI                                                                8

SEQ ID NO: 128          moltype = AA  length = 11
FEATURE                 Location/Qualifiers
source                  1..11
                        mol_type = protein
                        organism = synthetic construct
SEQUENCE: 128
TLDGRDGWVA Y                                                           11

SEQ ID NO: 129          moltype = AA  length = 8
FEATURE                 Location/Qualifiers
source                  1..8
                        mol_type = protein
                        organism = synthetic construct
SEQUENCE: 129
TGNIGSNY                                                                8

SEQ ID NO: 130          moltype =    length =
SEQUENCE: 130
000

SEQ ID NO: 131          moltype = AA  length = 8
FEATURE                 Location/Qualifiers
source                  1..8
                        mol_type = protein
                        organism = synthetic construct
SEQUENCE: 131
QSYSSGFI                                                                8

SEQ ID NO: 132          moltype = AA  length = 5
FEATURE                 Location/Qualifiers
source                  1..5
                        mol_type = protein
                        organism = synthetic construct
REGION                  5
                        note = The entire sequence of amino acids 1-5 can be
                         repeated one to five times
SEQUENCE: 132
GGGGS                                                                   5

SEQ ID NO: 133          moltype = AA  length = 5
FEATURE                 Location/Qualifiers
source                  1..5
                        mol_type = protein
                        organism = synthetic construct
REGION                  5
                        note = The entire sequence of amino acids 1-5 can be
                         repeated one to five times
SEQUENCE: 133
```

```
EAAAK                                                                                      5

SEQ ID NO: 134          moltype = AA  length = 5
FEATURE                 Location/Qualifiers
source                  1..5
                        mol_type = protein
                        organism = synthetic construct
SEQUENCE: 134
EAAAK                                                                                      5

SEQ ID NO: 135          moltype = AA  length = 10
FEATURE                 Location/Qualifiers
source                  1..10
                        mol_type = protein
                        organism = synthetic construct
SEQUENCE: 135
EAAAKEAAAK                                                                                10

SEQ ID NO: 136          moltype =     length =
SEQUENCE: 136
000

SEQ ID NO: 137          moltype = AA  length = 4
FEATURE                 Location/Qualifiers
source                  1..4
                        mol_type = protein
                        organism = synthetic construct
SEQUENCE: 137
PPPP                                                                                       4

SEQ ID NO: 138          moltype = AA  length = 5
FEATURE                 Location/Qualifiers
source                  1..5
                        mol_type = protein
                        organism = synthetic construct
SEQUENCE: 138
GPPPG                                                                                      5

SEQ ID NO: 139          moltype = AA  length = 7
FEATURE                 Location/Qualifiers
source                  1..7
                        mol_type = protein
                        organism = synthetic construct
SEQUENCE: 139
GGPPPGG                                                                                    7

SEQ ID NO: 140          moltype = AA  length = 6
FEATURE                 Location/Qualifiers
source                  1..6
                        mol_type = protein
                        organism = synthetic construct
SEQUENCE: 140
GPPPPG                                                                                     6

SEQ ID NO: 141          moltype = AA  length = 8
FEATURE                 Location/Qualifiers
source                  1..8
                        mol_type = protein
                        organism = synthetic construct
SEQUENCE: 141
GGPPPPGG                                                                                   8

SEQ ID NO: 142          moltype = AA  length = 6
FEATURE                 Location/Qualifiers
source                  1..6
                        mol_type = protein
                        organism = synthetic construct
REGION                  1..5
                        note = Up to four G residues may be deleted
REGION                  6
                        note = The entire sequence of amino acids can be repeated
                         one to five times
SEQUENCE: 142
GGGGGS                                                                                     6

SEQ ID NO: 143          moltype = AA  length = 9
FEATURE                 Location/Qualifiers
source                  1..9
                        mol_type = protein
```

```
                        organism = synthetic construct
REGION                  1..4
                        note = The amino acid residues 1-4 can be repeated one to
                         five times
SEQUENCE: 143
GGGSGGGGS                                                                      9

SEQ ID NO: 144          moltype = AA  length = 9
FEATURE                 Location/Qualifiers
source                  1..9
                        mol_type = protein
                        organism = synthetic construct
REGION                  5..9
                        note = The amino acid residues 5-9 can be repeated one to
                         five times
SEQUENCE: 144
GGGSGGGGS                                                                      9

SEQ ID NO: 145          moltype = AA  length = 9
FEATURE                 Location/Qualifiers
source                  1..9
                        mol_type = protein
                        organism = synthetic construct
REGION                  1..4
                        note = The amino acid residues 1-4 can be repeated one to
                         five times
REGION                  5..9
                        note = The amino acid residues 5-9 can be repeated one to
                         five times
SEQUENCE: 145
GGGSGGGGS                                                                      9

SEQ ID NO: 146          moltype = AA  length = 23
FEATURE                 Location/Qualifiers
source                  1..23
                        mol_type = protein
                        organism = synthetic construct
REGION                  1..20
                        note = Up to twenty G residues may be deleted
REGION                  1..21
                        note = The amino acid residues can be repeated one to
                         twenty times
SEQUENCE: 146
GGGGGGGGGG GGGGGGGGGG SGG                                                     23

SEQ ID NO: 147          moltype = AA  length = 21
FEATURE                 Location/Qualifiers
source                  1..21
                        mol_type = protein
                        organism = synthetic construct
REGION                  2..21
                        note = Up to twenty G residues may be deleted
REGION                  21
                        note = The entire sequence of amino acids can be repeated
                         one to twenty times
SEQUENCE: 147
SGGGGGGGGG GGGGGGGGGG G                                                       21

SEQ ID NO: 148          moltype = AA  length = 22
FEATURE                 Location/Qualifiers
source                  1..22
                        mol_type = protein
                        organism = synthetic construct
REGION                  3..22
                        note = Up to twenty G residues may be deleted
REGION                  22
                        note = The entire sequence of amino acids can be repeated
                         one to twenty times
SEQUENCE: 148
SEGGGGGGGG GGGGGGGGGG GG                                                      22

SEQ ID NO: 149          moltype = AA  length = 245
FEATURE                 Location/Qualifiers
source                  1..245
                        mol_type = protein
                        organism = synthetic construct
SEQUENCE: 149
DIQMTQSPSS LSASVGDRVT ITCSASSSVS YMHWYQQKSG KAPKLLIYDT SKLASGVPSR             60
FSGSGSGTDF TLTISSLQPE DFATYYCQQW SGYPLTFGQG TKLEIKGGGG SGGGGSGGGG            120
```

```
SGGGGSQVQL VQSGAEVKKP GASVKVSCKA SGYSFTGYTM NWVRQAPGQG LEWMGLITPY    180
NGASSYNQKF RGKATMTVDT STSTVYMELS SLRSEDTAVY YCARGGYDGR GFDYWGQGTL    240
VTVSS                                                                245

SEQ ID NO: 150          moltype = AA   length = 240
FEATURE                 Location/Qualifiers
source                  1..240
                        mol_type = protein
                        organism = synthetic construct
SEQUENCE: 150
QVQLVQSGAE VKKPGASVKV SCKASGYSFT GYTMNWVRQA PGQGLEWMGL ITPYNGASSY     60
NQKFRGKATM TVDTSTSTVY MELSSLRSED TAVYYCARGG YDGRGFDYWG QGTLVTVSSG    120
GGGSGGGGS GGGSDIQMTQ SPSSLSASVG DRVTITCSAS SSVSYMHWYQ QKSGKAPKLL    180
IYDTSKLASG VPSRFSGSGS GTDFTLTISS LQPEDFATYY CQQWSGYPLT FGQGTKLEIK    240

SEQ ID NO: 151          moltype = AA   length = 448
FEATURE                 Location/Qualifiers
source                  1..448
                        mol_type = protein
                        organism = synthetic construct
SEQUENCE: 151
QVQLVQSGAE VKKPGASVKV SCKASGYSFT GYTMNWVRQA PGQGLEWMGL ITPYNGASSY     60
NQKFRGKATM TVDTSTSTVY MELSSLRSED TAVYYCARGG YDGRGFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPEAAGGP    240
SVFLFPPKPK DTLMISRTPE VTCVVVSVSH EDPEVKFNWY VDGVEVHNAK TKPREEQYNS    300
TYRVVSVLTV LHQDWLNGKE YKCKVSNKAL PAPIEKTISK AKGQPREPQV YVLPPSRDEL    360
TKNQVSLLCL VKGFYPSDIA VEWESNGQPE NNYLTWPPVL DSDGSFFLYS KLTVDKSRWQ    420
QGNVFSCSVM HEALHNHYTQ KSLSLSPG                                       448

SEQ ID NO: 152          moltype = AA   length = 448
FEATURE                 Location/Qualifiers
source                  1..448
                        mol_type = protein
                        organism = synthetic construct
SEQUENCE: 152
QVQLVQSGAE VKKPGASVKV SCKASGYSFT GYTMNWVRQA PGQGLEWMGL ITPYNGASSY     60
NQKFRGKATM TVDTSTSTVY MELSSLRSED TAVYYCARGG YDGRGFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPEAAGGP    240
SVFLFPPKPK DTLMISRTPE VTCVVVSVSH EDPEVKFNWY VDGVEVHNAK TKPREEQYNS    300
TYRVVSVLTV LHQDWLNGKE YKCKVSNKAL PAPIEKTISK AKGQPREPQV YVYPPSRDEL    360
TKNQVSLTCL VKGFYPSDIA VEWESNGQPE NNYKTTPPVL DSDGSFALVS KLTVDKSRWQ    420
QGNVFSCSVM HEALHNHYTQ KSLSLSPG                                       448

SEQ ID NO: 153          moltype = AA   length = 213
FEATURE                 Location/Qualifiers
source                  1..213
                        mol_type = protein
                        organism = synthetic construct
SEQUENCE: 153
DIQMTQSPSS LSASVGDRVT ITCSASSSVS YMHWYQQKSG KAPKLLIYDT SKLASGVPSR     60
FSGSGSGTDF TLTISSLQPE DFATYYCQQW SGYPLTFGQG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 154          moltype = AA   length = 705
FEATURE                 Location/Qualifiers
source                  1..705
                        mol_type = protein
                        organism = synthetic construct
SEQUENCE: 154
QVQLVQSGAE VKKPGASVRV SCRASGYIFT ESGITWVRQA PGQGLEWMGW ISGYSGDTKY     60
AQKLQGRVTM TKDTSTTTAY MELRSLRYDD TAVYYCARDV QYSGSYLGAY YFDYWSPGTL    120
VTVSSGGGGS GGGGSGGGGS GGGQSVLTQP PSASGTPGQR VTISCSGSSS NIGTNYVYWY    180
QQFPGTAPKL LIYRSYQRPS GVPDRFSGSK SGSSASLAIS GLQSEDEADY YCATWDDSLD    240
GWVFGGGTKL TVLGGGGSEV QLVESGGGLV QPGGSLRLSC AASGVTFNYY GMSWIRQAPG    300
KGLEWVASIT SSGGRIYYPD SVKGRFTISR ENTQKTLYLQ MNSLRAEDTA VYYCTLDGRD    360
GWVAYWGQGT LVTVSSASTK GPSVFPLAPS SKSTSGGTAA LGCLVKDYFP EPVTVSWNSG    420
ALTSGVHTFP AVLQSSGLYS LSSVVTVPSS SLGTQTYICN VNHKPSNTKV DKKVEPKSCD    480
KTHTCPPCPA PEAAGGPSVF LFPPKPKDTL MISRTPEVTC VVVSVSHEDP EVKFNWYVDG    540
VEVHNAKTKP REEQYNSTYR VVSVLTVLHQ DWLNGKEYKC KVSNKALPAP IEKTISKAKG    600
QPREPQVYVY PPSRDELTKN QVSLTCLVKG FYPSDIAVEW ESNGQPENNY KTTPPVLDSD    660
GSFALVSKLT VDKSRWQQGN VFSCSVMHEA LHNHYTQKSL SLSPG                    705

SEQ ID NO: 155          moltype = AA   length = 486
FEATURE                 Location/Qualifiers
source                  1..486
                        mol_type = protein
```

```
                        organism = synthetic construct
SEQUENCE: 155
QVQLVQSGAE VKKPGASVRV SCRASGYIFT ESGITWVRQA PGQGLEWMGW ISGYSGDTKY    60
AQKLQGRVTM TKDTSTTTAY MELRSLRYDD TAVYYCARDV QYSGSYLGAY YFDYWSPGTL   120
VTVSSGGGGS GGGGSGGGGS GGGQSVLTQP PSASGTPGQR VTISCSGSSS NIGTNYVYWY   180
QQFPGTAPKL LIYRSYQRPS GVPDRFSGSK SGSSASLAIS GLQSEDEADY YCATWDDSLD   240
GWVFGGGTKL TVLAAEPKSS DKTHTCPPCP APEAAGGPSV FLFPPKPKDT LMISRTPEVT   300
CVVVSVSHED PEVKFNWYVD GVEVHNAKTK PREEQYNSTY RVVSVLTVLH QDWLNGKEYK   360
CKVSNKALPA PIEKTISKAK GQPREPQVYV LPPSRDELTK NQVSLLCLVK GFYPSDIAVE   420
WESNGQPENN YLTWPPVLDS DGSFFLYSKL TVDKSRWQQG NVFSCSVMHE ALHNHYTQKS   480
LSLSPG                                                              486

SEQ ID NO: 156          moltype = AA  length = 475
FEATURE                 Location/Qualifiers
source                  1..475
                        mol_type = protein
                        organism = synthetic construct
SEQUENCE: 156
EVQLVESGGG LVQPGGSLRL SCAASGVTFN YYGMSWIRQA PGKGLEWVAS ITSSGGRIYY    60
PDSVKGRFTI SRENTQKTLY LQMNSLRAED TAVYYCTLDG RDGWVAYWGQ GTLVTVSSGG   120
GGSGGGGSGG GGSNFMLTQP HSVSESPGKT VTISCKRNTG NIGSNYVNWY QQHEGSSPTT   180
IIYRNDKRPD GVSDRFSGSI DRSSKSASLT ISNLKTEDEA DYFCQSYSSG FIFGGGTKLT   240
VLAAEPKSSD KTHTCPPCPA PEAAGGPSVF LFPPKPKDTL MISRTPEVTC VVVSVSHEDP   300
EVKFNWYVDG VEVHNAKTKP REEQYNSTYR VVSVLTVLHQ DWLNGKEYKC KVSNKALPAP   360
IEKTISKAKG QPREPQVYVY PPSRDELTKN QVSLTCLVKG FYPSDIAVEW ESNGQPENNY   420
KTTPPVLDSD GSFALVSKLT VDKSRWQQGN VFSCSVMHEA LHNHYTQKSL SLSPG        475

SEQ ID NO: 157          moltype = AA  length = 676
FEATURE                 Location/Qualifiers
source                  1..676
                        mol_type = protein
                        organism = synthetic construct
SEQUENCE: 157
QVQLVQSGAE VKKPGASVKV SCKASGYSFT GYTMNWVRQA PGQGLEWMGL ITPYNGASSY    60
NQKFRGKATM TVDTSTSTVY MELSSLRSED TAVYYCARGG YDGRGFDYWG QGTLVTVSSA   120
STKGPSVFPR APSSKSTSGG TAALGCLVKD YFPEPVTVSW NSGALTSGVH TFPAVLQSSG   180
LYKLSSVVTV PSSSLGTQTY ICNVNHKPSN TKVDKKVEPK SCDKTHTGGE VQLVESGGGL   240
VQPGGSLRLS CAASGVTFNY YGMSWIRQAP GKGLEWVASI TSSGGRIYYP DSVKGRFTIS   300
RENTQKTLYL QMNSLRAEDT AVYYCTLDGR DGWVAYWGQG TLVTVSSAST KGPSVFPLAP   360
SSKSTSGGTA WLGCDTDYF PEPVTVSWNS GALTSGVHTF PAVLQSSGLY SLSSVVTVPS   420
SSLGTQTYIC NVNHKPSNTK VDKKVEPKSC DKTHTCPPCP APEAAGGPSV FLFPPKPKDT   480
LMISRTPEVT CVVVSVSHED PEVKFNWYVD GVEVHNAKTK PREEQYNSTY RVVSVLTVLH   540
QDWLNGKEYK CKVSNKALPA PIEKTISKAK GQPREPQVYV YPPSRDELTK NQVSLTCLVK   600
GFYPSDIAVE WESNGQPENN YKTTPPVLDS DGSFALVSKL TVDKSRWQQG NVFSCSVMHE   660
ALHNHYTQKS LSLSPG                                                   676

SEQ ID NO: 158          moltype = AA  length = 448
FEATURE                 Location/Qualifiers
source                  1..448
                        mol_type = protein
                        organism = synthetic construct
SEQUENCE: 158
QVQLVQSGAE VKKPGASVKV SCKASGYSFT GYTMNWVRQA PGQGLEWMGL ITPYNGASSY    60
NQKFRGKATM TVDTSTSTVY MELSSLRSED TAVYYCARGG YDGRGFDYWG QGTLVTVSSA   120
STKGPSVFPR APSSKSTSGG TAALGCLVKD YFPEPVTVSW NSGALTSGVH TFPAVLQSSG   180
LYKLSSVVTV PSSSLGTQTY ICNVNHKPSN TKVDKKVEPK SCDKTHTCPP CPAPEAAGGP   240
SVFLFPPKPK DTLMISRTPE VTCVVVSVSH EDPEVKFNWY VDGVEVHNAK TKPREEQYNS   300
TYRVVSVLTV LHQDWLNGKE YKCKVSNKAL PAPIEKTISK AKGQPREPQV YVLPPSRDEL   360
TKNQVSLLCL VKGFYPSDIA VEWESNGQPE NNYLTWPPVL DSDGSFFLYS KLTVDKSRWQ   420
QGNVFSCSVM HEALHNHYTQ KSLSLSPG                                      448

SEQ ID NO: 159          moltype = AA  length = 215
FEATURE                 Location/Qualifiers
source                  1..215
                        mol_type = protein
                        organism = synthetic construct
SEQUENCE: 159
NPMLTQPHSV SESPGKTVTI SCKRNTGNIG SNYVNWYQQH EGSSPTTIIY RNDKRPDGVS    60
DRFSGSIDRS SKSASLTISN LKTEDEADYF CQSYSSGFIF GGGTKLTVLG QPKAAPSVTL   120
FPPSSEQLQA NKARLVCLIS DFYPGAVTVA WKADSSPVKA GVETTTPSKQ SNNKYAASSY   180
LSLTPEQWKS HKSYSCQVTH EGSTVEKTVA PAECS                              215

SEQ ID NO: 160          moltype = AA  length = 213
FEATURE                 Location/Qualifiers
source                  1..213
                        mol_type = protein
                        organism = synthetic construct
SEQUENCE: 160
DIQMTQSPSS LSASVGDRVT ITCSASSSVS YMHWYQQKSG KAPKLLIYDT SKLASGVPSR    60
```

```
FSGSGSGTDF TLTISSLQPE DFATYYCQQW SGYPLTFGQG TKLEIKRTVA APSVFIFPPS    120
DEQLKSGTAS VGCWLNNFYP REAKVQWKVD NALQSGNSQE SVTEQDSKDS TYSLDSTLEL    180
SKADYEKHKV YACEVTHQGL SSPVTKSFNR GEC                                 213

SEQ ID NO: 161          moltype = AA   length = 692
FEATURE                 Location/Qualifiers
source                  1..692
                        mol_type = protein
                        organism = synthetic construct
SEQUENCE: 161
QVQLVQSGAE VKKPGASVKI SCKASGYSFT GYTMNWVRQA PGQGLEWIGL ITPYSGASSY     60
AQKFQGRATL TVDKSTSTAY MELSSLRSED TAVYYCARGG YDGRGFDYWG QGTLVTVSSG    120
GGGSGGGGSG GGGSEIVLTQ SPATLSLSPG ERVTMSCSAS SSVSYMHWYQ QKPGQAPRLW    180
IYDTSKLASG VPARFSGSGS GTDYTLTISS VEPEDFAVYY CQQWSGYPLT FGQGTKVEIK    240
GGGGSEVQLV ESGGGLVQPG GSLRLSCAAS GVTFNYYGMS WIRQAPGKGL EWVASITSSG    300
GRIYYPDSVK GRFTISRENT QKTLYLQMNS LRAEDTAVYY CTLDGRDGWV AYWGQGTLVT    360
VSSASTKGPS VFPLAPSSKS TSGGTAALGC LVKDYFPEPV TVSWNSGALT SGVHTFPAVL    420
QSSGLYSLSS VVTVPSSSLG TQTYICNVNH KPSNTKVDKK VEPKSCDKTH TCPPCPAPEA    480
AGGPSVFLFP PKPKDTLMIS RTPEVTCVVV SVSHEDPEVK FNWYVDGVEV HNAKTKPREE    540
QYNSTYRVVS VLTVLHQDWL NGKEYKCKVS NKALPAPIEK TISKAKGQPR EPQVYVYPPS    600
RDELTKNQVS LTCLVKGFYP SDIAVEWESN GQPENNYKTT PPVLDSDGSF ALVSKLTVDK    660
SRWQQGNVFS CSVMHEALHN HYTQKSLSLS PG                                  692

SEQ ID NO: 162          moltype = AA   length = 473
FEATURE                 Location/Qualifiers
source                  1..473
                        mol_type = protein
                        organism = synthetic construct
SEQUENCE: 162
QVQLVQSGAE VKKPGASVKI SCKASGYSFT GYTMNWVRQA PGQGLEWIGL ITPYSGASSY     60
AQKFQGRATL TVDKSTSTAY MELSSLRSED TAVYYCARGG YDGRGFDYWG QGTLVTVSSG    120
GGGSGGGGSG GGGSEIVLTQ SPATLSLSPG ERVTMSCSAS SSVSYMHWYQ QKPGQAPRLW    180
IYDTSKLASG VPARFSGSGS GTDYTLTISS VEPEDFAVYY CQQWSGYPLT FGQGTKVEIK    240
AAEPKSSDKT HTCPPCPAPE AAGGPSVFLF PPKPKDTLMI SRTPEVTCVV VSVSHEDPEV    300
KFNWYVDGVE VHNAKTKPRE EQYNSTYRVV SVLTVLHQDW LNGKEYKCKV SNKALPAPIE    360
KTISKAKGQP REPQVYVLPP SRDELTKNQV SLLCLVKGFY PSDIAVEWES NGQPENNYLT    420
WPPVLDSDGS FFLYSKLTVD KSRWQQGNVF SCSVMHEALH NHYTQKSLSL SPG           473

SEQ ID NO: 163          moltype = AA   length = 692
FEATURE                 Location/Qualifiers
source                  1..692
                        mol_type = protein
                        organism = synthetic construct
SEQUENCE: 163
EVQLLESGGG LVQPGGSVRI SCAASGYSFT GYTMNWVRQA PGKGLEWIGL ITPYSGASSY     60
ADSFKGRATL SVDNSKNTAY MQLNSLRAED TAVYYCARGG YDGRGFDYWG QGTLVTVSSG    120
GGGSGGGGSG GGGSDIQLTQ SPSSLSASVG DRVTMTCSAS SSVSYMHWYQ QKPGKAPKLW    180
IYDTSKLASG VPSRFSGSGS GTDYTLTISS VQPEDFATYY CQQWSKHPLT FGQGTKVEIK    240
GGGGSEVQLV ESGGGLVQPG GSLRLSCAAS GVTFNYYGMS WIRQAPGKGL EWVASITSSG    300
GRIYYPDSVK GRFTISRENT QKTLYLQMNS LRAEDTAVYY CTLDGRDGWV AYWGQGTLVT    360
VSSASTKGPS VFPLAPSSKS TSGGTAALGC LVKDYFPEPV TVSWNSGALT SGVHTFPAVL    420
QSSGLYSLSS VVTVPSSSLG TQTYICNVNH KPSNTKVDKK VEPKSCDKTH TCPPCPAPEA    480
AGGPSVFLFP PKPKDTLMIS RTPEVTCVVV SVSHEDPEVK FNWYVDGVEV HNAKTKPREE    540
QYNSTYRVVS VLTVLHQDWL NGKEYKCKVS NKALPAPIEK TISKAKGQPR EPQVYVYPPS    600
RDELTKNQVS LTCLVKGFYP SDIAVEWESN GQPENNYKTT PPVLDSDGSF ALVSKLTVDK    660
SRWQQGNVFS CSVMHEALHN HYTQKSLSLS PG                                  692

SEQ ID NO: 164          moltype = AA   length = 473
FEATURE                 Location/Qualifiers
source                  1..473
                        mol_type = protein
                        organism = synthetic construct
SEQUENCE: 164
EVQLLESGGG LVQPGGSVRI SCAASGYSFT GYTMNWVRQA PGKGLEWIGL ITPYSGASSY     60
ADSFKGRATL SVDNSKNTAY MQLNSLRAED TAVYYCARGG YDGRGFDYWG QGTLVTVSSG    120
GGGSGGGGSG GGGSDIQLTQ SPSSLSASVG DRVTMTCSAS SSVSYMHWYQ QKPGKAPKLW    180
IYDTSKLASG VPSRFSGSGS GTDYTLTISS VQPEDFATYY CQQWSKHPLT FGQGTKVEIK    240
AAEPKSSDKT HTCPPCPAPE AAGGPSVFLF PPKPKDTLMI SRTPEVTCVV VSVSHEDPEV    300
KFNWYVDGVE VHNAKTKPRE EQYNSTYRVV SVLTVLHQDW LNGKEYKCKV SNKALPAPIE    360
KTISKAKGQP REPQVYVLPP SRDELTKNQV SLLCLVKGFY PSDIAVEWES NGQPENNYLT    420
WPPVLDSDGS FFLYSKLTVD KSRWQQGNVF SCSVMHEALH NHYTQKSLSL SPG           473

SEQ ID NO: 165          moltype = AA   length = 673
FEATURE                 Location/Qualifiers
source                  1..673
                        mol_type = protein
                        organism = synthetic construct
SEQUENCE: 165
QVQLVQSGAE VKKPGASVKV SCKASGYSFT GYTMNWVRQA PGQGLEWMGL ITPYNGASSY     60
```

```
NQKFRGKATM TVDTSTSTVY MELSSLRSED TAVYYCARGG YDGRGFDYWG QGTLVTVSSA   120
STKGPSVFPL APSSKSTSGG TAALGCLVED YFPEPVTVSW NSGALTSGVH TFPAVLQSSG   180
LYSLSSVVTV PSSSLGTQTY ICNVNHKPSN TKVDEKVEPK SCDGGGGSGG GGSQAVVTQE   240
PSLTVSPGGT VTLTCGSSTG AVTTSNYANW VQEKPGQAFR GLIGGTNKRA PGTPARFSGS   300
LLGGKAALTL SGAQPEDEAE YYCALWYSNL WVFGGGTKLT VLSSASTKGP SVFPLAPSSK   360
STSGGTAALG CLVKDYFPEP VTVSWNSGAL TSGVHTFPAV LQSSGLYSLS SVVTVPSSSL   420
GTQTYICNVN HKPSNTKVDK KVEPKSCDKT HTCPPCPAPE AAGGPSVFLF PPKPKDTLMI   480
SRTPEVTCVV VDVSHEDPEV KFNWYVDGVE VHNAKTKPRE EQYNSTYRVV SVLTVLHQDW   540
LNGKEYKCKV SNKALGAPIE KTISKAKGQP REPQVYTLPP CRDELTKNQV SLWCLVKGFY   600
PSDIAVEWES NGQPENNYKT TPPVLDSDGS FFLYSKLTVD KSRWQQGNVF SCSVMHEALH   660
NHYTQKSLSL SPG                                                     673

SEQ ID NO: 166         moltype = AA length = 448
FEATURE                Location/Qualifiers
source                 1..448
                       mol_type = protein
                       organism = synthetic construct
SEQUENCE: 166
QVQLVQSGAE VKKPGASVKV SCKASGYSFT GYTMNWVRQA PGQGLEWMGL ITPYNGASSY    60
NQKFRGKATM TVDTSTSTVY MELSSLRSED TAVYYCARGG YDGRGFDYWG QGTLVTVSSA   120
STKGPSVFPL APSSKSTSGG TAALGCLVED YFPEPVTVSW NSGALTSGVH TFPAVLQSSG   180
LYSLSSVVTV PSSSLGTQTY ICNVNHKPSN TKVDEKVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL GAPIEKTISK AKGQPREPQV CTLPPSRDEL   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPG                                     448

SEQ ID NO: 167         moltype = AA length = 232
FEATURE                Location/Qualifiers
source                 1..232
                       mol_type = protein
                       organism = synthetic construct
SEQUENCE: 167
EVQLLESGGG LVQPGGSLRL SCAASGFTFS TYAMNWVRQA PGKGLEWVSR IRSKYNNYAT    60
YYADSVKGRF TISRDDSKNT LYLQMNSLRA EDTAVYYCVR HGNFGNSYVS WFAYWGQGTL   120
VTVSSASVAA PSVFIFPPSD EQLKSGTASV VCLLNNFYPR EAKVQWKVDN ALQSGNSQES   180
VTEQDSKDST YSLSSTLTLS KADYEKHKVY ACEVTHQGLS SPVTKSFNRG EC            232

SEQ ID NO: 168         moltype = AA length = 213
FEATURE                Location/Qualifiers
source                 1..213
                       mol_type = protein
                       organism = synthetic construct
SEQUENCE: 168
DIQMTQSPSS LSASVGDRVT ITCSASSSVS YMHWYQQKSG KAPKLLIYDT SKLASGVPSR    60
FSGSGSGTDF TLTISSLQPE DFATYYCQQW SKHPLTFGQG TKLEIKRTVA APSVFIFPPS   120
DRKLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 169         moltype = AA length = 504
FEATURE                Location/Qualifiers
source                 1..504
                       mol_type = protein
                       organism = synthetic construct
SEQUENCE: 169
QVQLVESGGG VVQAGGSLTL SCAASGFTFS IRAMRWYRQA PGTERDLVAV IYGSSTYYAD    60
AVKGRFTISR DNSKNTLYLQ MNSLRAEDTA VYYCNADTIG TARDYWGQGT LVTVSSGGGG   120
SGGGGSEVQL VESGGGLVQP GNSLRLSCAA SGFTFSKFGMS WVRQAPGKGL EWVSSISGSG   180
RDTLYADSVK GRFTISRDNA KTTLYLQMNS LRPEDTAVYY CTIGGSLSVS SQGTLVTVSS   240
GGGGSGGGSE VQLVESGGGL VQPGGSLKLS CAASGFTFNK YAINWVRQAP GKGLEWVARI   300
RSKYNNYATY YADQVKDRFT ISRDDSKNTA YLQMNNLKTE DTAVYYCVRH ANFGNSYISY   360
WAYWGQGTLV TVSSGGGGSG GGGSGGGGSQ TVVTQEPSLT VSPGGTVTLT CASSTGAVTS   420
GNYPNWVQQK PGQAPRGLIG GTKFLVPGTP ARFSGSLLGG KAALTSGVQ PEDEAEYYCT    480
LWYSNRWVFG GGTKLTVLHH HHHH                                         504

SEQ ID NO: 170         moltype = AA length = 585
FEATURE                Location/Qualifiers
source                 1..585
                       mol_type = protein
                       organism = synthetic construct
SEQUENCE: 170
DAHKSEVAHR FKDLGEENFK ALVLIAFAQY LQQCPFEDHV KLVNEVTEFA KTCVADESAE    60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
```

```
LVNRRPCFSA LEVDETYVPK EFNAETFTFH ADICTLSEKE RQIKKQTALV ELVKHKPKAT    540
KEQLKAVMDD FAAFVEKCCK ADDKETCFAE EGKKLVAASQ AALGL                   585

SEQ ID NO: 171           moltype = AA  length = 698
FEATURE                  Location/Qualifiers
source                   1..698
                         mol_type = protein
                         organism = synthetic construct
SEQUENCE: 171
DIQMTQSPSS LSASVGDRVT ITCSASSSVS YMHWYQQKSG KAPKLLIYDT SKLASGVPSR    60
FSGSGSGTDF TLTISSLQPE DFATYYCQQW SGYPLTFGQG TKLEIKGGGG SGGGGSGGGG   120
SGGGGSQVQL VQSGAEVKKP GASVKVSCKA SGYSFTGYTM NWVRQAPGQG LEWMGLITPY   180
NGASSYNQKF RGKATMTVDT STSTVYMELS SLRSEDTAVY YCARGGYDGR GFDYWGQGTL   240
VTVSSGGGGS EVQLVESGGG LVQPGGSLRL SCAASGVTFN YYGMSWIRQA PGKGLEWVAS   300
ITSSGGRIYY PDSVKGRFTI SRENTQKTLY LQMNSLRAED TAVYYCTLDG RDGWVAYWGQ   360
GTLVTVSSAS TKGPSVFPLA PSSKSTSGGT AALGCLVKDY FPEPVTVSWN SGALTSGVHT   420
FPAVLQSSGL YSLSSVVTVP SSSLGTQTYI CNVNHKPSNT KVDKKVEPKS CDKTHTCPPC   480
PAPEAAGGPS VFLFPPKPKD TLMISRTPEV TCVVVSVSHE DPEVKFNWYV DGVEVHNAKT   540
KPREEQYNST YRVVSVLTVL HQDWLNGKEY KCKVSNKALP APIEKTISKA KGQPREPQVY   600
VYPPSRDELT KNQVSLTCLV KGFYPSDIAV EWESNGQPEN NYKTTPPVLD SDGSFALVSK   660
LTVDKSRWQQ GNVFSCSVMH EALHNHYTQK SLSLSPGK                          698

SEQ ID NO: 172           moltype = AA  length = 479
FEATURE                  Location/Qualifiers
source                   1..479
                         mol_type = protein
                         organism = synthetic construct
SEQUENCE: 172
DIQMTQSPSS LSASVGDRVT ITCSASSSVS YMHWYQQKSG KAPKLLIYDT SKLASGVPSR    60
FSGSGSGTDF TLTISSLQPE DFATYYCQQW SGYPLTFGQG TKLEIKGGGG SGGGGSGGGG   120
SGGGGSQVQL VQSGAEVKKP GASVKVSCKA SGYSFTGYTM NWVRQAPGQG LEWMGLITPY   180
NGASSYNQKF RGKATMTVDT STSTVYMELS SLRSEDTAVY YCARGGYDGR GFDYWGQGTL   240
VTVSSAAEPK SSDKTHTCPP CPAPEAAGGP SVFLFPPKPK DTLMISRTPE VTCVVVSVSH   300
EDPEVKFNWY VDGVEVHNAK TKPREEQYNS TYRVVSVLTV LHQDWLNGKE YKCKVSNKAL   360
PAPIEKTISK AKGQPREPQV YVLPPSRDEL TKNQVSLLCL VKGFYPSDIA VEWESNGQPE   420
NNYLTWPPVL DSDGSFFLYS KLTVDKSRWQ QGNVFSCSVM HEALHNHYTQ KSLSLSPGK    479
```